United States Patent
Suzuki et al.

(10) Patent No.: US 11,076,595 B2
(45) Date of Patent: Aug. 3, 2021

(54) 1-(N,N-DISUBSTITUTED CARBAMOYL) 4-(SUBSTITUTED SULFONYL)TRIAZOLIN-5-ONE DERIVATIVE, 4-(N,N-DISUBSTITUTED CARBAMOYL) 1-(SUBSTITUTED SULFONYL)TRIAZOLIN-5-ONE DERIVATIVE, AND HERBICIDE CONTAINING SAID DERIVATIVE AS ACTIVE INGREDIENT

(71) Applicant: HOKKO CHEMICAL INDUSTRY CO., LTD., Tokyo (JP)

(72) Inventors: Jun Suzuki, Kanagawa (JP); Hitoshi Wakabayashi, Kanagawa (JP); Akihito Ootaka, Kanagawa (JP); Sho Sunagawa, Kanagawa (JP); Kohei Koyama, Kanagawa (JP); Satoshi Kanematsu, Kanagawa (JP)

(73) Assignee: HOKKO CHEMICAL INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 16/643,333

(22) PCT Filed: Aug. 31, 2018

(86) PCT No.: PCT/JP2018/032509
§ 371 (c)(1),
(2) Date: Feb. 28, 2020

(87) PCT Pub. No.: WO2019/045085
PCT Pub. Date: Mar. 7, 2019

(65) Prior Publication Data
US 2020/0367499 A1    Nov. 26, 2020

(30) Foreign Application Priority Data

Aug. 31, 2017 (JP) ............................. JP2017-167829
Aug. 31, 2017 (JP) ............................. JP2017-167830

(51) Int. Cl.
*A01N 43/653* (2006.01)
*C07D 249/12* (2006.01)

(52) U.S. Cl.
CPC ......... *A01N 43/653* (2013.01); *C07D 249/12* (2013.01)

(58) Field of Classification Search
CPC .. A01N 43/653; C07D 249/12; C07D 401/12; C07D 403/12; C07D 409/12
See application file for complete search history.

(56) References Cited

U.S. PATENT DOCUMENTS 5,061,311 A   10/1991  Findeisen et al.
5,147,445 A    9/1992  Takeuchi et al.
5,496,793 A    3/1996  Andree et al.
5,610,121 A    3/1997  Riebel et al.
2011/0245308 A1  10/2011  Brüggemeier et al.

FOREIGN PATENT DOCUMENTS

| DE | 2042660 | 3/1972 |
|----|---------|--------|
| DE | 42 17 719 | 12/1993 |
| DE | 10 2008 060 967 | 6/2010 |
| EP | 0 281 289 | 9/1988 |
| JP | 60-100561 | 6/1985 |
| JP | 63-255271 | 10/1988 |
| JP | 01-102070 | 4/1989 |
| JP | 01-121279 | 5/1989 |
| JP | 01-279876 | 11/1989 |

(Continued)

OTHER PUBLICATIONS

Wu, Q. et al., "Synthesis and Biological Activity of Novel Phenyltriazolinone Derivatives", Molecules, vol. 13, 2010, pp. 9024-9034.

(Continued)

*Primary Examiner* — Anna Pagonakis
(74) *Attorney, Agent, or Firm* — Wenderoth, Lind & Ponack, L.L.P.

(57) ABSTRACT

The present invention provides a 1-(N,N-disubstituted carbamoyl)4-(substituted sulfonyl)triazolin-5-one derivative represented by the following formula (1), a 4-(N,N-disubstituted carbamoyl)1-(substituted sulfonyl)triazolin-5-one derivative represented by the following formula (11), each of which exhibits an excellent herbicidal activity, and a herbicide characterized by containing the derivative as an active ingredient:

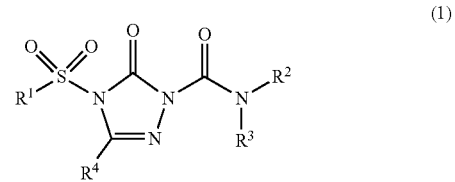

(1)

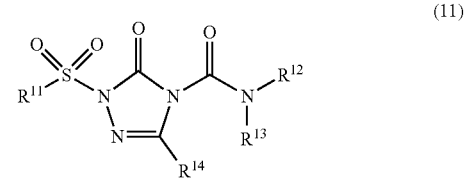

(11)

wherein in the formula (1), $R^1$ to $R^4$ represent predetermined substituents, and in the formula (11), $R^{11}$ to $R^{14}$ represent predetermined substituents.

12 Claims, No Drawings

(56) References Cited

FOREIGN PATENT DOCUMENTS

| JP | 02-1481 | 1/1990 |
|---|---|---|
| JP | 03-106865 | 5/1991 |
| JP | 03-279368 | 12/1991 |
| JP | 07-188187 | 7/1995 |
| JP | 2003-342265 | 12/2003 |
| JP | 2012-077078 | 4/2012 |
| WO | 88/06156 | 8/1988 |
| WO | 99/25700 | 5/1999 |
| WO | 2007/139968 | 12/2007 |
| WO | 2010/063402 | 6/2010 |
| WO | 2010/070523 | 6/2010 |
| WO | 2011/104332 | 9/2011 |
| WO | 2017/011445 | 1/2017 |

OTHER PUBLICATIONS

Wujec, M. et al., "New Derivatives of 3-[(4-Phenyl-5-Oxo-1,2,4-Triazolin-1-Yl)-Methyl]-4-Substituted 1,2,4-Triazolin-5-One" Heterocycles, vol. 68, No. 4, 2006, pp. 779-785.

Salah, B. B. et al., "Synthesis, Crystal Structure, and Antibacterial Activity of 1,2,4-Triazoles and 1,2,4-Triazol-3-one", Journal of Heterocyclic Chemistry, vol. 52, No. 6, 2015, pp. 1769-1775.

Şahin, D. et al., "Design and synthesis of new 1,2,4-triazole derivatives containing morpholine moiety as antimicrobial agents" Turkish Journal of Chemistry, vol. 36, No. 3, 2012, pp. 411-426.

Varmaghani, F. et al., "Electrochemical oxidation of 4-substituted urazoles in the presence of arylsulfinic acids: an efficient method for the synthesis of new sulfonamide derivatives", Green Chemistry, vol. 14, No. 4, 2012, pp. 963-967.

Şahin, D. et al., "Design and synthesis of some azole derivatives as potential antimicrobial agents" Medicinal Chemistry Research, vol. 21, No. 12, 2012, pp. 4485-4498.

Flanagan, M. E. et al., "Preparation, Gram-Negative Antibacterial Activity, and Hydrolytic Stability of Novel Siderophore-Conjugated Monocarbam Diols" ACS Medicinal Chemistry Letter, vol. 2, No. 5, 2011, pp. 385-390.

Bektaş, H. et al., "Synthesis and Antimicrobial Activities of Some New 1,2,4-Triazole Derivatives" Molecules, vol. 15, 2010, pp. 2427-2438.

Baxendale, I. R. et al., "The rapid preparation of 2-aminosulfonamide-1,3,4-oxadiazoles using polymer-supported reagents and microwave heating", Tetrahedron, vol. 61, No. 22, 2005, pp. 5323-5349.

Chouaieb, H. et al., "Novel Method for the Synthesis of 1,2,4-Triazoles and 1,2,4-Triazol-3-ones" Synthetic Communications, vol. 33(22), 2003, pp. 3861-3868.

Read G. et al., "Synthetic studies on 4,5-dihyrdo-3H-1,2,4-triazole-3,5-diones bearing fluorogenic residues at N-4", Journal of Chemical Society Perkin Transactions 1: Organic and Bio-organic Chemistry, No. 2, 1996, pp. 167-174.

"Synthesis and Structure-Activity Relationships of Monocarbams Leading to U-78608" Journal of Antibiotics, vol. 43, No. 9, 1990, pp. 1199-1203.

Aly, N.F. et al., "Acid Azides. Part XI* Synthesis and Decomposition of Hydrazidoic Acid Azides" Egyptian Journal of Chemistry, vol. 30, No. 5, 1987, pp. 421-428.

Ahmed, R. et al., "The Oxidation of Hydrazine Derivatives with 4-Phenyl-1,2,4-Triazoline-3,5-Dione" Tetrahedron, vol. 28, No. 19, 1972, pp. 4939-4946.

International Search Report dated Nov. 27, 2018 in corresponding International (PCT) Application No. PCT/JP2018/032509, with English Translation.

Written Opinion dated Nov. 27, 2018 in corresponding International (PCT) Application No. PCT/JP2018/032509, with English Translation.

International Preliminary Report on Patentability dated Mar. 3, 2020 in corresponding International (PCT) Application No. PCT/JP2018/032509.

1-(N,N-DISUBSTITUTED CARBAMOYL) 4-(SUBSTITUTED SULFONYL)TRIAZOLIN-5-ONE DERIVATIVE, 4-(N,N-DISUBSTITUTED CARBAMOYL) 1-(SUBSTITUTED SULFONYL)TRIAZOLIN-5-ONE DERIVATIVE, AND HERBICIDE CONTAINING SAID DERIVATIVE AS ACTIVE INGREDIENT

TECHNICAL FIELD

The present invention relates to a 1-(N,N-disubstituted carbamoyl)4-(substituted sulfonyl)triazolin-5-one derivative, a 4-(N,N-disubstituted carbamoyl)1-(substituted sulfonyl)triazolin-5-one derivative, and a herbicide containing the said derivative as an active ingredient and having a very excellent control effect against noxious weeds in an agricultural or horticultural cultivation setting or a non-crop land.

BACKGROUND ART

It is essential to use a herbicide so as to protect useful crops such as rice, wheat, corn, soybean, cotton and beet from weeds and increase the yield. In recent years, there is desired a selective herbicide capable of selectively withering only weeds without showing any phytotoxicity to crops in a field where such useful crops are coexistent with weeds. In addition, from the viewpoint of, for example, preventing environmental pollution and reducing an economic cost at the time of transportation and spraying, a chemical preparation exhibiting a herbicidal effect with a dose of being as low as possible is needed.

Meanwhile, 4-(substituted sulfonyl)triazolin-5-one derivatives having a chemical structure analogous to the present invention have been reported in Patent Literatures 1 to 3 and Non-Patent Literatures 1 and 2. However, there exist neither examples of the triazolin-5-one derivative substituted at the 1-position by a carbamoyl group of the present invention nor reports that these compounds exhibit a herbicidal activity.

In addition, 1-(substituted sulfonyl)triazolin-5-one derivatives having a chemical structure analogous to the present invention have been reported in Patent Literatures 4 to 14 and Non-Patent Literatures 3 to 15, but there exist neither examples of the 1-(substituted sulfonyl)triazolin-5-one derivative substituted at the 4-position by a carbamoyl group of the present invention nor reports that these compounds exhibit herbicidal activity.

BACKGROUND ART LITERATURE

Patent Literature

Patent Literature 1: JP-A-2012-077078
Patent Literature 2: WO2007/139968
Patent Literature 3: WO2010/070523
Patent Literature 4: WO2017/011445
Patent Literature 5: WO2011/104332
Patent Literature 6: WO2010/070523
Patent Literature 7: WO2010/063402
Patent Literature 8: German patent publication No. 2010/102008060967A
Patent Literature 9: JP-A-2003-342265
Patent Literature 10: German patent publication No. 1993/4217719A
Patent Literature 11: JP-A-1991-106865
Patent Literature 12: EP-A-1988-281289
Patent Literature 13: WO1988/06156
Patent Literature 14: German patent publication No. 1972/2042660A

Non-Patent Literature

Non-Patent Literature 1: Molecules, Vol. 13, 2010, pp. 9024-9034
Non-Patent Literature 2: Heterocycles, Vol. 68, No. 4, 2006, pp. 779-785
Non-Patent Literature 3: Journal of Heterocyclic Chemistry, Vol. 52, No. 6, 2015, pp. 1769-1775
Non-Patent Literature 4: Turkish Journal of Chemistry, Vol. 36, No. 3, 2012, pp. 411-426
Non-Patent Literature 5: Green Chemistry, Vol. 14, No. 4, 2012, pp. 963-967
Non-Patent Literature 6: Medicinal Chemistry Research, Vol. 21, No. 12, 2012, pp. 4485-4498
Non-Patent Literature 7: Medicinal Chemistry Letter, Vol. 2, No. 5, 2011, pp. 385-390
Non-Patent Literature 8: Molecules, Vol. 15, 2010, pp. 2427-2438
Non-Patent Literature 9: Tetrahedron, Vol. 61, No. 22, 2005, pp. 5323-5349
Non-Patent Literature 10: Synthetic Communications, Vol. 33, 2003, pp. 3861-3868
Non-Patent Literature 11: Physical and Chemical News, Vol. 5, No. 1, 2002, pp. 115-120
Non-Patent Literature 12: Journal of Chemical Society Perkin Transactions 1: Organic and Bio-organic Chemistry, No. 2, 1996, pp. 167-174
Non-Patent Literature 13: Journal of Antibiotics, Vol. 43, No. 9, 1990, pp. 1199-1203
Non-Patent Literature 14: Egyptian Journal of Chemistry, Vol. 30, No. 5, 1987, pp. 421-428
Non-Patent Literature 15: Tetrahedron, Vol. 28, No. 19, 1972, pp. 4939-4946

SUMMARY OF INVENTION

Technical Problem

An object of the present invention is to provide a herbicide having an excellent herbicidal activity.

Solution to Problem

As a result of many intensive studies so as to solve the above-described object, the inventors of the present invention have found that a 1-(N,N-disubstituted carbamoyl)4-(substituted sulfonyl)triazolin-5-one derivative represented by the following formula (1) and a 4-(N,N-disubstituted carbamoyl)1-(substituted sulfonyl)triazolin-5-one derivative represented by the following formula (11) exhibit an excellent herbicidal activity, and the present invention has been accomplished based on this finding.

Namely, the present invention is summarized as follows.

[1]A 1-(N,N-disubstituted carbamoyl)4-(substituted sulfonyl)triazolin-5-one derivative represented by formula (1):

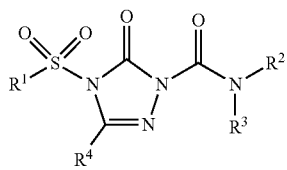

(1)

wherein in formula (1), $R^1$ represents a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C8 cycloalkyl group which may be substituted (the group may be monosubstituted or polysubstituted by a halogen atom, a C1-C6 alkyl group, a C1-C6 alkoxy group, a C3-C8 cycloalkyl group, a C3-C6 cycloalkyl C1-C6 alkyl group, a phenyl group, or a C7-C11 aralkyl group), a C3-C6 cycloalkyl C1-C6 alkyl group, a C1-C6 alkoxy C1-C6 alkyl group, a C1-C6 haloalkoxy C1-C6 alkyl group, a phenyl group which may be substituted (the group may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group), a C7-C11 aralkyl group which may be substituted (the group may be monosubstituted or polysubstituted by a halogen atom, a C1-C6 alkyl group, or a C1-C6 alkoxy group), a heterocyclic ring which may be substituted (the group may be monosubstituted or polysubstituted by a halogen atom, a C1-C6 alkyl group, or a C1-C6 alkoxy group), a C1-C6 alkylamino group, a di C1-C6 alkylamino group in which alkyl groups may be the same or different (the alkyl groups may also combine with each other via an alkylene group to form a 3-membered ring, a 4-membered ring, a 5-membered ring and a 6-membered ring), a tetrahydropyranyl group, a tetrahydrofuryl group, a tetrahydropyranylmethyl group, or a tetrahydrofurfuryl group; each of $R^2$ and $R^3$ independently represents a C1-C6 alkyl group, a C1-C6 haloalkyl group, a C2-C6 alkenyl group, a C2-C6 alkynyl group, a C3-C6 cycloalkyl group, a C3-C6 cycloalkyl C1-C6 alkyl group, a C1-C6 alkoxy C1-C6 alkyl group, a C1-C6 haloalkoxy C1-C6 alkyl group, a phenyl group which may be substituted (the group may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group), a C7-C11 aralkyl group which may be substituted (the group may be monosubstituted or polysubstituted by a halogen atom, a C1-C6 alkyl group, or a C1-C6 alkoxy group), or a heterocyclic ring which may be substituted (the group may be monosubstituted or polysubstituted by a halogen atom, a C1-C6 alkyl group, a C1-C6 haloalkyl group, or a C1-C6 alkoxy group), and when $R^2$ and $R^3$ are C1-C6 alkyl groups, these may also combine with each other to form a 3-membered ring, a 4-membered ring, a 5-membered ring, and a 6-membered ring with an alkylene group having from 2 to 5 carbon atoms as ring members; and $R^4$ represents a hydrogen atom, a halogen atom, a C1-C6 alkyl group, a C1-C6 haloalkyl group, a C1-C6 alkoxy group, or a C1-C6 haloalkoxy group.

[2] The 1-(N,N-disubstituted carbamoyl)4-(substituted sulfonyl)triazolin-5-one derivative according to [1], wherein in formula (1), $R^1$ represents a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C8 cycloalkyl group which may be substituted (the group may be monosubstituted or polysubstituted by a halogen atom, a C1-C6 alkyl group, a C1-C6 alkoxy group, a C3-C8 cycloalkyl group, a C3-C6 cycloalkyl C1-C6 alkyl group, a phenyl group, or a C7-C11 aralkyl group), a C3-C6 cycloalkyl C1-C6 alkyl group, a C1-C6 alkoxy C1-C6 alkyl group, a C1-C6 haloalkoxy C1-C6 alkyl group, a phenyl group which may be substituted (the group may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group), a C7-C11 aralkyl group which may be substituted (the group may be monosubstituted or polysubstituted by a halogen atom, a C1-C6 alkyl group, or a C1-C6 alkoxy group), a pyridine ring which may be substituted (the group may be monosubstituted or polysubstituted by a halogen atom, a C1-C6 alkyl group, or a C1-C6 alkoxy group), a thiophene ring which may be substituted (the group may be monosubstituted or polysubstituted by a halogen atom, a C1-C6 alkyl group, or a C1-C6 alkoxy group), a C1-C6 alkylamino group, a di C1-C6 alkylamino group in which alkyl groups may be the same or different (the alkyl groups may also combine with each other via an alkylene group to form a 3-membered ring, a 4-membered ring, a 5-membered ring and a 6-membered ring), a tetrahydropyranyl group, a tetrahydrofuryl group, a tetrahydropyranylmethyl group, or a tetrahydrofurfuryl group;

$R^2$ represents a C1-C6 alkyl group, a C1-C6 haloalkyl group, a C2-C6 alkenyl group, a C2-C6 alkynyl group, a C3-C6 cycloalkyl group, a C3-C6 cycloalkyl C1-C6 alkyl group, a C1-C6 alkoxy C1-C6 alkyl group, a C1-C6 haloalkoxy C1-C6 alkyl group, a phenyl group which may be substituted (the group may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group), a C7-C11 aralkyl group which may be substituted (the group may be monosubstituted or polysubstituted by a halogen atom, a C1-C6 alkyl group, or a C1-C6 alkoxy group), or a pyridine ring which may be substituted (the group may be monosubstituted or polysubstituted by a halogen atom, a C1-C6 alkyl group, a C1-C6 haloalkyl group, or a C1-C6 alkoxy group);

$R^3$ represents a C1-C6 alkyl group, a C3-C6 cycloalkyl group, a phenyl group which may be substituted (the group may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group), a C7-C11 aralkyl group which may be substituted (the group may be monosubstituted or polysubstituted by a halogen atom, a C1-C6 alkyl group, or a C1-C6 alkoxy group), a pyridine ring which may be substituted (the group may be monosubstituted or polysubstituted by a halogen atom, a C1-C6 alkyl group, a C1-C6 haloalkyl group, or a C1-C6 alkoxy group), an isoxazole ring which may be substituted (the group may be monosubstituted or polysubstituted by a halogen atom, a C1-C6 alkyl group, a C1-C6 haloalkyl group, or a C1-C6 alkoxy group), a thiazole ring which may be substituted (the group may be monosubstituted or polysubstituted by a halogen atom, a C1-C6 alkyl group, a C1-C6 haloalkyl group, or a C1-C6 alkoxy group), or a pyrazole ring which may be substituted (the group may be monosubstituted or polysubstituted by a halogen atom, a C1-C6 alkyl group, a C1-C6 haloalkyl group, or a C1-C6 alkoxy group), and when $R^2$ and $R^3$ are C1-C6 alkyl groups, these may also combine with each other to form a 3-membered ring, a 4-membered ring, a 5-membered ring, and a 6-membered ring with an alkylene group having from 2 to 5 carbon atoms as ring members; and $R^4$ represents a hydrogen atom, a halogen atom, a C1-C6 alkyl group, a C1-C6 haloalkyl group, a C1-C6 alkoxy group, or a C1-C6 haloalkoxy group.

[3] The 1-(N,N-disubstituted carbamoyl)4-(substituted sulfonyl)triazolin-5-one derivative according to [1] or [2], wherein in formula (1), $R^1$ represents a C1-C6 alkyl group, a C1-C6 haloalkyl group, a C2-C6 alkenyl group, a C3-C8 cycloalkyl group which may be substituted (the group may be monosubstituted or polysubstituted by a halogen atom, a C1-C6 alkyl group, a C1-C6 alkoxy group, a C3-C8 cycloalkyl group, a C3-C6 cycloalkyl C1-C6 alkyl group, a phenyl group, or a C7-C11 aralkyl group), a phenyl group which may be substituted (the group may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group), a C7-C11 aralkyl group which may be substituted (the group may be monosubstituted or polysubstituted by a halogen atom, a C1-C6 alkyl group, or a C1-C6 alkoxy group), a pyridine ring which may be substituted (the group may be monosubstituted or polysubstituted by a halogen atom, a C1-C6 alkyl group, or a C1-C6 alkoxy group), a thiophene ring which may be substituted (the group may be monosubstituted or polysubstituted by a halogen atom, a C1-C6 alkyl group, or a C1-C6 alkoxy group), a di C1-C6 alkylamino group in which alkyl groups may be the same or different (the alkyl groups may also combine with each other via an alkylene group to form a 3-membered ring, a 4-membered ring, a 5-membered ring and a 6-membered ring), a tetrahydropyranyl group, or a tetrahydrofuryl group;

$R^2$ represents a C1-C6 alkyl group;

$R^3$ represents a C1-C6 alkyl group, a phenyl group which may be substituted (the group may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group), a C7-C11 aralkyl group which may be substituted (the group may be monosubstituted or polysubstituted by a halogen atom, a C1-C6 alkyl group, or a C1-C6 alkoxy group), a pyridine ring which may be substituted (the group may be monosubstituted or polysubstituted by a C1-C6 alkyl group, a C1-C6 haloalkyl group, or a C1-C6 alkoxy group), or an isoxazole ring which may be substituted (the group may be monosubstituted or polysubstituted by a halogen atom, a C1-C6 alkyl group, a C1-C6 haloalkyl group, or a C1-C6 alkoxy group); and $R^4$ represents a hydrogen atom, a C1-C6 alkyl group, or a C1-C6 alkoxy group.

[4] A 4-(N,N-disubstituted carbamoyl)1-(substituted sulfonyl)triazolin-5-one derivative represented by formula (11):

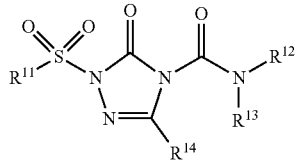

(11)

wherein in formula (11), $R^{11}$ represents a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C8 cycloalkyl group which may be substituted (the group may be monosubstituted or polysubstituted by a halogen atom, a C1-C6 alkyl group, a C1-C6 alkoxy group, a C3-C8 cycloalkyl group, a C3-C6 cycloalkyl C1-C6 alkyl group, a phenyl group, or a C7-C11 aralkyl group), a C3-C6 cycloalkyl C1-C6 alkyl group, a C1-C6 alkoxy C1-C6 alkyl group, a C1-C6 haloalkoxy C1-C6 alkyl group, a phenyl group which may be substituted (the group may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group), a C7-C11 aralkyl group which may be substituted (the group may be monosubstituted or polysubstituted by a halogen atom, a C1-C6 alkyl group, or a C1-C6 alkoxy group), a heterocyclic ring which may be substituted (the group may be monosubstituted or polysubstituted by a halogen atom, a C1-C6 alkyl group, or a C1-C6 alkoxy group), a C1-C6 alkylamino group, a di C1-C6 alkylamino group in which alkyl groups may be the same or different (the alkyl groups may also combine with each other via an alkylene group to form a 3-membered ring, a 4-membered ring, a 5-membered ring and a 6-membered ring), a tetrahydropyranyl group, a tetrahydrofuryl group, a tetrahydropyranylmethyl group, or a tetrahydrofurfuryl group;

each of $R^{12}$ and $R^{13}$ independently represents a C1-C6 alkyl group, a C1-C6 haloalkyl group, a C2-C6 alkenyl group, a C2-C6 alkynyl group, a C3-C6 cycloalkyl group, a C3-C6 cycloalkyl C1-C6 alkyl group, a C1-C6 alkoxy C1-C6 alkyl group, a C1-C6 haloalkoxy C1-C6 alkyl group, a phenyl group which may be substituted (the group may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group), a C7-C11 aralkyl group which may be substituted (the group may be monosubstituted or polysubstituted by a halogen atom, a C1-C6 alkyl group, or a C1-C6 alkoxy group), or a heterocyclic ring which may be substituted (the group may be monosubstituted or polysubstituted by a halogen atom, a C1-C6 alkyl group, a C1-C6 haloalkyl group, or a C1-C6 alkoxy group), and when $R^{12}$ and $R^{13}$ are a C1-C6 alkyl group, these may also combine with each other to form a 3-membered ring, a 4-membered ring, a 5-membered ring, and a 6-membered ring with an alkylene group having from 2 to 5 carbon atoms as ring members; and $R^{14}$ represents a hydrogen atom, a halogen atom, a C1-C6 alkyl group, a C1-C6 haloalkyl group, a C1-C6 alkoxy group, or a C1-C6 haloalkoxy group.

[5] The 4-(N,N-disubstituted carbamoyl)1-(substituted sulfonyl)triazolin-5-one derivative according to [4], wherein in formula (11), $R^{11}$ represents a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C8 cycloalkyl group which may be substituted (the group may be monosubstituted or polysubstituted by a halogen atom, a C1-C6 alkyl group, a C1-C6 alkoxy group, a C3-C8 cycloalkyl group, a C3-C6 cycloalkyl C1-C6 alkyl group, a phenyl group, or a C7-C11 aralkyl group), a C3-C6 cycloalkyl C1-C6 alkyl group, a C1-C6 alkoxy C1-C6 alkyl group, a C1-C6 haloalkoxy C1-C6 alkyl group, a phenyl group which may be substituted (the group may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group), a C7-C11 aralkyl group which may be substituted (the group may be monosubstituted or polysubstituted by a halogen atom, a C1-C6 alkyl group, or a C1-C6 alkoxy group), a pyridine ring which may be substituted (the group may be monosubstituted or polysubstituted by a halogen atom, a C1-C6 alkyl group, or a C1-C6 alkoxy group), a thiophene ring which may be substituted (the group may be monosubstituted or polysubstituted by a halogen atom, a C1-C6 alkyl group, or a C1-C6 alkoxy group), a C1-C6 alkylamino group, a di C1-C6 alkylamino group in which alkyl groups may be the same or different (the alkyl groups may also combine with each other via an alkylene group to form a 3-membered ring, a 4-membered ring, a 5-membered ring and a 6-membered ring), a tetrahydropyranyl group, a tetrahydrofuryl group, a tetrahydropyranylmethyl group, or a tetrahydrofurfuryl group;

$R^{12}$ represents a C1-C6 alkyl group, a C1-C6 haloalkyl group, a C2-C6 alkenyl group, a C2-C6 alkynyl group, a C3-C6 cycloalkyl group, a C3-C6 cycloalkyl C1-C6 alkyl group, a C1-C6 alkoxy C1-C6 alkyl group, a C1-C6 haloalkoxy C1-C6 alkyl group, a phenyl group which may be substituted (the group may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group), a C7-C11 aralkyl group which may be substituted (the group may be monosubstituted or polysubstituted by a halogen atom, a C1-C6 alkyl group, or a C1-C6 alkoxy group), or a pyridine ring which may be substituted (the group may be monosubstituted or polysubstituted by a halogen atom, a C1-C6 alkyl group, a C1-C6 haloalkyl group, or a C1-C6 alkoxy group);

$R^{13}$ represents a C1-C6 alkyl group, a C3-C6 cycloalkyl group, a phenyl group which may be substituted (the group may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group), a C7-C11 aralkyl group which may be substituted (the group may be monosubstituted or polysubstituted by a halogen atom, a C1-C6 alkyl group, or a C1-C6 alkoxy group), a pyridine ring which may be substituted (the group may be monosubstituted or polysubstituted by a halogen atom, a C1-C6 alkyl group, a C1-C6 haloalkyl group, or a C1-C6 alkoxy group), an isoxazole ring which may be substituted (the group may be monosubstituted or polysubstituted by a halogen atom, a C1-C6 alkyl group, a C1-C6 haloalkyl group, or a C1-C6 alkoxy group), a thiazole ring which may be substituted (the group may be monosubstituted or polysubstituted by a halogen atom, a C1-C6 alkyl group, a C1-C6 haloalkyl group, or a C1-C6 alkoxy group), or a pyrazole ring which may be substituted (the group may be monosubstituted or polysubstituted by a halogen atom, a C1-C6 alkyl group, a C1-C6 haloalkyl group, or a C1-C6 alkoxy group), and when $R^{12}$ and $R^{13}$ are C1-C6 alkyl groups, these may also combine with each other to form a 3-membered ring, a 4-membered ring, a 5-membered ring, and a 6-membered ring with an alkylene group having from 2 to 5 carbon atoms as ring members; and $R^{14}$ represents a hydrogen atom, a halogen atom, a C1-C6 alkyl group, a C1-C6 haloalkyl group, a C1-C6 alkoxy group, or a C1-C6 haloalkoxy group.

[6] The 4-(N,N-disubstituted carbamoyl)1-(substituted sulfonyl)triazolin-5-one derivative according to [4] or [5], wherein in formula (11), $R^{11}$ represents a C1-C6 alkyl group, a C1-C6 haloalkyl group, a C2-C6 alkenyl group, a C3-C8 cycloalkyl group which may be substituted (the group may be monosubstituted or polysubstituted by a halogen atom, a C1-C6 alkyl group, a C1-C6 alkoxy group, a C3-C8 cycloalkyl group, a C3-C6 cycloalkyl C1-C6 alkyl group, a phenyl group, or a C7-C11 aralkyl group), a phenyl group which may be substituted (the group may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group), a C7-C11 aralkyl group which may be substituted (the group may be monosubstituted or polysubstituted by a halogen atom, a C1-C6 alkyl group, or a C1-C6 alkoxy group), a pyridine ring which may be substituted (the group may be monosubstituted or polysubstituted by a halogen atom, a C1-C6 alkyl group, or a C1-C6 alkoxy group), a thiophene ring which may be substituted (the group may be monosubstituted or polysubstituted by a halogen atom, a C1-C6 alkyl group, or a C1-C6 alkoxy group), a di C1-C6 alkylamino group in which alkyl groups may be the same or different (the alkyl groups may also combine with each other via an alkylene group to form a 3-membered ring, a 4-membered ring, a 5-membered ring and a 6-membered ring), or a tetrahydropyranyl group;

$R^{12}$ represents a C1-C6 alkyl group or a C1-C6 haloalkyl group;

$R^{13}$ represents a C1-C6 alkyl group, a C3-C8 cycloalkyl group, a phenyl group which may be substituted (the group may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group), a C7-C11 aralkyl group which may be substituted (the group may be monosubstituted or polysubstituted by a halogen atom, a C1-C6 alkyl group, or a C1-C6 alkoxy group), a pyridine ring which may be substituted (the group may be monosubstituted or polysubstituted by a halogen atom, a C1-C6 alkyl group, a C1-C6 haloalkyl group, or a C1-C6 alkoxy group), or an isoxazole ring which may be substituted (the group may be monosubstituted or polysubstituted by a halogen atom, a C1-C6 alkyl group, a C1-C6 haloalkyl group, or a C1-C6 alkoxy group), and when $R^{12}$ and $R^{13}$ are C1-C6 alkyl groups, these may also combine with each other to form a 3-membered ring, a 4-membered ring, a 5-membered ring, and a 6-membered ring with an alkylene group having from 2 to 5 carbon atoms as ring members; and $R^{14}$ represents a hydrogen atom or a C1-C6 alkyl group.

[7] A herbicide containing as an active ingredient the 1-(N,N-disubstituted carbamoyl)4-(substituted sulfonyl)triazolin-5-one derivative according to any one of [1] to [3].

[8] A herbicide containing as an active ingredient at least one derivative selected from the 4-(N,N-disubstituted carbamoyl)1-(substituted sulfonyl)triazolin-5-one derivative according to any one of [4] to [6].

Effects of Invention

The novel 1-(N,N-disubstituted carbamoyl)4-(substituted sulfonyl)triazolin-5-one derivative of the present invention represented by formula (1), and the novel 4-(N,N-disubstituted carbamoyl)1-(substituted sulfonyl)triazolin-5-one derivative of the present invention represented by formula (11) show an excellent herbicidal effect.

DESCRIPTION OF EMBODIMENTS

A 1-(N,N-disubstituted carbamoyl)4-(substituted sulfonyl)triazolin-5-one derivative and a 4-(N,N-disubstituted carbamoyl)1-(substituted sulfonyl)triazolin-5-one derivative, according to the compounds of the present invention, a production method thereof, and a herbicide containing the derivative as an active ingredient are specifically described.

(1-(N,N-Disubstituted carbamoyl)4-(Substituted sulfonyl)triazolin-5-One Derivative Represented by Formula (1))

In the 1-(N,N-disubstituted carbamoyl)4-(substituted sulfonyl)triazolin-5-one derivative (1) of the present invention, examples of the halogen atom or the halogen atom as a substituent include fluorine, chlorine, bromine and iodine elements. The number of halogen atoms as a substituent may be 1 or 2 or more and in the case of 2 or more, respective halogen atoms may be the same or different. In addition, the substitution position of the halogen atom may be any position.

Examples of the C1-C6 alkyl group represented by $R^1$, $R^2$, $R^3$ or $R^4$ or the C1-C6 alkyl group as a substituent include a methyl group, an ethyl group, a n-propyl group, an isopropyl group, a 1,1-dimethylpropyl group, a 1,2-dimethylpropyl group, a 1-ethylpropyl group, a n-butyl group, an isobutyl group, a sec-butyl group, a tert-butyl group, a 2-methylbutyl group, a 3-methylbutyl group, a 1-ethylbutyl group, a 2-ethylbutyl group, a 1,1-dimethylbutyl group, a 1,2-dimethylbutyl group, a 2,3-dimethylbutyl group, a 3,3-dimethylbutyl group, a n-pentyl group, a neopentyl group, a 2-pentyl group, a 3-pentyl group, a tert-pentyl group, a 1-methylpentyl group, a 2-methylpentyl group, a 3-methylpentyl group, a 4-methylpentyl group, a n-hexyl group, an isohexyl group, a 2-hexyl group, a 3-hexyl group, etc. The number of C1-C6 alkyl groups as a substituent may be 1 or 2 or more and in the case of 2 or more, respective C1-C6 alkyl groups may be the same or different. In addition, the substitution position of the C1-C6 alkyl group may be any position.

Examples of the C1-C6 haloalkyl group represented by $R^1$, $R^2$, $R^3$ or $R^4$ or the C1-C6 haloalkyl group as a substituent include a monofluoromethyl group, a difluoromethyl group, a trifluoromethyl group, a 2,2,2-trifluoroethyl group, a monochloromethyl group, a 2-chloroethyl group, a trichloromethyl group, a 1-fluoroethyl group, a 2-fluoroethyl group, a 3,3,3-trifluoropropyl group, a 4,4,4-trifluorobutyl group, a 5,5,5-trifluoropentyl group, a 6-fluorohexyl group, a 6,6,6-trifluorohexyl group, etc. The number of C1-C6 haloalkyl groups as a substituent may be 1 or 2 or more and in the case of 2 or more, respective C1-C6 haloalkyl groups may be the same or different. In addition, the substitution position of the C1-C6 haloalkyl group may be any position.

Examples of the C2-C6 alkenyl group represented by $R^1$, $R^2$ or $R^3$ include a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, a 5-hexenyl group, etc.

Examples of the C2-C6 haloalkenyl group represented by $R^1$ include a 3,3-dichloro-2-propenyl group, a 3,3,3-trifluoro-1-propenyl group, a 4,4-difluoro-3-butenyl group, and a 3,4,4-trifluoro-3-butenyl group.

Examples of the C2-C6 alkynyl group represented by $R^1$, $R^2$ or $R^3$ include an ethynyl group, a 1-propynyl group, a propargyl group, a 1-butynyl group, a 2-butynyl group, a 3-butynyl group, a 1-methyl-2-propynyl group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group, a 1,1-dimethyl-2-butynyl group, etc.

Examples of the C2-C6 haloalkynyl group represented by $R^1$ include a fluoroethynyl group, a 3-fluoro-2-propynyl group, a 3-chloro-2-propynyl group, a 3-chloro-1-propynyl group, a 5-chloro-4-pentynyl group, a 3,3,3-trifluoro-1-propynyl group, a 3,3-difluoro-1-propynyl group, a 4,4,4-trifluoro-2-butynyl group, etc.

Examples of the C3-C8 cycloalkyl group moiety of the C3-C8 cycloalkyl group represented by $R^1$, which may be substituted, the C3-C8 cycloalkyl group represented by $R^2$ or $R^3$, or the C3-C8 cycloalkyl group as a substituent include a cyclopropyl group, a cyclobutyl group, a cyclopentyl group, a cyclohexyl group, a cycloheptyl group, a cyclooctyl group, etc. The number of C3-C8 cycloalkyl groups as a substituent may be 1 or 2 or more and in the case of 2 or more, respective C3-C8 cycloalkyl groups may be the same or different. In addition, the substitution position of the C3-C8 cycloalkyl group may be any position.

Examples of the C3-C6 cycloalkyl C1-C6 alkyl group represented by $R^1$, $R^2$ or $R^3$ or the C3-C6 cycloalkyl C1-C6 alkyl group as a substituent include a cyclopropylmethyl group, a cyclopropylethyl group, a 1-methylcyclopropylmethyl group, a 2-methylcyclopropylmethyl group, a 2,2-dimethylcyclopropylmethyl group, a cyclobutylmethyl group, a cyclopentylmethyl group, etc.

Examples of the C1-C6 alkoxy C1-C6 alkyl group represented by $R^1$, $R^2$ or $R^3$ include a methoxymethyl group, an ethoxymethyl group, a n-propoxymethyl group, an isopropoxymethyl group, a n-butoxymethyl group, a sec-butoxymethyl group, a tert-butoxymethyl group, a 1-pentyloxymethyl group, a 1-hexyloxymethyl group, a 2-methoxyethyl group, a 2-ethoxyethyl group, a 2-isopropoxyethyl group, a 2-isobutoxyethyl group, a 3-methoxypropyl group, a 2-methoxypropyl group, a 2-methoxy-1-methylethyl group, etc.

Examples of the C1-C6 haloalkoxy C1-C6 alkyl group represented by $R^1$, $R^2$ or $R^3$ include a trifluoromethoxymethyl group, a 2,2,2-trifluoroethoxymethyl group, a 2-(2,2,2-trifluoroethoxy)ethyl group, etc.

Examples of the C7-C11 aralkyl group moiety of the C7-C11 aralkyl group represented by $R^1$, $R^2$ or $R^3$, which may be substituted, or the C7-C11 aralkyl group as a substituent include a benzyl group, a 1-phenethyl group, a 2-phenethyl group, a 1-phenylpropyl group, a 2-phenylpropyl group, a 3-phenylpropyl group, a 1-phenyl-2-methylpropyl group, a 1-phenylbutyl group, a 1-phenylpentyl group, etc.

Examples of the heterocyclic moiety of the heterocyclic ring represented by $R^1$, $R^2$ or $R^3$, which may be substituted, include a pyridine ring (2-pyridyl group, 3-pyridyl group, 4-pyridyl group), a thiophene ring (2-thienyl group, 3-thienyl group), an oxazole ring (oxazol-2-yl group, oxazol-4-yl group, oxazol-5-yl group), an isoxazole ring (isoxazol-3-yl group, isoxazol-4-yl group, isoxazol-5-yl group), a thiazole ring (thiazol-2-yl group, thiazol-4-yl group, thiazol-5-yl group), an isothiazole ring (isothiazol-3-yl group, isothiazol- 4-yl group, isothiazol-5-yl group), a pyrazole ring (pyrazol-3-yl group, pyrazol-4-yl group, pyrazol-5-yl group), etc.

Examples of the C1-C6 alkylamino group represented by $R^1$ include a methylamino group, an ethylamino group, a n-propylamino group, an isopropylamino group, a n-butylamino group, an isobutylamino group, a sec-butylamino group, a tert-butylamino group, etc.

Examples of the di C1-C6 alkylamino group represented by $R^1$, in which alkyl groups may be the same or different, include a dimethylamino group, a methylethylamino group, a diethylamino group, a di n-propylamino group, a methyl n-propylamino group, a methylisopropylamino group, a methylisobutylamino group, an ethyl n-propylamino group, a diisopropylamino group, a di n-butylamino group, a diisobutylamino group, a di sec-butylamino group, a di tert-butylamino group, etc.

Examples of the tetrahydropyranyl group represented by $R^1$ include a 3-tetrahydropyranyl group and a 4-tetrahydropyranyl group.

Examples of the tetrahydrofuryl group represented by $R^1$ include a 2-tetrahydrofuryl group and a 3-tetrahydrofuryl group.

Examples of the tetrahydropyranylmethyl group represented by $R^1$ include a 3-tetrahydropyranylmethyl group and a 4-tetrahydropyranylmethyl group.

Examples of the tetrahydrofurfuryl group represented by $R^1$ include a 2-tetrahydrofurfuryl group and a 3-tetrahydrofurfuryl group.

Examples of the C1-C6 alkoxy group represented by $R^4$ or the C1-C6 alkoxy group as a substituent include a methoxy group, an ethoxy group, a n-propoxy group, an isopropoxy group, a n-butoxy group, an isobutoxy group, a sec-butoxy group, a tert-butoxy group, etc. The number of C1-C6 alkoxy groups as a substituent may be 1 or 2 or more and in the case of 2 or more, respective C1-C6 alkoxy groups may be the same or different. In addition, the substitution position of the C1-C6 alkoxy group may be any position.

Examples of the C1-C6 haloalkoxy group represented by $R^4$ or the C1-C6 haloalkoxy group as a substituent include a monofluoromethoxy group, a difluoromethoxy group, a trifluoromethoxy group, a 2,2,2-trifluoroethoxy group, a 2-chloroethoxy group, a trichloromethoxy group, a 1-fluoroethoxy group, a 2-fluoroethoxy group, etc. The number of C1-C6 haloalkoxy groups as a substituent may be 1 or 2 or more and in the case of 2 or more, respective C1-C6 haloalkoxy groups may be the same or different. In addition, the substitution position of the C1-C6 haloalkoxy group may be any position.

Examples of the C1-C6 alkylthio group as a substituent include a methylthio group, an ethylthio group, a n-propylthio group, an isopropylthio group, a n-butylthio group, a isobutylthio group, a sec-butylthio group, a tert-butylthio group, etc. The number of C1-C6 alkylthio groups as a substituent may be 1 or 2 or more and in the case of 2 or more, respective C1-C6 alkylthio groups may be the same or different. In addition, the substitution position of the C1-C6 alkylthio group may be any position.

Examples of the C1-C6 haloalkylthio group as a substituent include a trifluoromethylthio group, a 2,2,2-trifluoroethylthio group, etc. The number of C1-C6 haloalkylthio groups as a substituent may be 1 or 2 or more and in the case of 2 or more, respective C1-C6 haloalkylthio groups may be the same or different. In addition, the substitution position of the C1-C6 haloalkylthio group may be any position.

As a preferred embodiment of the compound represented by formula (1), $R^1$ is preferably, in addition to the substituent above, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C8 cycloalkyl group which may be substituted (the group may be monosubstituted or polysubstituted by a halogen atom, a C1-C6 alkyl group, a C1-C6 alkoxy group, a C3-C8 cycloalkyl group, a C3-C6 cycloalkyl C1-C6 alkyl group, a phenyl group, or a C7-C11 aralkyl group), a C3-C6 cycloalkyl C1-C6 alkyl group, a C1-C6 alkoxy C1-C6 alkyl group, a C1-C6 haloalkoxy C1-C6 alkyl group, a phenyl group which may be substituted (the group may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group), a C7-C11 aralkyl group which may be substituted (the group may be monosubstituted or polysubstituted by a halogen atom, a C1-C6 alkyl group, or a C1-C6 alkoxy group), a pyridine ring which may be substituted (the group may be monosubstituted or polysubstituted by a halogen atom, a C1-C6 alkyl group, or a C1-C6 alkoxy group), a thiophene ring which may be substituted (the group may be monosubstituted or polysubstituted by a halogen atom, a C1-C6 alkyl group, or a C1-C6 alkoxy group), a C1-C6 alkylamino group, a di C1-C6 alkylamino group in which alkyl groups may be the same or different (the alkyl groups may also combine with each other via an alkylene group to form a 3-membered ring, a 4-membered ring, a 5-membered ring and a 6-membered ring), a tetrahydropyranyl group, a tetrahydrofuryl group, a tetrahydropyranylmethyl group, or a tetrahydrofurfuryl group, and more preferably a C1-C6 alkyl group, a C1-C6 haloalkyl group, a C2-C6 alkenyl group, a C3-C8 cycloalkyl group which may be substituted (the group may be monosubstituted or polysubstituted by a halogen atom, a C1-C6 alkyl group, a C1-C6 alkoxy group, a C3-C8 cycloalkyl group, a C3-C6 cycloalkyl C1-C6 alkyl group, a phenyl group, or a C7-C11 aralkyl group), a phenyl group which may be substituted (the group may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group), a C7-C11 aralkyl group which may be substituted (the group may be monosubstituted or polysubstituted by a halogen atom, a C1-C6 alkyl group, or a C1-C6 alkoxy group), a pyridine ring which may be substituted (the group may be monosubstituted or polysubstituted by a halogen atom, a C1-C6 alkyl group, or a C1-C6 alkoxy group), a thiophene ring which may be substituted (the group may be monosubstituted or polysubstituted by a halogen atom, a C1-C6 alkyl group, or a C1-C6 alkoxy group), a di C1-C6 alkylamino group in which alkyl groups may be the same or different (the alkyl groups may also combine with each other via an alkylene group to form a 3-membered ring, a 4-membered ring, a 5-membered ring and a 6-membered ring), a tetrahydropyranyl group, or a tetrahydrofuryl group.

$R^2$ is preferably, in addition to the substituent above, a C1-C6 alkyl group, a C1-C6 haloalkyl group, a C2-C6 alkenyl group, a C2-C6 alkynyl group, a C3-C6 cycloalkyl group, a C3-C6 cycloalkyl C1-C6 alkyl group, a C1-C6 alkoxy C1-C6 alkyl group, a C1-C6 haloalkoxy C1-C6 alkyl group, a phenyl group which may be substituted (the group may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group), a C7-C11 aralkyl group which may be substituted (the group may be monosubstituted or polysubstituted by a halogen atom, a C1-C6 alkyl group, or a C1-C6 alkoxy group), or a pyridine ring which may be substituted (the group may be monosubstituted or polysubstituted by a halogen atom, a C1-C6 alkyl group, a C1-C6 haloalkyl group, or a C1-C6 alkoxy group), and more preferably a C1-C6 alkyl group.

$R^3$ is preferably, in addition to the substituent above, a C1-C6 alkyl group, a C3-C6 cycloalkyl group, a phenyl group which may be substituted (the group may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group), a C7-C11 aralkyl group which may be substituted (the group may be monosubstituted or polysubstituted by a halogen atom, a C1-C6 alkyl group, or a C1-C6 alkoxy group), a pyridine ring which may be substituted (the group may be monosubstituted or polysubstituted by a halogen atom, a C1-C6 alkyl group, a C1-C6 haloalkyl group, or a C1-C6 alkoxy group), an isoxazole ring which may be substituted (the group may be monosubstituted or polysubstituted by a halogen atom, a C1-C6 alkyl group, a C1-C6 haloalkyl group, or a C1-C6 alkoxy group), a thiazole ring which may be substituted (the group may be monosubstituted or polysubstituted by a halogen atom, a C1-C6 alkyl group, a C1-C6 haloalkyl group, or a C1-C6 alkoxy group), or a pyrazole ring which may be substituted (the group may be monosubstituted or polysubstituted by a halogen atom, a C1-C6 alkyl group, a C1-C6 haloalkyl group, or a C1-C6 alkoxy group), more preferably a C1-C6 alkyl group, a phenyl group which may be substituted (the group may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group), a C7-C11 aralkyl group which may be substituted (the group may be monosubstituted or polysubstituted by a halogen atom, a C1-C6 alkyl group, or a C1-C6 alkoxy group), a pyridine ring which may be substituted (the group may be monosubstituted or polysubstituted by a halogen atom, a C1-C6 alkyl group, a C1-C6 haloalkyl group, or a C1-C6 alkoxy group), or an isoxazole ring which may be substituted (the group may be monosubstituted or polysubstituted by a halogen atom, a C1-C6 alkyl group, a C1-C6 haloalkyl group, or a C1-C6 alkoxy group). Incidentally, when $R^2$ and $R^3$ area C1-C6 alkyl group, as described above, these may also combine with each other to form a 3-membered ring, a 4-membered ring, a 5-membered ring, and a 6-membered ring with an alkylene group having from 2 to 5 carbon atoms as ring members.

$R^4$ is preferably, in addition to the substituent above, a hydrogen atom, a halogen atom, a C1-C6 alkyl group, a C1-C6 haloalkyl group, a C1-C6 alkoxy group or a C1-C6 haloalkoxy group, and more preferably a hydrogen atom, a C1-C6 alkyl group, or a C1-C6 alkoxy group.

Another preferred embodiment of the present invention is a 1-(N,N-disubstituted carbamoyl)4-(substituted sulfonyl)triazolin-5-one derivative represented by formula (1):

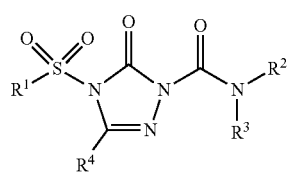

(1)

wherein in formula (1), $R^1$ represents a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C8 cycloalkyl group which may be substituted (the group may be monosubstituted or polysubstituted by a halogen atom, a C1-C6 alkyl group, a C1-C6 alkoxy group, a C3-C8 cycloalkyl group, a C3-C6 cycloalkyl C1-C6 alkyl group, a phenyl group, or an aralkyl group), a C3-C6 cycloalkyl C1-C6 alkyl group, a C1-C6 alkoxy C1-C6 alkyl group, a C1-C6 haloalkoxy C1-C6 alkyl group, a phenyl group which may be substituted (the group may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group), a C7-C11 aralkyl group which may be substituted (the group may be monosubstituted or polysubstituted by a halogen atom, a C1-C6 alkyl group, or a C1-C6 alkoxy group), a heterocyclic ring which may be substituted (the group may be monosubstituted or polysubstituted by a halogen atom, a C1-C6 alkyl group, or a C1-C6 alkoxy group), a C1-C6 alkylamino group, a di C1-C6 alkylamino group in which alkyl groups may be the same or different (the alkyl groups may also combine with each other via an alkylene group to form a 3-membered ring, a 4-membered ring, a 5-membered ring and a 6-membered ring), a tetrahydropyranyl group, a tetrahydrofuryl group, a tetrahydropyranylmethyl group, or a tetrahydrofurfuryl group;

each of $R^2$ and $R^3$ independently represents a C1-C6 alkyl group, a C1-C6 haloalkyl group, a C2-C6 alkenyl group, a C2-C6 alkynyl group, a C3-C6 cycloalkyl group, a C3-C6 cycloalkyl C1-C6 alkyl group, a C1-C6 alkoxy C1-C6 alkyl group, a C1-C6 haloalkoxy C1-C6 alkyl group, a phenyl group which may be substituted (the group may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group), a C7-C11 aralkyl group which may be substituted (the group may be monosubstituted or polysubstituted by a halogen atom, a C1-C6 alkyl group, or a C1-C6 alkoxy group), or a heterocyclic ring which may be substituted (the group may be monosubstituted or polysubstituted by a halogen atom, a C1-C6 alkyl group, or a C1-C6 alkoxy group), and when $R^2$ and $R^3$ are C1-C6 alkyl groups, these may also combine with each other to form a 3-membered ring, a 4-membered ring, a 5-membered ring, and a 6-membered ring with an alkylene group having from 2 to 5 carbon atoms as ring members; and $R^4$ represents a hydrogen atom, a halogen atom, a C1-C6 alkyl group, a C1-C6 haloalkyl group, a C1-C6 alkoxy group, or a C1-C6 haloalkoxy group.

The groups in $R^1$, $R^2$, $R^3$, and $R^4$ are each as described above.

Although representative examples of the 1-(N,N-disubstituted carbamoyl)4-(substituted sulfonyl)triazolin-5-one derivative represented by formula (1) are shown together in Table 1 below, the present invention is not limited to these compounds. These compounds include compounds containing optical isomers, E forms and Z forms. The compound number is referred to in the later description.

In the Table, respective notations below denote corresponding groups as follows.

"H" denotes a hydrogen atom, "Me" denotes a methyl group, "Et" denotes an ethyl group, "n-Pr" denotes a normal-propyl group, "i-Pr" denotes an isopropyl group, "c-Pr" denotes a cyclopropyl group, "s-Bu" denotes a sec-butyl group, "i-Bu" denotes an isobutyl group, "t-Bu" denotes a tert-butyl group, "c-Bu" denotes a cyclobutyl group, "c-Pen" denotes a cyclopentyl group, "c-Hex" denotes a cyclohexyl group, "Ph" denotes a phenyl group, "Bn" denotes a benzyl group, and "Py" denotes a pyridyl group.

TABLE 1

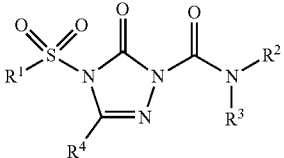

| No. | $R^1$ | $R^2$ | $R^3$ | $R^4$ |
|---|---|---|---|---|
| 1-1 | Me | Et | Et | H |
| 1-2 | Me | i-Pr | Ph | H |
| 1-3 | Me | i-Pr | 2-FPh | H |
| 1-4 | Me | i-Pr | 3-FPh | H |
| 1-5 | Me | i-Pr | 4-FPh | H |
| 1-6 | Me | i-Pr | 2-ClPh | H |
| 1-7 | Me | i-Pr | 3-ClPh | H |
| 1-8 | Me | i-Pr | 4-ClPh | H |
| 1-9 | Me | i-Pr | 2-$CF_3$Ph | H |
| 1-10 | Me | i-Pr | 3-$CF_3$Ph | H |
| 1-11 | Me | i-Pr | 4-$CF_3$Ph | H |
| 1-12 | Me | i-Pr | 2,3-$F_2$Ph | H |
| 1-13 | Me | i-Pr | 2,4-$F_2$Ph | H |
| 1-14 | Me | i-Pr | 2,5-$F_2$Ph | H |
| 1-15 | Me | i-Pr | 2,6-$F_2$Ph | H |
| 1-16 | Me | i-Pr | 2,3,4-$F_3$Ph | H |
| 1-17 | Me | i-Pr | 2,4,6-$F_3$Ph | H |
| 1-18 | Me | i-Pr | 2,3,5,6-$F_4$Ph | H |
| 1-19 | Me | i-Pr | 2,3,4,5,6-$F_5$Ph | H |
| 1-20 | Me | i-Pr | 2-Cl-4-FPh | H |
| 1-21 | Me | i-Pr | 2-F-4-ClPh | H |
| 1-22 | Me | i-Pr | 2-F-4-BrPh | H |
| 1-23 | Me | i-Pr | 2-Br-4-FPh | H |
| 1-24 | Me | i-Pr | 2-Cl-4-BrPh | H |
| 1-25 | Me | i-Pr | 2-Br-4-ClPh | H |
| 1-26 | Me | i-Pr | 2-Me-4-FPh | H |
| 1-27 | Me | i-Pr | 2-F-4-MePh | H |
| 1-28 | Me | i-Pr | 2-Me-4-ClPh | H |
| 1-29 | Me | i-Pr | 2-Cl-4-MePh | H |
| 1-30 | Me | i-Pr | 2-F-4-$CF_3$Ph | H |
| 1-31 | Me | i-Pr | 2-$CF_3$-4-FPh | H |
| 1-32 | Me | i-Pr | 2,3,5,6-$F_4$-4-$CF_3$Ph | H |
| 1-33 | Me | i-Pr | 2-Cl-4-$CF_3$Ph | H |
| 1-34 | Me | i-Pr | 2-$CF_3$-4-ClPh | H |
| 1-35 | Me | i-Pr | 2-Cl-4-CNPh | H |
| 1-36 | Me | i-Pr | 2-Cl-4-(SEt)Ph | H |
| 1-37 | Me | i-Pr | 2,4-$F_2$Bn | H |
| 1-38 | Me | i-Pr | 2-F-3-Py | H |
| 1-39 | Me | i-Pr | 6-F-3-Py | H |
| 1-40 | Me | i-Pr | 3-Cl-2-Py | H |
| 1-41 | Me | i-Pr | 5-Cl-2-Py | H |
| 1-42 | Me | i-Pr | 3,5-$Cl_2$-2-Py | H |
| 1-43 | Me | i-Pr | 3-Cl-5-$CF_3$-2-Py | H |
| 1-44 | Me | i-Pr | 2-Cl-3-Py | H |
| 1-45 | Me | i-Pr | 6-Cl-3-Py | H |
| 1-46 | Me | i-Pr | 2,6-$Cl_2$-3-Py | H |
| 1-47 | Me | i-Pr | 5-Me-isoxazol-3-yl | H |
| 1-48 | Me | i-Pr | 2,4-$F_2$Ph | Me |
| 1-49 | Et | Et | Et | H |
| 1-50 | Et | i-Pr | 2,4-$F_2$Ph | H |
| 1-51 | n-Pr | Et | Et | H |
| 1-52 | n-Pr | i-Pr | 2,4-$F_2$Ph | H |
| 1-53 | i-Pr | Et | Et | H |
| 1-54 | i-Pr | i-Pr | Ph | H |
| 1-55 | i-Pr | i-Pr | 2-FPh | H |
| 1-56 | i-Pr | i-Pr | 3-FPh | H |
| 1-57 | i-Pr | i-Pr | 4-FPh | H |
| 1-58 | i-Pr | i-Pr | 2-ClPh | H |
| 1-59 | i-Pr | i-Pr | 3-ClPh | H |
| 1-60 | i-Pr | i-Pr | 4-ClPh | H |
| 1-61 | i-Pr | i-Pr | 2-$CF_3$Ph | H |
| 1-62 | i-Pr | i-Pr | 3-$CF_3$Ph | H |
| 1-63 | i-Pr | i-Pr | 4-$CF_3$Ph | H |
| 1-64 | i-Pr | i-Pr | 2,3-$F_2$Ph | H |
| 1-65 | i-Pr | i-Pr | 2,4-$F_2$Ph | H |
| 1-66 | i-Pr | i-Pr | 2,5-$F_2$Ph | H |
| 1-67 | i-Pr | i-Pr | 2,6-$F_2$Ph | H |
| 1-68 | i-Pr | i-Pr | 2,3,4-$F_3$Ph | H |
| 1-69 | i-Pr | i-Pr | 2,4,6-$F_3$Ph | H |
| 1-70 | i-Pr | i-Pr | 2,3,5,6-$F_4$Ph | H |
| 1-71 | i-Pr | i-Pr | 2,3,4,5,6-$F_5$Ph | H |
| 1-72 | i-Pr | i-Pr | 2-Cl-4-FPh | H |
| 1-73 | i-Pr | i-Pr | 2-F-4-ClPh | H |
| 1-74 | i-Pr | i-Pr | 2-F-4-BrPh | H |
| 1-75 | i-Pr | i-Pr | 2-Br-4-FPh | H |
| 1-76 | i-Pr | i-Pr | 2-Cl-4-BrPh | H |
| 1-77 | i-Pr | i-Pr | 2-Br-4-ClPh | H |
| 1-78 | i-Pr | i-Pr | 2-Me-4-FPh | H |
| 1-79 | i-Pr | i-Pr | 2-F-4-MePh | H |
| 1-80 | i-Pr | i-Pr | 2-Me-4-ClPh | H |
| 1-81 | i-Pr | i-Pr | 2-Cl-4-MePh | H |
| 1-82 | i-Pr | i-Pr | 2-F-4-$CF_3$Ph | H |
| 1-83 | i-Pr | i-Pr | 2-$CF_3$-4-FPh | H |
| 1-84 | i-Pr | i-Pr | 2,3,5,6-$F_4$-4-$CF_3$Ph | H |
| 1-85 | i-Pr | i-Pr | 2-Cl-4-$CF_3$Ph | H |
| 1-86 | i-Pr | i-Pr | 2-$CF_3$-4-ClPh | H |
| 1-87 | i-Pr | i-Pr | 2-Cl-4-CNPh | H |
| 1-88 | i-Pr | i-Pr | 2-Cl-4-(SEt)Ph | H |
| 1-89 | i-Pr | i-Pr | 2,4-$F_2$Bn | H |
| 1-90 | i-Pr | i-Pr | 2-F-3-Py | H |
| 1-91 | i-Pr | i-Pr | 6-F-3-Py | H |
| 1-92 | i-Pr | i-Pr | 3-Cl-2-Py | H |
| 1-93 | i-Pr | i-Pr | 5-Cl-2-Py | H |
| 1-94 | i-Pr | i-Pr | 3,5-$Cl_2$-2-Py | H |
| 1-95 | i-Pr | i-Pr | 3-Cl-5-$CF_3$-2-Py | H |
| 1-96 | i-Pr | i-Pr | 2-Cl-3-Py | H |
| 1-97 | i-Pr | i-Pr | 6-Cl-3-Py | H |
| 1-98 | i-Pr | i-Pr | 2,6-$Cl_2$-3-Py | H |
| 1-99 | i-Pr | i-Pr | 5-Me-isoxazol-3-yl | H |
| 1-100 | i-Pr | i-Pr | 2,4-$F_2$Ph | Me |
| 1-101 | s-Bu | i-Pr | 2,4-$F_2$Ph | H |
| 1-102 | i-Bu | i-Pr | 2,4-$F_2$Ph | H |
| 1-103 | $CF_3$ | i-Pr | 2,4-$F_2$Ph | H |
| 1-104 | $CHF_2$ | i-Pr | 2,4-$F_2$Ph | H |
| 1-105 | $CH_2CF_3$ | i-Pr | 2,4-$F_2$Ph | H |
| 1-106 | $CH_2Cl$ | i-Pr | Ph | H |
| 1-107 | $CH_2Cl$ | i-Pr | 2-FPh | H |
| 1-108 | $CH_2Cl$ | i-Pr | 3-FPh | H |
| 1-109 | $CH_2Cl$ | i-Pr | 4-FPh | H |
| 1-110 | $CH_2Cl$ | i-Pr | 2-ClPh | H |
| 1-111 | $CH_2Cl$ | i-Pr | 3-ClPh | H |
| 1-112 | $CH_2Cl$ | i-Pr | 4-ClPh | H |
| 1-113 | $CH_2Cl$ | i-Pr | 2-$CF_3$Ph | H |
| 1-114 | $CH_2Cl$ | i-Pr | 3-$CF_3$Ph | H |
| 1-115 | $CH_2Cl$ | i-Pr | 4-$CF_3$Ph | H |
| 1-116 | $CH_2Cl$ | i-Pr | 2,3-$F_2$Ph | H |
| 1-117 | $CH_2Cl$ | i-Pr | 2,4-$F_2$Ph | H |
| 1-118 | $CH_2Cl$ | i-Pr | 2,5-$F_2$Ph | H |
| 1-119 | $CH_2Cl$ | i-Pr | 2,6-$F_2$Ph | H |
| 1-120 | $CH_2Cl$ | i-Pr | 2,3,4-$F_3$Ph | H |
| 1-121 | $CH_2Cl$ | i-Pr | 2,4,6-$F_3$Ph | H |
| 1-122 | $CH_2Cl$ | i-Pr | 2,3,5,6-$F_4$Ph | H |
| 1-123 | $CH_2Cl$ | i-Pr | 2,3,4,5,6-$F_5$Ph | H |
| 1-124 | $CH_2Cl$ | i-Pr | 2-Cl-4-FPh | H |
| 1-125 | $CH_2Cl$ | i-Pr | 2-F-4-ClPh | H |
| 1-126 | $CH_2Cl$ | i-Pr | 2-F-4-BrPh | H |
| 1-127 | $CH_2Cl$ | i-Pr | 2-Br-4-FPh | H |
| 1-128 | $CH_2Cl$ | i-Pr | 2-Cl-4-BrPh | H |
| 1-129 | $CH_2Cl$ | i-Pr | 2-Br-4-ClPh | H |
| 1-130 | $CH_2Cl$ | i-Pr | 2-Me-4-FPh | H |
| 1-131 | $CH_2Cl$ | i-Pr | 2-F-4-MePh | H |

TABLE 1-continued

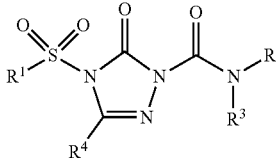

| No. | R¹ | R² | R³ | R⁴ |
|---|---|---|---|---|
| 1-132 | CH₂Cl | i-Pr | 2-Me-4-ClPh | H |
| 1-133 | CH₂Cl | i-Pr | 2-Cl-4-MePh | H |
| 1-134 | CH₂Cl | i-Pr | 2-F-4-CF₃Ph | H |
| 1-135 | CH₂Cl | i-Pr | 2-CF₃-4-FPh | H |
| 1-136 | CH₂Cl | i-Pr | 2,3,5,6-F₄-4-CF₃Ph | H |
| 1-137 | CH₂Cl | i-Pr | 2-Cl-4-CF₃Ph | H |
| 1-138 | CH₂Cl | i-Pr | 2-CF₃-4-ClPh | H |
| 1-139 | CH₂Cl | i-Pr | 2-Cl-4-CNPh | H |
| 1-140 | CH₂Cl | i-Pr | 2-Cl-4-(SEt)Ph | H |
| 1-141 | CH₂CH₂Cl | i-Pr | 2,4-F₂Ph | H |
| 1-142 | CH=CH₂ | i-Pr | 2,4-F₂Ph | H |
| 1-143 | CH₂CH=CH₂ | i-Pr | 2,4-F₂Ph | H |
| 1-144 | CH₂CH=CCl₂ | i-Pr | 2,4-F₂Ph | H |
| 1-145 | CH₂CH₂CH=CF₂ | i-Pr | 2,4-F₂Ph | H |
| 1-146 | CH₂C≡CH | i-Pr | 2,4-F₂Ph | H |
| 1-147 | CH₂C≡CCF₃ | i-Pr | 2,4-F₂Ph | H |
| 1-148 | c-Pr | Me | 2,4-F₂Ph | H |
| 1-149 | c-Pr | Et | 2,4-F₂Ph | H |
| 1-150 | c-Pr | i-Pr | 2,4-F₂Ph | H |
| 1-151 | c-Pr | s-Bu | 2,4-F₂Ph | H |
| 1-152 | c-Pr | CH₂CF₃ | 2,4-F₂Ph | H |
| 1-153 | c-Pr | CH₂CH=CH₂ | 2,4-F₂Ph | H |
| 1-154 | c-Pr | CH₂C≡CH | 2,4-F₂Ph | H |
| 1-155 | c-Pr | c-Pr | 2,4-F₂Ph | H |
| 1-156 | c-Pr | c-Hex | 2,4-F₂Ph | H |
| 1-157 | c-Pr | CH₂c-Pr | 2,4-F₂Ph | H |
| 1-158 | c-Pr | CH₂OMe | 2,4-F₂Ph | H |
| 1-159 | c-Pr | CH₂OCH₂CF₃ | 2,4-F₂Ph | H |
| 1-160 | c-Pr | Ph | 2,4-F₂Ph | H |
| 1-161 | c-Pr | Bn | 2,4-F₂Ph | H |
| 1-162 | c-Pr | 2-Py | 2,4-F₂Ph | H |
| 1-163 | c-Pr | —(CH₂)₅— | | H |
| 1-164 | c-Pr | —CH(Me)(CH₂)₄— | | H |
| 1-165 | Et | Et | Et | H |
| 1-166 | c-Pr | i-Pr | Et | H |
| 1-167 | c-Pr | i-Pr | c-Hex | H |
| 1-168 | c-Pr | i-Pr | Ph | H |
| 1-169 | c-Pr | i-Pr | 2-FPh | H |
| 1-170 | c-Pr | i-Pr | 3-FPh | H |
| 1-171 | c-Pr | i-Pr | 4-FPh | H |
| 1-172 | c-Pr | i-Pr | 2-ClPh | H |
| 1-173 | c-Pr | i-Pr | 3-ClPh | H |
| 1-174 | c-Pr | i-Pr | 4-ClPh | H |
| 1-175 | c-Pr | i-Pr | 4-BrPh | H |
| 1-176 | c-Pr | i-Pr | 2-CNPh | H |
| 1-177 | c-Pr | i-Pr | 4-CNPh | H |
| 1-178 | c-Pr | i-Pr | 2-NO₂Ph | H |
| 1-179 | c-Pr | i-Pr | 4-NO₂Ph | H |
| 1-180 | c-Pr | i-Pr | 2-MePh | H |
| 1-181 | c-Pr | i-Pr | 3-MePh | H |
| 1-182 | c-Pr | i-Pr | 4-MePh | H |
| 1-183 | c-Pr | i-Pr | 2-EtPh | H |
| 1-184 | c-Pr | i-Pr | 4-EtPh | H |
| 1-185 | c-Pr | i-Pr | 2-CF₃Ph | H |
| 1-186 | c-Pr | i-Pr | 3-CF₃Ph | H |
| 1-187 | c-Pr | i-Pr | 4-CF₃Ph | H |
| 1-188 | c-Pr | i-Pr | 2-OMePh | H |
| 1-189 | c-Pr | i-Pr | 3-OMePh | H |
| 1-190 | c-Pr | i-Pr | 4-OMePh | H |
| 1-191 | c-Pr | i-Pr | 2-OCF₃Ph | H |
| 1-192 | c-Pr | i-Pr | 3-OCF₃Ph | H |
| 1-193 | c-Pr | i-Pr | 4-OCF₃Ph | H |
| 1-194 | c-Pr | i-Pr | 2-SMePh | H |
| 1-195 | c-Pr | i-Pr | 4-SMePh | H |
| 1-196 | c-Pr | i-Pr | 2-SCF₃Ph | H |
| 1-197 | c-Pr | i-Pr | 4-SCF₃Ph | H |
| 1-198 | c-Pr | i-Pr | 2,3-F₂Ph | H |
| 1-199 | c-Pr | i-Pr | 2,5-F₂Ph | H |
| 1-200 | c-Pr | i-Pr | 2,6-F₂Ph | H |

TABLE 1-continued

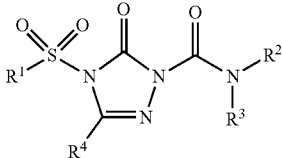

| No. | R¹ | R² | R³ | R⁴ |
|---|---|---|---|---|
| 1-201 | c-Pr | i-Pr | 3,4-F₂Ph | H |
| 1-202 | c-Pr | i-Pr | 3,5-F₂Ph | H |
| 1-203 | c-Pr | i-Pr | 2,3,4-F₃Ph | H |
| 1-204 | c-Pr | i-Pr | 2,4,6-F₃Ph | H |
| 1-205 | c-Pr | i-Pr | 3,4,5-F₃Ph | H |
| 1-206 | c-Pr | i-Pr | 2,3,5,6-F₄Ph | H |
| 1-207 | c-Pr | i-Pr | 2,3,4,5,6-F₅Ph | H |
| 1-208 | c-Pr | i-Pr | 2,3-Cl₂Ph | H |
| 1-209 | c-Pr | i-Pr | 2,4-Cl₂Ph | H |
| 1-210 | c-Pr | i-Pr | 2,5-Cl₂Ph | H |
| 1-211 | c-Pr | i-Pr | 2,6-Cl₂Ph | H |
| 1-212 | c-Pr | i-Pr | 3,4-Cl₂Ph | H |
| 1-213 | c-Pr | i-Pr | 3,5-Cl₂Ph | H |
| 1-214 | c-Pr | i-Pr | 2-Cl-4-FPh | H |
| 1-215 | c-Pr | i-Pr | 2-F-4-ClPh | H |
| 1-216 | c-Pr | i-Pr | 2-F-4-BrPh | H |
| 1-217 | c-Pr | i-Pr | 2-Br-4-FPh | H |
| 1-218 | c-Pr | i-Pr | 2-Cl-4-BrPh | H |
| 1-219 | c-Pr | i-Pr | 2-Br-4-ClPh | H |
| 1-220 | c-Pr | i-Pr | 2-Me-4-FPh | H |
| 1-221 | c-Pr | i-Pr | 2-F-4-MePh | H |
| 1-222 | c-Pr | i-Pr | 2-Me-4-ClPh | H |
| 1-223 | c-Pr | i-Pr | 2-Cl-4-MePh | H |
| 1-224 | c-Pr | i-Pr | 2,4-F₂-3-MePh | H |
| 1-225 | c-Pr | i-Pr | 2,4-F₂-5-MePh | H |
| 1-226 | c-Pr | i-Pr | 2-F-4-CF₃Ph | H |
| 1-227 | c-Pr | i-Pr | 2-CF₃-4-FPh | H |
| 1-228 | c-Pr | i-Pr | 2,3,5,6-F₄-4-CF₃Ph | H |
| 1-229 | c-Pr | i-Pr | 2-Cl-4-CF₃Ph | H |
| 1-230 | c-Pr | i-Pr | 2-CF₃-4-ClPh | H |
| 1-231 | c-Pr | i-Pr | 2-Cl-4-CNPh | H |
| 1-232 | c-Pr | i-Pr | 2-Cl-4-(SMe)Ph | H |
| 1-233 | c-Pr | i-Pr | 2-Cl-4-(SEt)Ph | H |
| 1-234 | c-Pr | i-Pr | Bn | H |
| 1-235 | c-Pr | i-Pr | 2-FBn | H |
| 1-236 | c-Pr | i-Pr | 3-FBn | H |
| 1-237 | c-Pr | i-Pr | 4-FBn | H |
| 1-238 | c-Pr | i-Pr | 2,4-F₂Bn | H |
| 1-239 | c-Pr | i-Pr | 4-MeBn | H |
| 1-240 | c-Pr | i-Pr | 4-OMeBn | H |
| 1-241 | i-Pr | i-Pr | 2-F-3-Py | H |
| 1-242 | i-Pr | i-Pr | 6-F-3-Py | H |
| 1-243 | c-Pr | i-Pr | 3-Cl-2-Py | H |
| 1-244 | c-Pr | i-Pr | 5-Cl-2-Py | H |
| 1-245 | c-Pr | i-Pr | 3,5-Cl₂-2-Py | H |
| 1-246 | c-Pr | i-Pr | 3-Cl-5-CF₃-2-Py | H |
| 1-247 | c-Pr | i-Pr | 2-Cl-3-Py | H |
| 1-248 | c-Pr | i-Pr | 6-Cl-3-Py | H |
| 1-249 | c-Pr | i-Pr | 2,6-Cl₂-3-Py | H |
| 1-250 | c-Pr | i-Pr | 5-Me-isoxazol-3-yl | H |
| 1-251 | c-Pr | i-Pr | 5-Cl-thiazol-2-yl | H |
| 1-252 | c-Pr | i-Pr | 1-Me-4-Cl-pyrazol-3-yl | H |
| 1-253 | c-Pr | i-Pr | 2,4-F₂Ph | F |
| 1-254 | c-Pr | i-Pr | 2,4-F₂Ph | Cl |
| 1-255 | c-Pr | i-Pr | 2,4-F₂Ph | Br |
| 1-256 | c-Pr | i-Pr | 2,4-F₂Ph | I |
| 1-257 | c-Pr | i-Pr | 2,4-F₂Ph | Me |
| 1-258 | c-Pr | i-Pr | 2,4-F₂Ph | Et |
| 1-259 | c-Pr | i-Pr | 2,4-F₂Ph | i-Pr |
| 1-260 | c-Pr | i-Pr | 2,4-F₂Ph | CHF₂ |
| 1-261 | c-Pr | i-Pr | 2,4-F₂Ph | CF₃ |
| 1-262 | c-Pr | i-Pr | 2,4-F₂Ph | OMe |
| 1-263 | c-Pr | i-Pr | 2,4-F₂Ph | OCF₃ |
| 1-264 | c-Bu | i-Pr | Ph | H |
| 1-265 | c-Bu | i-Pr | 2-FPh | H |
| 1-266 | c-Bu | i-Pr | 3-FPh | H |
| 1-267 | c-Bu | i-Pr | 4-FPh | H |
| 1-268 | c-Bu | i-Pr | 2,3-F₂Ph | H |

TABLE 1-continued

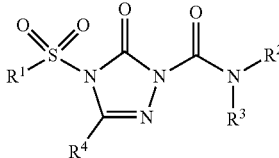

| No. | R¹ | R² | R³ | R⁴ |
|---|---|---|---|---|
| 1-269 | c-Bu | i-Pr | 2,4-F₂Ph | H |
| 1-270 | c-Bu | i-Pr | 2,5-F₂Ph | H |
| 1-271 | c-Bu | i-Pr | 2,6-F₂Ph | H |
| 1-272 | c-Bu | i-Pr | 2-Cl-4-FPh | H |
| 1-273 | c-Bu | i-Pr | 2-F-4-ClPh | H |
| 1-274 | c-Bu | i-Pr | 2-F-4-MePh | H |
| 1-275 | c-Bu | i-Pr | 2-Me-4-ClPh | H |
| 1-276 | c-Bu | i-Pr | 2-F-4-CF₃Ph | H |
| 1-277 | c-Bu | i-Pr | 2-CF₃-4-FPh | H |
| 1-278 | c-Bu | i-Pr | 2,4-F₂Ph | Me |
| 1-279 | c-Pen | i-Pr | Ph | H |
| 1-280 | c-Pen | i-Pr | 2-FPh | H |
| 1-281 | c-Pen | i-Pr | 3-FPh | H |
| 1-282 | c-Pen | i-Pr | 4-FPh | H |
| 1-283 | c-Pen | i-Pr | 2,3-F₂Ph | H |
| 1-284 | c-Pen | i-Pr | 2,4-F₂Ph | H |
| 1-285 | c-Pen | i-Pr | 2,5-F₂Ph | H |
| 1-286 | c-Pen | i-Pr | 2,6-F₂Ph | H |
| 1-287 | c-Pen | i-Pr | 2-Cl-4-FPh | H |
| 1-288 | c-Pen | i-Pr | 2-F-4-ClPh | H |
| 1-289 | c-Pen | i-Pr | 2-F-4-MePh | H |
| 1-290 | c-Pen | i-Pr | 2-Me-4-ClPh | H |
| 1-291 | c-Pen | i-Pr | 2-F-4-CF₃Ph | H |
| 1-292 | c-Pen | i-Pr | 2-CF₃-4-FPh | H |
| 1-293 | c-Pen | i-Pr | 2,4-F₂Ph | Me |
| 1-294 | c-Hex | Et | Et | H |
| 1-295 | c-Hex | i-Pr | Ph | H |
| 1-296 | c-Hex | i-Pr | 2-FPh | H |
| 1-297 | c-Hex | i-Pr | 3-FPh | H |
| 1-298 | c-Hex | i-Pr | 4-FPh | H |
| 1-299 | c-Hex | i-Pr | 2-ClPh | H |
| 1-300 | c-Hex | i-Pr | 3-ClPh | H |
| 1-301 | c-Hex | i-Pr | 4-ClPh | H |
| 1-302 | c-Hex | i-Pr | 2-CF₃Ph | H |
| 1-303 | c-Hex | i-Pr | 3-CF₃Ph | H |
| 1-304 | c-Hex | i-Pr | 4-CF₃Ph | H |
| 1-305 | c-Hex | i-Pr | 2,3-F₂Ph | H |
| 1-306 | c-Hex | i-Pr | 2,4-F₂Ph | H |
| 1-307 | c-Hex | i-Pr | 2,5-F₂Ph | H |
| 1-308 | c-Hex | i-Pr | 2,6-F₂Ph | H |
| 1-309 | c-Hex | i-Pr | 2,3,4-F₃Ph | H |
| 1-310 | c-Hex | i-Pr | 2,4,6-F₃Ph | H |
| 1-311 | c-Hex | i-Pr | 2,3,5,6-F₄Ph | H |
| 1-312 | c-Hex | i-Pr | 2,3,4,5,6-F₅Ph | H |
| 1-313 | c-Hex | i-Pr | 2-Cl-4-FPh | H |
| 1-314 | c-Hex | i-Pr | 2-F-4-ClPh | H |
| 1-315 | c-Hex | i-Pr | 2-F-4-BrPh | H |
| 1-316 | c-Hex | i-Pr | 2-Br-4-FPh | H |
| 1-317 | c-Hex | i-Pr | 2-Cl-4-BrPh | H |
| 1-318 | c-Hex | i-Pr | 2-Br-4-ClPh | H |
| 1-319 | c-Hex | i-Pr | 2-Me-4-FPh | H |
| 1-320 | c-Hex | i-Pr | 2-F-4-MePh | H |
| 1-321 | c-Hex | i-Pr | 2-Me-4-ClPh | H |
| 1-322 | c-Hex | i-Pr | 2-Cl-4-MePh | H |
| 1-323 | c-Hex | i-Pr | 2-F-4-CF₃Ph | H |
| 1-324 | c-Hex | i-Pr | 2-CF₃-4-FPh | H |
| 1-325 | c-Hex | i-Pr | 2,3,5,6-F₄-4-CF₃Ph | H |
| 1-326 | c-Hex | i-Pr | 2-Cl-4-CF₃Ph | H |
| 1-327 | c-Hex | i-Pr | 2-CF₃-4-ClPh | H |
| 1-328 | c-Hex | i-Pr | 2-Cl-4-CNPh | H |
| 1-329 | c-Hex | i-Pr | 2-Cl-4-(SEt)Ph | H |
| 1-330 | c-Hex | i-Pr | 2,4-F₂Bn | H |
| 1-331 | c-Hex | i-Pr | 3-Cl-2-Py | H |
| 1-332 | c-Hex | i-Pr | 5-Cl-2-Py | H |
| 1-333 | c-Hex | i-Pr | 3,5-Cl₂-2-Py | H |
| 1-334 | c-Hex | i-Pr | 3-Cl-5-CF₃-2-Py | H |
| 1-335 | c-Hex | i-Pr | 2-F-3-Py | H |
| 1-336 | c-Hex | i-Pr | 6-F-3-Py | H |
| 1-337 | c-Hex | i-Pr | 2-Cl-3-Py | H |

TABLE 1-continued

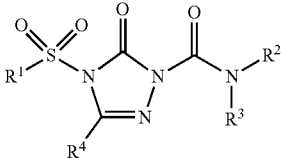

| No. | R¹ | R² | R³ | R⁴ |
|---|---|---|---|---|
| 1-338 | c-Hex | i-Pr | 6-Cl-3-Py | H |
| 1-339 | c-Hex | i-Pr | 2,6-Cl₂-3-Py | H |
| 1-340 | c-Hex | i-Pr | 5-Me-isoxazol-3-yl | H |
| 1-341 | c-Hex | i-Pr | 2,4-F₂Ph | Me |
| 1-342 | 1-F-c-Pr | i-Pr | 2,4-F₂Ph | H |
| 1-343 | 2,2-F₂-c-Pr | i-Pr | 2,4-F₂Ph | H |
| 1-344 | 2,2-Cl₂-c-Pr | i-Pr | 2,4-F₂Ph | H |
| 1-345 | 4,4-F₂-c-Hex | i-Pr | 2,4-F₂Ph | H |
| 1-346 | 1-Me-c-Pr | i-Pr | 2,4-F₂Ph | H |
| 1-347 | 2-Me-c-Pr | i-Pr | 2,4-F₂Ph | H |
| 1-348 | 2,2-Me₂-c-Pr | i-Pr | 2,4-F₂Ph | H |
| 1-349 | 3-Me-c-Pen | i-Pr | 2,4-F₂Ph | H |
| 1-350 | 4-Me-c-Hex | i-Pr | 2,4-F₂Ph | H |
| 1-351 | 4,4-Me₂-c-Hex | i-Pr | 2,4-F₂Ph | H |
| 1-352 | 1-OMe-c-Pr | i-Pr | 2,4-F₂Ph | H |
| 1-353 | 1-(c-Pr)-c-Pr | i-Pr | 2,4-F₂Ph | H |
| 1-354 | 1-(CH₂c-Pr)-c-Pr | i-Pr | 2,4-F₂Ph | H |
| 1-355 | 1-Ph-c-Pr | i-Pr | 2,4-F₂Ph | H |
| 1-356 | 1-Bn-c-Pr | i-Pr | 2,4-F₂Ph | H |
| 1-357 | CH₂c-Pr | i-Pr | 2,4-F₂Ph | H |
| 1-358 | CH₂c-Hex | i-Pr | 2,4-F₂Ph | H |
| 1-359 | CH₂OMe | i-Pr | 2,4-F₂Ph | H |
| 1-360 | CH₂OEt | i-Pr | 2,4-F₂Ph | H |
| 1-361 | CH₂Oi-Pr | i-Pr | 2,4-F₂Ph | H |
| 1-362 | CH₂CH₂OMe | i-Pr | 2,4-F₂Ph | H |
| 1-363 | CH(Me)CH₂OMe | i-Pr | 2,4-F₂Ph | H |
| 1-364 | CH₂CH(Me)OMe | i-Pr | 2,4-F₂Ph | H |
| 1-365 | CH₂OCH₂CF₃ | i-Pr | 2,4-F₂Ph | H |
| 1-366 | Ph | Et | Et | H |
| 1-367 | Ph | Et | c-Hex | H |
| 1-368 | Ph | i-Pr | Ph | H |
| 1-369 | Ph | i-Pr | 2-FPh | H |
| 1-370 | Ph | i-Pr | 3-FPh | H |
| 1-371 | Ph | i-Pr | 4-FPh | H |
| 1-372 | Ph | i-Pr | 2-ClPh | H |
| 1-373 | Ph | i-Pr | 3-ClPh | H |
| 1-374 | Ph | i-Pr | 4-ClPh | H |
| 1-375 | Ph | i-Pr | 4-MePh | H |
| 1-376 | Ph | i-Pr | 2-CF₃Ph | H |
| 1-377 | Ph | i-Pr | 3-CF₃Ph | H |
| 1-378 | Ph | i-Pr | 4-CF₃Ph | H |
| 1-379 | Ph | i-Pr | 2,3-F₂Ph | H |
| 1-380 | Ph | i-Pr | 2,4-F₂Ph | H |
| 1-381 | Ph | i-Pr | 2,5-F₂Ph | H |
| 1-382 | Ph | i-Pr | 2,6-F₂Ph | H |
| 1-383 | Ph | i-Pr | 2,3,4-F₃Ph | H |
| 1-384 | Ph | i-Pr | 2,4,6-F₃Ph | H |
| 1-385 | Ph | i-Pr | 2,3,5,6-F₄Ph | H |
| 1-386 | Ph | i-Pr | 2,3,4,5,6-F₅Ph | H |
| 1-387 | Ph | i-Pr | 2-Cl-4-FPh | H |
| 1-388 | Ph | i-Pr | 2-F-4-ClPh | H |
| 1-389 | Ph | i-Pr | 2-F-4-BrPh | H |
| 1-390 | Ph | i-Pr | 2-Br-4-FPh | H |
| 1-391 | Ph | i-Pr | 2-Cl-4-BrPh | H |
| 1-392 | Ph | i-Pr | 2-Br-4-ClPh | H |
| 1-393 | Ph | i-Pr | 2-Me-4-FPh | H |
| 1-394 | Ph | i-Pr | 2-F-4-MePh | H |
| 1-395 | Ph | i-Pr | 2-Me-4-ClPh | H |
| 1-396 | Ph | i-Pr | 2-Cl-4-MePh | H |
| 1-397 | Ph | i-Pr | 2-F-4-CF₃Ph | H |
| 1-398 | Ph | i-Pr | 2-CF₃-4-FPh | H |
| 1-399 | Ph | i-Pr | 2,3,5,6-F₄-4-CF₃Ph | H |
| 1-400 | Ph | i-Pr | 2-Cl-4-CF₃Ph | H |
| 1-401 | Ph | i-Pr | 2-CF₃-4-ClPh | H |
| 1-402 | Ph | i-Pr | 2-Cl-4-CNPh | H |
| 1-403 | Ph | i-Pr | 2-Cl-4-(SEt)Ph | H |
| 1-404 | 2-FPh | i-Pr | Ph | H |
| 1-405 | 2-FPh | i-Pr | 2-FPh | H |
| 1-406 | 2-FPh | i-Pr | 3-FPh | H |

TABLE 1-continued

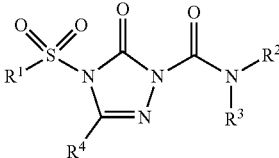

| No. | R¹ | R² | R³ | R⁴ |
|---|---|---|---|---|
| 1-407 | 2-FPh | i-Pr | 4-FPh | H |
| 1-408 | 2-FPh | i-Pr | 2-ClPh | H |
| 1-409 | 2-FPh | i-Pr | 3-ClPh | H |
| 1-410 | 2-FPh | i-Pr | 4-ClPh | H |
| 1-411 | 2-FPh | i-Pr | 2-CF₃Ph | H |
| 1-412 | 2-FPh | i-Pr | 3-CF₃Ph | H |
| 1-413 | 2-FPh | i-Pr | 4-CF₃Ph | H |
| 1-414 | 2-FPh | i-Pr | 2,3-F₂Ph | H |
| 1-415 | 2-FPh | i-Pr | 2,4-F₂Ph | H |
| 1-416 | 2-FPh | i-Pr | 2,5-F₂Ph | H |
| 1-417 | 2-FPh | i-Pr | 2,6-F₂Ph | H |
| 1-418 | 2-FPh | i-Pr | 2,3,4-F₃Ph | H |
| 1-419 | 2-FPh | i-Pr | 2,4,6-F₃Ph | H |
| 1-420 | 2-FPh | i-Pr | 2,3,5,6-F₄Ph | H |
| 1-421 | 2-FPh | i-Pr | 2,3,4,5,6-F₅Ph | H |
| 1-422 | 2-FPh | i-Pr | 2-Cl-4-FPh | H |
| 1-423 | 2-FPh | i-Pr | 2-F-4-ClPh | H |
| 1-424 | 2-FPh | i-Pr | 2-F-4-BrPh | H |
| 1-425 | 2-FPh | i-Pr | 2-Br-4-FPh | H |
| 1-426 | 2-FPh | i-Pr | 2-Cl-4-BrPh | H |
| 1-427 | 2-FPh | i-Pr | 2-Br-4-ClPh | H |
| 1-428 | 2-FPh | i-Pr | 2-Me-4-FPh | H |
| 1-429 | 2-FPh | i-Pr | 2-F-4-MePh | H |
| 1-430 | 2-FPh | i-Pr | 2-Me-4-ClPh | H |
| 1-431 | 2-FPh | i-Pr | 2-Cl-4-MePh | H |
| 1-432 | 2-FPh | i-Pr | 2-F-4-CF₃Ph | H |
| 1-433 | 2-FPh | i-Pr | 2-CF₃-4-FPh | H |
| 1-434 | 2-FPh | i-Pr | 2,3,5,6-F₄-4-CF₃Ph | H |
| 1-435 | 2-FPh | i-Pr | 2-Cl-4-CF₃Ph | H |
| 1-436 | 2-FPh | i-Pr | 2-CF₃-4-ClPh | H |
| 1-437 | 2-FPh | i-Pr | 2-Cl-4-CNPh | H |
| 1-438 | 2-FPh | i-Pr | 2-Cl-4-(SEt)Ph | H |
| 1-439 | 2-FPh | i-Pr | 6-Cl-3-Py | H |
| 1-440 | 2-FPh | i-Pr | 2,4-F₂Ph | Me |
| 1-441 | 3-FPh | i-Pr | Ph | H |
| 1-442 | 3-FPh | i-Pr | 2-FPh | H |
| 1-443 | 3-FPh | i-Pr | 3-FPh | H |
| 1-444 | 3-FPh | i-Pr | 4-FPh | H |
| 1-445 | 3-FPh | i-Pr | 2-ClPh | H |
| 1-446 | 3-FPh | i-Pr | 3-ClPh | H |
| 1-447 | 3-FPh | i-Pr | 4-ClPh | H |
| 1-448 | 3-FPh | i-Pr | 2-CF₃Ph | H |
| 1-449 | 3-FPh | i-Pr | 3-CF₃Ph | H |
| 1-450 | 3-FPh | i-Pr | 4-CF₃Ph | H |
| 1-451 | 3-FPh | i-Pr | 2,3-F₂Ph | H |
| 1-452 | 3-FPh | i-Pr | 2,4-F₂Ph | H |
| 1-453 | 3-FPh | i-Pr | 2,5-F₂Ph | H |
| 1-454 | 3-FPh | i-Pr | 2,6-F₂Ph | H |
| 1-455 | 3-FPh | i-Pr | 2,3,4-F₃Ph | H |
| 1-456 | 3-FPh | i-Pr | 2,4,6-F₃Ph | H |
| 1-457 | 3-FPh | i-Pr | 2,3,5,6-F₄Ph | H |
| 1-458 | 3-FPh | i-Pr | 2,3,4,5,6-F₅Ph | H |
| 1-459 | 3-FPh | i-Pr | 2-Cl-4-FPh | H |
| 1-460 | 3-FPh | i-Pr | 2-F-4-ClPh | H |
| 1-461 | 3-FPh | i-Pr | 2-F-4-BrPh | H |
| 1-462 | 3-FPh | i-Pr | 2-Br-4-FPh | H |
| 1-463 | 3-FPh | i-Pr | 2-Cl-4-BrPh | H |
| 1-464 | 3-FPh | i-Pr | 2-Br-4-ClPh | H |
| 1-465 | 3-FPh | i-Pr | 2-Me-4-FPh | H |
| 1-466 | 3-FPh | i-Pr | 2-F-4-MePh | H |
| 1-467 | 3-FPh | i-Pr | 2-Me-4-ClPh | H |
| 1-468 | 3-FPh | i-Pr | 2-Cl-4-MePh | H |
| 1-469 | 3-FPh | i-Pr | 2-F-4-CF₃Ph | H |
| 1-470 | 3-FPh | i-Pr | 2-CF₃-4-FPh | H |
| 1-471 | 3-FPh | i-Pr | 2,3,5,6-F₄-4-CF₃Ph | H |
| 1-472 | 3-FPh | i-Pr | 2-Cl-4-CF₃Ph | H |
| 1-473 | 3-FPh | i-Pr | 2-CF₃-4-ClPh | H |
| 1-474 | 3-FPh | i-Pr | 2-Cl-4-CNPh | H |
| 1-475 | 3-FPh | i-Pr | 2-Cl-4-(SEt)Ph | H |

TABLE 1-continued

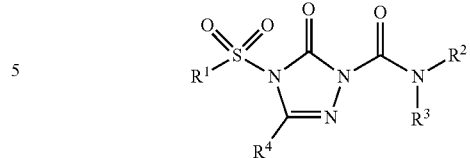

| No. | R¹ | R² | R³ | R⁴ |
|---|---|---|---|---|
| 1-476 | 3-FPh | i-Pr | 6-Cl-3-Py | H |
| 1-477 | 3-FPh | i-Pr | 2,4-F₂Ph | Me |
| 1-478 | 4-FPh | Et | Et | H |
| 1-479 | 4-FPh | i-Pr | Ph | H |
| 1-480 | 4-FPh | i-Pr | 2-FPh | H |
| 1-481 | 4-FPh | i-Pr | 3-FPh | H |
| 1-482 | 4-FPh | i-Pr | 4-FPh | H |
| 1-483 | 4-FPh | i-Pr | 2-ClPh | H |
| 1-484 | 4-FPh | i-Pr | 3-ClPh | H |
| 1-485 | 4-FPh | i-Pr | 4-ClPh | H |
| 1-486 | 4-FPh | i-Pr | 2-CF₃Ph | H |
| 1-487 | 4-FPh | i-Pr | 3-CF₃Ph | H |
| 1-488 | 4-FPh | i-Pr | 4-CF₃Ph | H |
| 1-489 | 4-FPh | i-Pr | 2,3-F₂Ph | H |
| 1-490 | 4-FPh | i-Pr | 2,4-F₂Ph | H |
| 1-491 | 4-FPh | i-Pr | 2,5-F₂Ph | H |
| 1-492 | 4-FPh | i-Pr | 2,6-F₂Ph | H |
| 1-493 | 4-FPh | i-Pr | 2,3,4-F₃Ph | H |
| 1-494 | 4-FPh | i-Pr | 2,4,6-F₃Ph | H |
| 1-495 | 4-FPh | i-Pr | 2,3,5,6-F₄Ph | H |
| 1-496 | 4-FPh | i-Pr | 2,3,4,5,6-F₅Ph | H |
| 1-497 | 4-FPh | i-Pr | 2-Cl-4-FPh | H |
| 1-498 | 4-FPh | i-Pr | 2-F-4-ClPh | H |
| 1-499 | 4-FPh | i-Pr | 2-F-4-BrPh | H |
| 1-500 | 4-FPh | i-Pr | 2-Br-4-FPh | H |
| 1-501 | 4-FPh | i-Pr | 2-Cl-4-BrPh | H |
| 1-502 | 4-FPh | i-Pr | 2-Br-4-ClPh | H |
| 1-503 | 4-FPh | i-Pr | 2-Me-4-FPh | H |
| 1-504 | 4-FPh | i-Pr | 2-F-4-MePh | H |
| 1-505 | 4-FPh | i-Pr | 2-Me-4-ClPh | H |
| 1-506 | 4-FPh | i-Pr | 2-Cl-4-MePh | H |
| 1-507 | 4-FPh | i-Pr | 2-F-4-CF₃Ph | H |
| 1-508 | 4-FPh | i-Pr | 2-CF₃-4-FPh | H |
| 1-509 | 4-FPh | i-Pr | 2,3,5,6-F₄-4-CF₃Ph | H |
| 1-510 | 4-FPh | i-Pr | 2-Cl-4-CF₃Ph | H |
| 1-511 | 4-FPh | i-Pr | 2-CF₃-4-ClPh | H |
| 1-512 | 4-FPh | i-Pr | 2-Cl-4-CNPh | H |
| 1-513 | 4-FPh | i-Pr | 2-Cl-4-(SEt)Ph | H |
| 1-514 | 4-FPh | i-Pr | 6-Cl-3-Py | H |
| 1-515 | 4-FPh | i-Pr | 2,4-F₂Ph | Me |
| 1-516 | 2-ClPh | Et | Et | H |
| 1-517 | 2-ClPh | i-Pr | Ph | H |
| 1-518 | 2-ClPh | i-Pr | 2-FPh | H |
| 1-519 | 2-ClPh | i-Pr | 3-FPh | H |
| 1-520 | 2-ClPh | i-Pr | 4-FPh | H |
| 1-521 | 2-ClPh | i-Pr | 2-ClPh | H |
| 1-522 | 2-ClPh | i-Pr | 3-ClPh | H |
| 1-523 | 2-ClPh | i-Pr | 4-ClPh | H |
| 1-524 | 2-ClPh | i-Pr | 2-CF₃Ph | H |
| 1-525 | 2-ClPh | i-Pr | 3-CF₃Ph | H |
| 1-526 | 2-ClPh | i-Pr | 4-CF₃Ph | H |
| 1-527 | 2-ClPh | i-Pr | 2,3-F₂Ph | H |
| 1-528 | 2-ClPh | i-Pr | 2,4-F₂Ph | H |
| 1-529 | 2-ClPh | i-Pr | 2,5-F₂Ph | H |
| 1-530 | 2-ClPh | i-Pr | 2,6-F₂Ph | H |
| 1-531 | 2-ClPh | i-Pr | 2,3,4-F₃Ph | H |
| 1-532 | 2-ClPh | i-Pr | 2,4,6-F₃Ph | H |
| 1-533 | 2-ClPh | i-Pr | 2,3,5,6-F₄Ph | H |
| 1-534 | 2-ClPh | i-Pr | 2,3,4,5,6-F₅Ph | H |
| 1-535 | 2-ClPh | i-Pr | 2-Cl-4-FPh | H |
| 1-536 | 2-ClPh | i-Pr | 2-F-4-ClPh | H |
| 1-537 | 2-ClPh | i-Pr | 2-F-4-BrPh | H |
| 1-538 | 2-ClPh | i-Pr | 2-Br-4-FPh | H |
| 1-539 | 2-ClPh | i-Pr | 2-Cl-4-BrPh | H |
| 1-540 | 2-ClPh | i-Pr | 2-Br-4-ClPh | H |
| 1-541 | 2-ClPh | i-Pr | 2-Me-4-FPh | H |
| 1-542 | 2-ClPh | i-Pr | 2-F-4-MePh | H |
| 1-543 | 2-ClPh | i-Pr | 2-Me-4-ClPh | H |
| 1-544 | 2-ClPh | i-Pr | 2-Cl-4-MePh | H |

TABLE 1-continued

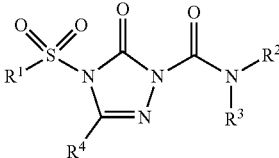

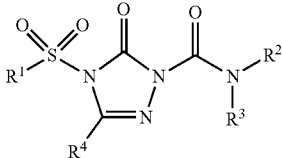

| No. | R¹ | R² | R³ | R⁴ |
|---|---|---|---|---|
| 1-545 | 2-ClPh | i-Pr | 2-F-4-CF₃Ph | H |
| 1-546 | 2-ClPh | i-Pr | 2-CF₃-4-FPh | H |
| 1-547 | 2-ClPh | i-Pr | 2,3,5,6-F₄-4-CF₃Ph | H |
| 1-548 | 2-ClPh | i-Pr | 2-Cl-4-CF₃Ph | H |
| 1-549 | 2-ClPh | i-Pr | 2-CF₃-4-ClPh | H |
| 1-550 | 2-ClPh | i-Pr | 2-Cl-4-CNPh | H |
| 1-551 | 2-ClPh | i-Pr | 2-Cl-4-(SEt)Ph | H |
| 1-552 | 2-ClPh | i-Pr | 2-F-3-Py | H |
| 1-553 | 2-ClPh | i-Pr | 6-F-3-Py | H |
| 1-554 | 2-ClPh | i-Pr | 5-Cl-2-Py | H |
| 1-555 | 2-ClPh | i-Pr | 2,4-F₂Ph | Me |
| 1-556 | 3-ClPh | Et | Et | H |
| 1-557 | 3-ClPh | i-Pr | Ph | H |
| 1-558 | 3-ClPh | i-Pr | 2-FPh | H |
| 1-559 | 3-ClPh | i-Pr | 3-FPh | H |
| 1-560 | 3-ClPh | i-Pr | 4-FPh | H |
| 1-561 | 3-ClPh | i-Pr | 2-ClPh | H |
| 1-562 | 3-ClPh | i-Pr | 3-ClPh | H |
| 1-563 | 3-ClPh | i-Pr | 4-ClPh | H |
| 1-564 | 3-ClPh | i-Pr | 2-CF₃Ph | H |
| 1-565 | 3-ClPh | i-Pr | 3-CF₃Ph | H |
| 1-566 | 3-ClPh | i-Pr | 4-CF₃Ph | H |
| 1-567 | 3-ClPh | i-Pr | 2,3-F₂Ph | H |
| 1-568 | 3-ClPh | i-Pr | 2,4-F₂Ph | H |
| 1-569 | 3-ClPh | i-Pr | 2,5-F₂Ph | H |
| 1-570 | 3-ClPh | i-Pr | 2,6-F₂Ph | H |
| 1-571 | 3-ClPh | i-Pr | 2,3,4-F₃Ph | H |
| 1-572 | 3-ClPh | i-Pr | 2,4,6-F₃Ph | H |
| 1-573 | 3-ClPh | i-Pr | 2,3,5,6-F₄Ph | H |
| 1-574 | 3-ClPh | i-Pr | 2,3,4,5,6-F₅Ph | H |
| 1-575 | 3-ClPh | i-Pr | 2-Cl-4-FPh | H |
| 1-576 | 3-ClPh | i-Pr | 2-F-4-ClPh | H |
| 1-577 | 3-ClPh | i-Pr | 2-F-4-BrPh | H |
| 1-578 | 3-ClPh | i-Pr | 2-Br-4-FPh | H |
| 1-579 | 3-ClPh | i-Pr | 2-Cl-4-BrPh | H |
| 1-580 | 3-ClPh | i-Pr | 2-Br-4-ClPh | H |
| 1-581 | 3-ClPh | i-Pr | 2-Me-4-FPh | H |
| 1-582 | 3-ClPh | i-Pr | 2-F-4-MePh | H |
| 1-583 | 3-ClPh | i-Pr | 2-Me-4-ClPh | H |
| 1-584 | 3-ClPh | i-Pr | 2-Cl-4-MePh | H |
| 1-585 | 3-ClPh | i-Pr | 2-F-4-CF₃Ph | H |
| 1-586 | 3-ClPh | i-Pr | 2-CF₃-4-FPh | H |
| 1-587 | 3-ClPh | i-Pr | 2,3,5,6-F₄-4-CF₃Ph | H |
| 1-588 | 3-ClPh | i-Pr | 2-Cl-4-CF₃Ph | H |
| 1-589 | 3-ClPh | i-Pr | 2-CF₃-4-ClPh | H |
| 1-590 | 3-ClPh | i-Pr | 2-Cl-4-CNPh | H |
| 1-591 | 3-ClPh | i-Pr | 2-Cl-4-(SEt)Ph | H |
| 1-592 | 3-ClPh | i-Pr | 2-F-3-Py | H |
| 1-593 | 3-ClPh | i-Pr | 6-F-3-Py | H |
| 1-594 | 3-ClPh | i-Pr | 5-Cl-2-Py | H |
| 1-595 | 3-ClPh | i-Pr | 2,6-Cl₂-3-Py | H |
| 1-596 | 3-ClPh | i-Pr | 2,4-F₂Ph | Me |
| 1-597 | 4-ClPh | Et | Et | H |
| 1-598 | 4-ClPh | i-Pr | Ph | H |
| 1-599 | 4-ClPh | i-Pr | 2-FPh | H |
| 1-600 | 4-ClPh | i-Pr | 3-FPh | H |
| 1-601 | 4-ClPh | i-Pr | 4-FPh | H |
| 1-602 | 4-ClPh | i-Pr | 2-ClPh | H |
| 1-603 | 4-ClPh | i-Pr | 3-ClPh | H |
| 1-604 | 4-ClPh | i-Pr | 4-ClPh | H |
| 1-605 | 4-ClPh | i-Pr | 2-CF₃Ph | H |
| 1-606 | 4-ClPh | i-Pr | 3-CF₃Ph | H |
| 1-607 | 4-ClPh | i-Pr | 4-CF₃Ph | H |
| 1-608 | 4-ClPh | i-Pr | 2,3-F₂Ph | H |
| 1-609 | 4-ClPh | i-Pr | 2,4-F₂Ph | H |
| 1-610 | 4-ClPh | i-Pr | 2,5-F₂Ph | H |
| 1-611 | 4-ClPh | i-Pr | 2,6-F₂Ph | H |
| 1-612 | 4-ClPh | i-Pr | 2,3,4-F₃Ph | H |
| 1-613 | 4-ClPh | i-Pr | 2,4,6-F₃Ph | H |
| 1-614 | 4-ClPh | i-Pr | 2,3,5,6-F₄Ph | H |
| 1-615 | 4-ClPh | i-Pr | 2,3,4,5,6-F₅Ph | H |
| 1-616 | 4-ClPh | i-Pr | 2-Cl-4-FPh | H |
| 1-617 | 4-ClPh | i-Pr | 2-F-4-ClPh | H |
| 1-618 | 4-ClPh | i-Pr | 2-F-4-BrPh | H |
| 1-619 | 4-ClPh | i-Pr | 2-Br-4-FPh | H |
| 1-620 | 4-ClPh | i-Pr | 2-Cl-4-BrPh | H |
| 1-621 | 4-ClPh | i-Pr | 2-Br-4-ClPh | H |
| 1-622 | 4-ClPh | i-Pr | 2-Me-4-FPh | H |
| 1-623 | 4-ClPh | i-Pr | 2-F-4-MePh | H |
| 1-624 | 4-ClPh | i-Pr | 2-Me-4-ClPh | H |
| 1-625 | 4-ClPh | i-Pr | 2-Cl-4-MePh | H |
| 1-626 | 4-ClPh | i-Pr | 2-F-4-CF₃Ph | H |
| 1-627 | 4-ClPh | i-Pr | 2-CF₃-4-FPh | H |
| 1-628 | 4-ClPh | i-Pr | 2,3,5,6-F₄-4-CF₃Ph | H |
| 1-629 | 4-ClPh | i-Pr | 2-Cl-4-CF₃Ph | H |
| 1-630 | 4-ClPh | i-Pr | 2-CF₃-4-ClPh | H |
| 1-631 | 4-ClPh | i-Pr | 2-Cl-4-CNPh | H |
| 1-632 | 4-ClPh | i-Pr | 2-Cl-4-(SEt)Ph | H |
| 1-633 | 4-ClPh | i-Pr | 2-F-3-Py | H |
| 1-634 | 4-ClPh | i-Pr | 6-F-3-Py | H |
| 1-635 | 4-ClPh | i-Pr | 5-Cl-2-Py | H |
| 1-636 | 4-ClPh | i-Pr | 2,6-Cl₂-3-Py | H |
| 1-637 | 4-ClPh | i-Pr | 2,4-F₂Bn | H |
| 1-638 | 4-ClPh | i-Pr | 2,4-F₂Ph | Me |
| 1-639 | 4-BrPh | Et | Et | H |
| 1-640 | 4-BrPh | i-Pr | 2,4-F₂Ph | H |
| 1-641 | 2-CNPh | i-Pr | 2,4-F₂Ph | H |
| 1-642 | 4-CNPh | i-Pr | 2,4-F₂Ph | H |
| 1-643 | 2-NO₂Ph | Et | Et | H |
| 1-644 | 2-NO₂Ph | i-Pr | 2,4-F₂Ph | H |
| 1-645 | 4-NO₂Ph | i-Pr | 2,4-F₂Ph | H |
| 1-646 | 2-MePh | Et | Et | H |
| 1-647 | 2-MePh | i-Pr | 2,4-F₂Ph | H |
| 1-648 | 3-MePh | Et | Et | H |
| 1-649 | 3-MePh | i-Pr | 2,4-F₂Ph | H |
| 1-650 | 4-MePh | Et | Et | H |
| 1-651 | 4-MePh | i-Pr | Ph | H |
| 1-652 | 4-MePh | i-Pr | 2-FPh | H |
| 1-653 | 4-MePh | i-Pr | 3-FPh | H |
| 1-654 | 4-MePh | i-Pr | 4-FPh | H |
| 1-655 | 4-MePh | i-Pr | 2-ClPh | H |
| 1-656 | 4-MePh | i-Pr | 3-ClPh | H |
| 1-657 | 4-MePh | i-Pr | 4-ClPh | H |
| 1-658 | 4-MePh | i-Pr | 2-CF₃Ph | H |
| 1-659 | 4-MePh | i-Pr | 3-CF₃Ph | H |
| 1-660 | 4-MePh | i-Pr | 4-CF₃Ph | H |
| 1-661 | 4-MePh | i-Pr | 2,3-F₂Ph | H |
| 1-662 | 4-MePh | i-Pr | 2,4-F₂Ph | H |
| 1-663 | 4-MePh | i-Pr | 2,5-F₂Ph | H |
| 1-664 | 4-MePh | i-Pr | 2,6-F₂Ph | H |
| 1-665 | 4-MePh | i-Pr | 2,3,4-F₃Ph | H |
| 1-666 | 4-MePh | i-Pr | 2,4,6-F₃Ph | H |
| 1-667 | 4-MePh | i-Pr | 2,3,5,6-F₄Ph | H |
| 1-668 | 4-MePh | i-Pr | 2,3,4,5,6-F₅Ph | H |
| 1-669 | 4-MePh | i-Pr | 2-Cl-4-FPh | H |
| 1-670 | 4-MePh | i-Pr | 2-F-4-ClPh | H |
| 1-671 | 4-MePh | i-Pr | 2-F-4-BrPh | H |
| 1-672 | 4-MePh | i-Pr | 2-Br-4-FPh | H |
| 1-673 | 4-MePh | i-Pr | 2-Cl-4-BrPh | H |
| 1-674 | 4-MePh | i-Pr | 2-Br-4-ClPh | H |
| 1-675 | 4-MePh | i-Pr | 2-Me-4-FPh | H |
| 1-676 | 4-MePh | i-Pr | 2-F-4-MePh | H |
| 1-677 | 4-MePh | i-Pr | 2-Me-4-ClPh | H |
| 1-678 | 4-MePh | i-Pr | 2-Cl-4-MePh | H |
| 1-679 | 4-MePh | i-Pr | 2-F-4-CF₃Ph | H |
| 1-680 | 4-MePh | i-Pr | 2-CF₃-4-FPh | H |
| 1-681 | 4-MePh | i-Pr | 2,3,5,6-F₄-4-CF₃Ph | H |
| 1-682 | 4-MePh | i-Pr | 2-Cl-4-CF₃Ph | H |

TABLE 1-continued

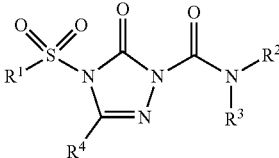

| No. | R¹ | R² | R³ | R⁴ |
|---|---|---|---|---|
| 1-683 | 4-MePh | i-Pr | 2-CF₃-4-ClPh | H |
| 1-684 | 4-MePh | i-Pr | 2-Cl-4-CNPh | H |
| 1-685 | 4-MePh | i-Pr | 2-Cl-4-(SEt)Ph | H |
| 1-686 | 4-MePh | i-Pr | 2-F-3-Py | H |
| 1-687 | 4-MePh | i-Pr | 6-F-3-Py | H |
| 1-688 | 4-MePh | i-Pr | 5-Cl-2-Py | H |
| 1-689 | 4-MePh | i-Pr | 6-Cl-3-Py | H |
| 1-690 | 4-MePh | i-Pr | 2,6-Cl₂-3-Py | H |
| 1-691 | 4-MePh | i-Pr | 2,4-F₂Bn | H |
| 1-692 | 4-MePh | i-Pr | 2,4-F₂Ph | Me |
| 1-693 | 2-EtPh | i-Pr | 2,4-F₂Ph | H |
| 1-694 | 4-EtPh | Et | Et | H |
| 1-695 | 4-EtPh | i-Pr | 2,4-F₂Ph | H |
| 1-696 | 2-(i-Pr)Ph | i-Pr | 2,4-F₂Ph | H |
| 1-697 | 4-(i-Pr)Ph | i-Pr | 2,4-F₂Ph | H |
| 1-698 | 2-(t-Bu)Ph | i-Pr | 2,4-F₂Ph | H |
| 1-699 | 4-(t-Bu)Ph | Et | Et | H |
| 1-700 | 4-(t-Bu)Ph | i-Pr | Ph | H |
| 1-701 | 4-(t-Bu)Ph | i-Pr | 2-FPh | H |
| 1-702 | 4-(t-Bu)Ph | i-Pr | 3-FPh | H |
| 1-703 | 4-(t-Bu)Ph | i-Pr | 4-FPh | H |
| 1-704 | 4-(t-Bu)Ph | i-Pr | 2-ClPh | H |
| 1-705 | 4-(t-Bu)Ph | i-Pr | 3-ClPh | H |
| 1-706 | 4-(t-Bu)Ph | i-Pr | 4-ClPh | H |
| 1-707 | 4-(t-Bu)Ph | i-Pr | 2-CF₃Ph | H |
| 1-708 | 4-(t-Bu)Ph | i-Pr | 3-CF₃Ph | H |
| 1-709 | 4-(t-Bu)Ph | i-Pr | 4-CF₃Ph | H |
| 1-710 | 4-(t-Bu)Ph | i-Pr | 2,3-F₂Ph | H |
| 1-711 | 4-(t-Bu)Ph | i-Pr | 2,4-F₂Ph | H |
| 1-712 | 4-(t-Bu)Ph | i-Pr | 2,5-F₂Ph | H |
| 1-713 | 4-(t-Bu)Ph | i-Pr | 2,6-F₂Ph | H |
| 1-714 | 4-(t-Bu)Ph | i-Pr | 2,3,4-F₃Ph | H |
| 1-715 | 4-(t-Bu)Ph | i-Pr | 2,4,6-F₃Ph | H |
| 1-716 | 4-(t-Bu)Ph | i-Pr | 2,3,5,6-F₄Ph | H |
| 1-717 | 4-(t-Bu)Ph | i-Pr | 2,3,4,5,6-F₅Ph | H |
| 1-718 | 4-(t-Bu)Ph | i-Pr | 2-Cl-4-FPh | H |
| 1-719 | 4-(t-Bu)Ph | i-Pr | 2-F-4-ClPh | H |
| 1-720 | 4-(t-Bu)Ph | i-Pr | 2-F-4-BrPh | H |
| 1-721 | 4-(t-Bu)Ph | i-Pr | 2-Br-4-FPh | H |
| 1-722 | 4-(t-Bu)Ph | i-Pr | 2-Cl-4-BrPh | H |
| 1-723 | 4-(t-Bu)Ph | i-Pr | 2-Br-4-ClPh | H |
| 1-724 | 4-(t-Bu)Ph | i-Pr | 2-Me-4-FPh | H |
| 1-725 | 4-(t-Bu)Ph | i-Pr | 2-F-4-MePh | H |
| 1-726 | 4-(t-Bu)Ph | i-Pr | 2-Me-4-ClPh | H |
| 1-727 | 4-(t-Bu)Ph | i-Pr | 2-Cl-4-MePh | H |
| 1-728 | 4-(t-Bu)Ph | i-Pr | 2-F-4-CF₃Ph | H |
| 1-729 | 4-(t-Bu)Ph | i-Pr | 2-CF₃-4-FPh | H |
| 1-730 | 4-(t-Bu)Ph | i-Pr | 2,3,5,6-F₄-4-CF₃Ph | H |
| 1-731 | 4-(t-Bu)Ph | i-Pr | 2-Cl-4-CF₃Ph | H |
| 1-732 | 4-(t-Bu)Ph | i-Pr | 2-CF₃-4-ClPh | H |
| 1-733 | 4-(t-Bu)Ph | i-Pr | 2-Cl-4-CNPh | H |
| 1-734 | 4-(t-Bu)Ph | i-Pr | 2-Cl-4-(SEt)Ph | H |
| 1-735 | 4-(t-Bu)Ph | i-Pr | 2-F-3-Py | H |
| 1-736 | 4-(t-Bu)Ph | i-Pr | 6-F-3-Py | H |
| 1-737 | 4-(t-Bu)Ph | i-Pr | 5-Cl-2-Py | H |
| 1-738 | 4-(t-Bu)Ph | i-Pr | 2,6-Cl₂-3-Py | H |
| 1-739 | 4-(t-Bu)Ph | i-Pr | 2,4-F₂Bn | H |
| 1-740 | 4-(t-Bu)Ph | i-Pr | 2,4-F₂Ph | Me |
| 1-741 | 2-CF₃Ph | Et | Et | H |
| 1-742 | 2-CF₃Ph | i-Pr | 2,4-F₂Ph | H |
| 1-743 | 3-CF₃Ph | i-Pr | Ph | H |
| 1-744 | 3-CF₃Ph | i-Pr | 2-FPh | H |
| 1-745 | 3-CF₃Ph | i-Pr | 3-FPh | H |
| 1-746 | 3-CF₃Ph | i-Pr | 4-FPh | H |
| 1-747 | 3-CF₃Ph | i-Pr | 2-ClPh | H |
| 1-748 | 3-CF₃Ph | i-Pr | 3-ClPh | H |
| 1-749 | 3-CF₃Ph | i-Pr | 4-ClPh | H |
| 1-750 | 3-CF₃Ph | i-Pr | 2-CF₃Ph | H |
| 1-751 | 3-CF₃Ph | i-Pr | 3-CF₃Ph | H |

TABLE 1-continued

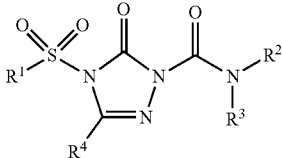

| No. | R¹ | R² | R³ | R⁴ |
|---|---|---|---|---|
| 1-752 | 3-CF₃Ph | i-Pr | 4-CF₃Ph | H |
| 1-753 | 3-CF₃Ph | i-Pr | 2,3-F₂Ph | H |
| 1-754 | 3-CF₃Ph | i-Pr | 2,4-F₂Ph | H |
| 1-755 | 3-CF₃Ph | i-Pr | 2,5-F₂Ph | H |
| 1-756 | 3-CF₃Ph | i-Pr | 2,6-F₂Ph | H |
| 1-757 | 3-CF₃Ph | i-Pr | 2,3,4-F₃Ph | H |
| 1-758 | 3-CF₃Ph | i-Pr | 2,4,6-F₃Ph | H |
| 1-759 | 3-CF₃Ph | i-Pr | 2,3,5,6-F₄Ph | H |
| 1-760 | 3-CF₃Ph | i-Pr | 2,3,4,5,6-F₅Ph | H |
| 1-761 | 3-CF₃Ph | i-Pr | 2-Cl-4-FPh | H |
| 1-762 | 3-CF₃Ph | i-Pr | 2-F-4-ClPh | H |
| 1-763 | 3-CF₃Ph | i-Pr | 2-F-4-BrPh | H |
| 1-764 | 3-CF₃Ph | i-Pr | 2-Br-4-FPh | H |
| 1-765 | 3-CF₃Ph | i-Pr | 2-Cl-4-BrPh | H |
| 1-766 | 3-CF₃Ph | i-Pr | 2-Br-4-ClPh | H |
| 1-767 | 3-CF₃Ph | i-Pr | 2-Me-4-FPh | H |
| 1-768 | 3-CF₃Ph | i-Pr | 2-F-4-MePh | H |
| 1-769 | 3-CF₃Ph | i-Pr | 2-Me-4-ClPh | H |
| 1-770 | 3-CF₃Ph | i-Pr | 2-Cl-4-MePh | H |
| 1-771 | 3-CF₃Ph | i-Pr | 2-F-4-CF₃Ph | H |
| 1-772 | 3-CF₃Ph | i-Pr | 2-CF₃-4-FPh | H |
| 1-773 | 3-CF₃Ph | i-Pr | 2,3,5,6-F₄-4-CF₃Ph | H |
| 1-774 | 3-CF₃Ph | i-Pr | 2-Cl-4-CF₃Ph | H |
| 1-775 | 3-CF₃Ph | i-Pr | 2-CF₃-4-ClPh | H |
| 1-776 | 3-CF₃Ph | i-Pr | 2-Cl-4-CNPh | H |
| 1-777 | 3-CF₃Ph | i-Pr | 2-Cl-4-(SEt)Ph | H |
| 1-778 | 3-CF₃Ph | i-Pr | 2,4-F₂Ph | Me |
| 1-779 | 4-CF₃Ph | Et | Et | H |
| 1-780 | 4-CF₃Ph | i-Pr | 2,4-F₂Ph | H |
| 1-781 | 2-OMePh | i-Pr | 2,4-F₂Ph | H |
| 1-782 | 4-OMePh | Et | Et | H |
| 1-783 | 4-OMePh | i-Pr | 2,4-F₂Ph | H |
| 1-784 | 2-OCF₃Ph | i-Pr | 2,4-F₂Ph | H |
| 1-785 | 2-OCF₃Ph | i-Pr | 2,4-F₂Ph | H |
| 1-786 | 4-OCF₃Ph | i-Pr | 2,4-F₂Ph | H |
| 1-787 | 2-SMePh | i-Pr | 2,4-F₂Ph | H |
| 1-788 | 4-SMePh | i-Pr | 2,4-F₂Ph | H |
| 1-789 | 2-SCF₃Ph | i-Pr | 2,4-F₂Ph | H |
| 1-790 | 4-SCF₃Ph | i-Pr | 2,4-F₂Ph | H |
| 1-791 | 2,3-F₂Ph | i-Pr | 2,4-F₂Ph | H |
| 1-792 | 2,4-F₂Ph | i-Pr | 2,4-F₂Ph | H |
| 1-793 | 2,5-F₂Ph | i-Pr | 2,4-F₂Ph | H |
| 1-794 | 2,6-F₂Ph | i-Pr | Ph | H |
| 1-795 | 2,6-F₂Ph | i-Pr | 2-FPh | H |
| 1-796 | 2,6-F₂Ph | i-Pr | 3-FPh | H |
| 1-797 | 2,6-F₂Ph | i-Pr | 4-FPh | H |
| 1-798 | 2,6-F₂Ph | i-Pr | 2-ClPh | H |
| 1-799 | 2,6-F₂Ph | i-Pr | 3-ClPh | H |
| 1-800 | 2,6-F₂Ph | i-Pr | 4-ClPh | H |
| 1-801 | 2,6-F₂Ph | i-Pr | 2-CF₃Ph | H |
| 1-802 | 2,6-F₂Ph | i-Pr | 3-CF₃Ph | H |
| 1-803 | 2,6-F₂Ph | i-Pr | 4-CF₃Ph | H |
| 1-804 | 2,6-F₂Ph | i-Pr | 2,3-F₂Ph | H |
| 1-805 | 2,6-F₂Ph | i-Pr | 2,4-F₂Ph | H |
| 1-806 | 2,6-F₂Ph | i-Pr | 2,5-F₂Ph | H |
| 1-807 | 2,6-F₂Ph | i-Pr | 2,6-F₂Ph | H |
| 1-808 | 2,6-F₂Ph | i-Pr | 2,3,4-F₃Ph | H |
| 1-809 | 2,6-F₂Ph | i-Pr | 2,4,6-F₃Ph | H |
| 1-810 | 2,6-F₂Ph | i-Pr | 2,3,5,6-F₄Ph | H |
| 1-811 | 2,6-F₂Ph | i-Pr | 2,3,4,5,6-F₅Ph | H |
| 1-812 | 2,6-F₂Ph | i-Pr | 2-Cl-4-FPh | H |
| 1-813 | 2,6-F₂Ph | i-Pr | 2-F-4-ClPh | H |
| 1-814 | 2,6-F₂Ph | i-Pr | 2-F-4-BrPh | H |
| 1-815 | 2,6-F₂Ph | i-Pr | 2-Br-4-FPh | H |
| 1-816 | 2,6-F₂Ph | i-Pr | 2-Cl-4-BrPh | H |
| 1-817 | 2,6-F₂Ph | i-Pr | 2-Br-4-ClPh | H |
| 1-818 | 2,6-F₂Ph | i-Pr | 2-Me-4-FPh | H |
| 1-819 | 2,6-F₂Ph | i-Pr | 2-F-4-MePh | H |
| 1-820 | 2,6-F₂Ph | i-Pr | 2-Me-4-ClPh | H |

TABLE 1-continued

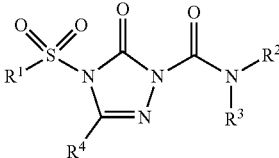

| No. | R¹ | R² | R³ | R⁴ |
|---|---|---|---|---|
| 1-821 | 2,6-F₂Ph | i-Pr | 2-Cl-4-MePh | H |
| 1-822 | 2,6-F₂Ph | i-Pr | 2-F-4-CF₃Ph | H |
| 1-823 | 2,6-F₂Ph | i-Pr | 2-CF₃-4-FPh | H |
| 1-824 | 2,6-F₂Ph | i-Pr | 2,3,5,6-F₄-4-CF₃Ph | H |
| 1-825 | 2,6-F₂Ph | i-Pr | 2-Cl-4-CF₃Ph | H |
| 1-826 | 2,6-F₂Ph | i-Pr | 2-CF₃-4-ClPh | H |
| 1-827 | 2,6-F₂Ph | i-Pr | 2-Cl-4-CNPh | H |
| 1-828 | 2,6-F₂Ph | i-Pr | 2-Cl-4-(SEt)Ph | H |
| 1-829 | 2,6-F₂Ph | i-Pr | 2,4-F₂Ph | Me |
| 1-830 | 3,4-F₂Ph | i-Pr | 2,4-F₂Ph | H |
| 1-831 | 3,5-F₂Ph | i-Pr | 2,4-F₂Ph | H |
| 1-832 | 2,3,4,5,6-F₅Ph | i-Pr | Ph | H |
| 1-833 | 2,3,4,5,6-F₅Ph | i-Pr | 2-FPh | H |
| 1-834 | 2,3,4,5,6-F₅Ph | i-Pr | 3-FPh | H |
| 1-835 | 2,3,4,5,6-F₅Ph | i-Pr | 4-FPh | H |
| 1-836 | 2,3,4,5,6-F₅Ph | i-Pr | 2-ClPh | H |
| 1-837 | 2,3,4,5,6-F₅Ph | i-Pr | 3-ClPh | H |
| 1-838 | 2,3,4,5,6-F₅Ph | i-Pr | 4-ClPh | H |
| 1-839 | 2,3,4,5,6-F₅Ph | i-Pr | 2-CF₃Ph | H |
| 1-840 | 2,3,4,5,6-F₅Ph | i-Pr | 3-CF₃Ph | H |
| 1-841 | 2,3,4,5,6-F₅Ph | i-Pr | 4-CF₃Ph | H |
| 1-842 | 2,3,4,5,6-F₅Ph | i-Pr | 2,3-F₂Ph | H |
| 1-843 | 2,3,4,5,6-F₅Ph | i-Pr | 2,4-F₂Ph | H |
| 1-844 | 2,3,4,5,6-F₅Ph | i-Pr | 2,5-F₂Ph | H |
| 1-845 | 2,3,4,5,6-F₅Ph | i-Pr | 2,6-F₂Ph | H |
| 1-846 | 2,3,4,5,6-F₅Ph | i-Pr | 2,3,4-F₃Ph | H |
| 1-847 | 2,3,4,5,6-F₅Ph | i-Pr | 2,4,6-F₃Ph | H |
| 1-848 | 2,3,4,5,6-F₅Ph | i-Pr | 2,3,5,6-F₄Ph | H |
| 1-849 | 2,3,4,5,6-F₅Ph | i-Pr | 2,3,4,5,6-F₅Ph | H |
| 1-850 | 2,3,4,5,6-F₅Ph | i-Pr | 2-Cl-4-FPh | H |
| 1-851 | 2,3,4,5,6-F₅Ph | i-Pr | 2-F-4-ClPh | H |
| 1-852 | 2,3,4,5,6-F₅Ph | i-Pr | 2-F-4-BrPh | H |
| 1-853 | 2,3,4,5,6-F₅Ph | i-Pr | 2-Br-4-FPh | H |
| 1-854 | 2,3,4,5,6-F₅Ph | i-Pr | 2-Cl-4-BrPh | H |
| 1-855 | 2,3,4,5,6-F₅Ph | i-Pr | 2-Br-4-ClPh | H |
| 1-856 | 2,3,4,5,6-F₅Ph | i-Pr | 2-Me-4-FPh | H |
| 1-857 | 2,3,4,5,6-F₅Ph | i-Pr | 2-F-4-MePh | H |
| 1-858 | 2,3,4,5,6-F₅Ph | i-Pr | 2-Me-4-ClPh | H |
| 1-859 | 2,3,4,5,6-F₅Ph | i-Pr | 2-Cl-4-MePh | H |
| 1-860 | 2,3,4,5,6-F₅Ph | i-Pr | 2-F-4-CF₃Ph | H |
| 1-861 | 2,3,4,5,6-F₅Ph | i-Pr | 2-CF₃-4-FPh | H |
| 1-862 | 2,3,4,5,6-F₅Ph | i-Pr | 2,3,5,6-F₄-4-CF₃Ph | H |
| 1-863 | 2,3,4,5,6-F₅Ph | i-Pr | 2-Cl-4-CF₃Ph | H |
| 1-864 | 2,3,4,5,6-F₅Ph | i-Pr | 2-CF₃-4-ClPh | H |
| 1-865 | 2,3,4,5,6-F₅Ph | i-Pr | 2-Cl-4-CNPh | H |
| 1-866 | 2,3,4,5,6-F₅Ph | i-Pr | 2-Cl-4-(SEt)Ph | H |
| 1-867 | 2,3,4,5,6-F₅Ph | i-Pr | 2,4-F₂Ph | Me |
| 1-868 | 2,3-Cl₂Ph | i-Pr | 2,4-F₂Ph | H |
| 1-869 | 2,4-Cl₂Ph | Et | Et | H |
| 1-870 | 2,4-Cl₂Ph | i-Pr | 2,4-F₂Ph | H |
| 1-871 | 2,5-Cl₂Ph | i-Pr | 2,4-F₂Ph | H |
| 1-872 | 2,6-Cl₂Ph | i-Pr | 2,4-F₂Ph | H |
| 1-873 | 3,4-Cl₂Ph | Et | Et | H |
| 1-874 | 3,4-Cl₂Ph | i-Pr | 2,4-F₂Ph | H |
| 1-875 | 3,5-Cl₂Ph | i-Pr | 2,4-F₂Ph | H |
| 1-876 | 2-Cl-4-FPh | i-Pr | 2,4-F₂Ph | H |
| 1-877 | 2-F-4-ClPh | i-Pr | 2,4-F₂Ph | H |
| 1-878 | 2,3-Me₂Ph | i-Pr | 2,4-F₂Ph | H |
| 1-879 | 2,4-Me₂Ph | i-Pr | 2,4-F₂Ph | H |
| 1-880 | 2,5-Me₂Ph | i-Pr | 2,4-F₂Ph | H |
| 1-881 | 2,6-Me₂Ph | i-Pr | 2,4-F₂Ph | H |
| 1-882 | 3,4-Me₂Ph | i-Pr | 2,4-F₂Ph | H |
| 1-883 | 3,5-Me₂Ph | i-Pr | 2,4-F₂Ph | H |
| 1-884 | 2,4,6-Me₃Ph | Et | Et | H |
| 1-885 | 2,4,6-Me₃Ph | i-Pr | Ph | H |
| 1-886 | 2,4,6-Me₃Ph | i-Pr | 2-FPh | H |
| 1-887 | 2,4,6-Me₃Ph | i-Pr | 3-FPh | H |
| 1-888 | 2,4,6-Me₃Ph | i-Pr | 4-FPh | H |
| 1-889 | 2,4,6-Me₃Ph | i-Pr | 2-ClPh | H |
| 1-890 | 2,4,6-Me₃Ph | i-Pr | 3-ClPh | H |
| 1-891 | 2,4,6-Me₃Ph | i-Pr | 4-ClPh | H |
| 1-892 | 2,4,6-Me₃Ph | i-Pr | 2-CF₃Ph | H |
| 1-893 | 2,4,6-Me₃Ph | i-Pr | 3-CF₃Ph | H |
| 1-894 | 2,4,6-Me₃Ph | i-Pr | 4-CF₃Ph | H |
| 1-895 | 2,4,6-Me₃Ph | i-Pr | 2,3-F₂Ph | H |
| 1-896 | 2,4,6-Me₃Ph | i-Pr | 2,4-F₂Ph | H |
| 1-897 | 2,4,6-Me₃Ph | i-Pr | 2,5-F₂Ph | H |
| 1-898 | 2,4,6-Me₃Ph | i-Pr | 2,6-F₂Ph | H |
| 1-899 | 2,4,6-Me₃Ph | i-Pr | 2,3,4-F₃Ph | H |
| 1-900 | 2,4,6-Me₃Ph | i-Pr | 2,4,6-F₃Ph | H |
| 1-901 | 2,4,6-Me₃Ph | i-Pr | 2,3,5,6-F₄Ph | H |
| 1-902 | 2,4,6-Me₃Ph | i-Pr | 2,3,4,5,6-F₅Ph | H |
| 1-903 | 2,4,6-Me₃Ph | i-Pr | 2-Cl-4-FPh | H |
| 1-904 | 2,4,6-Me₃Ph | i-Pr | 2-F-4-ClPh | H |
| 1-905 | 2,4,6-Me₃Ph | i-Pr | 2-F-4-BrPh | H |
| 1-906 | 2,4,6-Me₃Ph | i-Pr | 2-Br-4-FPh | H |
| 1-907 | 2,4,6-Me₃Ph | i-Pr | 2-Cl-4-BrPh | H |
| 1-908 | 2,4,6-Me₃Ph | i-Pr | 2-Br-4-ClPh | H |
| 1-909 | 2,4,6-Me₃Ph | i-Pr | 2-Me-4-FPh | H |
| 1-910 | 2,4,6-Me₃Ph | i-Pr | 2-F-4-MePh | H |
| 1-911 | 2,4,6-Me₃Ph | i-Pr | 2-Me-4-ClPh | H |
| 1-912 | 2,4,6-Me₃Ph | i-Pr | 2-Cl-4-MePh | H |
| 1-913 | 2,4,6-Me₃Ph | i-Pr | 2-F-4-CF₃Ph | H |
| 1-914 | 2,4,6-Me₃Ph | i-Pr | 2-CF₃-4-FPh | H |
| 1-915 | 2,4,6-Me₃Ph | i-Pr | 2,3,5,6-F₄-4-CF₃Ph | H |
| 1-916 | 2,4,6-Me₃Ph | i-Pr | 2-Cl-4-CF₃Ph | H |
| 1-917 | 2,4,6-Me₃Ph | i-Pr | 2-CF₃-4-ClPh | H |
| 1-918 | 2,4,6-Me₃Ph | i-Pr | 2-Cl-4-CNPh | H |
| 1-919 | 2,4,6-Me₃Ph | i-Pr | 2-Cl-4-(SEt)Ph | H |
| 1-920 | 2,4,6-Me₃Ph | i-Pr | 2,4-F₂Bn | H |
| 1-921 | 2,4,6-Me₃Ph | i-Pr | 2-F-3-Py | H |
| 1-922 | 2,4,6-Me₃Ph | i-Pr | 6-F-3-Py | H |
| 1-923 | 2,4,6-Me₃Ph | i-Pr | 3-Cl-2-Py | H |
| 1-924 | 2,4,6-Me₃Ph | i-Pr | 5-Cl-2-Py | H |
| 1-925 | 2,4,6-Me₃Ph | i-Pr | 3,5-Cl₂-2-Py | H |
| 1-926 | 2,4,6-Me₃Ph | i-Pr | 3-Cl-5-CF₃-2-Py | H |
| 1-927 | 2,4,6-Me₃Ph | i-Pr | 2-Cl-3-Py | H |
| 1-928 | 2,4,6-Me₃Ph | i-Pr | 6-Cl-3-Py | H |
| 1-929 | 2,4,6-Me₃Ph | i-Pr | 2,6-Cl₂-3-Py | H |
| 1-930 | 2,4,6-Me₃Ph | i-Pr | 5-Me-isoxazol-3-yl | H |
| 1-931 | 2,4,6-Me₃Ph | i-Pr | 2,4-F₂Ph | Me |
| 1-932 | 2,4,6-(i-Pr)₃Ph | i-Pr | Ph | H |
| 1-933 | 2,4,6-(i-Pr)₃Ph | i-Pr | 2-FPh | H |
| 1-934 | 2,4,6-(i-Pr)₃Ph | i-Pr | 3-FPh | H |
| 1-935 | 2,4,6-(i-Pr)₃Ph | i-Pr | 4-FPh | H |
| 1-936 | 2,4,6-(i-Pr)₃Ph | i-Pr | 2-ClPh | H |
| 1-937 | 2,4,6-(i-Pr)₃Ph | i-Pr | 3-ClPh | H |
| 1-938 | 2,4,6-(i-Pr)₃Ph | i-Pr | 4-ClPh | H |
| 1-939 | 2,4,6-(i-Pr)₃Ph | i-Pr | 2-CF₃Ph | H |
| 1-940 | 2,4,6-(i-Pr)₃Ph | i-Pr | 3-CF₃Ph | H |
| 1-941 | 2,4,6-(i-Pr)₃Ph | i-Pr | 4-CF₃Ph | H |
| 1-942 | 2,4,6-(i-Pr)₃Ph | i-Pr | 2,3-F₂Ph | H |
| 1-943 | 2,4,6-(i-Pr)₃Ph | i-Pr | 2,4-F₂Ph | H |
| 1-944 | 2,4,6-(i-Pr)₃Ph | i-Pr | 2,5-F₂Ph | H |
| 1-945 | 2,4,6-(i-Pr)₃Ph | i-Pr | 2,6-F₂Ph | H |
| 1-946 | 2,4,6-(i-Pr)₃Ph | i-Pr | 2,3,4-F₃Ph | H |
| 1-947 | 2,4,6-(i-Pr)₃Ph | i-Pr | 2,4,6-F₃Ph | H |
| 1-948 | 2,4,6-(i-Pr)₃Ph | i-Pr | 2,3,5,6-F₄Ph | H |
| 1-949 | 2,4,6-(i-Pr)₃Ph | i-Pr | 2,3,4,5,6-F₅Ph | H |
| 1-950 | 2,4,6-(i-Pr)₃Ph | i-Pr | 2-Cl-4-FPh | H |
| 1-951 | 2,4,6-(i-Pr)₃Ph | i-Pr | 2-F-4-ClPh | H |
| 1-952 | 2,4,6-(i-Pr)₃Ph | i-Pr | 2-F-4-BrPh | H |
| 1-953 | 2,4,6-(i-Pr)₃Ph | i-Pr | 2-Br-4-FPh | H |
| 1-954 | 2,4,6-(i-Pr)₃Ph | i-Pr | 2-Cl-4-BrPh | H |
| 1-955 | 2,4,6-(i-Pr)₃Ph | i-Pr | 2-Br-4-ClPh | H |
| 1-956 | 2,4,6-(i-Pr)₃Ph | i-Pr | 2-Me-4-FPh | H |
| 1-957 | 2,4,6-(i-Pr)₃Ph | i-Pr | 2-F-4-MePh | H |
| 1-958 | 2,4,6-(i-Pr)₃Ph | i-Pr | 2-Me-4-ClPh | H |

TABLE 1-continued

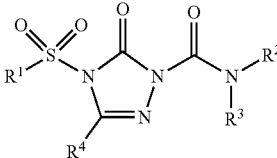 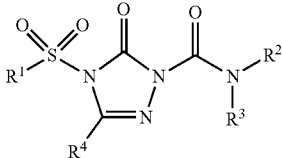

| No. | R¹ | R² | R³ | R⁴ |
|---|---|---|---|---|
| 1-959 | 2,4,6-(i-Pr)₃Ph | i-Pr | 2-Cl-4-MePh | H |
| 1-960 | 2,4,6-(i-Pr)₃Ph | i-Pr | 2-F-4-CF₃Ph | H |
| 1-961 | 2,4,6-(i-Pr)₃Ph | i-Pr | 2-CF₃-4-FPh | H |
| 1-962 | 2,4,6-(i-Pr)₃Ph | i-Pr | 2,3,5,6-F₄-4-CF₃Ph | H |
| 1-963 | 2,4,6-(i-Pr)₃Ph | i-Pr | 2-Cl-4-CF₃Ph | H |
| 1-964 | 2,4,6-(i-Pr)₃Ph | i-Pr | 2-CF₃-4-ClPh | H |
| 1-965 | 2,4,6-(i-Pr)₃Ph | i-Pr | 2-Cl-4-CNPh | H |
| 1-966 | 2,4,6-(i-Pr)₃Ph | i-Pr | 2-Cl-4-(SEt)Ph | H |
| 1-967 | 2,4,6-(i-Pr)₃Ph | i-Pr | 2,4-F₂Ph | Me |
| 1-968 | Bn | Et | Et | H |
| 1-969 | Bn | i-Pr | Ph | H |
| 1-970 | Bn | i-Pr | 2-FPh | H |
| 1-971 | Bn | i-Pr | 3-FPh | H |
| 1-972 | Bn | i-Pr | 4-FPh | H |
| 1-973 | Bn | i-Pr | 2-ClPh | H |
| 1-974 | Bn | i-Pr | 3-ClPh | H |
| 1-975 | Bn | i-Pr | 4-ClPh | H |
| 1-976 | Bn | i-Pr | 2-CF₃Ph | H |
| 1-977 | Bn | i-Pr | 3-CF₃Ph | H |
| 1-978 | Bn | i-Pr | 4-CF₃Ph | H |
| 1-979 | Bn | i-Pr | 2,3-F₂Ph | H |
| 1-980 | Bn | i-Pr | 2,4-F₂Ph | H |
| 1-981 | Bn | i-Pr | 2,5-F₂Ph | H |
| 1-982 | Bn | i-Pr | 2,6-F₂Ph | H |
| 1-983 | Bn | i-Pr | 2,3,4-F₃Ph | H |
| 1-984 | Bn | i-Pr | 2,4,6-F₃Ph | H |
| 1-985 | Bn | i-Pr | 2,3,5,6-F₄Ph | H |
| 1-986 | Bn | i-Pr | 2,3,4,5,6-F₅Ph | H |
| 1-987 | Bn | i-Pr | 2-Cl-4-FPh | H |
| 1-988 | Bn | i-Pr | 2-F-4-ClPh | H |
| 1-989 | Bn | i-Pr | 2-F-4-BrPh | H |
| 1-990 | Bn | i-Pr | 2-Br-4-FPh | H |
| 1-991 | Bn | i-Pr | 2-Cl-4-BrPh | H |
| 1-992 | Bn | i-Pr | 2-Br-4-ClPh | H |
| 1-993 | Bn | i-Pr | 2-Me-4-FPh | H |
| 1-994 | Bn | i-Pr | 2-F-4-MePh | H |
| 1-995 | Bn | i-Pr | 2-Me-4-ClPh | H |
| 1-996 | Bn | i-Pr | 2-Cl-4-MePh | H |
| 1-997 | Bn | i-Pr | 2-F-4-CF₃Ph | H |
| 1-998 | Bn | i-Pr | 2-CF₃-4-FPh | H |
| 1-999 | Bn | i-Pr | 2,3,5,6-F₄-4-CF₃Ph | H |
| 1-1000 | Bn | i-Pr | 2-Cl-4-CF₃Ph | H |
| 1-1001 | Bn | i-Pr | 2-CF₃-4-ClPh | H |
| 1-1002 | Bn | i-Pr | 2-Cl-4-CNPh | H |
| 1-1003 | Bn | i-Pr | 2-Cl-4-(SEt)Ph | H |
| 1-1004 | Bn | i-Pr | 6-Cl-3-Py | H |
| 1-1005 | Bn | i-Pr | 2,4-F₂Ph | Me |
| 1-1006 | 4-FBn | i-Pr | 2,4-F₂Ph | H |
| 1-1007 | 4-MeBn | i-Pr | 2,4-F₂Ph | H |
| 1-1008 | 4-OMeBn | i-Pr | 2,4-F₂Ph | H |
| 1-1009 | 2-Py | i-Pr | 2,4-F₂Ph | H |
| 1-1010 | 3-Py | Et | Et | H |
| 1-1011 | 3-Py | i-Pr | Ph | H |
| 1-1012 | 3-Py | i-Pr | 2-FPh | H |
| 1-1013 | 3-Py | i-Pr | 3-FPh | H |
| 1-1014 | 3-Py | i-Pr | 4-FPh | H |
| 1-1015 | 3-Py | i-Pr | 2-ClPh | H |
| 1-1016 | 3-Py | i-Pr | 3-ClPh | H |
| 1-1017 | 3-Py | i-Pr | 4-ClPh | H |
| 1-1018 | 3-Py | i-Pr | 2-CF₃Ph | H |
| 1-1019 | 3-Py | i-Pr | 3-CF₃Ph | H |
| 1-1020 | 3-Py | i-Pr | 4-CF₃Ph | H |
| 1-1021 | 3-Py | i-Pr | 2,3-F₂Ph | H |
| 1-1022 | 3-Py | i-Pr | 2,4-F₂Ph | H |
| 1-1023 | 3-Py | i-Pr | 2,5-F₂Ph | H |
| 1-1024 | 3-Py | i-Pr | 2,6-F₂Ph | H |
| 1-1025 | 3-Py | i-Pr | 2,3,4-F₃Ph | H |
| 1-1026 | 3-Py | i-Pr | 2,4,6-F₃Ph | H |
| 1-1027 | 3-Py | i-Pr | 2,3,5,6-F₄Ph | H |
| 1-1028 | 3-Py | i-Pr | 2,3,4,5,6-F₅Ph | H |
| 1-1029 | 3-Py | i-Pr | 2-Cl-4-FPh | H |
| 1-1030 | 3-Py | i-Pr | 2-F-4-ClPh | H |
| 1-1031 | 3-Py | i-Pr | 2-F-4-BrPh | H |
| 1-1032 | 3-Py | i-Pr | 2-Br-4-FPh | H |
| 1-1033 | 3-Py | i-Pr | 2-Cl-4-BrPh | H |
| 1-1034 | 3-Py | i-Pr | 2-Br-4-ClPh | H |
| 1-1035 | 3-Py | i-Pr | 2-Me-4-FPh | H |
| 1-1036 | 3-Py | i-Pr | 2-F-4-MePh | H |
| 1-1037 | 3-Py | i-Pr | 2-Me-4-ClPh | H |
| 1-1038 | 3-Py | i-Pr | 2-Cl-4-MePh | H |
| 1-1039 | 3-Py | i-Pr | 2-F-4-CF₃Ph | H |
| 1-1040 | 3-Py | i-Pr | 2-CF₃-4-FPh | H |
| 1-1041 | 3-Py | i-Pr | 2,3,5,6-F₄-4-CF₃Ph | H |
| 1-1042 | 3-Py | i-Pr | 2-Cl-4-CF₃Ph | H |
| 1-1043 | 3-Py | i-Pr | 2-CF₃-4-ClPh | H |
| 1-1044 | 3-Py | i-Pr | 2-Cl-4-CNPh | H |
| 1-1045 | 3-Py | i-Pr | 2-Cl-4-(SEt)Ph | H |
| 1-1046 | 3-Py | i-Pr | 6-Cl-3-Py | H |
| 1-1047 | 3-Py | i-Pr | 2,4-F₂Ph | Me |
| 1-1048 | 4-Py | i-Pr | 2,4-F₂Ph | H |
| 1-1049 | 2-thienyl | i-Pr | Ph | H |
| 1-1050 | 2-thienyl | i-Pr | 2-FPh | H |
| 1-1051 | 2-thienyl | i-Pr | 3-FPh | H |
| 1-1052 | 2-thienyl | i-Pr | 4-FPh | H |
| 1-1053 | 2-thienyl | i-Pr | 2-ClPh | H |
| 1-1054 | 2-thienyl | i-Pr | 3-ClPh | H |
| 1-1055 | 2-thienyl | i-Pr | 4-ClPh | H |
| 1-1056 | 2-thienyl | i-Pr | 2-CF₃Ph | H |
| 1-1057 | 2-thienyl | i-Pr | 3-CF₃Ph | H |
| 1-1058 | 2-thienyl | i-Pr | 4-CF₃Ph | H |
| 1-1059 | 2-thienyl | i-Pr | 2,3-F₂Ph | H |
| 1-1060 | 2-thienyl | i-Pr | 2,4-F₂Ph | H |
| 1-1061 | 2-thienyl | i-Pr | 2,5-F₂Ph | H |
| 1-1062 | 2-thienyl | i-Pr | 2,6-F₂Ph | H |
| 1-1063 | 2-thienyl | i-Pr | 2,3,4-F₃Ph | H |
| 1-1064 | 2-thienyl | i-Pr | 2,4,6-F₃Ph | H |
| 1-1065 | 2-thienyl | i-Pr | 2,3,5,6-F₄Ph | H |
| 1-1066 | 2-thienyl | i-Pr | 2,3,4,5,6-F₅Ph | H |
| 1-1067 | 2-thienyl | i-Pr | 2-Cl-4-FPh | H |
| 1-1068 | 2-thienyl | i-Pr | 2-F-4-ClPh | H |
| 1-1069 | 2-thienyl | i-Pr | 2-F-4-BrPh | H |
| 1-1070 | 2-thienyl | i-Pr | 2-Br-4-FPh | H |
| 1-1071 | 2-thienyl | i-Pr | 2-Cl-4-BrPh | H |
| 1-1072 | 2-thienyl | i-Pr | 2-Br-4-ClPh | H |
| 1-1073 | 2-thienyl | i-Pr | 2-Me-4-FPh | H |
| 1-1074 | 2-thienyl | i-Pr | 2-F-4-MePh | H |
| 1-1075 | 2-thienyl | i-Pr | 2-Me-4-ClPh | H |
| 1-1076 | 2-thienyl | i-Pr | 2-Cl-4-MePh | H |
| 1-1077 | 2-thienyl | i-Pr | 2-F-4-CF₃Ph | H |
| 1-1078 | 2-thienyl | i-Pr | 2-CF₃-4-FPh | H |
| 1-1079 | 2-thienyl | i-Pr | 2,3,5,6-F₄-4-CF₃Ph | H |
| 1-1080 | 2-thienyl | i-Pr | 2-Cl-4-CF₃Ph | H |
| 1-1081 | 2-thienyl | i-Pr | 2-CF₃-4-ClPh | H |
| 1-1082 | 2-thienyl | i-Pr | 2-Cl-4-CNPh | H |
| 1-1083 | 2-thienyl | i-Pr | 2-Cl-4-(SEt)Ph | H |
| 1-1084 | 2-thienyl | i-Pr | 2,4-F₂Bn | H |
| 1-1085 | 2-thienyl | i-Pr | 2,4-F₂Ph | Me |
| 1-1086 | 3-thienyl | i-Pr | 2,4-F₂Ph | H |
| 1-1087 | 5-Br-2-thienyl | i-Pr | 2,4-F₂Ph | H |
| 1-1088 | 3-Me-2-thienyl | i-Pr | 2,4-F₂Ph | H |
| 1-1089 | NHMe | i-Pr | 2,4-F₂Ph | H |
| 1-1090 | NHEt | i-Pr | 2,4-F₂Ph | H |
| 1-1091 | NMe₂ | Et | Et | H |
| 1-1092 | NMe₂ | i-Pr | Ph | H |
| 1-1093 | NMe₂ | i-Pr | 2-FPh | H |
| 1-1094 | NMe₂ | i-Pr | 3-FPh | H |
| 1-1095 | NMe₂ | i-Pr | 4-FPh | H |
| 1-1096 | NMe₂ | i-Pr | 2-ClPh | H |

TABLE 1-continued

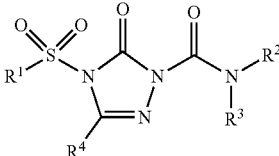

| No. | R¹ | R² | R³ | R⁴ |
|---|---|---|---|---|
| 1-1097 | NMe₂ | i-Pr | 3-ClPh | H |
| 1-1098 | NMe₂ | i-Pr | 4-ClPh | H |
| 1-1099 | NMe₂ | i-Pr | 2-CF₃Ph | H |
| 1-1100 | NMe₂ | i-Pr | 3-CF₃Ph | H |
| 1-1101 | NMe₂ | i-Pr | 4-CF₃Ph | H |
| 1-1102 | NMe₂ | i-Pr | 2,3-F₂Ph | H |
| 1-1103 | NMe₂ | i-Pr | 2,4-F₂Ph | H |
| 1-1104 | NMe₂ | i-Pr | 2,5-F₂Ph | H |
| 1-1105 | NMe₂ | i-Pr | 2,6-F₂Ph | H |
| 1-1106 | NMe₂ | i-Pr | 2,3,4-F₃Ph | H |
| 1-1107 | NMe₂ | i-Pr | 2,4,6-F₃Ph | H |
| 1-1108 | NMe₂ | i-Pr | 2,3,5,6-F₄Ph | H |
| 1-1109 | NMe₂ | i-Pr | 2,3,4,5,6-F₅Ph | H |
| 1-1110 | NMe₂ | i-Pr | 2-Cl-4-FPh | H |
| 1-1111 | NMe₂ | i-Pr | 2-F-4-ClPh | H |
| 1-1112 | NMe₂ | i-Pr | 2-F-4-BrPh | H |
| 1-1113 | NMe₂ | i-Pr | 2-Br-4-FPh | H |
| 1-1114 | NMe₂ | i-Pr | 2-Cl-4-BrPh | H |
| 1-1115 | NMe₂ | i-Pr | 2-Br-4-ClPh | H |
| 1-1116 | NMe₂ | i-Pr | 2-Me-4-FPh | H |
| 1-1117 | NMe₂ | i-Pr | 2-F-4-MePh | H |
| 1-1118 | NMe₂ | i-Pr | 2-Me-4-ClPh | H |
| 1-1119 | NMe₂ | i-Pr | 2-Cl-4-MePh | H |
| 1-1120 | NMe₂ | i-Pr | 2-F-4-CF₃Ph | H |
| 1-1121 | NMe₂ | i-Pr | 2-CF₃-4-FPh | H |
| 1-1122 | NMe₂ | i-Pr | 2,3,5,6-F₄-4-CF₃Ph | H |
| 1-1123 | NMe₂ | i-Pr | 2-Cl-4-CF₃Ph | H |
| 1-1124 | NMe₂ | i-Pr | 2-CF₃-4-ClPh | H |
| 1-1125 | NMe₂ | i-Pr | 2-Cl-4-CNPh | H |
| 1-1126 | NMe₂ | i-Pr | 2-Cl-4-(SEt)Ph | H |
| 1-1127 | NMe₂ | i-Pr | 2,4-F₂Bn | H |
| 1-1128 | NMe₂ | i-Pr | 2-F-3-Py | H |
| 1-1129 | NMe₂ | i-Pr | 6-F-3-Py | H |
| 1-1130 | NMe₂ | i-Pr | 3-Cl-2-Py | H |
| 1-1131 | NMe₂ | i-Pr | 5-Cl-2-Py | H |
| 1-1132 | NMe₂ | i-Pr | 3,5-Cl₂-2-Py | H |
| 1-1133 | NMe₂ | i-Pr | 3-Cl-5-CF₃-2-Py | H |
| 1-1134 | NMe₂ | i-Pr | 2-Cl-3-Py | H |
| 1-1135 | NMe₂ | i-Pr | 6-Cl-3-Py | H |
| 1-1136 | NMe₂ | i-Pr | 2,6-Cl₂-3-Py | H |
| 1-1137 | NMe₂ | i-Pr | 5-Me-isoxazol-3-yl | H |
| 1-1138 | NMe₂ | i-Pr | 2,4-F₂Ph | Me |
| 1-1139 | N(Me)Et | i-Pr | 2,4-F₂Ph | H |
| 1-1140 | NEt₂ | i-Pr | 2,4-F₂Ph | H |
| 1-1141 | N(Me)i-Pr | i-Pr | 2,4-F₂Ph | H |
| 1-1142 | N(Me)i-Bu | i-Pr | 2,4-F₂Ph | H |
| 1-1143 | 1-piperidinyl | i-Pr | 2,4-F₂Ph | H |
| 1-1144 | 3-tetrahydropyranyl | i-Pr | 2,4-F₂Ph | H |
| 1-1145 | 4-tetrahydropyranyl | i-Pr | Ph | H |
| 1-1146 | 4-tetrahydropyranyl | i-Pr | 2-FPh | H |
| 1-1147 | 4-tetrahydropyranyl | i-Pr | 3-FPh | H |
| 1-1148 | 4-tetrahydropyranyl | i-Pr | 4-FPh | H |
| 1-1149 | 4-tetrahydropyranyl | i-Pr | 2,3-F₂Ph | H |
| 1-1150 | 4-tetrahydropyranyl | i-Pr | 2,4-F₂Ph | H |
| 1-1151 | 4-tetrahydropyranyl | i-Pr | 2,5-F₂Ph | H |
| 1-1152 | 4-tetrahydropyranyl | i-Pr | 2,6-F₂Ph | H |
| 1-1153 | 4-tetrahydropyranyl | i-Pr | 2-Cl-4-FPh | H |
| 1-1154 | 4-tetrahydropyranyl | i-Pr | 2-F-4-ClPh | H |
| 1-1155 | 4-tetrahydropyranyl | i-Pr | 2-F-4-MePh | H |
| 1-1156 | 4-tetrahydropyranyl | i-Pr | 2-Me-4-ClPh | H |
| 1-1157 | 4-tetrahydropyranyl | i-Pr | 2-F-4-CF₃Ph | H |
| 1-1158 | 4-tetrahydropyranyl | i-Pr | 2-CF₃-4-FPh | H |
| 1-1159 | 4-tetrahydropyranyl | i-Pr | 2,4-F₂Ph | Me |
| 1-1160 | 2-tetrahydrofuryl | i-Pr | 2,4-F₂Ph | H |
| 1-1161 | 3-tetrahydrofuryl | i-Pr | 2,4-F₂Ph | H |
| 1-1162 | 3-tetrahydropyranyl-methyl | i-Pr | 2,4-F₂Ph | H |
| 1-1163 | 4-tetrahydropyranyl-methyl | i-Pr | 2,4-F₂Ph | H |

TABLE 1-continued

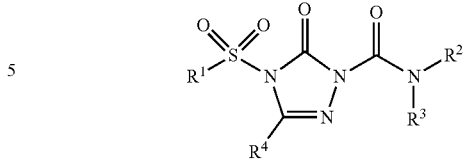

| No. | R¹ | R² | R³ | R⁴ |
|---|---|---|---|---|
| 1-1164 | 2-tetrahydrofurfuryl | i-Pr | 2,4-F₂Ph | H |
| 1-1165 | 3-tetrahydrofurfuryl | i-Pr | 2,4-F₂Ph | H |

Although the production method of the 1-(N,N-disubstituted carbamoyl)4-(substituted sulfonyl)triazolin-5-one derivative (1) of the present invention is described in detail below, the present invention is not limited to these methods. In this connection, as for the reactor, other than a magnetic stirrer or a mechanical stirrer, a reaction using a microwave synthesizer is also possible.

[Production Method 1]

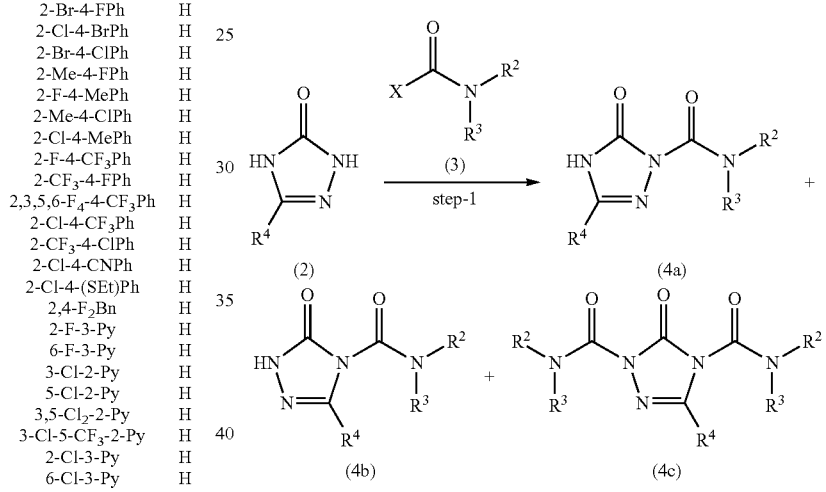

($R^2$, $R^3$ and $R^4$ have the same meanings as above, and X represents a halogen atom).

Step-1 is a step of reacting a triazolin-5-one derivative represented by formula (2) with a halogenated N,N-disubstituted carbamoyl derivative represented by formula (3), in some cases in the presence of a base, to produce a 1-(N,N-disubstituted carbamoyl)triazolin-5-one derivative (4a). The triazolin-5-one derivative represented by formula (2) and the halogenated N,N-disubstituted carbamoyl derivative represented by formula (3) are known in some cases and are available from Tokyo Chemical Industry Co., Ltd., etc. Alternatively, these can also be easily produced from available reagents according to a known method described in *Lectures on Experimental Chemistry, Organic Syntheses,* etc.

This reaction may be performed in the presence of a base. As the base, for example, an organic base such as triethylamine, diisopropylethylamine, tributylamine, N-methylmorpholine, N,N-dimethylaniline, N,N-diethylaniline, 4-tert-butyl-N,N-dimethylaniline, pyridine, picoline and lutidine, and an alkali metal salt such as sodium carbonate, potassium carbonate, cesium carbonate, sodium hydrogencarbonate, potassium hydrogencarbonate, sodium acetate, potassium acetate, sodium methoxide, sodium ethoxide, potassiumtert-butoxide, sodium hydride, potassium hydride, sodium amide, butyllithium, tert-butyllithium, lithium diisopropylamide, trimethylsilyl lithium and lithium hexamethyldisilazide can be used. Among these bases, a metal base such as potassium carbonate and cesium carbonate is preferred in view of good yield. The reaction is performed using the base in an amount of 0.1 to 5 equivalents relative to the substrate, and a target compound can thereby be obtained in good yield. The reaction substrate (3) is used usually in an amount of 1 to 5 equivalents relative to the substrate (2).

This reaction is preferably conducted in the presence of a solvent. As the solvent used, a solvent which does not adversely affect the reaction can be used, and an aromatic hydrocarbon-based solvent such as benzene, toluene, xylene and chlorobenzene, an aliphatic hydrocarbon-based solvent such as pentane, hexane and octane, an ether-based solvent such as diethyl ether, diisopropyl ether, cyclopentylmethyl ether, tetrahydrofuran, dimethoxyethane and 1,4-dioxane, a ketone-based solvent such as acetone, methyl ethyl ketone and cyclohexanone, a halogen-based solvent such as chloroform and dichloromethane, a nitrile-based solvent such as acetonitrile and propionitrile, an ester-based solvent such as ethyl acetate, propyl acetate, butyl acetate and methyl propionate, an amide-based solvent such as N,N-dimethylformamide, N,N-dimethylacetamide and N-methylpyrrolidone, an alcohol-based solvent such as methanol, ethanol, 1-propanol, 2-propanol and tert-butanol, dimethylsulfoxide, water, or a mixed solvent thereof may be used. Furthermore, in order to promote the progress of the reaction, a phase transfer catalyst such as quaternary ammonium salt may also be added.

The reaction can be performed at a temperature appropriately selected from the range of −78° C. to 200° C., although this varies depending on reaction conditions. After the completion of the reaction, although a target compound can be obtained by a normal post-treatment operation, in this step, a compound (4b) and a compound (4c) are sometimes produced as by-products. If desired, purification by column chromatography or recrystallization, etc. may also be performed to isolate a 1-(N,N-disubstituted carbamoyl)triazolin-5-one derivative (4a).

[Production Method 2]

Step-2 is a step of reacting a 1-(N,N-disubstituted carbamoyl)triazolin-5-one derivative represented by formula (4a) with a sulfonyl compound represented by formula (5), in some cases in the presence of a base, to produce a 1-(N,N-disubstituted carbamoyl)4-(substituted sulfonyl)triazolin-5-one derivative.

This reaction may be performed in the presence of a base. As the base, for example, an organic base such as triethylamine, diisopropylethylamine, tributylamine, N-methylmorpholine, N,N-dimethylaniline, N,N-diethylaniline, 4-tert-butyl-N,N-dimethylaniline, pyridine, picoline and lutidine, and an alkali metal salt such as sodium carbonate, potassium carbonate, cesium carbonate, sodium hydrogencarbonate, potassium hydrogencarbonate, sodium acetate, potassium acetate, sodium methoxide, sodium ethoxide, potassium-tert-butoxide, sodium hydride, potassium hydride, sodium amide, butyllithium, tert-butyllithium, lithium diisopropylamide, trimethylsilyl lithium and lithium hexamethyldisilazide can be used. The reaction is performed using the base in an amount of 0.1 to 5 equivalents relative to the substrate, and a target compound can thereby be obtained in good yield. The reaction substrate (5) is used usually in an amount of 1 to 5 equivalents relative to the substrate (4a).

This reaction is preferably conducted in a solvent. As the solvent, a solvent which does not adversely affect the reaction can be used, and an aromatic hydrocarbon-based solvent such as benzene, toluene, xylene and chlorobenzene, an aliphatic hydrocarbon-based solvent such as pentane, hexane and octane, an ether-based solvent such as diethyl ether, diisopropyl ether, cyclopentylmethyl ether, tetrahydrofuran, dimethoxyethane and 1,4-dioxane, a ketone-based solvent such as acetone, methyl ethyl ketone and cyclohexanone, a halogen-based solvent such as chloroform and dichloromethane, a nitrile-based solvent such as acetonitrile and propionitrile, an ester-based solvent such as ethyl acetate, propyl acetate, butyl acetate and methyl propionate, an amide-based solvent such as N,N-dimethylformamide, N,N-dimethylacetamide and N-methylpyrrolidone, an alcohol-based solvent such as methanol, ethanol, 1-propanol, 2-propanol and tert-butanol, dimethylsulfoxide, water, or a mixed solvent thereof may be used.

The reaction can be performed at a temperature appropriately selected from the range of −78° C. to 200° C., although this varies depending on a base used or reaction conditions. After the completion of the reaction, a target compound can be obtained by a normal post-treatment operation, and, if desired, purification by column chromatography or recrystallization, etc. may also be performed.

[Production Method 3]

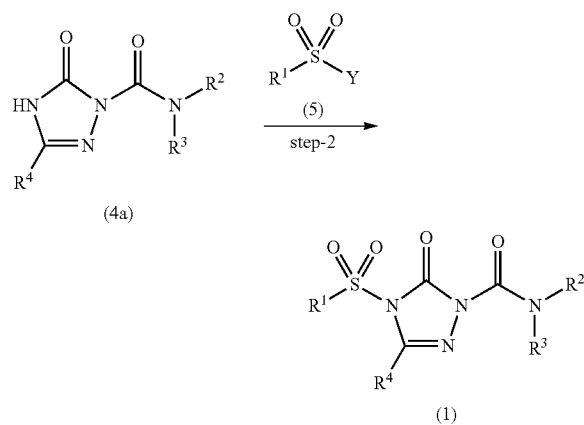

($R^1$, $R^2$, $R^3$ and $R^4$ have the same meanings as above, and Y represents a leaving group such as a halogen atom, a methanesulfonyloxy group, a trifluoromethanesulfonyloxy group and a toluenesulfonyloxy group).

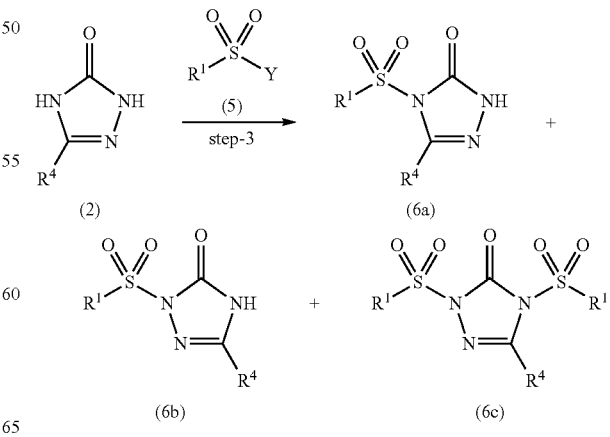

($R^1$, $R^4$ and Y have the same meanings as above).

Step-3 is a step of reacting a triazolin-5-one derivative represented by formula (2) with a sulfonyl compound represented by formula (5), in some cases in the presence of a base, to produce a 4-(substituted sulfonyl)triazolin-5-one derivative (6a).

This reaction may be performed in the presence of a base. As the base, for example, an organic base such as triethylamine, diisopropylethylamine, tributylamine, N-methylmorpholine, N,N-dimethylaniline, N,N-diethylaniline, 4-tert-butyl-N,N-dimethylaniline, pyridine, picoline and lutidine, and an alkali metal salt such as sodium carbonate, potassium carbonate, cesium carbonate, sodium hydrogencarbonate, potassium hydrogencarbonate, sodium acetate, potassium acetate, sodium methoxide, sodium ethoxide, potassium-tert-butoxide, sodium hydride, potassium hydride, sodium amide, butyllithium, tert-butyllithium, lithium diisopropylamide, trimethylsilyl lithium and lithium hexamethyldisilazide can be used. The reaction is performed using the base in an amount of 0.1 to 5 equivalents relative to the substrate, and a target compound can thereby be obtained in good yield. The reaction substrate (5) is used usually in an amount of 1 to 5 equivalents relative to the substrate (2).

This reaction is preferably conducted in a solvent. As the solvent used, a solvent which does not adversely affect the reaction can be used, and an aromatic hydrocarbon-based solvent such as benzene, toluene, xylene and chlorobenzene, an aliphatic hydrocarbon-based solvent such as pentane, hexane and octane, an ether-based solvent such as diethyl ether, diisopropyl ether, cyclopentylmethyl ether, tetrahydrofuran, dimethoxyethane and 1,4-dioxane, a ketone-based solvent such as acetone, methyl ethyl ketone and cyclohexanone, a halogen-based solvent such as chloroform and dichloromethane, a nitrile-based solvent such as acetonitrile and propionitrile, an ester-based solvent such as ethyl acetate, propyl acetate, butyl acetate and methyl propionate, an amide-based solvent such as N,N-dimethylformamide, N,N-dimethylacetamide and N-methylpyrrolidone, an alcohol-based solvent such as methanol, ethanol, 1-propanol, 2-propanol and tert-butanol, dimethylsulfoxide, water, or a mixed solvent thereof may be used.

The reaction can be performed at a temperature appropriately selected from the range of −78° C. to 200° C., although this varies depending on reaction conditions. After the completion of the reaction, although a target compound can be obtained by a normal post-treatment operation, in this step, a compound (6b) and a compound (6c) are sometimes produced as by-products. If desired, purification by column chromatography or recrystallization, etc. may also be performed to isolate a 4-(substituted sulfonyl)triazolin-5-one derivative (6a).

[Production Method 4]

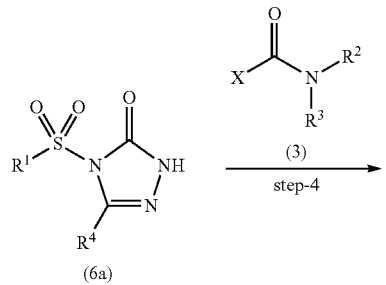

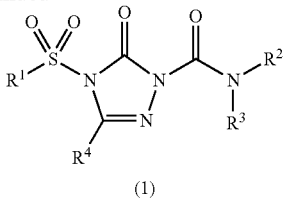

($R^1$, $R^2$, $R^3$, $R^4$ and X have the same meanings as above).

Step-4 is a step of reacting a 4-(substituted sulfonyl)triazolin-5-one derivative represented by formula (6a) with a halogenated disubstituted carbamoyl derivative represented by formula (3), in some cases in the presence of abase, to produce a 1-(N,N-disubstituted carbamoyl)4-(substituted sulfonyl)triazolin-5-one derivative (1).

This reaction may be performed in the presence of a base. As the base, for example, an organic base such as triethylamine, diisopropylethylamine, tributylamine, N-methylmorpholine, N,N-dimethylaniline, N,N-diethylaniline, 4-tert-butyl-N,N-dimethylaniline, pyridine, picoline and lutidine, and an alkali metal salt such as sodium carbonate, potassium carbonate, cesium carbonate, sodium hydrogencarbonate, potassium hydrogencarbonate, sodium acetate, potassium acetate, sodium methoxide, sodium ethoxide, potassium-tert-butoxide, sodium hydride, potassium hydride, sodium amide, butyllithium, tert-butyllithium, lithium diisopropylamide, trimethylsilyl lithium and lithium hexamethyldisilazide can be used. The reaction is performed using the base in an amount of 0.1 to 5 equivalents relative to the substrate, and a target compound can thereby be obtained in good yield. The reaction substrate (3) is used usually in an amount of 1 to 5 equivalents relative to the substrate (6a).

This reaction is preferably conducted in a solvent. As the solvent, a solvent which does not adversely affect the reaction can be used, and an aromatic hydrocarbon-based solvent such as benzene, toluene, xylene and chlorobenzene, an aliphatic hydrocarbon-based solvent such as pentane, hexane and octane, an ether-based solvent such as diethyl ether, diisopropyl ether, cyclopentylmethyl ether, tetrahydrofuran, dimethoxyethane and 1,4-dioxane, a ketone-based solvent such as acetone, methyl ethyl ketone and cyclohexanone, a halogen-based solvent such as chloroform and dichloromethane, a nitrile-based solvent such as acetonitrile and propionitrile, an ester-based solvent such as ethyl acetate, propyl acetate, butyl acetate and methyl propionate, an amide-based solvent such as N,N-dimethylformamide, N,N-dimethylacetamide and N-methylpyrrolidone, an alcohol-based solvent such as methanol, ethanol, 1-propanol, 2-propanol and tert-butanol, dimethylsulfoxide, water, or a mixed solvent thereof may be used.

The reaction can be performed at a temperature appropriately selected from the range of −78° C. to 200° C., although this varies depending on a base used or reaction conditions. After the completion of the reaction, a target compound can be obtained by a normal post-treatment operation, and, if desired, purification by column chromatography or recrystallization, etc. may also be performed.

[Production Method 5]

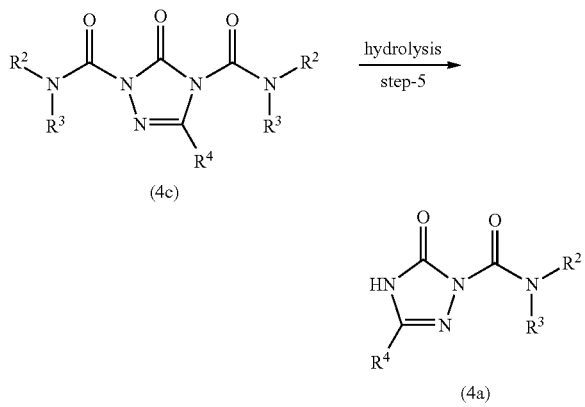

($R^2$, $R^3$ and $R^4$ have the same meanings as above).

Step-5 is a step of hydrolyzing a 1,4-di(N,N-disubstituted carbamoyl)triazolin-5-one derivative represented by formula (4c) by using an acid or a base to produce a 1-(N,N-disubstituted carbamoyl)triazolin-5-one derivative (4a).

As the acid used in this reaction, hydrochloric acid, sulfuric acid, acetic acid, etc. can be used. The reaction is performed using the acid in an amount of 0.1 to 10 equivalents relative to the substrate, and a target compound can thereby be obtained in good yield.

As the base used in this reaction, for example, an alkali metal salt such as sodium carbonate, potassium carbonate, sodium hydrogencarbonate, potassium hydrogencarbonate, sodium acetate, potassium acetate, sodium methoxide, sodium ethoxide, potassium-tert-butoxide, sodium hydride, potassium hydride, sodium amide, butyllithium, tert-butyllithium, lithium diisopropylamide, trimethylsilyl lithium, lithium hexamethyldisilazide, sodium hydroxide and potassium hydroxide can be used. The reaction is performed using the base in an amount of 0.1 to 10 equivalents relative to the substrate, and a target compound can thereby be obtained in good yield.

This reaction is preferably conducted in a solvent. As the solvent, a solvent which does not adversely affect the reaction can be used, and an aromatic hydrocarbon-based solvent such as benzene, toluene, xylene and chlorobenzene, an aliphatic hydrocarbon-based solvent such as pentane, hexane and octane, an ether-based solvent such as diethyl ether, diisopropyl ether, cyclopentylmethyl ether, tetrahydrofuran, dimethoxyethane and 1,4-dioxane, a ketone-based solvent such as acetone, methyl ethyl ketone and cyclohexanone, a halogen-based solvent such as chloroform and dichloromethane, a nitrile-based solvent such as acetonitrile and propionitrile, an ester-based solvent such as ethyl acetate, propyl acetate, butyl acetate and methyl propionate, an amide-based solvent such as N,N-dimethylformamide, N,N-dimethylacetamide and N-methylpyrrolidone, an alcohol-based solvent such as methanol, ethanol, 1-propanol, 2-propanol and tert-butanol, dimethylsulfoxide, water, or a mixed solvent thereof may be used.

The reaction can be performed at a temperature appropriately selected from the range of −78° C. to 200° C., although this varies depending on reaction conditions. After the completion of the reaction, a target compound can be obtained by a normal post-treatment operation, and, if desired, purification by column chromatography or recrystallization, etc. may also be performed.

[Production Method 6]

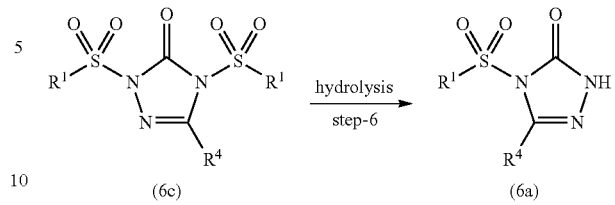

($R^1$ and $R^4$ have the same meanings as above).

Step-6 is a step of hydrolyzing a 1,4-di(substituted sulfonyl)triazolin-5-one derivative represented by formula (6c) by using an acid or a base to produce a 4-(substituted sulfonyl)triazolin-5-one derivative (6a).

As the acid used in this reaction, hydrochloric acid, sulfuric acid, acetic acid, etc. can be used. The reaction is performed using the acid in an amount of 0.1 to 10 equivalents relative to the substrate, and a target compound can thereby be obtained in good yield.

As the base used in this reaction, for example, an alkali metal salt such as sodium carbonate, potassium carbonate, sodium hydrogencarbonate, potassium hydrogencarbonate, sodium acetate, potassium acetate, sodium methoxide, sodium ethoxide, potassium-tert-butoxide, sodium hydride, potassium hydride, sodium amide, butyllithium, tert-butyllithium, lithium diisopropylamide, trimethylsilyl lithium, lithium hexamethyldisilazide, sodium hydroxide and potassium hydroxide can be used. The reaction is performed using the base in an amount of 0.1 to 10 equivalents relative to the substrate, and a target compound can thereby be obtained in good yield.

This reaction is preferably conducted in a solvent. As the solvent, a solvent which does not adversely affect the reaction can be used, and an aromatic hydrocarbon-based solvent such as benzene, toluene, xylene and chlorobenzene, an aliphatic hydrocarbon-based solvent such as pentane, hexane and octane, an ether-based solvent such as diethyl ether, diisopropyl ether, cyclopentylmethyl ether, tetrahydrofuran, dimethoxyethane and 1,4-dioxane, a ketone-based solvent such as acetone, methyl ethyl ketone and cyclohexanone, a halogen-based solvent such as chloroform and dichloromethane, a nitrile-based solvent such as acetonitrile and propionitrile, an ester-based solvent such as ethyl acetate, propyl acetate, butyl acetate and methyl propionate, an amide-based solvent such as N,N-dimethylformamide, N,N-dimethylacetamide and N-methylpyrrolidone, an alcohol-based solvent such as methanol, ethanol, 1-propanol, 2-propanol and tert-butanol, dimethylsulfoxide, water, or a mixed solvent thereof may be used.

The reaction can be performed at a temperature appropriately selected from the range of −78° C. to 200° C., although this varies depending on the reaction conditions. After the completion of the reaction, a target compound can be obtained by a normal post-treatment operation, and, if desired, purification by column chromatography or recrystallization, etc. may also be performed.

The compound represented by formula (1) of the present invention can be analyzed, confirmed and identified by a melting point, infrared absorption spectrum, $^1$H-NMR, $^{13}$C-NMR, mass spectrometry, X-ray structural analysis, etc. as needed.

In this connection, the compound represented by formula (1) of the present invention is not limited to the above-described production methods and can be produced by any organic synthesis technique.

(4-(N,N-Disubstituted carbamoyl)1-(Substituted sulfonyl)triazolin-5-One Derivative Represented by Formula (11))

In the 4-(N,N-disubstituted carbamoyl)1-(substituted sulfonyl)triazolin-5-one derivative (11) of the present invention, examples of the halogen atom or the halogen atom as a substituent include fluorine, chlorine, bromine and iodine elements. The number of halogen atoms as a substituent may be 1 or 2 or more and in the case of 2 or more, respective halogen atoms may be the same or different. In addition, the substitution position of the halogen atom may be any position.

Examples of the C1-C6 alkyl group represented by $R^{11}$, $R^{12}$, $R^{13}$ or $R^1$ or the C1-C6 alkyl group as a substituent include a methyl group, an ethyl group, a n-propyl group, an isopropyl group, a 1,1-dimethylpropyl group, a 1,2-dimethylpropyl group, a 1-ethylpropyl group, a n-butyl group, an isobutyl group, a sec-butyl group, a tert-butyl group, a 2-methylbutyl group, a 3-methylbutyl group, a 1-ethylbutyl group, a 2-ethylbutyl group, a 1,1-dimethylbutyl group, 1,2-dimethylbutyl group, a 2,3-dimethylbutyl group, a 3,3-dimethylbutyl group, a n-pentyl group, a neopentyl group, a 2-pentyl group, a 3-pentyl group, a tert-pentyl group, a 1-methylpentyl group, a 2-methylpentyl group, a 3-methylpentyl group, a 4-methylpentyl group, a n-hexyl group, an isohexyl group, a 2-hexyl group, a 3-hexyl group, etc. The number of C1-C6 alkyl groups as a substituent may be 1 or 2 or more and in the case of 2 or more, respective C1-C6 alkyl groups may be the same or different. In addition, the substitution position of the C1-C6 alkyl group may be any position.

Examples of the C1-C6 haloalkyl group represented by R, $R^{12}$, $R^{13}$ or $R^1$ or the C1-C6 haloalkyl group as a substituent include a monofluoromethyl group, a difluoromethyl group, a trifluoromethyl group, a 2,2,2-trifluoroethyl group, a monochloromethyl group, a 2-chloroethyl group, a trichloromethyl group, a 1-fluoroethyl group, a 2-fluoroethyl group, a 3,3,3-trifluoropropyl group, a 4,4,4-trifluorobutyl group, a 5,5,5-trifluoropentyl group, a 6-fluorohexyl group, a 6,6,6-trifluorohexyl group, etc. The number of C1-C6 haloalkyl groups as a substituent may be 1 or 2 or more and in the case of 2 or more, respective C1-C6 haloalkyl groups may be the same or different. In addition, the substitution position of the C1-C6 haloalkyl group may be any position.

Examples of the C2-C6 alkenyl group represented by $R^{11}$, $R^{12}$ or $R^{13}$ include a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, a 5-hexenyl group, etc.

Examples of the C2-C6 haloalkenyl group represented by $R^{11}$ include a 3,3-dichloro-2-propenyl group, a 3,3,3-trifluoro-1-propenyl group, a 4,4-difluoro-3-butenyl group, and a 3,4,4-trifluoro-3-butenyl group.

Examples of the C2-C6 alkynyl group represented by $R^{11}$, $R^{12}$ or $R^{13}$ include an ethynyl group, a 1-propynyl group, a propargyl group, a 1-butynyl group, a 2-butynyl group, a 3-butynyl group, a 1-methyl-2-propynyl group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group, a 1,1-dimethyl-2-butynyl group, etc.

Examples of the C2-C6 haloalkynyl group represented by $R^{11}$ include a fluoroethynyl group, a 3-fluoro-2-propynyl group, a 3-chloro-2-propynyl group, a 3-chloro-1-propynyl group, a 5-chloro-4-pentynyl group, a 3,3,3-trifluoro-1-propynyl group, a 3,3-difluoro-1-propynyl group, a 4,4,4-trifluoro-2-butynyl group, etc.

Examples of the C3-C8 cycloalkyl group moiety of the C3-C8 cycloalkyl group represented by $R^{11}$, which may be substituted, the C3-C8 cycloalkyl group represented by $R^{12}$ or $R^{13}$, or the C3-C8 cycloalkyl group as a substituent include a cyclopropyl group, a cyclobutyl group, a cyclopentyl group, a cyclohexyl group, a cycloheptyl group, a cyclooctyl group, etc. The number of C3-C8 cycloalkyl groups as a substituent may be 1 or 2 or more and in the case of 2 or more, respective C3-C8 cycloalkyl groups may be the same or different. In addition, the substitution position of the C3-C8 cycloalkyl group may be any position.

Examples of the C3-C6 cycloalkyl C1-C6 alkyl group represented by $R^{11}$, $R^{12}$ or $R^{13}$ or the C3-C6 cycloalkyl C1-C6 alkyl group as a substituent include a cyclopropylmethyl group, a cyclopropylethyl group, a 1-methylcyclopropylmethyl group, a 2-methylcyclopropylmethyl group, a 2,2-dimethylcyclopropylmethyl group, a cyclobutylmethyl group, a cyclopentylmethyl group, etc.

Examples of the C1-C6 alkoxy C1-C6 alkyl group represented by $R^{11}$, $R^{12}$ or $R^{13}$ include a methoxymethyl group, an ethoxymethyl group, a n-propoxymethyl group, an isopropoxymethyl group, a n-butoxymethyl group, a sec-butoxymethyl group, a tert-butoxymethyl group, a 1-pentyloxymethyl group, a 1-hexyloxymethyl group, a 2-methoxyethyl group, a 2-ethoxyethyl group, a 2-isopropoxyethyl group, a 2-isobutoxyethyl group, a 3-methoxypropyl group, a 2-methoxypropyl group, a 2-methoxy-1-methylethyl group, etc.

Examples of the C1-C6 haloalkoxy C1-C6 alkyl group represented by $R^{11}$, $R^{12}$ or $R^{13}$ include a trifluoromethoxymethyl group, a 2,2,2-trifluoroethoxymethyl group, a 2-(2,2,2-trifluoroethoxy)ethyl group, etc.

Examples of the C7-C11 aralkyl group moiety of the C7-C11 aralkyl group represented by $R^{11}$, $R^{12}$ or $R^{13}$, which may be substituted, or the C7-C11 aralkyl group as a substituent include a benzyl group, a 1-phenethyl group, a 2-phenethyl group, a 1-phenylpropyl group, a 2-phenylpropyl group, a 3-phenylpropyl group, a 1-phenyl-2-methylpropyl group, a 1-phenylbutyl group, a 1-phenylpentyl group, etc.

Examples of the heterocyclic moiety of the heterocyclic ring represented by R, $R^{12}$ or $R^{13}$, which may be substituted, include a pyridine ring (2-pyridyl group, 3-pyridyl group, 4-pyridyl group), a thiophene ring (2-thienyl group, 3-thienyl group), an oxazole ring (oxazol-2-yl group, oxazol-4-yl group, oxazol-5-yl group), an isoxazole ring (isoxazol-3-yl group, isoxazol-4-yl group, isoxazol-5-yl group), a thiazole ring (thiazol-2-yl group, thiazol-4-yl group, thiazol-5-yl group), an isothiazole ring (isothiazol-3-yl group, isothiazol-4-yl group, isothiazol-5-yl group), a pyrazole ring (pyrazol-3-yl group, pyrazol-4-yl group, pyrazol-5-yl group), etc.

Examples of the C1-C6 alkylamino group represented by $R^{11}$ include a methylamino group, an ethylamino group, a n-propylamino group, an isopropylamino group, a n-butylamino group, an isobutylamino group, a sec-butylamino group, a tert-butylamino group, etc.

Examples of the di C1-C6 alkylamino group represented by $R^{11}$, which may be the same or different, include a dimethylamino group, a methylethylamino group, a diethylamino group, a di n-propylamino group, a methyl n-propylamino group, a methylisopropylamino group, a methylisobutylamino group, an ethyl n-propylamino group, a diisopropylamino group, a di n-butylamino group, a diisobutylamino group, a di sec-butylamino group, a di tert-butylamino group, etc.

Examples of the tetrahydropyranyl group represented by $R^{11}$ include a 3-tetrahydropyranyl group and a 4-tetrahydropyranyl group.

Examples of the tetrahydrofuryl group represented by $R^{11}$ include a 2-tetrahydrofuryl group and a 3-tetrahydrofuryl group.

Examples of the tetrahydropyranylmethyl group represented by $R^{11}$ include a 3-tetrahydropyranylmethyl group and a 4-tetrahydropyranylmethyl group.

Examples of the tetrahydrofurfuryl group represented by $R^{11}$ include a 2-tetrahydrofurfuryl group and a 3-tetrahydrofurfuryl group.

Examples of the C1-C6 alkoxy group represented by $R^{14}$ or the C1-C6 alkoxy group as a substituent include a methoxy group, an ethoxy group, a n-propoxy group, an isopropoxy group, a n-butoxy group, an isobutoxy group, a sec-butoxy group, a tert-butoxy group, etc.

The number of C1-C6 alkoxy groups as a substituent may be 1 or 2 or more and in the case of 2 or more, respective C1-C6 alkoxy groups may be the same or different. In addition, the substitution position of the C1-C6 alkoxy group may be any position.

Examples of the C1-C6 haloalkoxy group represented by $R^{14}$ or the C1-C6 haloalkoxy group as a substituent include a monofluoromethoxy group, a difluoromethoxy group, a trifluoromethoxy group, a 2,2,2-trifluoroethoxy group, a 2-chloroethoxy group, a trichloromethoxy group, a 1-fluoroethoxy group, a 2-fluoroethoxy group, etc. The number of C1-C6 haloalkoxy groups as a substituent may be 1 or 2 or more and in the case of 2 or more, respective C1-C6 haloalkoxy groups may be the same or different. In addition, the substitution position of the C1-C6 haloalkoxy group may be any position.

Examples of the C1-C6 alkylthio group as a substituent include a methylthio group, an ethylthio group, a n-propylthio group, an isopropylthio group, a n-butylthio group, an isobutylthio group, a sec-butylthio group, a tert-butylthio group, etc. The number of C1-C6 alkylthio groups as a substituent may be 1 or 2 or more and in the case of 2 or more, respective C1-C6 alkylthio groups may be the same or different. In addition, the substitution position of the C1-C6 alkylthio group may be any position.

Examples of the C1-C6 haloalkylthio group as a substituent include a trifluoromethylthio group, a 2,2,2-trifluoroethylthio group, etc. The number of C1-C6 haloalkylthio groups as a substituent may be 1 or 2 or more and in the case of 2 or more, respective C1-C6 haloalkylthio groups may be the same or different. In addition, the substitution position of the C1-C6 haloalkylthio group may be any position.

As a preferred embodiment of the compound represented by formula (11), $R^{11}$ is preferably, in addition to the substituent above, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C8 cycloalkyl group which may be substituted (the group may be monosubstituted or polysubstituted by a halogen atom, a C1-C6 alkyl group, a C1-C6 alkoxy group, a C3-C8 cycloalkyl group, a C3-C6 cycloalkyl C1-C6 alkyl group, a phenyl group, or a C7-C11 aralkyl group), a C3-C6 cycloalkyl C1-C6 alkyl group, a C1-C6 alkoxy C1-C6 alkyl group, a C1-C6 haloalkoxy C1-C6 alkyl group, a phenyl group which may be substituted (the group may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group), a C7-C11 aralkyl group which may be substituted (the group may be monosubstituted or polysubstituted by a halogen atom, a C1-C6 alkyl group, or a C1-C6 alkoxy group), a pyridine ring which may be substituted (the group may be monosubstituted or polysubstituted by a halogen atom, a C1-C6 alkyl group, or a C1-C6 alkoxy group), a thiophene ring which may be substituted (the group may be monosubstituted or polysubstituted by a halogen atom, a C1-C6 alkyl group, or a C1-C6 alkoxy group), a C1-C6 alkylamino group, a di C1-C6 alkylamino group in which alkyl groups may be the same or different (the alkyl groups may also combine with each other via an alkylene group to form a 3-membered ring, a 4-membered ring, a 5-membered ring and a 6-membered ring), a tetrahydropyranyl group, a tetrahydrofuryl group, a tetrahydropyranylmethyl group, or a tetrahydrofurfuryl group, and more preferably a C1-C6 alkyl group, a C1-C6 haloalkyl group, a C2-C6 alkenyl group, a C3-C8 cycloalkyl group which may be substituted (the group may be monosubstituted or polysubstituted by a halogen atom, a C1-C6 alkyl group, a C1-C6 alkoxy group, a C3-C8 cycloalkyl group, a C3-C6 cycloalkyl C1-C6 alkyl group, a phenyl group, or a C7-C11 aralkyl group), a phenyl group which may be substituted (the group may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group), a C7-C11 aralkyl group which may be substituted (the group may be monosubstituted or polysubstituted by a halogen atom, a C1-C6 alkyl group, or a C1-C6 alkoxy group), a pyridine ring which may be substituted (the group may be monosubstituted or polysubstituted by a halogen atom, a C1-C6 alkyl group, or a C1-C6 alkoxy group), a thiophene ring which may be substituted (the group may be monosubstituted or polysubstituted by a halogen atom, a C1-C6 alkyl group, or a C1-C6 alkoxy group), a di C1-C6 alkylamino group in which alkyl groups may be the same or different (the alkyl groups may also combine with each other via an alkylene group to form a 3-membered ring, a 4-membered ring, a 5-membered ring and a 6-membered ring), or a tetrahydropyranyl group.

$R^{12}$ is preferably, in addition to the substituent above, a C1-C6 alkyl group, a C1-C6 haloalkyl group, a C2-C6 alkenyl group, a C2-C6 alkynyl group, a C3-C6 cycloalkyl group, a C3-C6 cycloalkyl C1-C6 alkyl group, a C1-C6 alkoxy C1-C6 alkyl group, a C1-C6 haloalkoxy C1-C6 alkyl group, a phenyl group which may be substituted (the group may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group), a C7-C11 aralkyl group which may be substituted (the group may be monosubstituted or polysubstituted by a halogen atom, a C1-C6 alkyl group, or a C1-C6 alkoxy group), or a pyridine ring which may be substituted (the group may be monosubstituted or polysubstituted by a halogen atom, a C1-C6 alkyl group, a C1-C6 haloalkyl group, or a C1-C6 alkoxy group), and more preferably a C1-C6 alkyl group or a C1-C6 haloalkyl group.

$R^{13}$ is preferably, in addition to the substituent above, a C1-C6 alkyl group, a C3-C6 cycloalkyl group, a phenyl group which may be substituted (the group may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group), a C7-C11 aralkyl group which may be substituted (the group may be monosubstituted or polysubstituted by a halogen atom, a C1-C6 alkyl group, or a C1-C6 alkoxy group), a pyridine ring which may be substituted (the group may be monosubstituted or polysubstituted by a halogen atom, a C1-C6 alkyl group, a C1-C6 haloalkyl group, or a C1-C6 alkoxy group), an isoxazole ring which may be substituted (the group may be monosubstituted or polysubstituted by a halogen atom, a C1-C6 alkyl group, a C1-C6 haloalkyl group, or a C1-C6 alkoxy group), a thiazole ring which may be substituted (the group may be monosubstituted or polysubstituted by a halogen atom, a C1-C6 alkyl group, a C1-C6 haloalkyl group, or a C1-C6 alkoxy group), or a pyrazole ring which may be substituted (the group may be monosubstituted or polysubstituted by a halogen atom, a C1-C6 alkyl group, a C1-C6 haloalkyl group, or a C1-C6 alkoxy group), and more preferably a C1-C6 alkyl group, a C3-C8 cycloalkyl group, a phenyl group which may be substituted (the group may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group), a C7-C11 aralkyl group which may be substituted (the group may be monosubstituted or polysubstituted by a halogen atom, a C1-C6 alkyl group, or a C1-C6 alkoxy group), a pyridine ring which may be substituted (the group may be monosubstituted or polysubstituted by a halogen atom, a C1-C6 alkyl group, a C1-C6 haloalkyl group, or a C1-C6 alkoxy group), or an isoxazole ring which may be substituted (the group may be monosubstituted or polysubstituted by a halogen atom, a C1-C6 alkyl group, a C1-C6 haloalkyl group, or a C1-C6 alkoxy group). In this connection, when $R^{12}$ and $R^{13}$ are a C1-C6 alkyl group, as described above, these may also combine with each other to form a 3-membered ring, a 4-membered ring, a 5-membered ring, and a 6-membered ring with an alkylene group having from 2 to 5 carbon atoms as ring members.

$R^{14}$ is preferably, in addition to the substituent above, a hydrogen atom, a halogen atom, a C1-C6 alkyl group, a C1-C6 haloalkyl group, a C1-C6 alkoxy group or a C1-C6 haloalkoxy group, more preferably a hydrogen atom or a C1-C6 alkyl group.

Another preferred embodiment of the present invention is a 4-(N,N-disubstituted carbamoyl)1-(substituted sulfonyl) triazolin-5-one derivative represented by formula (11):

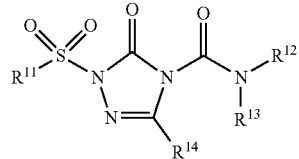

(11)

wherein in formula (11), $R^{11}$ represents a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C8 cycloalkyl group which may be substituted (the group may be monosubstituted or polysubstituted by a halogen atom, a C1-C6 alkyl group, a C1-C6 alkoxy group, a C3-C8 cycloalkyl group, a C3-C6 cycloalkyl C1-C6 alkyl group, a phenyl group, or an aralkyl group), a C3-C6 cycloalkyl C1-C6 alkyl group, a C1-C6 alkoxy C1-C6 alkyl group, a C1-C6 haloalkoxy C1-C6 alkyl group, a phenyl group which may be substituted (the group may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group), a C7-C11 aralkyl group which may be substituted (the group may be monosubstituted or polysubstituted by a halogen atom, a C1-C6 alkyl group, or a C1-C6 alkoxy group), a heterocyclic ring which may be substituted (the group may be monosubstituted or polysubstituted by a halogen atom, a C1-C6 alkyl group, or a C1-C6 alkoxy group), a C1-C6 alkylamino group, a di C1-C6 alkylamino group in which alkyl groups may be the same or different (the alkyl groups may also combine with each other via an alkylene group to form a 3-membered ring, a 4-membered ring, a 5-membered ring and a 6-membered ring), a tetrahydropyranyl group, a tetrahydrofuryl group, a tetrahydropyranylmethyl group, or a tetrahydrofurfuryl group;

each of $R^{12}$ and $R^{13}$ independently represents a C1-C6 alkyl group, a C1-C6 haloalkyl group, a C2-C6 alkenyl group, a C2-C6 alkynyl group, a C3-C6 cycloalkyl group, a C3-C6 cycloalkyl C1-C6 alkyl group, a C1-C6 alkoxy C1-C6 alkyl group, a C1-C6 haloalkoxy C1-C6 alkyl group, a phenyl group which may be substituted (the group may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group), a C7-C11 aralkyl group which may be substituted (the group may be monosubstituted or polysubstituted by a halogen atom, a C1-C6 alkyl group, or a C1-C6 alkoxy group), or a heterocyclic ring which may be substituted (the group may be monosubstituted or polysubstituted by a halogen atom, a C1-C6 alkyl group, or a C1-C6 alkoxy group), and when $R^{12}$ and $R^{13}$ are C1-C6 alkyl groups, these may also combine with each other to form a 3-membered ring, a 4-membered ring, a 5-membered ring, and a 6-membered ring with an alkylene group having from 2 to 5 carbon atoms as ring members; and $R^{14}$ represents a hydrogen atom, a halogen atom, a C1-C6 alkyl group, a C1-C6 haloalkyl group, a C1-C6 alkoxy group, or a C1-C6 haloalkoxy group.

The groups in $R^{11}$, $R^{12}$, $R^{13}$, and $R^{14}$ are each as described above.

Although representative examples of the 4-(N,N-disubstituted carbamoyl)1-(substituted sulfonyl)triazolin-5-one derivative represented by formula (11) are shown together in Table 2 below, the present invention is not limited to these compounds. These compounds include compounds containing optical isomers, E forms and Z forms. The compound number is referred to in the later description.

In the Table, respective notations below denote corresponding groups as follows.

"H" denotes hydrogen atom, "Me" denotes a methyl group, "Et" denotes an ethyl group, "n-Pr" denotes a normal-propyl group, "i-Pr" denotes an isopropyl group, "c-Pr" denotes a cyclopropyl group, "s-Bu" denotes a sec-butyl group, "i-Bu" denotes an isobutyl group, "t-Bu" denotes a tert-butyl group, "c-Bu" denotes a cyclobutyl group, "c-Pen" denotes a cyclopentyl group, "c-Hex" denotes a cyclohexyl group, "Ph" denotes a phenyl group, "Bn" denotes a benzyl group, and "Py" denotes a pyridyl group.

TABLE 2

| No. | $R^{11}$ | $R^{12}$ | $R^{13}$ | $R^{14}$ |
|---|---|---|---|---|
| 11-1 | Me | i-Pr | Ph | H |
| 11-2 | Me | i-Pr | 2-FPh | H |
| 11-3 | Me | i-Pr | 3-FPh | H |
| 11-4 | Me | i-Pr | 4-FPh | H |
| 11-5 | Me | i-Pr | 2-ClPh | H |
| 11-6 | Me | i-Pr | 3-ClPh | H |
| 11-7 | Me | i-Pr | 4-ClPh | H |
| 11-8 | Me | i-Pr | 2-CF$_3$Ph | H |
| 11-9 | Me | i-Pr | 3-CF$_3$Ph | H |
| 11-10 | Me | i-Pr | 4-CF$_3$Ph | H |
| 11-11 | Me | i-Pr | 2,3-F$_2$Ph | H |
| 11-12 | Me | i-Pr | 2,4-F$_2$Ph | H |
| 11-13 | Me | i-Pr | 2,5-F$_2$Ph | H |
| 11-14 | Me | i-Pr | 2,6-F$_2$Ph | H |
| 11-15 | Me | i-Pr | 2,3,4-F$_3$Ph | H |
| 11-16 | Me | i-Pr | 2,4,6-F$_3$Ph | H |
| 11-17 | Me | i-Pr | 2,3,5,6-F$_4$Ph | H |
| 11-18 | Me | i-Pr | 2,3,4,5,6-F$_5$Ph | H |
| 11-19 | Me | i-Pr | 2-Cl-4-FPh | H |
| 11-20 | Me | i-Pr | 2-F-4-ClPh | H |
| 11-21 | Me | i-Pr | 2-F-4-BrPh | H |
| 11-22 | Me | i-Pr | 2-Br-4-FPh | H |
| 11-23 | Me | i-Pr | 2-Cl-4-BrPh | H |
| 11-24 | Me | i-Pr | 2-Br-4-ClPh | H |
| 11-25 | Me | i-Pr | 2-Me-4-FPh | H |
| 11-26 | Me | i-Pr | 2-F-4-MePh | H |
| 11-27 | Me | i-Pr | 2-Me-4-ClPh | H |
| 11-28 | Me | i-Pr | 2-Cl-4-MePh | H |
| 11-29 | Me | i-Pr | 2-F-4-CF$_3$Ph | H |
| 11-30 | Me | i-Pr | 2-CF$_3$-4-FPh | H |
| 11-31 | Me | i-Pr | 2,3,5,6-F$_4$-4-CF$_3$Ph | H |
| 11-32 | Me | i-Pr | 2-Cl-4-CF$_3$Ph | H |
| 11-33 | Me | i-Pr | 2-CF$_3$-4-ClPh | H |
| 11-34 | Me | i-Pr | 2-Cl-4-CNPh | H |
| 11-35 | Me | i-Pr | 2-Cl-4-(SEt)Ph | H |
| 11-36 | Me | i-Pr | 2,4-F$_2$Bn | H |
| 11-37 | Me | i-Pr | 3-Cl-2-Py | H |
| 11-38 | Me | i-Pr | 5-Cl-2-Py | H |
| 11-39 | Me | i-Pr | 3,5-Cl$_2$-2-Py | H |
| 11-40 | Me | i-Pr | 3-Cl-5-CF$_3$-2-Py | H |
| 11-41 | Me | i-Pr | 2-Cl-3-Py | H |
| 11-42 | Me | i-Pr | 6-Cl-3-Py | H |
| 11-43 | Me | i-Pr | 2,6-Cl$_2$-3-Py | H |
| 11-44 | Me | i-Pr | 5-Me-isoxazol-3-yl | H |
| 11-45 | Me | i-Pr | 2,4-F$_2$Ph | Me |
| 11-46 | Et | i-Pr | 2,4-F$_2$Ph | H |
| 11-47 | n-Pr | i-Pr | 2,4-F$_2$Ph | H |
| 11-48 | i-Pr | i-Pr | Ph | H |
| 11-49 | i-Pr | i-Pr | 2-FPh | H |
| 11-50 | i-Pr | i-Pr | 3-FPh | H |
| 11-51 | i-Pr | i-Pr | 4-FPh | H |
| 11-52 | i-Pr | i-Pr | 2-ClPh | H |
| 11-53 | i-Pr | i-Pr | 3-ClPh | H |
| 11-54 | i-Pr | i-Pr | 4-ClPh | H |
| 11-55 | i-Pr | i-Pr | 2-CF$_3$Ph | H |
| 11-56 | i-Pr | i-Pr | 3-CF$_3$Ph | H |
| 11-57 | i-Pr | i-Pr | 4-CF$_3$Ph | H |
| 11-58 | i-Pr | i-Pr | 2,3-F$_2$Ph | H |
| 11-59 | i-Pr | i-Pr | 2,4-F$_2$Ph | H |
| 11-60 | i-Pr | i-Pr | 2,5-F$_2$Ph | H |
| 11-61 | i-Pr | i-Pr | 2,6-F$_2$Ph | H |
| 11-62 | i-Pr | i-Pr | 2,3,4-F$_3$Ph | H |
| 11-63 | i-Pr | i-Pr | 2,4,6-F$_3$Ph | H |
| 11-64 | i-Pr | i-Pr | 2,3,5,6-F$_4$Ph | H |
| 11-65 | i-Pr | i-Pr | 2,3,4,5,6-F$_5$Ph | H |
| 11-66 | i-Pr | i-Pr | 2-Cl-4-FPh | H |
| 11-67 | i-Pr | i-Pr | 2-F-4-ClPh | H |
| 11-68 | i-Pr | i-Pr | 2-F-4-BrPh | H |
| 11-69 | i-Pr | i-Pr | 2-Br-4-FPh | H |
| 11-70 | i-Pr | i-Pr | 2-Cl-4-BrPh | H |
| 11-71 | i-Pr | i-Pr | 2-Br-4-ClPh | H |
| 11-72 | i-Pr | i-Pr | 2-Me-4-FPh | H |
| 11-73 | i-Pr | i-Pr | 2-F-4-MePh | H |
| 11-74 | i-Pr | i-Pr | 2-Me-4-ClPh | H |
| 11-75 | i-Pr | i-Pr | 2-Cl-4-MePh | H |
| 11-76 | i-Pr | i-Pr | 2-F-4-CF$_3$Ph | H |
| 11-77 | i-Pr | i-Pr | 2-CF$_3$-4-FPh | H |
| 11-78 | i-Pr | i-Pr | 2,3,5,6-F$_4$-4-CF$_3$Ph | H |

TABLE 2-continued

| No. | R¹¹ | R¹² | R¹³ | R¹⁴ |
|---|---|---|---|---|
| 11-79 | i-Pr | i-Pr | 2-Cl-4-CF$_3$Ph | H |
| 11-80 | i-Pr | i-Pr | 2-CF$_3$-4-ClPh | H |
| 11-81 | i-Pr | i-Pr | 2-Cl-4-CNPh | H |
| 11-82 | i-Pr | i-Pr | 2-Cl-4-(SEt)Ph | H |
| 11-83 | i-Pr | i-Pr | 2,4-F$_2$Bn | H |
| 11-84 | i-Pr | i-Pr | 3-Cl-2-Py | H |
| 11-85 | i-Pr | i-Pr | 5-Cl-2-Py | H |
| 11-86 | i-Pr | i-Pr | 3,5-Cl$_2$-2-Py | H |
| 11-87 | i-Pr | i-Pr | 3-Cl-5-CF$_3$-2-Py | H |
| 11-88 | i-Pr | i-Pr | 2-Cl-3-Py | H |
| 11-89 | i-Pr | i-Pr | 6-Cl-3-Py | H |
| 11-90 | i-Pr | i-Pr | 2,6-Cl$_2$-3-Py | H |
| 11-91 | i-Pr | i-Pr | 5-Me-isoxazol-3-yl | H |
| 11-92 | i-Pr | i-Pr | 2,4-F$_2$Ph | Me |
| 11-93 | s-Bu | i-Pr | 2,4-F$_2$Ph | H |
| 11-94 | i-Bu | i-Pr | 2,4-F$_2$Ph | H |
| 11-95 | CF$_3$ | i-Pr | 2,4-F$_2$Ph | H |
| 11-96 | CHF$_2$ | i-Pr | 2,4-F$_2$Ph | H |
| 11-97 | CH$_2$CF$_3$ | i-Pr | 2,4-F$_2$Ph | H |
| 11-98 | CH$_2$Cl | i-Pr | Ph | H |
| 11-99 | CH$_2$Cl | i-Pr | 2-FPh | H |
| 11-100 | CH$_2$Cl | i-Pr | 3-FPh | H |
| 11-101 | CH$_2$Cl | i-Pr | 4-FPh | H |
| 11-102 | CH$_2$Cl | i-Pr | 2-ClPh | H |
| 11-103 | CH$_2$Cl | i-Pr | 3-ClPh | H |
| 11-104 | CH$_2$Cl | i-Pr | 4-ClPh | H |
| 11-105 | CH$_2$Cl | i-Pr | 2-CF$_3$Ph | H |
| 11-106 | CH$_2$Cl | i-Pr | 3-CF$_3$Ph | H |
| 11-107 | CH$_2$Cl | i-Pr | 4-CF$_3$Ph | H |
| 11-108 | CH$_2$Cl | i-Pr | 2,3-F$_2$Ph | H |
| 11-109 | CH$_2$Cl | i-Pr | 2,4-F$_2$Ph | H |
| 11-110 | CH$_2$Cl | i-Pr | 2,5-F$_2$Ph | H |
| 11-111 | CH$_2$Cl | i-Pr | 2,6-F$_2$Ph | H |
| 11-112 | CH$_2$Cl | i-Pr | 2,3,4-F$_3$Ph | H |
| 11-113 | CH$_2$Cl | i-Pr | 2,4,6-F$_3$Ph | H |
| 11-114 | CH$_2$Cl | i-Pr | 2,3,5,6-F$_4$Ph | H |
| 11-115 | CH$_2$Cl | i-Pr | 2,3,4,5,6-F$_5$Ph | H |
| 11-116 | CH$_2$Cl | i-Pr | 2-Cl-4-FPh | H |
| 11-117 | CH$_2$Cl | i-Pr | 2-F-4-ClPh | H |
| 11-118 | CH$_2$Cl | i-Pr | 2-F-4-BrPh | H |
| 11-119 | CH$_2$Cl | i-Pr | 2-Br-4-FPh | H |
| 11-120 | CH$_2$Cl | i-Pr | 2-Cl-4-BrPh | H |
| 11-121 | CH$_2$Cl | i-Pr | 2-Br-4-ClPh | H |
| 11-122 | CH$_2$Cl | i-Pr | 2-Me-4-FPh | H |
| 11-123 | CH$_2$Cl | i-Pr | 2-F-4-MePh | H |
| 11-124 | CH$_2$Cl | i-Pr | 2-Me-4-ClPh | H |
| 11-125 | CH$_2$Cl | i-Pr | 2-Cl-4-MePh | H |
| 11-126 | CH$_2$Cl | i-Pr | 2-F-4-CF$_3$Ph | H |
| 11-127 | CH$_2$Cl | i-Pr | 2-CF$_3$-4-FPh | H |
| 11-128 | CH$_2$Cl | i-Pr | 2,3,5,6-F$_4$-4-CF$_3$Ph | H |
| 11-129 | CH$_2$Cl | i-Pr | 2-Cl-4-CF$_3$Ph | H |
| 11-130 | CH$_2$Cl | i-Pr | 2-CF$_3$-4-ClPh | H |
| 11-131 | CH$_2$Cl | i-Pr | 2-Cl-4-CNPh | H |
| 11-132 | CH$_2$Cl | i-Pr | 2-Cl-4-(SEt)Ph | H |
| 11-133 | CH$_2$CH$_2$Cl | i-Pr | 2,4-F$_2$Ph | H |
| 11-134 | CH=CH$_2$ | i-Pr | 2,4-F$_2$Ph | H |
| 11-135 | CH$_2$CH=CH$_2$ | i-Pr | 2,4-F$_2$Ph | H |
| 11-136 | CH$_2$CH=CCl$_2$ | i-Pr | 2,4-F$_2$Ph | H |
| 11-137 | CH$_2$CH$_2$CH=CF$_2$ | i-Pr | 2,4-F$_2$Ph | H |
| 11-138 | CH$_2$C≡CH | i-Pr | 2,4-F$_2$Ph | H |
| 11-139 | CH$_2$C≡CCF$_3$ | i-Pr | 2,4-F$_2$Ph | H |
| 11-140 | c-Pr | Me | 2,4-F$_2$Ph | H |
| 11-141 | c-Pr | Et | 2,4-F$_2$Ph | H |
| 11-142 | c-Pr | i-Pr | 2,4-F$_2$Ph | H |
| 11-143 | c-Pr | s-Bu | 2,4-F$_2$Ph | H |
| 11-144 | c-Pr | CH$_2$CF$_3$ | 2,4-F$_2$Ph | H |
| 11-145 | c-Pr | CH$_2$CH=CH$_2$ | 2,4-F$_2$Ph | H |
| 11-146 | c-Pr | CH$_2$C≡CH | 2,4-F$_2$Ph | H |
| 11-147 | c-Pr | c-Pr | 2,4-F$_2$Ph | H |
| 11-148 | c-Pr | c-Hex | 2,4-F$_2$Ph | H |
| 11-149 | c-Pr | CH$_2$c-Pr | 2,4-F$_2$Ph | H |
| 11-150 | c-Pr | CH$_2$OMe | 2,4-F$_2$Ph | H |
| 11-151 | c-Pr | CH$_2$OCH$_2$CF$_3$ | 2,4-F$_2$Ph | H |
| 11-152 | c-Pr | Ph | 2,4-F$_2$Ph | H |
| 11-153 | c-Pr | Bn | 2,4-F$_2$Ph | H |
| 11-154 | c-Pr | 2-Py | 2,4-F$_2$Ph | H |
| 11-155 | c-Pr | —(CH$_2$)$_5$— | | H |
| 11-156 | c-Pr | —CH(Me)(CH$_2$)$_4$— | | H |

TABLE 2-continued

| No. | R11 | R12 | R13 | R14 |
|---|---|---|---|---|
| 11-157 | c-Pr | i-Pr | Et | H |
| 11-158 | c-Pr | i-Pr | c-Hex | H |
| 11-159 | c-Pr | i-Pr | Ph | H |
| 11-160 | c-Pr | i-Pr | 2-FPh | H |
| 11-161 | c-Pr | i-Pr | 3-FPh | H |
| 11-162 | c-Pr | i-Pr | 4-FPh | H |
| 11-163 | c-Pr | i-Pr | 2-ClPh | H |
| 11-164 | c-Pr | i-Pr | 3-ClPh | H |
| 11-165 | c-Pr | i-Pr | 4-ClPh | H |
| 11-166 | c-Pr | i-Pr | 4-BrPh | H |
| 11-167 | c-Pr | i-Pr | 2-CNPh | H |
| 11-168 | c-Pr | i-Pr | 4-CNPh | H |
| 11-169 | c-Pr | i-Pr | 2-NO$_2$Ph | H |
| 11-170 | c-Pr | i-Pr | 4-NO$_2$Ph | H |
| 11-171 | c-Pr | i-Pr | 2-MePh | H |
| 11-172 | c-Pr | i-Pr | 3-MePh | H |
| 11-173 | c-Pr | i-Pr | 4-MePh | H |
| 11-174 | c-Pr | i-Pr | 2-EtPh | H |
| 11-175 | c-Pr | i-Pr | 4-EtPh | H |
| 11-176 | c-Pr | i-Pr | 2-CF$_3$Ph | H |
| 11-177 | c-Pr | i-Pr | 3-CF$_3$Ph | H |
| 11-178 | c-Pr | i-Pr | 4-CF$_3$Ph | H |
| 11-179 | c-Pr | i-Pr | 2-OMePh | H |
| 11-180 | c-Pr | i-Pr | 3-OMePh | H |
| 11-181 | c-Pr | i-Pr | 4-OMePh | H |
| 11-182 | c-Pr | i-Pr | 2-OCF$_3$Ph | H |
| 11-183 | c-Pr | i-Pr | 3-OCF$_3$Ph | H |
| 11-184 | c-Pr | i-Pr | 4-OCF$_3$Ph | H |
| 11-185 | c-Pr | i-Pr | 2-SMePh | H |
| 11-186 | c-Pr | i-Pr | 4-SMePh | H |
| 11-187 | c-Pr | i-Pr | 2-SCF$_3$Ph | H |
| 11-188 | c-Pr | i-Pr | 4-SCF$_3$Ph | H |
| 11-189 | c-Pr | i-Pr | 2,3-F$_2$Ph | H |
| 11-190 | c-Pr | i-Pr | 2,5-F$_2$Ph | H |
| 11-191 | c-Pr | i-Pr | 2,6-F$_2$Ph | H |
| 11-192 | c-Pr | i-Pr | 3,4-F$_2$Ph | H |
| 11-193 | c-Pr | i-Pr | 3,5-F$_2$Ph | H |
| 11-194 | c-Pr | i-Pr | 2,3,4-F$_3$Ph | H |
| 11-195 | c-Pr | i-Pr | 2,4,6-F$_3$Ph | H |
| 11-196 | c-Pr | i-Pr | 3,4,5-F$_3$Ph | H |
| 11-197 | c-Pr | i-Pr | 2,3,5,6-F$_4$Ph | H |
| 11-198 | c-Pr | i-Pr | 2,3,4,5,6-F$_5$Ph | H |
| 11-199 | c-Pr | i-Pr | 2,3-Cl$_2$Ph | H |
| 11-200 | c-Pr | i-Pr | 2,4-Cl$_2$Ph | H |
| 11-201 | c-Pr | i-Pr | 2,5-Cl$_2$Ph | H |
| 11-202 | c-Pr | i-Pr | 2,6-Cl$_2$Ph | H |
| 11-203 | c-Pr | i-Pr | 3,4-Cl$_2$Ph | H |
| 11-204 | c-Pr | i-Pr | 3,5-Cl$_2$Ph | H |
| 11-205 | c-Pr | i-Pr | 2-Cl-4-FPh | H |
| 11-206 | c-Pr | i-Pr | 2-F-4-ClPh | H |
| 11-207 | c-Pr | i-Pr | 2-F-4-BrPh | H |
| 11-208 | c-Pr | i-Pr | 2-Br-4-FPh | H |
| 11-209 | c-Pr | i-Pr | 2-Cl-4-BrPh | H |
| 11-210 | c-Pr | i-Pr | 2-Br-4-ClPh | H |
| 11-211 | c-Pr | i-Pr | 2-Me-4-FPh | H |
| 11-212 | c-Pr | i-Pr | 2-F-4-MePh | H |
| 11-213 | c-Pr | i-Pr | 2-Me-4-ClPh | H |
| 11-214 | c-Pr | i-Pr | 2-Cl-4-MePh | H |
| 11-215 | c-Pr | i-Pr | 2,4-F$_2$-3-MePh | H |
| 11-216 | c-Pr | i-Pr | 2,4-F$_2$-5-MePh | H |
| 11-217 | c-Pr | i-Pr | 2-F-4-CF$_3$Ph | H |
| 11-218 | c-Pr | i-Pr | 2-CF$_3$-4-FPh | H |
| 11-219 | c-Pr | i-Pr | 2,3,5,6-F$_4$-4-CF$_3$Ph | H |
| 11-220 | c-Pr | i-Pr | 2-Cl-4-CF$_3$Ph | H |
| 11-221 | c-Pr | i-Pr | 2-CF$_3$-4-ClPh | H |
| 11-222 | c-Pr | i-Pr | 2-Cl-4-CNPh | H |
| 11-223 | c-Pr | i-Pr | 2-Cl-4-(SMe)Ph | H |
| 11-224 | c-Pr | i-Pr | 2-Cl-4-(SEt)Ph | H |
| 11-225 | c-Pr | i-Pr | Bn | H |
| 11-226 | c-Pr | i-Pr | 2-FBn | H |
| 11-227 | c-Pr | i-Pr | 3-FBn | H |
| 11-228 | c-Pr | i-Pr | 4-FBn | H |
| 11-229 | c-Pr | i-Pr | 2,4-F$_2$Bn | H |
| 11-230 | c-Pr | i-Pr | 4-MeBn | H |
| 11-231 | c-Pr | i-Pr | 4-OMeBn | H |
| 11-232 | c-Pr | i-Pr | 3-Cl-2-Py | H |
| 11-233 | c-Pr | i-Pr | 5-Cl-2-Py | H |
| 11-234 | c-Pr | i-Pr | 3,5-Cl$_2$-2-Py | H |

TABLE 2-continued

| No. | R11 | R12 | R13 | R14 |
|---|---|---|---|---|
| 11-235 | c-Pr | i-Pr | 3-Cl-5-CF$_3$-2-Py | H |
| 11-236 | c-Pr | i-Pr | 2-Cl-3-Py | H |
| 11-237 | c-Pr | i-Pr | 6-Cl-3-Py | H |
| 11-238 | c-Pr | i-Pr | 2,6-Cl$_2$-3-Py | H |
| 11-239 | c-Pr | i-Pr | 5-Me-isoxazol-3-yl | H |
| 11-240 | c-Pr | i-Pr | 5-Cl-thiazol-2-yl | H |
| 11-241 | c-Pr | i-Pr | 1-Me-4-Cl-pyrazol-3-yl | H |
| 11-242 | c-Pr | i-Pr | 2,4-F$_2$Ph | F |
| 11-243 | c-Pr | i-Pr | 2,4-F$_2$Ph | Cl |
| 11-244 | c-Pr | i-Pr | 2,4-F$_2$Ph | Br |
| 11-245 | c-Pr | i-Pr | 2,4-F$_2$Ph | I |
| 11-246 | c-Pr | i-Pr | 2,4-F$_2$Ph | Me |
| 11-247 | c-Pr | i-Pr | 2,4-F$_2$Ph | Et |
| 11-248 | c-Pr | i-Pr | 2,4-F$_2$Ph | i-Pr |
| 11-249 | c-Pr | i-Pr | 2,4-F$_2$Ph | CHF$_2$ |
| 11-250 | c-Pr | i-Pr | 2,4-F$_2$Ph | CF$_3$ |
| 11-251 | c-Pr | i-Pr | 2,4-F$_2$Ph | OMe |
| 11-252 | c-Pr | i-Pr | 2,4-F$_2$Ph | OCF$_3$ |
| 11-253 | c-Bu | i-Pr | Ph | H |
| 11-254 | c-Bu | i-Pr | 2-FPh | H |
| 11-255 | c-Bu | i-Pr | 3-FPh | H |
| 11-256 | c-Bu | i-Pr | 4-FPh | H |
| 11-257 | c-Bu | i-Pr | 2,3-F$_2$Ph | H |
| 11-258 | c-Bu | i-Pr | 2,4-F$_2$Ph | H |
| 11-259 | c-Bu | i-Pr | 2,5-F$_2$Ph | H |
| 11-260 | c-Bu | i-Pr | 2,6-F$_2$Ph | H |
| 11-261 | c-Bu | i-Pr | 2-Cl-4-FPh | H |
| 11-262 | c-Bu | i-Pr | 2-F-4-ClPh | H |
| 11-263 | c-Bu | i-Pr | 2-F-4-MePh | H |
| 11-264 | c-Bu | i-Pr | 2-Me-4-ClPh | H |
| 11-265 | c-Bu | i-Pr | 2-F-4-CF$_3$Ph | H |
| 11-266 | c-Bu | i-Pr | 2-CF$_3$-4-FPh | H |
| 11-267 | c-Bu | i-Pr | 2,4-F$_2$Ph | Me |
| 11-268 | c-Pen | i-Pr | Ph | H |
| 11-269 | c-Pen | i-Pr | 2-FPh | H |
| 11-270 | c-Pen | i-Pr | 3-FPh | H |
| 11-271 | c-Pen | i-Pr | 4-FPh | H |
| 11-272 | c-Pen | i-Pr | 2,3-F$_2$Ph | H |
| 11-273 | c-Pen | i-Pr | 2,4-F$_2$Ph | H |
| 11-274 | c-Pen | i-Pr | 2,5-F$_2$Ph | H |
| 11-275 | c-Pen | i-Pr | 2,6-F$_2$Ph | H |
| 11-276 | c-Pen | i-Pr | 2-Cl-4-FPh | H |
| 11-277 | c-Pen | i-Pr | 2-F-4-ClPh | H |
| 11-278 | c-Pen | i-Pr | 2-F-4-MePh | H |
| 11-279 | c-Pen | i-Pr | 2-Me-4-ClPh | H |
| 11-280 | c-Pen | i-Pr | 2-F-4-CF$_3$Ph | H |
| 11-281 | c-Pen | i-Pr | 2-CF$_3$-4-FPh | H |
| 11-282 | c-Pen | i-Pr | 2,4-F$_2$Ph | Me |
| 11-283 | c-Hex | i-Pr | Ph | H |
| 11-284 | c-Hex | i-Pr | 2-FPh | H |
| 11-285 | c-Hex | i-Pr | 3-FPh | H |
| 11-286 | c-Hex | i-Pr | 4-FPh | H |
| 11-287 | c-Hex | i-Pr | 2-ClPh | H |
| 11-288 | c-Hex | i-Pr | 3-ClPh | H |
| 11-289 | c-Hex | i-Pr | 4-ClPh | H |
| 11-290 | c-Hex | i-Pr | 2-CF$_3$Ph | H |
| 11-291 | c-Hex | i-Pr | 3-CF$_3$Ph | H |
| 11-292 | c-Hex | i-Pr | 4-CF$_3$Ph | H |
| 11-293 | c-Hex | i-Pr | 2,3-F$_2$Ph | H |
| 11-294 | c-Hex | i-Pr | 2,4-F$_2$Ph | H |
| 11-295 | c-Hex | i-Pr | 2,5-F$_2$Ph | H |
| 11-296 | c-Hex | i-Pr | 2,6-F$_2$Ph | H |
| 11-297 | c-Hex | i-Pr | 2,3,4-F$_3$Ph | H |
| 11-298 | c-Hex | i-Pr | 2,4,6-F$_3$Ph | H |
| 11-299 | c-Hex | i-Pr | 2,3,5,6-F$_4$Ph | H |
| 11-300 | c-Hex | i-Pr | 2,3,4,5,6-F$_5$Ph | H |
| 11-301 | c-Hex | i-Pr | 2-Cl-4-FPh | H |
| 11-302 | c-Hex | i-Pr | 2-F-4-ClPh | H |
| 11-303 | c-Hex | i-Pr | 2-F-4-BrPh | H |
| 11-304 | c-Hex | i-Pr | 2-Br-4-FPh | H |
| 11-305 | c-Hex | i-Pr | 2-Cl-4-BrPh | H |
| 11-306 | c-Hex | i-Pr | 2-Br-4-ClPh | H |
| 11-307 | c-Hex | i-Pr | 2-Me-4-FPh | H |
| 11-308 | c-Hex | i-Pr | 2-F-4-MePh | H |
| 11-309 | c-Hex | i-Pr | 2-Me-4-ClPh | H |
| 11-310 | c-Hex | i-Pr | 2-Cl-4-MePh | H |
| 11-311 | c-Hex | i-Pr | 2-F-4-CF$_3$Ph | H |
| 11-312 | c-Hex | i-Pr | 2-CF$_3$-4-FPh | H |

TABLE 2-continued

| No. | R11 | R12 | R13 | R14 |
|---|---|---|---|---|
| 11-313 | c-Hex | i-Pr | 2,3,5,6-F4-4-CF3Ph | H |
| 11-314 | c-Hex | i-Pr | 2-Cl-4-CF3Ph | H |
| 11-315 | c-Hex | i-Pr | 2-CF3-4-ClPh | H |
| 11-316 | c-Hex | i-Pr | 2-Cl-4-CNPh | H |
| 11-317 | c-Hex | i-Pr | 2-Cl-4-(SEt)Ph | H |
| 11-318 | c-Hex | i-Pr | 2,4-F2Bn | H |
| 11-319 | c-Hex | i-Pr | 3-Cl-2-Py | H |
| 11-320 | c-Hex | i-Pr | 5-Cl-2-Py | H |
| 11-321 | c-Hex | i-Pr | 3,5-Cl2-2-Py | H |
| 11-322 | c-Hex | i-Pr | 3-Cl-5-CF3-2-Py | H |
| 11-323 | c-Hex | i-Pr | 2-Cl-3-Py | H |
| 11-324 | c-Hex | i-Pr | 6-Cl-3-Py | H |
| 11-325 | c-Hex | i-Pr | 2,6-Cl2-3-Py | H |
| 11-326 | c-Hex | i-Pr | 5-Me-isoxazol-3-yl | H |
| 11-327 | c-Hex | i-Pr | 2,4-F2Ph | Me |
| 11-328 | 1-F-c-Pr | i-Pr | 2,4-F2Ph | H |
| 11-329 | 2,2-F2-c-Pr | i-Pr | 2,4-F2Ph | H |
| 11-330 | 2,2-Cl2-c-Pr | i-Pr | 2,4-F2Ph | H |
| 11-331 | 4,4-F2-c-Hex | i-Pr | 2,4-F2Ph | H |
| 11-332 | 1-Me-c-Pr | i-Pr | 2,4-F2Ph | H |
| 11-333 | 2-Me-c-Pr | i-Pr | 2,4-F2Ph | H |
| 11-334 | 2,2-Me2-c-Pr | i-Pr | 2,4-F2Ph | H |
| 11-335 | 3-Me-c-Pen | i-Pr | 2,4-F2Ph | H |
| 11-336 | 4-Me-c-Hex | i-Pr | 2,4-F2Ph | H |
| 11-337 | 4,4-Me2-c-Hex | i-Pr | 2,4-F2Ph | H |
| 11-338 | 1-OMe-c-Pr | i-Pr | 2,4-F2Ph | H |
| 11-339 | 1-(c-Pr)-c-Pr | i-Pr | 2,4-F2Ph | H |
| 11-340 | 1-(CH2c-Pr)-c-Pr | i-Pr | 2,4-F2Ph | H |
| 11-341 | 1-Ph-c-Pr | i-Pr | 2,4-F2Ph | H |
| 11-342 | 1-Bn-c-Pr | i-Pr | 2,4-F2Ph | H |
| 11-343 | CH2c-Pr | i-Pr | 2,4-F2Ph | H |
| 11-344 | CH2c-Hex | i-Pr | 2,4-F2Ph | H |
| 11-345 | CH2OMe | i-Pr | 2,4-F2Ph | H |
| 11-346 | CH2OEt | i-Pr | 2,4-F2Ph | H |
| 11-347 | CH2Oi-Pr | i-Pr | 2,4-F2Ph | H |
| 11-348 | CH2CH2OMe | i-Pr | 2,4-F2Ph | H |
| 11-349 | CH(Me)CH2OMe | i-Pr | 2,4-F2Ph | H |
| 11-350 | CH2CH(Me)OMe | i-Pr | 2,4-F2Ph | H |
| 11-351 | CH2OCH2CF3 | i-Pr | 2,4-F2Ph | H |
| 11-352 | Ph | Et | Et | H |
| 11-353 | Ph | Et | c-Hex | H |
| 11-354 | Ph |  | —CH(Me)(CH2)4— | H |
| 11-355 | Ph | i-Pr | Ph | H |
| 11-356 | Ph | i-Pr | 2-FPh | H |
| 11-357 | Ph | i-Pr | 3-FPh | H |
| 11-358 | Ph | i-Pr | 4-FPh | H |
| 11-359 | Ph | i-Pr | 2-ClPh | H |
| 11-360 | Ph | i-Pr | 3-ClPh | H |
| 11-361 | Ph | i-Pr | 4-ClPh | H |
| 11-362 | Ph | i-Pr | 4-MePh | H |
| 11-363 | Ph | i-Pr | 2-CF3Ph | H |
| 11-364 | Ph | i-Pr | 3-CF3Ph | H |
| 11-365 | Ph | i-Pr | 4-CF3Ph | H |
| 11-366 | Ph | i-Pr | 2,3-F2Ph | H |
| 11-367 | Ph | i-Pr | 2,4-F2Ph | H |
| 11-368 | Ph | i-Pr | 2,5-F2Ph | H |
| 11-369 | Ph | i-Pr | 2,6-F2Ph | H |
| 11-370 | Ph | i-Pr | 2,3,4-F3Ph | H |
| 11-371 | Ph | i-Pr | 2,4,6-F3Ph | H |
| 11-372 | Ph | i-Pr | 2,3,5,6-F4Ph | H |
| 11-373 | Ph | i-Pr | 2,3,4,5,6-F5Ph | H |
| 11-374 | Ph | i-Pr | 2-Cl-4-FPh | H |
| 11-375 | Ph | i-Pr | 2-F-4-ClPh | H |
| 11-376 | Ph | i-Pr | 2-F-4-BrPh | H |
| 11-377 | Ph | i-Pr | 2-Br-4-FPh | H |
| 11-378 | Ph | i-Pr | 2-Cl-4-BrPh | H |
| 11-379 | Ph | i-Pr | 2-Br-4-ClPh | H |
| 11-380 | Ph | i-Pr | 2-Me-4-FPh | H |
| 11-381 | Ph | i-Pr | 2-F-4-MePh | H |
| 11-382 | Ph | i-Pr | 2-Me-4-ClPh | H |
| 11-383 | Ph | i-Pr | 2-Cl-4-MePh | H |
| 11-384 | Ph | i-Pr | 2-F-4-CF3Ph | H |
| 11-385 | Ph | i-Pr | 2-CF3-4-FPh | H |
| 11-386 | Ph | i-Pr | 2,3,5,6-F4-4-CF3Ph | H |
| 11-387 | Ph | i-Pr | 2-Cl-4-CF3Ph | H |
| 11-388 | Ph | i-Pr | 2-CF3-4-ClPh | H |
| 11-389 | Ph | i-Pr | 2-Cl-4-CNPh | H |
| 11-390 | Ph | i-Pr | 2-Cl-4-(SEt)Ph | H |

TABLE 2-continued

| No. | R11 | R12 | R13 | R14 |
|---|---|---|---|---|
| 11-391 | 2-FPh | i-Pr | Ph | H |
| 11-392 | 2-FPh | i-Pr | 2-FPh | H |
| 11-393 | 2-FPh | i-Pr | 3-FPh | H |
| 11-394 | 2-FPh | i-Pr | 4-FPh | H |
| 11-395 | 2-FPh | i-Pr | 2-ClPh | H |
| 11-396 | 2-FPh | i-Pr | 3-ClPh | H |
| 11-397 | 2-FPh | i-Pr | 4-ClPh | H |
| 11-398 | 2-FPh | i-Pr | 2-$CF_3$Ph | H |
| 11-399 | 2-FPh | i-Pr | 3-$CF_3$Ph | H |
| 11-400 | 2-FPh | i-Pr | 4-$CF_3$Ph | H |
| 11-401 | 2-FPh | i-Pr | 2,3-$F_2$Ph | H |
| 11-402 | 2-FPh | i-Pr | 2,4-$F_2$Ph | H |
| 11-403 | 2-FPh | i-Pr | 2,5-$F_2$Ph | H |
| 11-404 | 2-FPh | i-Pr | 2,6-$F_2$Ph | H |
| 11-405 | 2-FPh | i-Pr | 2,3,4-$F_3$Ph | H |
| 11-406 | 2-FPh | i-Pr | 2,4,6-$F_3$Ph | H |
| 11-407 | 2-FPh | i-Pr | 2,3,5,6-$F_4$Ph | H |
| 11-408 | 2-FPh | i-Pr | 2,3,4,5,6-$F_5$Ph | H |
| 11-409 | 2-FPh | i-Pr | 2-Cl-4-FPh | H |
| 11-410 | 2-FPh | i-Pr | 2-F-4-ClPh | H |
| 11-411 | 2-FPh | i-Pr | 2-F-4-BrPh | H |
| 11-412 | 2-FPh | i-Pr | 2-Br-4-FPh | H |
| 11-413 | 2-FPh | i-Pr | 2-Cl-4-BrPh | H |
| 11-414 | 2-FPh | i-Pr | 2-Br-4-ClPh | H |
| 11-415 | 2-FPh | i-Pr | 2-Me-4-FPh | H |
| 11-416 | 2-FPh | i-Pr | 2-F-4-MePh | H |
| 11-417 | 2-FPh | i-Pr | 2-Me-4-ClPh | H |
| 11-418 | 2-FPh | i-Pr | 2-Cl-4-MePh | H |
| 11-419 | 2-FPh | i-Pr | 2-F-4-$CF_3$Ph | H |
| 11-420 | 2-FPh | i-Pr | 2-$CF_3$-4-FPh | H |
| 11-421 | 2-FPh | i-Pr | 2,3,5,6-$F_4$-4-$CF_3$Ph | H |
| 11-422 | 2-FPh | i-Pr | 2-Cl-4-$CF_3$Ph | H |
| 11-423 | 2-FPh | i-Pr | 2-$CF_3$-4-ClPh | H |
| 11-424 | 2-FPh | i-Pr | 2-Cl-4-CNPh | H |
| 11-425 | 2-FPh | i-Pr | 2-Cl-4-(SEt)Ph | H |
| 11-426 | 2-FPh | i-Pr | 2,4-$F_2$Ph | Me |
| 11-427 | 3-FPh | i-Pr | Ph | H |
| 11-428 | 3-FPh | i-Pr | 2-FPh | H |
| 11-429 | 3-FPh | i-Pr | 3-FPh | H |
| 11-430 | 3-FPh | i-Pr | 4-FPh | H |
| 11-431 | 3-FPh | i-Pr | 2-ClPh | H |
| 11-432 | 3-FPh | i-Pr | 3-ClPh | H |
| 11-433 | 3-FPh | i-Pr | 4-ClPh | H |
| 11-434 | 3-FPh | i-Pr | 2-$CF_3$Ph | H |
| 11-435 | 3-FPh | i-Pr | 3-$CF_3$Ph | H |
| 11-436 | 3-FPh | i-Pr | 4-$CF_3$Ph | H |
| 11-437 | 3-FPh | i-Pr | 2,3-$F_2$Ph | H |
| 11-438 | 3-FPh | i-Pr | 2,4-$F_2$Ph | H |
| 11-439 | 3-FPh | i-Pr | 2,5-$F_2$Ph | H |
| 11-440 | 3-FPh | i-Pr | 2,6-$F_2$Ph | H |
| 11-441 | 3-FPh | i-Pr | 2,3,4-$F_3$Ph | H |
| 11-442 | 3-FPh | i-Pr | 2,4,6-$F_3$Ph | H |
| 11-443 | 3-FPh | i-Pr | 2,3,5,6-$F_4$Ph | H |
| 11-444 | 3-FPh | i-Pr | 2,3,4,5,6-$F_5$Ph | H |
| 11-445 | 3-FPh | i-Pr | 2-Cl-4-FPh | H |
| 11-446 | 3-FPh | i-Pr | 2-F-4-ClPh | H |
| 11-447 | 3-FPh | i-Pr | 2-F-4-BrPh | H |
| 11-448 | 3-FPh | i-Pr | 2-Br-4-FPh | H |
| 11-449 | 3-FPh | i-Pr | 2-Cl-4-BrPh | H |
| 11-450 | 3-FPh | i-Pr | 2-Br-4-ClPh | H |
| 11-451 | 3-FPh | i-Pr | 2-Me-4-FPh | H |
| 11-452 | 3-FPh | i-Pr | 2-F-4-MePh | H |
| 11-453 | 3-FPh | i-Pr | 2-Me-4-ClPh | H |
| 11-454 | 3-FPh | i-Pr | 2-Cl-4-MePh | H |
| 11-455 | 3-FPh | i-Pr | 2-F-4-$CF_3$Ph | H |
| 11-456 | 3-FPh | i-Pr | 2-$CF_3$-4-FPh | H |
| 11-457 | 3-FPh | i-Pr | 2,3,5,6-$F_4$-4-$CF_3$Ph | H |
| 11-458 | 3-FPh | i-Pr | 2-Cl-4-$CF_3$Ph | H |
| 11-459 | 3-FPh | i-Pr | 2-$CF_3$-4-ClPh | H |
| 11-460 | 3-FPh | i-Pr | 2-Cl-4-CNPh | H |
| 11-461 | 3-FPh | i-Pr | 2-Cl-4-(SEt)Ph | H |
| 11-462 | 3-FPh | i-Pr | 2,4-$F_2$Ph | Me |
| 11-463 | 4-FPh | Et | Et | H |
| 11-464 | 4-FPh | i-Pr | Ph | H |
| 11-465 | 4-FPh | i-Pr | 2-FPh | H |
| 11-466 | 4-FPh | i-Pr | 3-FPh | H |
| 11-467 | 4-FPh | i-Pr | 4-FPh | H |
| 11-468 | 4-FPh | i-Pr | 2-ClPh | H |

TABLE 2-continued

| No. | R$^{11}$ | R$^{12}$ | R$^{13}$ | R$^{14}$ |
|---|---|---|---|---|
| 11-469 | 4-FPh | i-Pr | 3-ClPh | H |
| 11-470 | 4-FPh | i-Pr | 4-ClPh | H |
| 11-471 | 4-FPh | i-Pr | 2-CF$_3$Ph | H |
| 11-472 | 4-FPh | i-Pr | 3-CF$_3$Ph | H |
| 11-473 | 4-FPh | i-Pr | 4-CF$_3$Ph | H |
| 11-474 | 4-FPh | i-Pr | 2,3-F$_2$Ph | H |
| 11-475 | 4-FPh | i-Pr | 2,4-F$_2$Ph | H |
| 11-476 | 4-FPh | i-Pr | 2,5-F$_2$Ph | H |
| 11-477 | 4-FPh | i-Pr | 2,6-F$_2$Ph | H |
| 11-478 | 4-FPh | i-Pr | 2,3,4-F$_3$Ph | H |
| 11-479 | 4-FPh | i-Pr | 2,4,6-F$_3$Ph | H |
| 11-480 | 4-FPh | i-Pr | 2,3,5,6-F$_4$Ph | H |
| 11-481 | 4-FPh | i-Pr | 2,3,4,5,6-F$_5$Ph | H |
| 11-482 | 4-FPh | i-Pr | 2-Cl-4-FPh | H |
| 11-483 | 4-FPh | i-Pr | 2-F-4-ClPh | H |
| 11-484 | 4-FPh | i-Pr | 2-F-4-BrPh | H |
| 11-485 | 4-FPh | i-Pr | 2-Br-4-FPh | H |
| 11-486 | 4-FPh | i-Pr | 2-Cl-4-BrPh | H |
| 11-487 | 4-FPh | i-Pr | 2-Br-4-ClPh | H |
| 11-488 | 4-FPh | i-Pr | 2-Me-4-FPh | H |
| 11-489 | 4-FPh | i-Pr | 2-F-4-MePh | H |
| 11-490 | 4-FPh | i-Pr | 2-Me-4-ClPh | H |
| 11-491 | 4-FPh | i-Pr | 2-Cl-4-MePh | H |
| 11-492 | 4-FPh | i-Pr | 2-F-4-CF$_3$Ph | H |
| 11-493 | 4-FPh | i-Pr | 2-CF$_3$-4-FPh | H |
| 11-494 | 4-FPh | i-Pr | 2,3,5,6-F$_4$-4-CF$_3$Ph | H |
| 11-495 | 4-FPh | i-Pr | 2-Cl-4-CF$_3$Ph | H |
| 11-496 | 4-FPh | i-Pr | 2-CF$_3$-4-ClPh | H |
| 11-497 | 4-FPh | i-Pr | 2-Cl-4-CNPh | H |
| 11-498 | 4-FPh | i-Pr | 2-Cl-4-(SEt)Ph | H |
| 11-499 | 4-FPh | i-Pr | 2,4-F$_2$Ph | Me |
| 11-500 | 2-ClPh | Et | Et | H |
| 11-501 | 2-ClPh | i-Pr | Ph | H |
| 11-502 | 2-ClPh | i-Pr | 2-FPh | H |
| 11-503 | 2-ClPh | i-Pr | 3-FPh | H |
| 11-504 | 2-ClPh | i-Pr | 4-FPh | H |
| 11-505 | 2-ClPh | i-Pr | 2-ClPh | H |
| 11-506 | 2-ClPh | i-Pr | 3-ClPh | H |
| 11-507 | 2-ClPh | i-Pr | 4-ClPh | H |
| 11-508 | 2-ClPh | i-Pr | 2-CF$_3$Ph | H |
| 11-509 | 2-ClPh | i-Pr | 3-CF$_3$Ph | H |
| 11-510 | 2-ClPh | i-Pr | 4-CF$_3$Ph | H |
| 11-511 | 2-ClPh | i-Pr | 2,3-F$_2$Ph | H |
| 11-512 | 2-ClPh | i-Pr | 2,4-F$_2$Ph | H |
| 11-513 | 2-ClPh | i-Pr | 2,5-F$_2$Ph | H |
| 11-514 | 2-ClPh | i-Pr | 2,6-F$_2$Ph | H |
| 11-515 | 2-ClPh | i-Pr | 2,3,4-F$_3$Ph | H |
| 11-516 | 2-ClPh | i-Pr | 2,4,6-F$_3$Ph | H |
| 11-517 | 2-ClPh | i-Pr | 2,3,5,6-F$_4$Ph | H |
| 11-518 | 2-ClPh | i-Pr | 2,3,4,5,6-F$_5$Ph | H |
| 11-519 | 2-ClPh | i-Pr | 2-Cl-4-FPh | H |
| 11-520 | 2-ClPh | i-Pr | 2-F-4-ClPh | H |
| 11-521 | 2-ClPh | i-Pr | 2-F-4-BrPh | H |
| 11-522 | 2-ClPh | i-Pr | 2-Br-4-FPh | H |
| 11-523 | 2-ClPh | i-Pr | 2-Cl-4-BrPh | H |
| 11-524 | 2-ClPh | i-Pr | 2-Br-4-ClPh | H |
| 11-525 | 2-ClPh | i-Pr | 2-Me-4-FPh | H |
| 11-526 | 2-ClPh | i-Pr | 2-F-4-MePh | H |
| 11-527 | 2-ClPh | i-Pr | 2-Me-4-ClPh | H |
| 11-528 | 2-ClPh | i-Pr | 2-Cl-4-MePh | H |
| 11-529 | 2-ClPh | i-Pr | 2-F-4-CF$_3$Ph | H |
| 11-530 | 2-ClPh | i-Pr | 2-CF$_3$-4-FPh | H |
| 11-531 | 2-ClPh | i-Pr | 2,3,5,6-F$_4$-4-CF$_3$Ph | H |
| 11-532 | 2-ClPh | i-Pr | 2-Cl-4-CF$_3$Ph | H |
| 11-533 | 2-ClPh | i-Pr | 2-CF$_3$-4-ClPh | H |
| 11-534 | 2-ClPh | i-Pr | 2-Cl-4-CNPh | H |
| 11-535 | 2-ClPh | i-Pr | 2-Cl-4-(SEt)Ph | H |
| 11-536 | 2-ClPh | i-Pr | 5-Cl-2-Py | H |
| 11-537 | 2-ClPh | i-Pr | 2,4-F$_2$Ph | Me |
| 11-538 | 3-ClPh | Et | Et | H |
| 11-539 | 3-ClPh | i-Pr | Ph | H |
| 11-540 | 3-ClPh | i-Pr | 2-FPh | H |
| 11-541 | 3-ClPh | i-Pr | 3-FPh | H |
| 11-542 | 3-ClPh | i-Pr | 4-FPh | H |
| 11-543 | 3-ClPh | i-Pr | 2-ClPh | H |
| 11-544 | 3-ClPh | i-Pr | 3-ClPh | H |
| 11-545 | 3-ClPh | i-Pr | 4-ClPh | H |
| 11-546 | 3-ClPh | i-Pr | 2-CF$_3$Ph | H |

TABLE 2-continued

| No. | R11 | R12 | R13 | R14 |
|---|---|---|---|---|
| 11-547 | 3-ClPh | i-Pr | 3-CF$_3$Ph | H |
| 11-548 | 3-ClPh | i-Pr | 4-CF$_3$Ph | H |
| 11-549 | 3-ClPh | i-Pr | 2,3-F$_2$Ph | H |
| 11-550 | 3-ClPh | i-Pr | 2,4-F$_2$Ph | H |
| 11-551 | 3-ClPh | i-Pr | 2,5-F$_2$Ph | H |
| 11-552 | 3-ClPh | i-Pr | 2,6-F$_2$Ph | H |
| 11-553 | 3-ClPh | i-Pr | 2,3,4-F$_3$Ph | H |
| 11-554 | 3-ClPh | i-Pr | 2,4,6-F$_3$Ph | H |
| 11-555 | 3-ClPh | i-Pr | 2,3,5,6-F$_4$Ph | H |
| 11-556 | 3-ClPh | i-Pr | 2,3,4,5,6-F$_5$Ph | H |
| 11-557 | 3-ClPh | i-Pr | 2-Cl-4-FPh | H |
| 11-558 | 3-ClPh | i-Pr | 2-F-4-ClPh | H |
| 11-559 | 3-ClPh | i-Pr | 2-F-4-BrPh | H |
| 11-560 | 3-ClPh | i-Pr | 2-Br-4-FPh | H |
| 11-561 | 3-ClPh | i-Pr | 2-Cl-4-BrPh | H |
| 11-562 | 3-ClPh | i-Pr | 2-Br-4-ClPh | H |
| 11-563 | 3-ClPh | i-Pr | 2-Me-4-FPh | H |
| 11-564 | 3-ClPh | i-Pr | 2-F-4-MePh | H |
| 11-565 | 3-ClPh | i-Pr | 2-Me-4-ClPh | H |
| 11-566 | 3-ClPh | i-Pr | 2-Cl-4-MePh | H |
| 11-567 | 3-ClPh | i-Pr | 2-F-4-CF$_3$Ph | H |
| 11-568 | 3-ClPh | i-Pr | 2-CF$_3$-4-FPh | H |
| 11-569 | 3-ClPh | i-Pr | 2,3,5,6-F$_4$-4-CF$_3$Ph | H |
| 11-570 | 3-ClPh | i-Pr | 2-Cl-4-CF$_3$Ph | H |
| 11-571 | 3-ClPh | i-Pr | 2-CF$_3$-4-ClPh | H |
| 11-572 | 3-ClPh | i-Pr | 2-Cl-4-CNPh | H |
| 11-573 | 3-ClPh | i-Pr | 2-Cl-4-(SEt)Ph | H |
| 11-574 | 3-ClPh | i-Pr | 5-Cl-2-Py | H |
| 11-575 | 3-ClPh | i-Pr | 2,4-F$_2$Ph | Me |
| 11-576 | 4-ClPh | Et | Et | H |
| 11-577 | 4-ClPh | i-Pr | Ph | H |
| 11-578 | 4-ClPh | i-Pr | 2-FPh | H |
| 11-579 | 4-ClPh | i-Pr | 3-FPh | H |
| 11-580 | 4-ClPh | i-Pr | 4-FPh | H |
| 11-581 | 4-ClPh | i-Pr | 2-ClPh | H |
| 11-582 | 4-ClPh | i-Pr | 3-ClPh | H |
| 11-583 | 4-ClPh | i-Pr | 4-ClPh | H |
| 11-584 | 4-ClPh | i-Pr | 2-CF$_3$Ph | H |
| 11-585 | 4-ClPh | i-Pr | 3-CF$_3$Ph | H |
| 11-586 | 4-ClPh | i-Pr | 4-CF$_3$Ph | H |
| 11-587 | 4-ClPh | i-Pr | 2,3-F$_2$Ph | H |
| 11-588 | 4-ClPh | i-Pr | 2,4-F$_2$Ph | H |
| 11-589 | 4-ClPh | i-Pr | 2,5-F$_2$Ph | H |
| 11-590 | 4-ClPh | i-Pr | 2,6-F$_2$Ph | H |
| 11-591 | 4-ClPh | i-Pr | 2,3,4-F$_3$Ph | H |
| 11-592 | 4-ClPh | i-Pr | 2,4,6-F$_3$Ph | H |
| 11-593 | 4-ClPh | i-Pr | 2,3,5,6-F$_4$Ph | H |
| 11-594 | 4-ClPh | i-Pr | 2,3,4,5,6-F$_5$Ph | H |
| 11-595 | 4-ClPh | i-Pr | 2-Cl-4-FPh | H |
| 11-596 | 4-ClPh | i-Pr | 2-F-4-ClPh | H |
| 11-597 | 4-ClPh | i-Pr | 2-F-4-BrPh | H |
| 11-598 | 4-ClPh | i-Pr | 2-Br-4-FPh | H |
| 11-599 | 4-ClPh | i-Pr | 2-Cl-4-BrPh | H |
| 11-600 | 4-ClPh | i-Pr | 2-Br-4-ClPh | H |
| 11-601 | 4-ClPh | i-Pr | 2-Me-4-FPh | H |
| 11-602 | 4-ClPh | i-Pr | 2-F-4-MePh | H |
| 11-603 | 4-ClPh | i-Pr | 2-Me-4-ClPh | H |
| 11-604 | 4-ClPh | i-Pr | 2-Cl-4-MePh | H |
| 11-605 | 4-ClPh | i-Pr | 2-F-4-CF$_3$Ph | H |
| 11-606 | 4-ClPh | i-Pr | 2-CF$_3$-4-FPh | H |
| 11-607 | 4-ClPh | i-Pr | 2,3,5,6-F$_4$-4-CF$_3$Ph | H |
| 11-608 | 4-ClPh | i-Pr | 2-Cl-4-CF$_3$Ph | H |
| 11-609 | 4-ClPh | i-Pr | 2-CF$_3$-4-ClPh | H |
| 11-610 | 4-ClPh | i-Pr | 2-Cl-4-CNPh | H |
| 11-611 | 4-ClPh | i-Pr | 2-Cl-4-(SEt)Ph | H |
| 11-612 | 4-ClPh | i-Pr | 5-Cl-2-Py | H |
| 11-613 | 4-ClPh | i-Pr | 2,4-F$_2$Bn | H |
| 11-614 | 4-ClPh | i-Pr | 2,4-F$_2$Ph | Me |
| 11-615 | 4-BrPh | Et | Et | H |
| 11-616 | 4-BrPh | i-Pr | 2,4-F$_2$Ph | H |
| 11-617 | 2-CNPh | i-Pr | 2,4-F$_2$Ph | H |
| 11-618 | 4-CNPh | i-Pr | 2,4-F$_2$Ph | H |
| 11-619 | 2-NO$_2$Ph | Et | Et | H |
| 11-620 | 2-NO$_2$Ph | i-Pr | 2,4-F$_2$Ph | H |
| 11-621 | 4-NO$_2$Ph | i-Pr | 2,4-F$_2$Ph | H |
| 11-622 | 2-MePh | Et | Et | H |
| 11-623 | 2-MePh | i-Pr | 2,4-F$_2$Ph | H |
| 11-624 | 3-MePh | i-Pr | 2,4-F$_2$Ph | H |

TABLE 2-continued

| No. | $R^{11}$ | $R^{12}$ | $R^{13}$ | $R^{14}$ |
|---|---|---|---|---|
| 11-625 | 4-MePh | Et | Et | H |
| 11-626 | 4-MePh | i-Pr | Ph | H |
| 11-627 | 4-MePh | i-Pr | 2-FPh | H |
| 11-628 | 4-MePh | i-Pr | 3-FPh | H |
| 11-629 | 4-MePh | i-Pr | 4-FPh | H |
| 11-630 | 4-MePh | i-Pr | 2-ClPh | H |
| 11-631 | 4-MePh | i-Pr | 3-ClPh | H |
| 11-632 | 4-MePh | i-Pr | 4-ClPh | H |
| 11-633 | 4-MePh | i-Pr | 2-CF$_3$Ph | H |
| 11-634 | 4-MePh | i-Pr | 3-CF$_3$Ph | H |
| 11-635 | 4-MePh | i-Pr | 4-CF$_3$Ph | H |
| 11-636 | 4-MePh | i-Pr | 2,3-F$_2$Ph | H |
| 11-637 | 4-MePh | i-Pr | 2,4-F$_2$Ph | H |
| 11-638 | 4-MePh | i-Pr | 2,5-F$_2$Ph | H |
| 11-639 | 4-MePh | i-Pr | 2,6-F$_2$Ph | H |
| 11-640 | 4-MePh | i-Pr | 2,3,4-F$_3$Ph | H |
| 11-641 | 4-MePh | i-Pr | 2,4,6-F$_3$Ph | H |
| 11-642 | 4-MePh | i-Pr | 2,3,5,6-F$_4$Ph | H |
| 11-643 | 4-MePh | i-Pr | 2,3,4,5,6-F$_5$Ph | H |
| 11-644 | 4-MePh | i-Pr | 2-Cl-4-FPh | H |
| 11-645 | 4-MePh | i-Pr | 2-F-4-ClPh | H |
| 11-646 | 4-MePh | i-Pr | 2-F-4-BrPh | H |
| 11-647 | 4-MePh | i-Pr | 2-Br-4-FPh | H |
| 11-648 | 4-MePh | i-Pr | 2-Cl-4-BrPh | H |
| 11-649 | 4-MePh | i-Pr | 2-Br-4-ClPh | H |
| 11-650 | 4-MePh | i-Pr | 2-Me-4-FPh | H |
| 11-651 | 4-MePh | i-Pr | 2-F-4-MePh | H |
| 11-652 | 4-MePh | i-Pr | 2-Me-4-ClPh | H |
| 11-653 | 4-MePh | i-Pr | 2-Cl-4-MePh | H |
| 11-654 | 4-MePh | i-Pr | 2-F-4-CF$_3$Ph | H |
| 11-655 | 4-MePh | i-Pr | 2-CF$_3$-4-FPh | H |
| 11-656 | 4-MePh | i-Pr | 2,3,5,6-F$_4$-4-CF$_3$Ph | H |
| 11-657 | 4-MePh | i-Pr | 2-Cl-4-CF$_3$Ph | H |
| 11-658 | 4-MePh | i-Pr | 2-CF$_3$-4-ClPh | H |
| 11-659 | 4-MePh | i-Pr | 2-Cl-4-CNPh | H |
| 11-660 | 4-MePh | i-Pr | 2-Cl-4-(SEt)Ph | H |
| 11-661 | 4-MePh | i-Pr | 5-Cl-2-Py | H |
| 11-662 | 4-MePh | i-Pr | 2,4-F$_2$Bn | H |
| 11-663 | 4-MePh | i-Pr | 2,4-F$_2$Ph | Me |
| 11-664 | 2-EtPh | i-Pr | 2,4-F$_2$Ph | H |
| 11-665 | 4-EtPh | Et | Et | H |
| 11-666 | 4-EtPh | i-Pr | 2,4-F$_2$Ph | H |
| 11-667 | 2-(i-Pr)Ph | i-Pr | 2,4-F$_2$Ph | H |
| 11-668 | 4-(i-Pr)Ph | i-Pr | 2,4-F$_2$Ph | H |
| 11-669 | 2-(t-Bu)Ph | i-Pr | 2,4-F$_2$Ph | H |
| 11-670 | 4-(t-Bu)Ph | Et | Et | H |
| 11-671 | 4-(t-Bu)Ph | i-Pr | Ph | H |
| 11-672 | 4-(t-Bu)Ph | i-Pr | 2-FPh | H |
| 11-673 | 4-(t-Bu)Ph | i-Pr | 3-FPh | H |
| 11-674 | 4-(t-Bu)Ph | i-Pr | 4-FPh | H |
| 11-675 | 4-(t-Bu)Ph | i-Pr | 2-ClPh | H |
| 11-676 | 4-(t-Bu)Ph | i-Pr | 3-ClPh | H |
| 11-677 | 4-(t-Bu)Ph | i-Pr | 4-ClPh | H |
| 11-678 | 4-(t-Bu)Ph | i-Pr | 2-CF$_3$Ph | H |
| 11-679 | 4-(t-Bu)Ph | i-Pr | 3-CF$_3$Ph | H |
| 11-680 | 4-(t-Bu)Ph | i-Pr | 4-CF$_3$Ph | H |
| 11-681 | 4-(t-Bu)Ph | i-Pr | 2,3-F$_2$Ph | H |
| 11-682 | 4-(t-Bu)Ph | i-Pr | 2,4-F$_2$Ph | H |
| 11-683 | 4-(t-Bu)Ph | i-Pr | 2,5-F$_2$Ph | H |
| 11-684 | 4-(t-Bu)Ph | i-Pr | 2,6-F$_2$Ph | H |
| 11-685 | 4-(t-Bu)Ph | i-Pr | 2,3,4-F$_3$Ph | H |
| 11-686 | 4-(t-Bu)Ph | i-Pr | 2,4,6-F$_3$Ph | H |
| 11-687 | 4-(t-Bu)Ph | i-Pr | 2,3,5,6-F$_4$Ph | H |
| 11-688 | 4-(t-Bu)Ph | i-Pr | 2,3,4,5,6-F$_5$Ph | H |
| 11-689 | 4-(t-Bu)Ph | i-Pr | 2-Cl-4-FPh | H |
| 11-690 | 4-(t-Bu)Ph | i-Pr | 2-F-4-ClPh | H |
| 11-691 | 4-(t-Bu)Ph | i-Pr | 2-F-4-BrPh | H |
| 11-692 | 4-(t-Bu)Ph | i-Pr | 2-Br-4-FPh | H |
| 11-693 | 4-(t-Bu)Ph | i-Pr | 2-Cl-4-BrPh | H |
| 11-694 | 4-(t-Bu)Ph | i-Pr | 2-Br-4-ClPh | H |
| 11-695 | 4-(t-Bu)Ph | i-Pr | 2-Me-4-FPh | H |
| 11-696 | 4-(t-Bu)Ph | i-Pr | 2-F-4-MePh | H |
| 11-697 | 4-(t-Bu)Ph | i-Pr | 2-Me-4-ClPh | H |
| 11-698 | 4-(t-Bu)Ph | i-Pr | 2-Cl-4-MePh | H |
| 11-699 | 4-(t-Bu)Ph | i-Pr | 2-F-4-CF$_3$Ph | H |
| 11-700 | 4-(t-Bu)Ph | i-Pr | 2-CF$_3$-4-FPh | H |
| 11-701 | 4-(t-Bu)Ph | i-Pr | 2,3,5,6-F$_4$-4-CF$_3$Ph | H |
| 11-702 | 4-(t-Bu)Ph | i-Pr | 2-Cl-4-CF$_3$Ph | H |

TABLE 2-continued

| No. | R$^{11}$ | R$^{12}$ | R$^{13}$ | R$^{14}$ |
|---|---|---|---|---|
| 11-703 | 4-(t-Bu)Ph | i-Pr | 2-CF$_3$-4-ClPh | H |
| 11-704 | 4-(t-Bu)Ph | i-Pr | 2-Cl-4-CNPh | H |
| 11-705 | 4-(t-Bu)Ph | i-Pr | 2-Cl-4-(SEt)Ph | H |
| 11-706 | 4-(t-Bu)Ph | i-Pr | 5-Cl-2-Py | H |
| 11-707 | 4-(t-Bu)Ph | i-Pr | 2,6-Cl$_2$-3-Py | H |
| 11-708 | 4-(t-Bu)Ph | i-Pr | 2,4-F$_2$Bn | H |
| 11-709 | 4-(t-Bu)Ph | i-Pr | 2,4-F$_2$Ph | Me |
| 11-710 | 2-CF$_3$Ph | Et | Et | H |
| 11-711 | 2-CF$_3$Ph | i-Pr | 2,4-F$_2$Ph | H |
| 11-712 | 3-CF$_3$Ph | i-Pr | Ph | H |
| 11-713 | 3-CF$_3$Ph | i-Pr | 2-FPh | H |
| 11-714 | 3-CF$_3$Ph | i-Pr | 3-FPh | H |
| 11-715 | 3-CF$_3$Ph | i-Pr | 4-FPh | H |
| 11-716 | 3-CF$_3$Ph | i-Pr | 2-ClPh | H |
| 11-717 | 3-CF$_3$Ph | i-Pr | 3-ClPh | H |
| 11-718 | 3-CF$_3$Ph | i-Pr | 4-ClPh | H |
| 11-719 | 3-CF$_3$Ph | i-Pr | 2-CF$_3$Ph | H |
| 11-720 | 3-CF$_3$Ph | i-Pr | 3-CF$_3$Ph | H |
| 11-721 | 3-CF$_3$Ph | i-Pr | 4-CF$_3$Ph | H |
| 11-722 | 3-CF$_3$Ph | i-Pr | 2,3-F$_2$Ph | H |
| 11-723 | 3-CF$_3$Ph | i-Pr | 2,4-F$_2$Ph | H |
| 11-724 | 3-CF$_3$Ph | i-Pr | 2,5-F$_2$Ph | H |
| 11-725 | 3-CF$_3$Ph | i-Pr | 2,6-F$_2$Ph | H |
| 11-726 | 3-CF$_3$Ph | i-Pr | 2,3,4-F$_3$Ph | H |
| 11-727 | 3-CF$_3$Ph | i-Pr | 2,4,6-F$_3$Ph | H |
| 11-728 | 3-CF$_3$Ph | i-Pr | 2,3,5,6-F$_4$Ph | H |
| 11-729 | 3-CF$_3$Ph | i-Pr | 2,3,4,5,6-F$_5$Ph | H |
| 11-730 | 3-CF$_3$Ph | i-Pr | 2-Cl-4-FPh | H |
| 11-731 | 3-CF$_3$Ph | i-Pr | 2-F-4-ClPh | H |
| 11-732 | 3-CF$_3$Ph | i-Pr | 2-F-4-BrPh | H |
| 11-733 | 3-CF$_3$Ph | i-Pr | 2-Br-4-FPh | H |
| 11-734 | 3-CF$_3$Ph | i-Pr | 2-Cl-4-BrPh | H |
| 11-735 | 3-CF$_3$Ph | i-Pr | 2-Br-4-ClPh | H |
| 11-736 | 3-CF$_3$Ph | i-Pr | 2-Me-4-FPh | H |
| 11-737 | 3-CF$_3$Ph | i-Pr | 2-F-4-MePh | H |
| 11-738 | 3-CF$_3$Ph | i-Pr | 2-Me-4-ClPh | H |
| 11-739 | 3-CF$_3$Ph | i-Pr | 2-Cl-4-MePh | H |
| 11-740 | 3-CF$_3$Ph | i-Pr | 2-F-4-CF$_3$Ph | H |
| 11-741 | 3-CF$_3$Ph | i-Pr | 2-CF$_3$-4-FPh | H |
| 11-742 | 3-CF$_3$Ph | i-Pr | 2,3,5,6-F$_4$-4-CF$_3$Ph | H |
| 11-743 | 3-CF$_3$Ph | i-Pr | 2-Cl-4-CF$_3$Ph | H |
| 11-744 | 3-CF$_3$Ph | i-Pr | 2-CF$_3$-4-ClPh | H |
| 11-745 | 3-CF$_3$Ph | i-Pr | 2-Cl-4-CNPh | H |
| 11-746 | 3-CF$_3$Ph | i-Pr | 2-Cl-4-(SEt)Ph | H |
| 11-747 | 3-CF$_3$Ph | i-Pr | 2,4-F$_2$Ph | Me |
| 11-748 | 4-CF$_3$Ph | Et | Et | H |
| 11-749 | 4-CF$_3$Ph | i-Pr | 2,4-F$_2$Ph | H |
| 11-750 | 2-OMePh | i-Pr | 2,4-F$_2$Ph | H |
| 11-751 | 4-OMePh | i-Pr | 2,4-F$_2$Ph | H |
| 11-752 | 2-OCF$_3$Ph | i-Pr | 2,4-F$_2$Ph | H |
| 11-753 | 2-OCF$_3$Ph | i-Pr | 2,4-F$_2$Ph | H |
| 11-754 | 4-OCF$_3$Ph | i-Pr | 2,4-F$_2$Ph | H |
| 11-755 | 2-SMePh | i-Pr | 2,4-F$_2$Ph | H |
| 11-756 | 4-SMePh | i-Pr | 2,4-F$_2$Ph | H |
| 11-757 | 2-SCF$_3$Ph | i-Pr | 2,4-F$_2$Ph | H |
| 11-758 | 4-SCF$_3$Ph | i-Pr | 2,4-F$_2$Ph | H |
| 11-759 | 2,3-F$_2$Ph | i-Pr | 2,4-F$_2$Ph | H |
| 11-760 | 2,4-F$_2$Ph | i-Pr | 2,4-F$_2$Ph | H |
| 11-761 | 2,5-F$_2$Ph | i-Pr | 2,4-F$_2$Ph | H |
| 11-762 | 2,6-F$_2$Ph | i-Pr | Ph | H |
| 11-763 | 2,6-F$_2$Ph | i-Pr | 2-FPh | H |
| 11-764 | 2,6-F$_2$Ph | i-Pr | 3-FPh | H |
| 11-765 | 2,6-F$_2$Ph | i-Pr | 4-FPh | H |
| 11-766 | 2,6-F$_2$Ph | i-Pr | 2-ClPh | H |
| 11-767 | 2,6-F$_2$Ph | i-Pr | 3-ClPh | H |
| 11-768 | 2,6-F$_2$Ph | i-Pr | 4-ClPh | H |
| 11-769 | 2,6-F$_2$Ph | i-Pr | 2-CF$_3$Ph | H |
| 11-770 | 2,6-F$_2$Ph | i-Pr | 3-CF$_3$Ph | H |
| 11-771 | 2,6-F$_2$Ph | i-Pr | 4-CF$_3$Ph | H |
| 11-772 | 2,6-F$_2$Ph | i-Pr | 2,3-F$_2$Ph | H |
| 11-773 | 2,6-F$_2$Ph | i-Pr | 2,4-F$_2$Ph | H |
| 11-774 | 2,6-F$_2$Ph | i-Pr | 2,5-F$_2$Ph | H |
| 11-775 | 2,6-F$_2$Ph | i-Pr | 2,6-F$_2$Ph | H |
| 11-776 | 2,6-F$_2$Ph | i-Pr | 2,3,4-F$_3$Ph | H |
| 11-777 | 2,6-F$_2$Ph | i-Pr | 2,4,6-F$_3$Ph | H |
| 11-778 | 2,6-F$_2$Ph | i-Pr | 2,3,5,6-F$_4$Ph | H |
| 11-779 | 2,6-F$_2$Ph | i-Pr | 2,3,4,5,6-F$_5$Ph | H |
| 11-780 | 2,6-F$_2$Ph | i-Pr | 2-Cl-4-FPh | H |

TABLE 2-continued

| No. | R$^{11}$ | R$^{12}$ | R$^{13}$ | R$^{14}$ |
|---|---|---|---|---|
| 11-781 | 2,6-F$_2$Ph | i-Pr | 2-F-4-ClPh | H |
| 11-782 | 2,6-F$_2$Ph | i-Pr | 2-F-4-BrPh | H |
| 11-783 | 2,6-F$_2$Ph | i-Pr | 2-Br-4-FPh | H |
| 11-784 | 2,6-F$_2$Ph | i-Pr | 2-Cl-4-BrPh | H |
| 11-785 | 2,6-F$_2$Ph | i-Pr | 2-Br-4-ClPh | H |
| 11-786 | 2,6-F$_2$Ph | i-Pr | 2-Me-4-FPh | H |
| 11-787 | 2,6-F$_2$Ph | i-Pr | 2-F-4-MePh | H |
| 11-788 | 2,6-F$_2$Ph | i-Pr | 2-Me-4-ClPh | H |
| 11-789 | 2,6-F$_2$Ph | i-Pr | 2-Cl-4-MePh | H |
| 11-790 | 2,6-F$_2$Ph | i-Pr | 2-F-4-CF$_3$Ph | H |
| 11-791 | 2,6-F$_2$Ph | i-Pr | 2-CF$_3$-4-FPh | H |
| 11-792 | 2,6-F$_2$Ph | i-Pr | 2,3,5,6-F$_4$-4-CF$_3$Ph | H |
| 11-793 | 2,6-F$_2$Ph | i-Pr | 2-Cl-4-CF$_3$Ph | H |
| 11-794 | 2,6-F$_2$Ph | i-Pr | 2-CF$_3$-4-ClPh | H |
| 11-795 | 2,6-F$_2$Ph | i-Pr | 2-Cl-4-CNPh | H |
| 11-796 | 2,6-F$_2$Ph | i-Pr | 2-Cl-4-(SEt)Ph | H |
| 11-797 | 2,6-F$_2$Ph | i-Pr | 2,4-F$_2$Ph | Me |
| 11-798 | 3,4-F$_2$Ph | i-Pr | 2,4-F$_2$Ph | H |
| 11-799 | 3,5-F$_2$Ph | i-Pr | 2,4-F$_2$Ph | H |
| 11-800 | 2,3,4,5,6-F$_5$Ph | i-Pr | Ph | H |
| 11-801 | 2,3,4,5,6-F$_5$Ph | i-Pr | 2-FPh | H |
| 11-802 | 2,3,4,5,6-F$_5$Ph | i-Pr | 3-FPh | H |
| 11-803 | 2,3,4,5,6-F$_5$Ph | i-Pr | 4-FPh | H |
| 11-804 | 2,3,4,5,6-F$_5$Ph | i-Pr | 2-ClPh | H |
| 11-805 | 2,3,4,5,6-F$_5$Ph | i-Pr | 3-ClPh | H |
| 11-806 | 2,3,4,5,6-F$_5$Ph | i-Pr | 4-ClPh | H |
| 11-807 | 2,3,4,5,6-F$_5$Ph | i-Pr | 2-CF$_3$Ph | H |
| 11-808 | 2,3,4,5,6-F$_5$Ph | i-Pr | 3-CF$_3$Ph | H |
| 11-809 | 2,3,4,5,6-F$_5$Ph | i-Pr | 4-CF$_3$Ph | H |
| 11-810 | 2,3,4,5,6-F$_5$Ph | i-Pr | 2,3-F$_2$Ph | H |
| 11-811 | 2,3,4,5,6-F$_5$Ph | i-Pr | 2,4-F$_2$Ph | H |
| 11-812 | 2,3,4,5,6-F$_5$Ph | i-Pr | 2,5-F$_2$Ph | H |
| 11-813 | 2,3,4,5,6-F$_5$Ph | i-Pr | 2,6-F$_2$Ph | H |
| 11-814 | 2,3,4,5,6-F$_5$Ph | i-Pr | 2,3,4-F$_3$Ph | H |
| 11-815 | 2,3,4,5,6-F$_5$Ph | i-Pr | 2,4,6-F$_3$Ph | H |
| 11-816 | 2,3,4,5,6-F$_5$Ph | i-Pr | 2,3,5,6-F$_4$Ph | H |
| 11-817 | 2,3,4,5,6-F$_5$Ph | i-Pr | 2,3,4,5,6-F$_5$Ph | H |
| 11-818 | 2,3,4,5,6-F$_5$Ph | i-Pr | 2-Cl-4-FPh | H |
| 11-819 | 2,3,4,5,6-F$_5$Ph | i-Pr | 2-F-4-ClPh | H |
| 11-820 | 2,3,4,5,6-F$_5$Ph | i-Pr | 2-F-4-BrPh | H |
| 11-821 | 2,3,4,5,6-F$_5$Ph | i-Pr | 2-Br-4-FPh | H |
| 11-822 | 2,3,4,5,6-F$_5$Ph | i-Pr | 2-Cl-4-BrPh | H |
| 11-823 | 2,3,4,5,6-F$_5$Ph | i-Pr | 2-Br-4-ClPh | H |
| 11-824 | 2,3,4,5,6-F$_5$Ph | i-Pr | 2-Me-4-FPh | H |
| 11-825 | 2,3,4,5,6-F$_5$Ph | i-Pr | 2-F-4-MePh | H |
| 11-826 | 2,3,4,5,6-F$_5$Ph | i-Pr | 2-Me-4-ClPh | H |
| 11-827 | 2,3,4,5,6-F$_5$Ph | i-Pr | 2-Cl-4-MePh | H |
| 11-828 | 2,3,4,5,6-F$_5$Ph | i-Pr | 2-F-4-CF$_3$Ph | H |
| 11-829 | 2,3,4,5,6-F$_5$Ph | i-Pr | 2-CF$_3$-4-FPh | H |
| 11-830 | 2,3,4,5,6-F$_5$Ph | i-Pr | 2,3,5,6-F$_4$-4-CF$_3$Ph | H |
| 11-831 | 2,3,4,5,6-F$_5$Ph | i-Pr | 2-Cl-4-CF$_3$Ph | H |
| 11-832 | 2,3,4,5,6-F$_5$Ph | i-Pr | 2-CF$_3$-4-ClPh | H |
| 11-833 | 2,3,4,5,6-F$_5$Ph | i-Pr | 2-Cl-4-CNPh | H |
| 11-834 | 2,3,4,5,6-F$_5$Ph | i-Pr | 2-Cl-4-(SEt)Ph | H |
| 11-835 | 2,3,4,5,6-F$_5$Ph | i-Pr | 2,4-F$_2$Ph | Me |
| 11-836 | 2,3-Cl$_2$Ph | i-Pr | 2,4-F$_2$Ph | H |
| 11-837 | 2,4-Cl$_2$Ph | Et | Et | H |
| 11-838 | 2,4-Cl$_2$Ph | i-Pr | 2,4-F$_2$Ph | H |
| 11-839 | 2,5-Cl$_2$Ph | i-Pr | 2,4-F$_2$Ph | H |
| 11-840 | 2,6-Cl$_2$Ph | i-Pr | 2,4-F$_2$Ph | H |
| 11-841 | 3,4-Cl$_2$Ph | Et | Et | H |
| 11-842 | 3,4-Cl$_2$Ph | i-Pr | 2,4-F$_2$Ph | H |
| 11-843 | 3,5-Cl$_2$Ph | i-Pr | 2,4-F$_2$Ph | H |
| 11-844 | 2-Cl-4-FPh | i-Pr | 2,4-F$_2$Ph | H |
| 11-845 | 2-F-4-ClPh | i-Pr | 2,4-F$_2$Ph | H |
| 11-846 | 2,3-Me$_2$Ph | i-Pr | 2,4-F$_2$Ph | H |
| 11-847 | 2,4-Me$_2$Ph | i-Pr | 2,4-F$_2$Ph | H |
| 11-848 | 2,5-Me$_2$Ph | i-Pr | 2,4-F$_2$Ph | H |
| 11-849 | 2,6-Me$_2$Ph | i-Pr | 2,4-F$_2$Ph | H |
| 11-850 | 3,4-Me$_2$Ph | i-Pr | 2,4-F$_2$Ph | H |
| 11-851 | 3,5-Me$_2$Ph | i-Pr | 2,4-F$_2$Ph | H |
| 11-852 | 2,4,6-Me$_3$Ph | i-Pr | Ph | H |
| 11-853 | 2,4,6-Me$_3$Ph | i-Pr | 2-FPh | H |
| 11-854 | 2,4,6-Me$_3$Ph | i-Pr | 3-FPh | H |
| 11-855 | 2,4,6-Me$_3$Ph | i-Pr | 4-FPh | H |
| 11-856 | 2,4,6-Me$_3$Ph | i-Pr | 2-ClPh | H |
| 11-857 | 2,4,6-Me$_3$Ph | i-Pr | 3-ClPh | H |
| 11-858 | 2,4,6-Me$_3$Ph | i-Pr | 4-ClPh | H |

TABLE 2-continued

| No. | R11 | R12 | R13 | R14 |
|---|---|---|---|---|
| 11-859 | 2,4,6-Me3Ph | i-Pr | 2-CF3Ph | H |
| 11-860 | 2,4,6-Me3Ph | i-Pr | 3-CF3Ph | H |
| 11-861 | 2,4,6-Me3Ph | i-Pr | 4-CF3Ph | H |
| 11-862 | 2,4,6-Me3Ph | i-Pr | 2,3-F2Ph | H |
| 11-863 | 2,4,6-Me3Ph | i-Pr | 2,4-F2Ph | H |
| 11-864 | 2,4,6-Me3Ph | i-Pr | 2,5-F2Ph | H |
| 11-865 | 2,4,6-Me3Ph | i-Pr | 2,6-F2Ph | H |
| 11-866 | 2,4,6-Me3Ph | i-Pr | 2,3,4-F3Ph | H |
| 11-867 | 2,4,6-Me3Ph | i-Pr | 2,4,6-F3Ph | H |
| 11-868 | 2,4,6-Me3Ph | i-Pr | 2,3,5,6-F4Ph | H |
| 11-869 | 2,4,6-Me3Ph | i-Pr | 2,3,4,5,6-F5Ph | H |
| 11-870 | 2,4,6-Me3Ph | i-Pr | 2-Cl-4-FPh | H |
| 11-871 | 2,4,6-Me3Ph | i-Pr | 2-F-4-ClPh | H |
| 11-872 | 2,4,6-Me3Ph | i-Pr | 2-F-4-BrPh | H |
| 11-873 | 2,4,6-Me3Ph | i-Pr | 2-Br-4-FPh | H |
| 11-874 | 2,4,6-Me3Ph | i-Pr | 2-Cl-4-BrPh | H |
| 11-875 | 2,4,6-Me3Ph | i-Pr | 2-Br-4-ClPh | H |
| 11-876 | 2,4,6-Me3Ph | i-Pr | 2-Me-4-FPh | H |
| 11-877 | 2,4,6-Me3Ph | i-Pr | 2-F-4-MePh | H |
| 11-878 | 2,4,6-Me3Ph | i-Pr | 2-Me-4-ClPh | H |
| 11-879 | 2,4,6-Me3Ph | i-Pr | 2-Cl-4-MePh | H |
| 11-880 | 2,4,6-Me3Ph | i-Pr | 2-F-4-CF3Ph | H |
| 11-881 | 2,4,6-Me3Ph | i-Pr | 2-CF3-4-FPh | H |
| 11-882 | 2,4,6-Me3Ph | i-Pr | 2,3,5,6-F4-4-CF3Ph | H |
| 11-883 | 2,4,6-Me3Ph | i-Pr | 2-Cl-4-CF3Ph | H |
| 11-884 | 2,4,6-Me3Ph | i-Pr | 2-CF3-4-ClPh | H |
| 11-885 | 2,4,6-Me3Ph | i-Pr | 2-Cl-4-CNPh | H |
| 11-886 | 2,4,6-Me3Ph | i-Pr | 2-Cl-4-(SEt)Ph | H |
| 11-887 | 2,4,6-Me3Ph | i-Pr | 2,4-F2Bn | H |
| 11-888 | 2,4,6-Me3Ph | i-Pr | 3-Cl-2-Py | H |
| 11-889 | 2,4,6-Me3Ph | i-Pr | 5-Cl-2-Py | H |
| 11-890 | 2,4,6-Me3Ph | i-Pr | 3,5-Cl2-2-Py | H |
| 11-891 | 2,4,6-Me3Ph | i-Pr | 3-Cl-5-CF3-2-Py | H |
| 11-892 | 2,4,6-Me3Ph | i-Pr | 2-Cl-3-Py | H |
| 11-893 | 2,4,6-Me3Ph | i-Pr | 6-Cl-3-Py | H |
| 11-894 | 2,4,6-Me3Ph | i-Pr | 2,6-Cl2-3-Py | H |
| 11-895 | 2,4,6-Me3Ph | i-Pr | 5-Me-isoxazol-3-yl | H |
| 11-896 | 2,4,6-Me3Ph | i-Pr | 2,4-F2Ph | Me |
| 11-897 | 2,4,6-(i-Pr)3Ph | i-Pr | Ph | H |
| 11-898 | 2,4,6-(i-Pr)3Ph | i-Pr | 2-FPh | H |
| 11-899 | 2,4,6-(i-Pr)3Ph | i-Pr | 3-FPh | H |
| 11-900 | 2,4,6-(i-Pr)3Ph | i-Pr | 4-FPh | H |
| 11-901 | 2,4,6-(i-Pr)3Ph | i-Pr | 2-ClPh | H |
| 11-902 | 2,4,6-(i-Pr)3Ph | i-Pr | 3-ClPh | H |
| 11-903 | 2,4,6-(i-Pr)3Ph | i-Pr | 4-ClPh | H |
| 11-904 | 2,4,6-(i-Pr)3Ph | i-Pr | 2-CF3Ph | H |
| 11-905 | 2,4,6-(i-Pr)3Ph | i-Pr | 3-CF3Ph | H |
| 11-906 | 2,4,6-(i-Pr)3Ph | i-Pr | 4-CF3Ph | H |
| 11-907 | 2,4,6-(i-Pr)3Ph | i-Pr | 2,3-F2Ph | H |
| 11-908 | 2,4,6-(i-Pr)3Ph | i-Pr | 2,4-F2Ph | H |
| 11-909 | 2,4,6-(i-Pr)3Ph | i-Pr | 2,5-F2Ph | H |
| 11-910 | 2,4,6-(i-Pr)3Ph | i-Pr | 2,6-F2Ph | H |
| 11-911 | 2,4,6-(i-Pr)3Ph | i-Pr | 2,3,4-F3Ph | H |
| 11-912 | 2,4,6-(i-Pr)3Ph | i-Pr | 2,4,6-F3Ph | H |
| 11-913 | 2,4,6-(i-Pr)3Ph | i-Pr | 2,3,5,6-F4Ph | H |
| 11-914 | 2,4,6-(i-Pr)3Ph | i-Pr | 2,3,4,5,6-F5Ph | H |
| 11-915 | 2,4,6-(i-Pr)3Ph | i-Pr | 2-Cl-4-FPh | H |
| 11-916 | 2,4,6-(i-Pr)3Ph | i-Pr | 2-F-4-ClPh | H |
| 11-917 | 2,4,6-(i-Pr)3Ph | i-Pr | 2-F-4-BrPh | H |
| 11-918 | 2,4,6-(i-Pr)3Ph | i-Pr | 2-Br-4-FPh | H |
| 11-919 | 2,4,6-(i-Pr)3Ph | i-Pr | 2-Cl-4-BrPh | H |
| 11-920 | 2,4,6-(i-Pr)3Ph | i-Pr | 2-Br-4-ClPh | H |
| 11-921 | 2,4,6-(i-Pr)3Ph | i-Pr | 2-Me-4-FPh | H |
| 11-922 | 2,4,6-(i-Pr)3Ph | i-Pr | 2-F-4-MePh | H |
| 11-923 | 2,4,6-(i-Pr)3Ph | i-Pr | 2-Me-4-ClPh | H |
| 11-924 | 2,4,6-(i-Pr)3Ph | i-Pr | 2-Cl-4-MePh | H |
| 11-925 | 2,4,6-(i-Pr)3Ph | i-Pr | 2-F-4-CF3Ph | H |
| 11-926 | 2,4,6-(i-Pr)3Ph | i-Pr | 2-CF3-4-FPh | H |
| 11-927 | 2,4,6-(i-Pr)3Ph | i-Pr | 2,3,5,6-F4-4-CF3Ph | H |
| 11-928 | 2,4,6-(i-Pr)3Ph | i-Pr | 2-Cl-4-CF3Ph | H |
| 11-929 | 2,4,6-(i-Pr)3Ph | i-Pr | 2-CF3-4-ClPh | H |
| 11-930 | 2,4,6-(i-Pr)3Ph | i-Pr | 2-Cl-4-CNPh | H |
| 11-931 | 2,4,6-(i-Pr)3Ph | i-Pr | 2-Cl-4-(SEt)Ph | H |
| 11-932 | 2,4,6-(i-Pr)3Ph | i-Pr | 2,4-F2Ph | Me |
| 11-933 | Bn | i-Pr | Ph | H |
| 11-934 | Bn | i-Pr | 2-FPh | H |
| 11-935 | Bn | i-Pr | 3-FPh | H |
| 11-936 | Bn | i-Pr | 4-FPh | H |

TABLE 2-continued

| No. | $R^{11}$ | $R^{12}$ | $R^{13}$ | $R^{14}$ |
|---|---|---|---|---|
| 11-937 | Bn | i-Pr | 2-ClPh | H |
| 11-938 | Bn | i-Pr | 3-ClPh | H |
| 11-939 | Bn | i-Pr | 4-ClPh | H |
| 11-940 | Bn | i-Pr | 2-CF$_3$Ph | H |
| 11-941 | Bn | i-Pr | 3-CF$_3$Ph | H |
| 11-942 | Bn | i-Pr | 4-CF$_3$Ph | H |
| 11-943 | Bn | i-Pr | 2,3-F$_2$Ph | H |
| 11-944 | Bn | i-Pr | 2,4-F$_2$Ph | H |
| 11-945 | Bn | i-Pr | 2,5-F$_2$Ph | H |
| 11-946 | Bn | i-Pr | 2,6-F$_2$Ph | H |
| 11-947 | Bn | i-Pr | 2,3,4-F$_3$Ph | H |
| 11-948 | Bn | i-Pr | 2,4,6-F$_3$Ph | H |
| 11-949 | Bn | i-Pr | 2,3,5,6-F$_4$Ph | H |
| 11-950 | Bn | i-Pr | 2,3,4,5,6-F$_5$Ph | H |
| 11-951 | Bn | i-Pr | 2-Cl-4-FPh | H |
| 11-952 | Bn | i-Pr | 2-F-4-ClPh | H |
| 11-953 | Bn | i-Pr | 2-F-4-BrPh | H |
| 11-954 | Bn | i-Pr | 2-Br-4-FPh | H |
| 11-955 | Bn | i-Pr | 2-Cl-4-BrPh | H |
| 11-956 | Bn | i-Pr | 2-Br-4-ClPh | H |
| 11-957 | Bn | i-Pr | 2-Me-4-FPh | H |
| 11-958 | Bn | i-Pr | 2-F-4-MePh | H |
| 11-959 | Bn | i-Pr | 2-Me-4-ClPh | H |
| 11-960 | Bn | i-Pr | 2-Cl-4-MePh | H |
| 11-961 | Bn | i-Pr | 2-F-4-CF$_3$Ph | H |
| 11-962 | Bn | i-Pr | 2-CF$_3$-4-FPh | H |
| 11-963 | Bn | i-Pr | 2,3,5,6-F$_4$-4-CF$_3$Ph | H |
| 11-964 | Bn | i-Pr | 2-Cl-4-CF$_3$Ph | H |
| 11-965 | Bn | i-Pr | 2-CF$_3$-4-ClPh | H |
| 11-966 | Bn | i-Pr | 2-Cl-4-CNPh | H |
| 11-967 | Bn | i-Pr | 2-Cl-4-(SEt)Ph | H |
| 11-968 | Bn | i-Pr | 2,4-F$_2$Ph | Me |
| 11-969 | 4-FBn | i-Pr | 2,4-F$_2$Ph | H |
| 11-970 | 4-MeBn | i-Pr | 2,4-F$_2$Ph | H |
| 11-971 | 4-OMeBn | i-Pr | 2,4-F$_2$Ph | H |
| 11-972 | 2-Py | i-Pr | 2,4-F$_2$Ph | H |
| 11-973 | 3-Py | Et | Et | H |
| 11-974 | 3-Py | i-Pr | Ph | H |
| 11-975 | 3-Py | i-Pr | 2-FPh | H |
| 11-976 | 3-Py | i-Pr | 3-FPh | H |
| 11-977 | 3-Py | i-Pr | 4-FPh | H |
| 11-978 | 3-Py | i-Pr | 2-ClPh | H |
| 11-979 | 3-Py | i-Pr | 3-ClPh | H |
| 11-980 | 3-Py | i-Pr | 4-ClPh | H |
| 11-981 | 3-Py | i-Pr | 2-CF$_3$Ph | H |
| 11-982 | 3-Py | i-Pr | 3-CF$_3$Ph | H |
| 11-983 | 3-Py | i-Pr | 4-CF$_3$Ph | H |
| 11-984 | 3-Py | i-Pr | 2,3-F$_2$Ph | H |
| 11-985 | 3-Py | i-Pr | 2,4-F$_2$Ph | H |
| 11-986 | 3-Py | i-Pr | 2,5-F$_2$Ph | H |
| 11-987 | 3-Py | i-Pr | 2,6-F$_2$Ph | H |
| 11-988 | 3-Py | i-Pr | 2,3,4-F$_3$Ph | H |
| 11-989 | 3-Py | i-Pr | 2,4,6-F$_3$Ph | H |
| 11-990 | 3-Py | i-Pr | 2,3,5,6-F$_4$Ph | H |
| 11-991 | 3-Py | i-Pr | 2,3,4,5,6-F$_5$Ph | H |
| 11-992 | 3-Py | i-Pr | 2-Cl-4-FPh | H |
| 11-993 | 3-Py | i-Pr | 2-F-4-ClPh | H |
| 11-994 | 3-Py | i-Pr | 2-F-4-BrPh | H |
| 11-995 | 3-Py | i-Pr | 2-Br-4-FPh | H |
| 11-996 | 3-Py | i-Pr | 2-Cl-4-BrPh | H |
| 11-997 | 3-Py | i-Pr | 2-Br-4-ClPh | H |
| 11-998 | 3-Py | i-Pr | 2-Me-4-FPh | H |
| 11-999 | 3-Py | i-Pr | 2-F-4-MePh | H |
| 11-1000 | 3-Py | i-Pr | 2-Me-4-ClPh | H |
| 11-1001 | 3-Py | i-Pr | 2-Cl-4-MePh | H |
| 11-1002 | 3-Py | i-Pr | 2-F-4-CF$_3$Ph | H |
| 11-1003 | 3-Py | i-Pr | 2-CF$_3$-4-FPh | H |
| 11-1004 | 3-Py | i-Pr | 2,3,5,6-F$_4$-4-CF$_3$Ph | H |
| 11-1005 | 3-Py | i-Pr | 2-Cl-4-CF$_3$Ph | H |
| 11-1006 | 3-Py | i-Pr | 2-CF$_3$-4-ClPh | H |
| 11-1007 | 3-Py | i-Pr | 2-Cl-4-CNPh | H |
| 11-1008 | 3-Py | i-Pr | 2-Cl-4-(SEt)Ph | H |
| 11-1009 | 3-Py | i-Pr | 2,4-F$_2$Ph | Me |
| 11-1010 | 4-Py | i-Pr | 2,4-F$_2$Ph | H |
| 11-1011 | 2-thienyl | i-Pr | Ph | H |
| 11-1012 | 2-thienyl | i-Pr | 2-FPh | H |
| 11-1013 | 2-thienyl | i-Pr | 3-FPh | H |
| 11-1014 | 2-thienyl | i-Pr | 4-FPh | H |

TABLE 2-continued

| No. | R¹¹ | R¹² | R¹³ | R¹⁴ |
|---|---|---|---|---|
| 11-1015 | 2-thienyl | i-Pr | 2-ClPh | H |
| 11-1016 | 2-thienyl | i-Pr | 3-ClPh | H |
| 11-1017 | 2-thienyl | i-Pr | 4-ClPh | H |
| 11-1018 | 2-thienyl | i-Pr | 2-CF$_3$Ph | H |
| 11-1019 | 2-thienyl | i-Pr | 3-CF$_3$Ph | H |
| 11-1020 | 2-thienyl | i-Pr | 4-CF$_3$Ph | H |
| 11-1021 | 2-thienyl | i-Pr | 2,3-F$_2$Ph | H |
| 11-1022 | 2-thienyl | i-Pr | 2,4-F$_2$Ph | H |
| 11-1023 | 2-thienyl | i-Pr | 2,5-F$_2$Ph | H |
| 11-1024 | 2-thienyl | i-Pr | 2,6-F$_2$Ph | H |
| 11-1025 | 2-thienyl | i-Pr | 2,3,4-F$_3$Ph | H |
| 11-1026 | 2-thienyl | i-Pr | 2,4,6-F$_3$Ph | H |
| 11-1027 | 2-thienyl | i-Pr | 2,3,5,6-F$_4$Ph | H |
| 11-1028 | 2-thienyl | i-Pr | 2,3,4,5,6-F$_5$Ph | H |
| 11-1029 | 2-thienyl | i-Pr | 2-Cl-4-FPh | H |
| 11-1030 | 2-thienyl | i-Pr | 2-F-4-ClPh | H |
| 11-1031 | 2-thienyl | i-Pr | 2-F-4-BrPh | H |
| 11-1032 | 2-thienyl | i-Pr | 2-Br-4-FPh | H |
| 11-1033 | 2-thienyl | i-Pr | 2-Cl-4-BrPh | H |
| 11-1034 | 2-thienyl | i-Pr | 2-Br-4-ClPh | H |
| 11-1035 | 2-thienyl | i-Pr | 2-Me-4-FPh | H |
| 11-1036 | 2-thienyl | i-Pr | 2-F-4-MePh | H |
| 11-1037 | 2-thienyl | i-Pr | 2-Me-4-ClPh | H |
| 11-1038 | 2-thienyl | i-Pr | 2-Cl-4-MePh | H |
| 11-1039 | 2-thienyl | i-Pr | 2-F-4-CF$_3$Ph | H |
| 11-1040 | 2-thienyl | i-Pr | 2-CF$_3$-4-FPh | H |
| 11-1041 | 2-thienyl | i-Pr | 2,3,5,6-F$_4$-4-CF$_3$Ph | H |
| 11-1042 | 2-thienyl | i-Pr | 2-Cl-4-CF$_3$Ph | H |
| 11-1043 | 2-thienyl | i-Pr | 2-CF$_3$-4-ClPh | H |
| 11-1044 | 2-thienyl | i-Pr | 2-Cl-4-CNPh | H |
| 11-1045 | 2-thienyl | i-Pr | 2-Cl-4-(SEt)Ph | H |
| 11-1046 | 2-thienyl | i-Pr | 2,4-F$_2$Bn | H |
| 11-1047 | 2-thienyl | i-Pr | 2,4-F$_2$Ph | Me |
| 11-1048 | 3-thienyl | i-Pr | 2,4-F$_2$Ph | H |
| 11-1049 | 5-Br-2-thienyl | i-Pr | 2,4-F$_2$Ph | H |
| 11-1050 | 3-Me-2-thienyl | i-Pr | 2,4-F$_2$Ph | H |
| 11-1051 | NHMe | i-Pr | 2,4-F$_2$Ph | H |
| 11-1052 | NHEt | i-Pr | 2,4-F$_2$Ph | H |
| 11-1053 | NMe$_2$ | i-Pr | Ph | H |
| 11-1054 | NMe$_2$ | i-Pr | 2-FPh | H |
| 11-1055 | NMe$_2$ | i-Pr | 3-FPh | H |
| 11-1056 | NMe$_2$ | i-Pr | 4-FPh | H |
| 11-1057 | NMe$_2$ | i-Pr | 2-ClPh | H |
| 11-1058 | NMe$_2$ | i-Pr | 3-ClPh | H |
| 11-1059 | NMe$_2$ | i-Pr | 4-ClPh | H |
| 11-1060 | NMe$_2$ | i-Pr | 2-CF$_3$Ph | H |
| 11-1061 | NMe$_2$ | i-Pr | 3-CF$_3$Ph | H |
| 11-1062 | NMe$_2$ | i-Pr | 4-CF$_3$Ph | H |
| 11-1063 | NMe$_2$ | i-Pr | 2,3-F$_2$Ph | H |
| 11-1064 | NMe$_2$ | i-Pr | 2,4-F$_2$Ph | H |
| 11-1065 | NMe$_2$ | i-Pr | 2,5-F$_2$Ph | H |
| 11-1066 | NMe$_2$ | i-Pr | 2,6-F$_2$Ph | H |
| 11-1067 | NMe$_2$ | i-Pr | 2,3,4-F$_3$Ph | H |
| 11-1068 | NMe$_2$ | i-Pr | 2,4,6-F$_3$Ph | H |
| 11-1069 | NMe$_2$ | i-Pr | 2,3,5,6-F$_4$Ph | H |
| 11-1070 | NMe$_2$ | i-Pr | 2,3,4,5,6-F$_5$Ph | H |
| 11-1071 | NMe$_2$ | i-Pr | 2-Cl-4-FPh | H |
| 11-1072 | NMe$_2$ | i-Pr | 2-F-4-ClPh | H |
| 11-1073 | NMe$_2$ | i-Pr | 2-F-4-BrPh | H |
| 11-1074 | NMe$_2$ | i-Pr | 2-Br-4-FPh | H |
| 11-1075 | NMe$_2$ | i-Pr | 2-Cl-4-BrPh | H |
| 11-1076 | NMe$_2$ | i-Pr | 2-Br-4-ClPh | H |
| 11-1077 | NMe$_2$ | i-Pr | 2-Me-4-FPh | H |
| 11-1078 | NMe$_2$ | i-Pr | 2-F-4-MePh | H |
| 11-1079 | NMe$_2$ | i-Pr | 2-Me-4-ClPh | H |
| 11-1080 | NMe$_2$ | i-Pr | 2-Cl-4-MePh | H |
| 11-1081 | NMe$_2$ | i-Pr | 2-F-4-CF$_3$Ph | H |
| 11-1082 | NMe$_2$ | i-Pr | 2-CF$_3$-4-FPh | H |
| 11-1083 | NMe$_2$ | i-Pr | 2,3,5,6-F$_4$-4-CF$_3$Ph | H |
| 11-1084 | NMe$_2$ | i-Pr | 2-Cl-4-CF$_3$Ph | H |
| 11-1085 | NMe$_2$ | i-Pr | 2-CF$_3$-4-ClPh | H |
| 11-1086 | NMe$_2$ | i-Pr | 2-Cl-4-CNPh | H |
| 11-1087 | NMe$_2$ | i-Pr | 2-Cl-4-(SEt)Ph | H |
| 11-1088 | NMe$_2$ | i-Pr | 2,4-F$_2$Bn | H |
| 11-1089 | NMe$_2$ | i-Pr | 3-Cl-2-Py | H |
| 11-1090 | NMe$_2$ | i-Pr | 5-Cl-2-Py | H |
| 11-1091 | NMe$_2$ | i-Pr | 3,5-Cl$_2$-2-Py | H |
| 11-1092 | NMe$_2$ | i-Pr | 3-Cl-5-CF$_3$-2-Py | H |

TABLE 2-continued

| No. | R11 | R12 | R13 | R14 |
|---|---|---|---|---|
| 11-1093 | NMe2 | i-Pr | 2-Cl-3-Py | H |
| 11-1094 | NMe2 | i-Pr | 6-Cl-3-Py | H |
| 11-1095 | NMe2 | i-Pr | 2,6-Cl2-3-Py | H |
| 11-1096 | NMe2 | i-Pr | 5-Me-isoxazol-3-yl | H |
| 11-1097 | NMe2 | i-Pr | 2,4-F2Ph | Me |
| 11-1098 | N(Me)Et | i-Pr | 2,4-F2Ph | H |
| 11-1099 | NEt2 | i-Pr | 2,4-F2Ph | H |
| 11-1100 | N(Me)i-Pr | i-Pr | 2,4-F2Ph | H |
| 11-1101 | N(Me)i-Bu | i-Pr | 2,4-F2Ph | H |
| 11-1102 | 1-piperidinyl | i-Pr | 2,4-F2Ph | H |
| 11-1103 | 3-tetrahydropyranyl | i-Pr | 2,4-F2Ph | H |
| 11-1104 | 4-tetrahydropyranyl | i-Pr | Ph | H |
| 11-1105 | 4-tetrahydropyranyl | i-Pr | 2-FPh | H |
| 11-1106 | 4-tetrahydropyranyl | i-Pr | 3-FPh | H |
| 11-1107 | 4-tetrahydropyranyl | i-Pr | 4-FPh | H |
| 11-1108 | 4-tetrahydropyranyl | i-Pr | 2,3-F2Ph | H |
| 11-1109 | 4-tetrahydropyranyl | i-Pr | 2,4-F2Ph | H |
| 11-1110 | 4-tetrahydropyranyl | i-Pr | 2,5-F2Ph | H |
| 11-1111 | 4-tetrahydropyranyl | i-Pr | 2,6-F2Ph | H |
| 11-1112 | 4-tetrahydropyranyl | i-Pr | 2-Cl-4-FPh | H |
| 11-1113 | 4-tetrahydropyranyl | i-Pr | 2-F-4-ClPh | H |
| 11-1114 | 4-tetrahydropyranyl | i-Pr | 2-F-4-MePh | H |
| 11-1115 | 4-tetrahydropyranyl | i-Pr | 2-Me-4-ClPh | H |
| 11-1116 | 4-tetrahydropyranyl | i-Pr | 2-F-4-CF3Ph | H |
| 11-1117 | 4-tetrahydropyranyl | i-Pr | 2-CF3-4-FPh | H |
| 11-1118 | 4-tetrahydropyranyl | i-Pr | 2,4-F2Ph | Me |
| 11-1119 | 2-tetrahydrofuryl | i-Pr | 2,4-F2Ph | H |
| 11-1120 | 3-tetrahydrofuryl | i-Pr | 2,4-F2Ph | H |
| 11-1121 | 3-tetrahydropyranylmethyl | i-Pr | 2,4-F2Ph | H |
| 11-1122 | 4-tetrahydropyranylmethyl | i-Pr | 2,4-F2Ph | H |
| 11-1123 | 2-tetrahydrofurfuryl | i-Pr | 2,4-F2Ph | H |
| 11-1124 | 3-tetrahydrofurfuryl | i-Pr | 2,4-F2Ph | H |
| 11-1125 | Me | Me | 2,4-F2Ph | H |
| 11-1126 | Et | Me | 2,4-F2Ph | H |
| 11-1127 | i-Pr | Me | 2,4-F2Ph | H |
| 11-1128 | CH2Cl | Me | 2,4-F2Ph | H |
| 11-1129 | c-Hex | Me | 2,4-F2Ph | H |
| 11-1130 | NMe2 | Me | 2,4-F2Ph | H |
| 11-1131 | 4-MePh | Me | 2,4-F2Ph | H |
| 11-1132 | 2-ClPh | Me | 2,4-F2Ph | H |
| 11-1133 | 3-ClPh | Me | 2,4-F2Ph | H |
| 11-1134 | 4-ClPh | Me | 2,4-F2Ph | H |
| 11-1135 | 2-FPh | Me | 2,4-F2Ph | H |
| 11-1136 | 3-FPh | Me | 2,4-F2Ph | H |
| 11-1137 | 4-FPh | Me | 2,4-F2Ph | H |
| 11-1138 | 2,6-F2Ph | Me | 2,4-F2Ph | H |
| 11-1139 | 2,3,4,5,6-F5Ph | Me | 2,4-F2Ph | H |
| 11-1140 | 2,4,6-Me3Ph | Me | 2,4-F2Ph | H |
| 11-1141 | 4-(t-Bu)Ph | Me | 2,4-F2Ph | H |
| 11-1142 | 2,4,6-(i-Pr)3Ph | Me | 2,4-F2Ph | H |
| 11-1143 | 4-OMePh | Me | 2,4-F2Ph | H |
| 11-1144 | 3-CF3Ph | Me | 2,4-F2Ph | H |
| 11-1145 | Bn | Me | 2,4-F2Ph | H |
| 11-1146 | 3-Py | Me | 2,4-F2Ph | H |
| 11-1147 | 2-thienyl | Me | 2,4-F2Ph | H |
| 11-1148 | Et | i-Pr | 2,3-F2Ph | H |
| 11-1149 | 4-OMePh | i-Pr | 2,3-F2Ph | H |
| 11-1150 | Et | i-Pr | 2,6-F2Ph | H |
| 11-1151 | 4-OMePh | i-Pr | 2,6-F2Ph | H |
| 11-1152 | Et | i-Pr | 2,3,4-F3Ph | H |
| 11-1153 | 4-OMePh | i-Pr | 2,3,4-F3Ph | H |
| 11-1154 | Et | i-Pr | 2,4,6-F3Ph | H |
| 11-1155 | 4-OMePh | i-Pr | 2,4,6-F3Ph | H |
| 11-1156 | c-Hex | CH2CF3 | 2,4-F2Ph | H |
| 11-1157 | 2,4,6-Me3Ph | CH2CF3 | 2,4-F2Ph | H |
| 11-1158 | c-Pr | i-Pr | 2,4-F2Ph | t-Bu |

Although the production method of the 4-(N,N-disubstituted carbamoyl)1-(substituted sulfonyl)triazolin-5-one derivative (11) of the present invention is described in detail below, but the present invention is not limited to these methods. In this connection, as for the reactor, other than a magnetic stirrer or a mechanical stirrer, a reaction using a microwave synthesizer is also possible.

[Production Method 11]

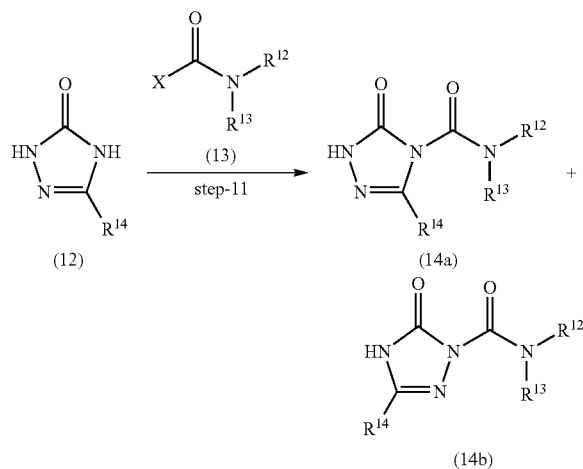

($R^{12}$, $R^{13}$ an $R^{14}$ have the same meanings as above, and $X^1$ represents a halogen atom).

Step-11 is a step of reacting a triazolin-5-one derivative represented by formula (12) with a halogenated N,N-disubstituted carbamoyl derivative represented by formula (13), in some cases in the presence of a base, to produce a 4-(N,N-disubstituted carbamoyl)triazolin-5-one derivative (14a). The triazolin-5-one derivative represented by formula (12) and the halogenated N,N-disubstituted carbamoyl derivative represented by formula (13) are known in some cases and are available from Tokyo Chemical Industry Co., Ltd., etc. Alternatively, these can also be easily produced from available reagents according to a known method described in *Lectures on Experimental Chemistry* issued on Jan. 31, 2007, by Maruzen Publishing Co., Ltd., *Organic Syntheses* issued on Apr. 24, 2017, by John Wiley & Sons, Inc., etc.

This reaction may be performed in the presence of a base. As the base, for example, an organic base such as triethylamine, diisopropyl ethyl amine, tributylamine, N-methylmorpholine, N,N-dimethylaniline, N,N-di ethylaniline, 4-tert-butyl-N,N-dimethylaniline, pyridine, picoline and lutidine, and alkali metal salt such as sodium carbonate, potassium carbonate, cesium carbonate sodium hydrogencarbonate potassium hydrogencarbonate, sodium acetate, potassium acetate, sodium methoxide, sodium ethoxide, potassium-tert-butoxide, sodium hydride, potassium hydride, sodium amide, butyllithium, tert-butyllithium, lithium diisopropylamide, trimethylsilyl lithium and lithium hexamethyldisilazide can be used. Among these bases, a metal base such as potassium carbonate and cesium carbonate is preferred in view of good yield. The reaction is performed using the base in an amount of 0.1 to 5 equivalents relative to the substrate, and a target compound can thereby be obtained in good yield. The reaction substrate (13) is used usually in an amount of 0.1 to 5 equivalents relative to the substrate (12).

This reaction is preferably conducted in the presence of a solvent. As the solvent used, a solvent which does not adversely affect the reaction can be used, and an aromatic hydrocarbon-based solvent such as benzene, toluene, xylene and chlorobenzene, an aliphatic hydrocarbon-based solvent such as pentane, hexane and octane, an ether-based solvent such as diethyl ether, diisopropyl ether, cyclopentylmethyl ether, tetrahydrofuran, dimethoxyethane and 1,4-dioxane, a ketone-based solvent such as acetone, methyl ethyl ketone and cyclohexanone, a halogen-based solvent such as chloroform and dichloromethane, a nitrile-based solvent such as acetonitrile and propionitrile, an ester-based solvent such as ethyl acetate, propyl acetate, butyl acetate and methyl propionate, an amide-based solvent such as N,N-dimethylformamide, N,N-dimethylacetamide and N-methylpyrrolidone, an alcohol-based solvent such as methanol, ethanol, 1-propanol, 2-propanol and tert-butanol, dimethylsulfoxide, water, or a mixed solvent thereof may be used. Furthermore, in order to promote the progress of the reaction, a phase transfer catalyst such as quaternary ammonium salt may also be added.

The reaction can be performed at a temperature appropriately selected from the range of −78° C. to 200° C., although this varies depending on reaction conditions. After the completion of the reaction, although a target compound can be obtained by a normal post-treatment operation, in this step, a compound (14b) is sometimes produced as a by-product. If desired, purification by column chromatography or recrystallization, etc. may also be performed to isolate a 4-(N,N-disubstituted carbamoyl)triazolin-5-one derivative (14a).

[Production Method 12]

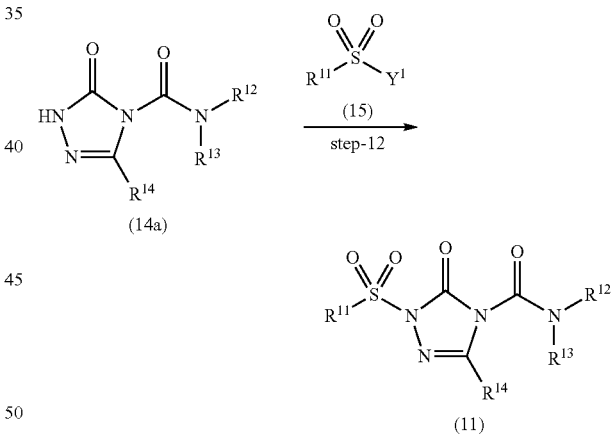

($R^{11}$, $R^{12}$, $R^{13}$ and $R^{14}$ have the same meanings as above, and Y represents a leaving group such as halogen atom, methanesulfonyloxy group, trifluoromethanesulfonyloxy group and toluenesulfonyloxy group).

Step-12 is a step of reacting a 4-(N,N-disubstituted carbamoyl)triazolin-5-one derivative represented by formula (14a) with a sulfonyl compound represented by formula (15), in some cases in the presence of a base, to produce a 4-(N,N-disubstituted carbamoyl)1-(substituted sulfonyl)triazolin-5-one derivative.

This reaction may be performed in the presence of a base. As the base, for example, an organic base such as triethylamine, diisopropylethylamine, tributylamine, N-methylmorpholine, N,N-dimethylaniline, N,N-diethylaniline, 4-tert-butyl-N,N-dimethylaniline, pyridine, picoline and lutidine, and an alkali metal salt such as sodium carbonate, potassium carbonate, cesium carbonate, sodium hydrogencarbonate, potassium hydrogencarbonate, sodium acetate, potassium acetate, sodium methoxide, sodium ethoxide, potassium-tert-butoxide, sodium hydride, potassium hydride, sodium amide, butyllithium, tert-butyllithium, lithium diisopropylamide, trimethylsilyl lithium and lithium hexamethyldisilazide can be used. The reaction is performed using the base in an amount of 0.1 to 5 equivalents relative to the substrate, and a target compound can thereby be obtained in good yield. The reaction substrate (15) is used usually in an amount of 1 to 5 equivalents relative to the substrate (14a).

This reaction is preferably conducted in a solvent. As the solvent, a solvent which does not adversely affect the reaction can be used, and an aromatic hydrocarbon-based solvent such as benzene, toluene, xylene and chlorobenzene, an aliphatic hydrocarbon-based solvent such as pentane, hexane and octane, an ether-based solvent such as diethyl ether, diisopropyl ether, cyclopentylmethyl ether, tetrahydrofuran, dimethoxyethane and 1,4-dioxane, a ketone-based solvent such as acetone, methyl ethyl ketone and cyclohexanone, a halogen-based solvent such as chloroform and dichloromethane, a nitrile-based solvent such as acetonitrile and propionitrile, an ester-based solvent such as ethyl acetate, propyl acetate, butyl acetate and methyl propionate, an amide-based solvent such as N,N-dimethylformamide, N,N-dimethylacetamide and N-methylpyrrolidone, an alcohol-based solvent such as methanol, ethanol, 1-propanol, 2-propanol and tert-butanol, dimethylsulfoxide, water, or a mixed solvent thereof may be used.

The reaction can be performed at a temperature appropriately selected from the range of −78° C. to 200° C., although this varies depending on the base used or the reaction conditions. After the completion of the reaction, a target compound can be obtained by a normal post-treatment operation, and, if desired, purification by column chromatography or recrystallization, etc. may also be performed.

[Production Method 13]

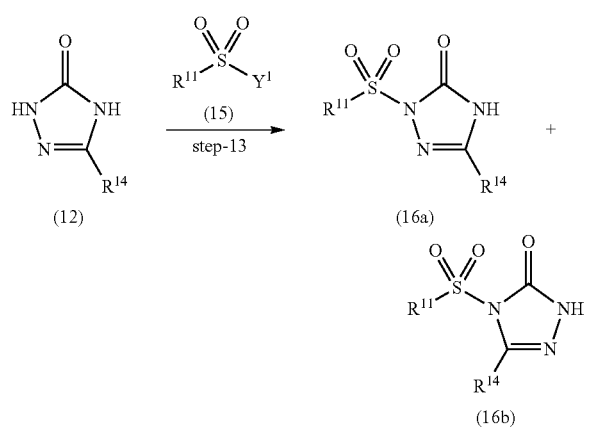

($R^{11}$, $R^{14}$, and $Y^1$ have the same meanings as above).

Step-13 is a step of reacting a triazolin-5-one derivative represented by formula (12) with a sulfonyl compound represented by formula (15), in some cases in the presence of a base, to produce a 1-(substituted sulfonyl)triazolin-5-one derivative (16a).

This reaction may be performed in the presence of a base. As the base, for example, an organic base such as triethylamine, diisopropylethylamine, tributylamine, N-methylmorpholine, N,N-dimethylaniline, N,N-diethylaniline, 4-tert-butyl-N,N-dimethylaniline, pyridine, picoline and lutidine, and an alkali metal salt such as sodium carbonate, potassium carbonate, sodium hydrogencarbonate, potassium hydrogencarbonate, sodium acetate, potassium acetate, sodium methoxide, sodium ethoxide, potassium-tert-butoxide, sodium hydride, potassium hydride, sodium amide, butyllithium, tert-butyllithium, lithium diisopropylamide, trimethylsilyl lithium and lithium hexamethyldisilazide can be used. The reaction is performed using the base in an amount of 0.1 to 5 equivalents relative to the substrate, and a target compound can thereby be obtained in good yield. The reaction substrate (15) is used usually in an amount of 1 to 5 equivalents relative to the substrate (12).

This reaction is preferably conducted in a solvent. As the solvent, a solvent which does not adversely affect the reaction can be used, and an aromatic hydrocarbon-based solvent such as benzene, toluene, xylene and chlorobenzene, an aliphatic hydrocarbon-based solvent such as pentane, hexane and octane, an ether-based solvent such as diethyl ether, diisopropyl ether, cyclopentylmethyl ether, tetrahydrofuran, dimethoxyethane and 1,4-dioxane, a ketone-based solvent such as acetone, methyl ethyl ketone and cyclohexanone, a halogen-based solvent such as chloroform and dichloromethane, a nitrile-based solvent such as acetonitrile and propionitrile, an ester-based solvent such as ethyl acetate, propyl acetate, butyl acetate and methyl propionate, an amide-based solvent such as N,N-dimethylformamide, N,N-dimethylacetamide and N-methylpyrrolidone, an alcohol-based solvent such as methanol, ethanol, 1-propanol, 2-propanol and tert-butanol, dimethylsulfoxide, water, or a mixed solvent thereof may be used.

The reaction can be performed at a temperature appropriately selected from the range of −78° C. to 200° C., although this varies depending on the reaction conditions. After the completion of the reaction, although a target compound can be obtained by a normal post-treatment operation, in this step, a compound (16b) is sometimes produced as a by-product. If desired, purification by column chromatography or recrystallization, etc. may also be performed to isolate a 1-(substituted sulfonyl)triazolin-5-one derivative (16a).

[Production Method 14]

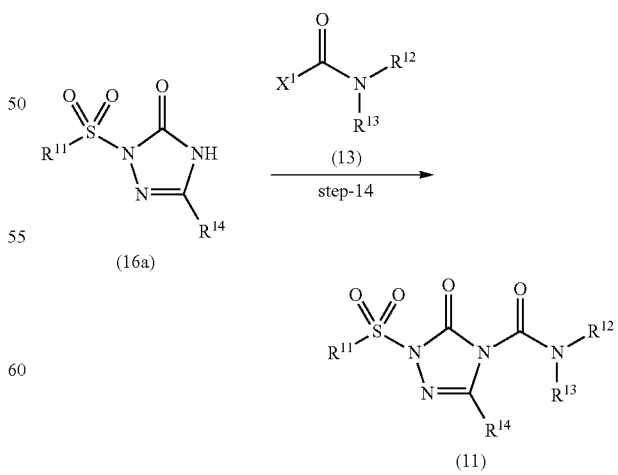

($R^{11}$, $R^{12}$, $R^{13}$, $R^{14}$, and $X^1$ have the same meanings as above).

Step-14 is a step of reacting a 1-(substituted sulfonyl)triazolin-5-one derivative represented by formula (16a) with a halogenated disubstituted carbamoyl derivative represented by formula (13), in some cases in the presence of a base, to produce a 4-(N,N-disubstituted carbamoyl)1-(substituted sulfonyl)triazolin-5-one derivative (11).

This reaction may be performed in the presence of a base. As the base, for example, an organic base such as triethylamine, diisopropylethylamine, tributylamine, N-methylmorpholine, N,N-dimethylaniline, N,N-diethylaniline, 4-tert-butyl-N,N-dimethylaniline, pyridine, picoline and lutidine, and an alkali metal salt such as sodium carbonate, potassium carbonate, sodium hydrogencarbonate, potassium hydrogencarbonate, sodium acetate, potassium acetate, sodium methoxide, sodium ethoxide, potassium-tert-butoxide, sodium hydride, potassium hydride, sodium amide, butyllithium, tert-butyllithium, lithium diisopropylamide, trimethylsilyl lithium and lithium hexamethyldisilazide can be used. The reaction is performed using the base in an amount of 0.1 to 5 equivalents relative to the substrate, and a target compound can thereby be obtained in good yield. The reaction substrate (13) is used usually in an amount of 1 to 5 equivalents relative to the substrate (16a).

This reaction is preferably conducted in a solvent. As the solvent, a solvent which does not adversely affect the reaction can be used, and an aromatic hydrocarbon-based solvent such as benzene, toluene, xylene and chlorobenzene, an aliphatic hydrocarbon-based solvent such as pentane, hexane and octane, an ether-based solvent such as diethyl ether, diisopropyl ether, cyclopentylmethyl ether, tetrahydrofuran, dimethoxyethane and 1,4-dioxane, a ketone-based solvent such as acetone, methyl ethyl ketone and cyclohexanone, a halogen-based solvent such as chloroform and dichloromethane, a nitrile-based solvent such as acetonitrile and propionitrile, an ester-based solvent such as ethyl acetate, propyl acetate, butyl acetate and methyl propionate, an amide-based solvent such as N,N-dimethylformamide, N,N-dimethylacetamide and N-methylpyrrolidone, an alcohol-based solvent such as methanol, ethanol, 1-propanol, 2-propanol and tert-butanol, dimethylsulfoxide, water, or a mixed solvent thereof may be used.

The reaction can be performed at a temperature appropriately selected from the range of −78° C. to 200° C., although this varies depending on the base used or the reaction conditions. After the completion of the reaction, a target compound can be obtained by a normal post-treatment operation, and, if desired, purification by column chromatography or recrystallization, etc. may also be performed.

The compound represented by formula (11) of the present invention can be analyzed, confirmed and identified by the melting point, infrared absorption spectrum, $^1$H-NMR, $^{13}$C-NMR, mass spectrometry, X-ray structural analysis, etc. as needed.

In this connection, the compound represented by formula (11) of the present invention is not limited to the above-described production methods and can be produced by any organic synthesis technique.

The compound represented by formula (1) and the compound represented by formula (11) of the present invention (hereinafter, sometimes referred to as the "compound of the present invention") exhibit an excellent herbicidal activity as demonstrated in the later-described Test Examples as well as an excellent selective herbicidal activity between weeds and crops shown below. Therefore, they can be used for a wide range of objects such as weeds in paddy fields and upland fields. Specific examples of the weed include the followings.

Specifically, the compounds can control various noxious weeds, for example, gramineae such as *Echinochloa crusgalli, Echinochloa* oryzicola, crabgrass (Difitaria *sanguinalis, Digitaria ischaem, Digitaria adscendens, Digitaria microbachne, Digitaria horizontalis*), *Setaria Viridis, Setaria faberi, Setaria lutescens, Eleusine indica, Avena fatua, Sorghum halepense, Aropyron repens, Brachiaria plantaginea, Panicum maximum, Panicum purpurascens, Panicum dichotomiflorum, Leptochloa chinensis, Leptochloa panicea, Poa annua, Alopecurus aequalis, Alopecurus myosuroides, Avena spica-venti, Agropyron tsukushiense, Brachiaria platyphylla, Cenchrus echinatus, Lolium multiflorum, Cynodon dactylon, Beckmannia syzigache, Bromus catharticus, Leersia japonica, Leersia sayanuka, Lolium rigidum, Paspalum distichum* and *Phleum pratense*; cyperaceae such as *Cyperus iria, Cyperus rotundus, Cyperus esculentus, Scirpus hotarui, Cyperus serotinus, Cyperus serotinus, Eleocharis acicularis, Eleocharis kuroguwai, Cyperus flaccidus, Kyllinga brevifolia* and *Scirpus* juncoides; alismataceae such as *Sagittaria pygmaea, Sagittaria trifolia* and *Alisma canaliculatum*; pontderiaceae such as *Monochoria vaginalis, Heteranthera limosa* and *Monochoria kosakowii*; linderniaceae such as *Lindernia pyxidaria*; plantaginaceae such as *Plantago asiatica, Gratiola japonica, Dopatrium junceum* and *Veronica polita*; lythraceae such as *Rotala india, Ammannia multiflora* and *Rotala indica*; elatinaceae such as *Elatine triandra*; malvaceae such as *Abutiol theophrsti* and *Sida spinosa*; compositae such as *Xanthium* strumarim, *Ambrosia elatior, Breea serosa, Galinsoga ciliata, Matricaria chamomilla, Taraxacum officinale, Erigeron Canadensis, Bidens frondosa, Bidens pilosa, Bidens tripartita*, Gnaphalium affine and *Senecio vulgaris*; lamiaceae such as *Lamium* amplexinale weber; solanaceae such as *Solanum nigrum* and *Datura stramonium*; amarathaceae such as *Amaranthus viridis, Chenopodium album, Kochia scoparia* and *Amaranthus hybridus*; polygonaceeae such as *Polygonum lapathifolium, Polygonum persicaria, Polygonum convolvulus, Polygonum aviculare, Persicaria longiseta* and *Persicaria nepalensis*; crpurea such as *Cardamine flexuosa, Capsella bursapastoris, Brassica juncea* and *Rorippa* indica; convolvulaceae such as *Ipomoea purpurea, Convolvulus arvensis, Ipomoea hederacea, Calystegia pubescens* and *Ipomoea coccinea*; portulacaceae such as portulacaceae; fabaceae such as *Cassia obtusifolia, Aeschynomene indica, Sesbania exaltata, Trifolium repens* and *Vicia sativa*; carypha *australis* such as *Stellaria media, Stellaria neglecta* and *Stellaria uliginosa*; euphoribiaceae such as *Euphorbia helioscopia* and Acalypha *australis*; commelinaceae such as *Commelina communis* and *Murdannia keisak*; potamogetonaceae such as *Potamogeton distinctus*; araceae such as *Spirodela polyrhiza*; cucurbitaceae such as *Sicyos angulatus*; rubiaceae such as *Galium spurium*; apiaceae such as *Oenanthe javanica*; violaceae such as Viola mandshuria; onagraceae such as *Ludwigia* epilobioides and *Oenothera odorata*); oxalidaceae such as Oxalis *corniculata*; equisetaceae such as Equisetum *arvense*; and zygnemataceae such as Spirogyra sp. Accordingly, they are effectively used, for example, in the case of selectively controlling noxious weeds or non-selectively controlling noxious weeds in the cultivation of useful crops such as *Oryza sativa* L., *Zea mays, Glycine max, Gossypium* spp., *Triticum* spp., *Hordeum Vulgare*, Secalecereale, *Avena sativa, Sorghum bicolor, Brassica napus, Helianthus annuus, Beta Vulgaris, Saccharum officinarum, Zoysia japonicaa, Arachis hypogaea, Linum usitatissmum, Nicotiana tabacum* and *Coffea* spp.

Note that the application of the herbicide of the present invention is not limited to the above-exemplified grasses and crops.

The compound of the present invention may be mixed with, if desired, at the time of formulation or spraying, other herbicides, various insecticides, acaricides, nematicides, fungicides (mildewcide, bactericide, antiviral agent, plant resistance inducing agent), bird repellents, plant growth regulators, safeners, fertilizers, soil conditioners, synergists, etc. to provide a mixed formulation or may be mixed and applied as a tankmix at the time of spraying.

In particular, by the use and application in combination with other herbicide, it is possible not only to reduce the dose of the herbicide used and achieve labor-saving but also to expect spreading of an application target (a herbicidal spectrum) due to the cooperative action of both agents and furthermore, realization of more enhanced effect due to the synergistic action of both agents. At this time, a plurality of known herbicides or safeners may also be combined and blended.

Out of the above-described optional ingredients, although representative examples of the herbicide are shown below, the present invention is not limited thereto.

(1) A compound believed to exhibit a herbicidal effect by disturbing hormone activities of plants, for example, a phenoxy-based compound such as 2,4-D, 2,4-D-butotyl, 2,4-D-butyl, 2,4-D-dimethylammonimum, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, 2,4-D choline salt, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl, mecoprop-P-potassium, naproanilide, clomeprop and HIA-1; an aromatic carboxylic acid-based compound such as 2,3,6-TBA, dicamba, dicamba-butotyl, dicamba-diglycolamine, dicamba-dimethylammonium, dicamba-diolamine, dicamba-isopropylammonium, dicamba-potassium, dicamba-sodium, picloram, picloram-dimethylammonium, picloram-isoctyl, picloram-potassium, picloram-triisopropanolammonium, picloram-triisopropylammonium, picloram-trolamine, tricolopyr, tricolopyr-butotyl, tricolopyr-triethylammonium, clopyralid, clopyralid-olamine, clopyralid-potassium, clopyralid-triisopropanolammonium, aminopyralid, aminocyclopyrachlor, aminocyclopyrachlor, halauxifen, florpyrauxifen, halauxifen-methyl and DAS-534; and others including naptalam, naptalam-sodium, benazolin, benazolin-ethyl, quinclorac, quinmerac, diflufenzopyr, diflufenzopyr-sodium, fluroxypyr, fluroxypyr-2-butoxy-1-methylethyl, fluroxypyr-meptyl, chlorflurenol, chlorflurenol-methyl, and clacyfos.

(2) A compound believed to exhibit a herbicidal effect by inhibiting the photosynthesis of plants, for example, a urea-based compound such as chlorotoluron, diuron, fluometuron, linuron, isoproturon, metobenzuron, tebuthiuron, dimefuron, isouron, karbutilate, methabenztiazuron, metoxuron, metobromuron, monolinuron, neburon, siduron, terbumeton and trietazine; triazine-based compound such as simazine, atrazine, atratone, simetryn, prometryn, dimethametryn, hexazinone, metribuzin, terbuthylazine, cyanazine, ametryn, cybutryne, terbutryn, propazine, metamitron and prometon; a uracil-based compound such as bromacil, bromacil-lithium, lenacil and terbacil; an anilide-based compound such as propanil and cypromid; a carbamate-based compound such as swep, desmedipham and phenmedipham; a hydroxybenzonitrile-based compound such as bromoxynil, bromoxynil-octanoate, bromoxynil-heptanoate, ioxynil, ioxynil-octanoate, ioxynil-potassium and ioxynil-sodium; and others including pyridate, bentazone, bentazone-sodium, amicarbazone, methazole, pentanochlor and phenmedipham.

(3) A quaternary ammonium salt-based compound such as paraquat and diquat, which is believed to show rapid herbicidal efficacy by being converted to a free radical by itself in the plant body and forming an active oxygen.

(4) A compound believed to exhibit a herbicidal effect by inhibiting chlorophyll biosynthesis of plants and abnormally accumulating a photosensitizing peroxide substance in the plant body, for example, a diphenylether-based compound such as nitrofen, chlomethoxyfen, bifenox, acifluorfen, acifluorfen-sodium, fomesafen, fomesafen-sodium, oxyfluorfen, lactofen, aclonifen, ethoxyfen-ethyl, fluoroglycofen-ethyl and fluoroglycofen; a cyclic imide-based compound such as chlorphthalim, flumioxazin, flumiclorac, flumiclorac-pentyl, cinidon-ethyl, fluthiacet-methyl and EK-5385; and others including oxadiargyl, oxadiazon, sulfentrazone, carfentrazone-ethyl, thidiazimin, pentoxazone, azafenidin, isopropazole, pyraflufen-ethyl, benzfendizone, butafenacil, saflufenacil, fluazolate, profluazol, flufenpyr-ethyl, bencarbazone, tiafenacil, pyrachlonil, trifludimoxazin, HNPC-B4047, IR-6396, EK-5498, SYN-523 and compounds described in WO2008/008763 (FMC).

(5) A compound believed to exhibit a herbicidal effect characterized by bleaching activities by inhibiting pigment biosynthesis of carotenoid etc. in plants, for example, a pyridazinone-based compound such as norflurazon, chloridazon and metflurazon; a pyrazole-based compound such as pyrazolynate, pyrazoxyfen, benzofenap, topramezone, pyrasulfotole and tolpyralate; and others including amitrole, fluridone, flurtamone, diflufenican, methoxyphenone, clomazone, bixlozone, sulcotrione, mesotrione, tembotrione, tefuryltrione, fenquinotrione, lancotrione, cyclopyrimorate, isoxaflutole, difenzoquat, difenzoquat-metilsulfate, isoxachlortole, benzobicyclon, bicyclopyron, picolinafen, beflubutamid, ketospiradox, ketospiradox-potassium and compounds described in JP2012/2571 (Sumitomo Chemical Co., Ltd.)

(6) A compound believed to exhibit a herbicidal effect on plants by inhibiting fatty acid biosynthesis, for example, an aryloxyphenoxypropionic acid-based compound such as diclofop-methyl, dichlorprop, pyriphenop-sodium, fluazifop-butyl, fluazifop, fluazifop-P, fluazifop-P-butyl, haloxyfop, haloxyfop-etotyl, haloxyfop-P, haloxyfop-P-methyl, quizalofop-ethyl, quizalofop-P, quizalofop-P-ethyl, quizalofop-P-tefuryl, cyhalofop-butyl, fenoxaprop-ethyl, fenoxaprop-P, fenoxaprop-P-ethyl, metamifop-propyl, metamifop, clodinafop-propargyl, propaquizafop, HNPC-A8169 and SYP-1924; a cyclohexanedione-based compound such as alloxydim-sodium, alloxydim, clethodim, sethoxydim, tralkoxydim, butroxydim, tepraloxydim, profoxydim and cycloxydim; a phenylpyrazoline-based compound such as pinoxaden; etc.

(7) A compound believed to exhibit a herbicidal effect by inhibiting amino acid biosynthesis of plants, for example, a sulfonium urea compound such as chlorimuron-ethyl, chlorimuron, sulfometuron-methyl, sulfometuron, primisulfuron-methyl, primisulfuron, bensulfuron-methyl, bensulfuron, chlorsulfuron, metsulfuron-methyl, metsulfuron, cinosulfuron, pyrazosulfuron-ethyl, pyrazosulfuron, flazasulfuron, rimsulfuron, nicosulfuron, imazosulfuron, flucetosulfuron, flazasufuron, cyclosulfamuron, prosulfuron, flupyrsulfuron-methyl-sodium, flupyrsulfuron, triflusulfuron, flupyrsulfuron-methyl-sodium, flupyrsulfuron, triflusulfuron-methyl, triflusulfuron, halosulfuron-methyl, halosulfuron, thifensulfuron-methyl, thifensulfuron, ethoxysulfuron, oxasulfuron, ethametsulfuron, ethametsulfuron-methyl, iodosulfuron, iodosulfuron-methyl-sodium, sulfosulfuron, triasulfuron, tribenuron-methyl, tribenuron, tritosulfuron, foramsulfuron, trifloxysulfuron, trifloxysulfuron-sodium, mesosulfuron-metthyl, mesosulfuron, orthosulfamuron, amidosulfuron, azimsulfuron, propyrisulfuron, metazosulfuron, methiopyrsulfuron, monosulfuron-methyl, orsosulfuron, iofensulfuron and iofensulfuron-sodium; a triazolopyrimidinesulfonamide-based compound such as flumetsulam, metosulam, diclosulam, cloransulam-methyl, florasulam, penoxsulam and pyroxsulam; an imidazolinone-based compound such as imazapyr, imazapyr-isopropylammonium, imazethapyr, imazethapyr-ammonium, imazaquin, imazaquin-ammonium, imazamox, imazamox-ammonium, imazamethabenz, imazamethabenz-methyl and imazapic; a pyrimidinylsalicylic acid-based compound such as pyrithiobac-sodium, bispyribac-sodium, pyriminobac-methyl, pyribenzoxim, pyriftalid, pyrimisulfan and triafamone; a sulfonylaminocarbonyltriazolinone-based compound such as flucarbazone, flucarbazone-sodium, propoxycarbazone-sodium, propoxycarbazone and thiencarbazone-methyl; and others including glyphosate, glyphosate-sodium, glyphosate-potassium, glyphosate-ammonium, glyphosate-isopropylammonium, glyphosate-trimesium, glyphosate-sesquisodim, glufosinate, glufosinate-ammonium, glufosinate-P, glufosinate-P-ammonium, glufosinate-P-sodium, bilanafos, and bilanafos-sodium.

(8) A compound believed to exhibit a herbicidal effect by inhibiting a cell mitosis of plants, for example, a dinitroaniline-based compound such as trifluralin, oryzalin, nitralin, pendimethalin, ethalfluralin, benfluralin, prodiamine, butralin and dinitramine; an amide-based compound such as bensulide, napropamide, napropamide-M, propyzamide and pronamide; an organic phosphorus-based compound such as amiprofos-methyl, butamifos, anilofos and piperophos; a phenyl carbamate-based compound such as propham, chlorpropham, barban and carbetamide; a cumylamine-based compound such as daimuron, cumyluron, bromobutide and methyldymron; and others including asulam, asulam-sodium, dithiopyr, thiazopyr, chlorthal-dimethyl, chlorthal, diphenamid, flamprop-M-methyl, flamprop-M, and flamprop-M-isopropyl.

(9) A compound believed to exhibit a herbicidal effect by inhibiting protein biosynthesis or lipid biosynthesis of plants, for example, a chloroacetamide-based compound such as alachlor, metazachlor, butachlor, pretilachlor, metolachlor, S-metolachlor, thenylchlor, pethoxamid, acetochlor, propachlor, dimethenamide, dimethenamide-P, propisochlor and dimethachlor; a thiocarbamate-based compound such as molinate, dimepiperate, pyributicarb, EPTC, butylate, vernolate, cycloate, prosulfocarb, esprocarb, thiobencarb, diallate, tri-allate and orbencarb; and others including etobenzanid, mefenacet, flufenacet, tridiphane, cafenstrole, fentrazamide, ipfencarbazone, oxaziclomefone, indanofan, benfuresate, pyroxasulfone, fenoxasulfone, methiozolin, dalapon, dalapon-sodium, TCA-sodium, and trichloroacetic acid.

(10) A compound believed to exhibit a herbicidal effect by inhibiting cellulose biosynthesis of plants, such as dichlobenil, triaziflam, indaziflam, flupoxam and isoxaben.

(11) Other herbicides, such as MSMA, DSMA, CMA, endothall, endothall-dipotassium, endothall-sodium, endothall-mono(N,N-dimethylalkylammonium), ethofumesate, cinmethylin, sodium chlorate, pelargonic acid, nonanoic acid, fosamine, fosamine-ammonium, acrolein, ammonium sulfamate, borax, chloroacetic acid, sodium chloroacetate, cyanamide, methylarsonic acid, dimethylarsinic acid, sodium dimethylarsinate, dinoterb, dinoterb-ammonium, dinoterb-diolamine, dinoterb-acetate, DNOC, ferrous sulfate, flupropanate, flupropanate-sodium, mefluidide, mefluidide-diolamine, metam, metam-ammonium, metam-potassium, metam-sodium, methyl isothiocyanate, pentachlorophenol, sodium pentachlorophenoxide, pentachlorophenol laurate, quinoclamine, sulfuric acid, urea sulfate, zanthinosin, herbimycin, unguinol, metatyrosine, sarmentine, thaxtomin A, mevalocidin, alpha-limonene, pyribambenz-propyl, pyribambenz-isopropyl, JS-913, KHG-23844, H-9201, SIOC-0163, SIOC-0171, SIOC-0172, SIOC-0285, SIOC-0426, SIOC-H-057, ZJ-0166, ZJ-1835, ZJ-0453, ZJ-0777, ZJ-0862 and compounds described in WO2008/096398 (KUMIAI CHEMICAL INDUSTRY CO., LTD.).

(12) Those believed to exhibit a herbicidal effect by being parasitic on plants, such as *Xanthomonas campestris Epicoccosirus nematosorus, Epicoccosirus nematosperus, Exserohilum monoseras* and *Drechsrela monoceras*.

In using the compound of the present invention as a herbicide, the compound may be used as it is or after being formulated. At the time of formulation, an appropriate carrier, adjuvant, surfactant, binder, stabilizer, etc. described in *Pesticide Formulation Guide* (edited by: Pesticide Science Society of Japan, Agricultural Formulation and Application Committee, issued by: Japan Plant Protection Association, 1997) may also be blended.

The herbicide containing the compound of the present invention can be formulated into any form that is generally employed as a form of the herbicide. For example, although the herbicide can be used in the form of granule, microgranule, fine granule, wettable powder, water-dispersible granule (dry flowable) formulation, emulsifiable concentrate, soluble powder, sol (flowable) formulation, liquid formulation, dust, coarse dust, DL (driftless type) dust, flow dust, oil solution, microcapsule, paste, jumbo formulation, etc., the present invention is not limited thereto.

As the carrier used in the formulation, as long as it is a carrier conventionally used in general for the pesticide formulation, either a solid carrier or a liquid carrier may be used. Although the carrier is not limited to specific carries, specifically, includes the followings. The solid carrier includes, for example, a mineral powder (e.g., kaolin, bentonite, clay, montmorillonite, talc, diatomaceous earth, mica, vermiculite, quartz, calcium carbonate, phosphorite, white carbon, slaked lime, silica sand, acid white clay, zeolite, sepiolite, pulverized expanded perlite, silas balloon, alumina balloon, phenol resin, epoxy resin, a microsphere formed of polyacrylonitrile, polyurethane, etc.), a vegetable powder (e.g., soybean flour, wheat flour, wood meal, tobacco powder, starch, crystalline cellulose), a macromolecular compound (e.g., petroleum resin, polyvinyl chloride, ketone resin), alumina, silicates, glucose, sucrose, lactose, a sugar polymer, ammonium sulfate, sodium chloride, potassium chloride, urea, high-dispersible silicic acid, and waxes.

The liquid carrier includes, for example, water, alcohols (e.g., methyl alcohol, ethyl alcohol, n-propyl alcohol, isopropyl alcohol, butanol, ethylene glycol, benzyl alcohol), aromatic hydrocarbons (e.g., toluene, benzene, xylene, ethylbenzene, methylnaphthalene), ethers (e.g., ethyl ether, ethylene oxide, dioxane, tetrahydrofuran), ketones (e.g., acetone, methyl ethyl ketone, cyclohexanone, methyl isobutyl ketone, isophorone), esters (e.g., ethyl acetate, butyl acetate, ethylene glycol acetate, amyl acetate), acid amides (e.g., dimethylformamide, dimethylacetamide), nitriles (e.g., acetonitrile, propionitrile, acrylonitrile), sulfoxides (e.g., dimethylsulfoxide), alcohol ethers (e.g., ethylene glycol monomethyl ether, ethylene glycol monoethyl ether), aliphatic and alicyclic hydrocarbons (e.g., n-hexane, cyclohexane), industrial gasoline (e.g., petroleum ether, solvent naphtha), and petroleum fractions (e.g., paraffins, kerosene, gas oil).

In addition, in the case of formulating the herbicide as an emulsifiable concentrate, wettable powder, flowable formulation, etc., various kinds of surfactants are blended for the purpose of emulsification, dispersion, solubilization, wetting, foaming, lubrication, spreading, etc. Although the surfactant includes, for example, a nonionic surfactant such as polyoxyethylene alkyl ether, polyoxyethylene alkyl ester, polyoxyethylene sorbitan alkyl ester, polyoxyethylene alkylaryl ether, polyoxyethylene polyoxypropylene block copolymer and polyoxyethylene styrylphenyl ether, an anionic surfactant such as alkylbenzene sulfonate, alkyl sulfosuccinate, alkylsulfate, polyoxyethylene alkylsulfate, aryl sulfonate, alkylnaphthalene sulfonate, polyoxyethylene styrylphenyl ether sulfate, lignin sulfonate, naphthalenesulfonic acid-formaldehyde condensate and polycarboxylate, a cationic surfactant such as alkylamines (e.g., laurylamine, stearyl trimethyl ammonium chloride), polyoxyethylene alkylamines, alkylpyridinium salt, alkyltrimethylammonium salt and alkyldimethylammonium salt, and an amphoteric surfactant such as carboxylic acid (betaine type) and sulfuric ester salt, the present invention is not limited to these examples.

Other than those described above, various adjuvants, additives, etc. such as polyvinyl alcohol (PVA), carboxymethyl cellulose (CMC), gum arabic, polyvinyl acetate, sodium alginate, gelatin, tragacanth gum, dextrin, hydroxypropylmethyl cellulose (HPMC) and methyl cellulose (MC) can be used.

The preferable method for using a herbicide containing the compound of the present invention as an active ingredient includes a soil treatment, a water surface treatment, a foliage treatment, etc., and a particularly excellent effect can be achieved by application before germination and up to the time of plumule of weeds to be controlled.

Although the application rate of the compound of the present invention as a herbicide differs depending on an application situation, an application time, an application method, a target weed, a cultivated crop, etc., in general, as the amount of the active ingredient, it is suitably on the order of 0.001 to 10 Kg, and preferably on the order of 0.01 to 1 Kg, per hectare (ha).

EXAMPLES

Although the present invention is described more specifically below by referring to Synthesis Examples, Formulation Examples and Test Examples of the compound of the present invention, the present invention is not limited thereto.

Synthesis Example 1

Synthesis of 4-cyclopropylsulfonyl-N-(2,4-difluorophenyl)-N-isopropyl-5-oxo-1,2,4-triazole-1-carboxamide (1-150)

Cesium carbonate (693 mg, 2.13 mmol) and cyclopropanesulfonyl chloride (299 mg, 2.13 mmol) were added to an N,N-dimethylformamide solution (5 ml) of N-(2,4-difluorophenyl)-N-isopropyl-5-oxo-4H-1,2,4-triazole-1-carboxamie (500 mg, 1.77 mmol), and the solution was stirred at room temperature (25° C.) for 2 hours. Water was poured in the reaction mixture, and the resulting solution was extracted with ethyl acetate. The extract was washed with saturated brine, dried with anhydrous sodium sulfate and then concentrated under reduced pressure. The concentrate was purified by silica gel column chromatography (eluting solvent: ethyl acetate/n-hexane=1/2) to obtain the title compound (yielded: 400 mg, yield: 58%) as a white solid.

The $^1$H NMR spectrum (CDCl$_3$) σ (ppm) value, melting point (° C.), etc. of the compounds according to the present invention produced based on this Synthesis Example and the Production Methods above are shown in Table 3. The $^1$H NMR data was measured by JNM-ECS400 Spectrometer (manufactured by JEOL Ltd.).

TABLE 3

| No. | Physical Properties (mp. ° C.) | Shape | $^1$HNMR Spectrum σ ppm: |
|---|---|---|---|
| 1-1 | 81.7-85.3 | solid | |
| 1-3 | 134-143 | solid | |
| 1-13 | 143-145 | solid | 7.61(1H, s), 7.28-7.22(1H, m), 6.91-6.85(2H, m), 4.70-4.63(1H, m), 3.36(3H, s), 1.27-1.21(6H, m). |
| 1-20 | | amorphous | |
| 1-27 | | amorphous | |
| 1-29 | 144-149 | solid | |
| 1-35 | | solid | |
| 1-38 | | amorphous | |
| 1-39 | | oil | |
| 1-45 | 165-168 | solid | |
| 1-46 | 153-160 | solid | |
| 1-49 | | oil | |
| 1-50 | | oil | |
| 1-51 | | oil | |
| 1-52 | | oil | |
| 1-53 | | oil | 8.51(1H, s), 3.83-3.73(1H, m), 3.47-3.36(4H, m), 1.43(6H, d, 8.0 Hz), 1.29-1.20(6H, m). |

TABLE 3-continued

| No. | Physical Properties (mp. ° C.) | Shape | ¹HNMR Spectrum σ ppm: |
|---|---|---|---|
| 1-54 | 92-94 | solid | |
| 1-55 | | oil | |
| 1-65 | 105-107 | oil | 7.58(1H, s), 7.30-7.24(1H, m), 6.90-6.84(2H, m), 4.70-4.63(1H, m), 3.81-3.74(1H, m), 1.34-1.17(12H, m). |
| 1-72 | | amorphous | |
| 1-73 | | oil | |
| 1-79 | | amorphous | |
| 1-81 | | oil | |
| 1-87 | | oil | |
| 1-90 | | oil | |
| 1-91 | | oil | |
| 1-93 | | oil | |
| 1-97 | | oil | |
| 1-98 | | oil | |
| 1-99 | | oil | |
| 1-101 | | gum | |
| 1-102 | | oil | |
| 1-103 | | oil | |
| 1-107 | | oil | |
| 1-117 | | oil | |
| 1-131 | | amorphous | |
| 1-139 | | oil | |
| 1-142 | 112-114 | solid | 7.60(1H, s), 7.30-7.22(1H, m), 6.87(2H, t, 8.0 Hz), 6.77-6.65(2H, m), 6.36(1H, d, 9.2 Hz), 4.70-4.61(1H, m), 1.32-1.15(6H, m). |
| 1-150 | 144-146 | solid | 7.62(1H, s), 7.30-7.24(1H, m), 6.90-6.85(2H, m), 4.70-4.63(1H, m), 2.91-2.85(1H, m), 1.48-1.46(2H, m), 1.28-1.14(8H, m). |
| 1-165 | | oil | 8.50(1H, s), 3.47-3.36(4H, m), 2.87-2.79(1H, m), 1.59-1.57(2H, m), 1.33-1.20(8H, m). |
| 1-168 | 102-104 | solid | |
| 1-169 | 106-110 | solid | 7.52(1H, s), 7.32-7.25(2H, m), 7.15-7.08(2H, m), 4.68-4.65(1H, m), 2.88-2.84(1H, m), 1.46-1.43(2H, m), 1.28-1.15(8H, m). |
| 1-170 | | oil | |
| 1-171 | 107-119 | solid | 7.55(1H, s), 7.18-7.15(2H, m), 7.05-7.01(2H, m), 4.74-4.67(1H, m), 2.86-2.80(1H, m), 1.47-1.43(2H, m), 1.27-1.12(8H, m). |
| 1-198 | | oil | 7.54(1H, s), 7.21-7.15(1H, m), 7.10-7.00(2H, m), 4.70-4.60(1H, m), 2.93-2.86(1H, m), 1.49(2H, br), 1.30-1.18(8H, m). |
| 1-200 | 149-152 | solid | 7.49(1H, s), 7.32-7.24(1H, m), 6.94(2H, t, 8.0 Hz), 4.59-4.48(1H, m), 2.95-2.88(1H, m), 1.49-1.44(2H, m), 1.31(6H, d, 6.4 Hz), 1.22-1.16(2H, m). |
| 1-203 | | oil | 7.56(1H, s), 7.03-6.92(2H, m), 4.69-4.59(1H, m), 2.92-2.86(1H, m), 1.52-1.18(10H, m). |
| 1-204 | | oil | 7.54(1H, s), 6.74(2H, t, 8.0 Hz), 4.61-4.50(1H, m), 2.98-2.91(1H, m), 1.49(2H, br), 1.30-1.21(8H, m). |
| 1-206 | | oil | |
| 1-214 | 92-102 | solid | 7.55(1H, s), 7.43-7.39(1H, m), 7.16-7.15(1H, m), 7.03-6.99(1H, m), 4.67-4.61(1H, m), 2.90-2.85(1H, m), 1.56-1.19(10H, m). |
| 1-215 | | oil | |
| 1-218 | 162-164 | solid | |
| 1-219 | | oil | |
| 1-220 | | oil | |
| 1-221 | 92-94 | solid | |
| 1-223 | 135-140 | solid | |
| 1-226 | | oil | |
| 1-229 | | candy | |
| 1-231 | | oil | |
| 1-238 | | candy | |
| 1-241 | | oil | |
| 1-242 | | oil | |
| 1-244 | | oil | 8.39(1H, d, J = 2.8 Hz), 7.66(1H, dd, J = 8.8, 2.8 Hz), 7.53(1H, s), 7.10(1H, d, J = 8.8 Hz), 4.74-4.68(1H, m), 2.92-2.86(1H, m), 1.51-1.47(2H, m), 1.36(6H, d, J = 7.2 Hz), 1.22-1.18(2H, m). |
| 1-248 | | oil | |
| 1-249 | | amorphous | |
| 1-250 | 117-119 | solid | |
| 1-257 | | oil | 7.30-7.21(1H, m), 6.91-6.85(1H, m), 6.82-6.75(1H, m), 4.78-4.66(1H, m), 2.80-2.75(1H, m), 2.62(3H, s), 1.34-1.10(10H, m). |
| 1-262 | | oil | |
| 1-269 | | gum | 7.58(1H, s), 7.28-7.23(1H, m), 6.90-6.84(2H, m), 4.69-4.62(1H, m), 4.38-4.30(1H, m), 2.63-2.48(2H, m), 2.35-2.26(2H, m), 2.08-2.00(2H, m), 1.28-1.20(6H, m). |
| 1-284 | | oil | 7.59(1H, s), 7.29-7.22(1H, m), 6.90-6.85(2H, m), 4.70-4.63(1H, m), 4.09-4.03(1H, m), 1.99-1.94(4H, m), 1.84-1.77(2H, m), 1.71-1.65(2H, m), 1.27-1.21(6H, m). |
| 1-294 | | oil | |
| 1-295 | | solid | |
| 1-296 | 178-180 | solid | |

TABLE 3-continued

| No. | Physical Properties (mp. °C.) | Shape | ¹HNMR Spectrum σ ppm: |
|---|---|---|---|
| 1-298 | | candy | |
| 1-305 | 133-138 | solid | |
| 1-306 | 130-132 | solid | 7.57(1H, s), 7.31-7.26(1H, m), 6.90-6.84(2H, m), 4.68-4.65(1H, m), 3.51-3.45(1H, m), 1.92-1.85(4H, m), 1.51-1.48(2H, m), 1.28-1.15(10H, m). |
| 1-308 | 148-150 | solid | |
| 1-309 | | oil | |
| 1-310 | 133-137 | solid | |
| 1-311 | | oil | |
| 1-313 | 114-121 | solid | |
| 1-314 | | oil | |
| 1-318 | | oil | |
| 1-319 | | oil | |
| 1-320 | | amorphous | |
| 1-322 | | oil | |
| 1-323 | | oil | |
| 1-326 | | candy | |
| 1-328 | | oil | |
| 1-338 | | oil | |
| 1-366 | | amorphous | |
| 1-405 | 172-176 | solid | |
| 1-415 | | solid | |
| 1-422 | | amorphous | |
| 1-429 | | amorphous | |
| 1-431 | | oil | |
| 1-437 | | oil | |
| 1-439 | 163-166 | solid | |
| 1-442 | 129-132 | solid | |
| 1-452 | | solid | |
| 1-459 | | amorphous | |
| 1-466 | | amorphous | |
| 1-468 | 115-121 | solid | |
| 1-474 | | solid | |
| 1-476 | 162-168 | solid | |
| 1-479 | 195-197 | solid | |
| 1-480 | 159-161 | solid | |
| 1-490 | | solid | 8.05-8.02(2H, m), 7.70(1H, s), 7.29-7.23(2H, m), 7.23-7.15(1H, m), 6.80-6.76(2H, m), 4.63-4.57(1H, m), 1.27-1.17(6H, m). |
| 1-497 | | amorphous | |
| 1-504 | | amorphous | |
| 1-506 | 168-171 | solid | |
| 1-512 | 149-156 | solid | |
| 1-515 | 142-150 | solid | |
| 1-516 | 119.7-122.4 | solid | |
| 1-528 | | solid | |
| 1-535 | | amorphous | |
| 1-542 | | amorphous | |
| 1-550 | | solid | |
| 1-552 | 152-154 | solid | |
| 1-553 | | oil | |
| 1-556 | 86.3-88.8 | solid | |
| 1-568 | | solid | |
| 1-575 | | amorphous | |
| 1-582 | | amorphous | |
| 1-590 | | solid | |
| 1-592 | | oil | |
| 1-593 | | oil | |
| 1-595 | | amorphous | |
| 1-597 | | oil | |
| 1-599 | 137-143 | solid | |
| 1-601 | 163-166 | solid | |
| 1-609 | | solid | |
| 1-616 | | amorphous | |
| 1-623 | | amorphous | |
| 1-629 | 155-158 | solid | |
| 1-633 | | oil | |
| 1-634 | | oil | |
| 1-636 | 152-157 | solid | |
| 1-637 | | candy | |
| 1-640 | | oil | |
| 1-642 | 153-155 | solid | |
| 1-644 | | solid | |
| 1-646 | 105-110 | solid | |
| 1-647 | | solid | |
| 1-648 | 112-117 | solid | |
| 1-649 | 130-132 | solid | |

TABLE 3-continued

| No. | Physical Properties (mp. ° C.) | Shape | ¹HNMR Spectrum σ ppm: |
|---|---|---|---|
| 1-650 | 97-100 | solid | |
| 1-651 | 136-138 | solid | |
| 1-652 | 113-117 | solid | |
| 1-662 | | solid | 7.85(2H, d, J = 8.8 Hz), 7.71(1H, s), 7.35(2H, d, J = 8.8 Hz), 7.21-7.17(1H, m), 6.77-6.72(2H, m), 4.61-4.58(1H, m), 2.47(3H, s), 1.24-1.15(6H, m). |
| 1-669 | | amorphous | |
| 1-676 | | amorphous | |
| 1-684 | | solid | |
| 1-686 | 114-116 | solid | |
| 1-687 | | oil | |
| 1-689 | | oil | |
| 1-690 | 168.2-174.3 | solid | |
| 1-694 | 79.3-85.3 | solid | |
| 1-695 | | oil | |
| 1-699 | 119.3-125.2 | solid | |
| 1-700 | | amorphous | |
| 1-701 | 120-126 | solid | |
| 1-703 | | candy | |
| 1-711 | | oil | |
| 1-718 | | amorphous | |
| 1-725 | | amorphous | |
| 1-733 | | oil | |
| 1-735 | 162-164 | solid | |
| 1-736 | | oil | |
| 1-742 | | solid | |
| 1-746 | | candy | |
| 1-768 | | amorphous | |
| 1-774 | 133-137 | solid | |
| 1-779 | 149.8-153.3 | solid | |
| 1-780 | | solid | |
| 1-782 | 89-94 | solid | |
| 1-783 | 158-160 | solid | |
| 1-786 | | oil | |
| 1-795 | 140-142 | solid | |
| 1-819 | | amorphous | |
| 1-835 | 162-168 | solid | |
| 1-857 | | amorphous | |
| 1-868 | | solid | |
| 1-870 | | solid | |
| 1-871 | | solid | |
| 1-872 | | solid | |
| 1-874 | | amorphous | |
| 1-875 | | solid | |
| 1-879 | 124-126 | solid | |
| 1-884 | 128-136 | solid | |
| 1-885 | 132-135 | solid | |
| 1-886 | 118-122 | solid | |
| 1-888 | 157-160 | solid | |
| 1-895 | 168-170 | solid | |
| 1-896 | 127.4-132.2 | solid | 7.78(1H, s), 7.13-7.07(1H, m), 6.97(2H, s), 6.78-6.73(1H, m), 6.65-6.61(1H, m), 4.63-4.56(1H, m), 2.49(6H, s), 2.34(3H, s), 1.24-1.14(6H, m). |
| 1-898 | 186-187 | solid | |
| 1-899 | 142-144 | solid | |
| 1-900 | 147-150 | solid | |
| 1-901 | 131-133 | solid | |
| 1-903 | 157-160 | solid | |
| 1-904 | 160-163 | solid | |
| 1-907 | 132-142 | solid | |
| 1-908 | | amorphous | |
| 1-909 | 119-121 | solid | |
| 1-910 | 161-163 | solid | |
| 1-913 | 109-111 | solid | |
| 1-916 | | candy | |
| 1-918 | | amorphous | |
| 1-921 | 122-124 | solid | |
| 1-922 | | oil | |
| 1-933 | | oil | |
| 1-950 | | amorphous | |
| 1-957 | | amorphous | |
| 1-965 | | oil | |
| 1-968 | 115.8-118.6 | solid | |

TABLE 3-continued

| No. | Physical Properties (mp. ° C.) | Shape | $^1$HNMR Spectrum σ ppm: |
|---|---|---|---|
| 1-970 | 168-170 | solid | |
| 1-994 | | amorphous | |
| 1-1002 | | oil | |

In the following, Reference Examples illustrate synthesis examples of synthesizing the starting materials in the syntheses above from commercial products, but the present invention is not limited thereto.

Reference Example 1

Synthesis of 1,4-dihydro-1,2,4-triazol-5-one

A 88% formic acid solution (500 ml) of semicarbazide hydrochloride (505 g, 4.53 mol) was stirred at 75° C. for 6 hours. The reaction mixture was concentrated under a reduced pressure, and water was added to the obtained sold, followed by heating up to 90° C. This aqueous solution was cooled to room temperature (25° C.), and the precipitated solid was filtered and dried to obtain the title compound (yielded: 314 g, yield: 81%) as a white solid.

Melting point: 234 to 236° C.

$^1$H NMR spectrum (DMSO-d6) σ: 11.5 (1H, br. s), 11.2 (1H, br. s), 7.69 (1H, s).

Reference Example 2

Synthesis of N,N-bis(2,4-difluorophenyl)-N,N-diisopropyl-5-oxo-1,2,4-triazole-1,4-dicarboxamide Potassium carbonate (13.6 g, 98.8 mmol) and N-(2,4-difluorophenyl)-N-isopropylcarbamoyl chloride (23.1 g, 98.8 mmol) (prepared by the method described in WO 1998/38176) were added at room temperature (25° C.) to an N,N-dimethylformamide solution (20 ml) of 1,4-dihydro-1,2,4-triazol-5-one (4.00 g, 47.0 mmol) synthesized in Reference Example 1, and the solution was stirred at 90° C. for 3 hours. The reaction mixture was poured in an aqueous dilute hydrochloric acid solution and extracted with ethyl acetate. The extract was washed with saturated brine, dried with anhydrous sodium sulfate and then concentrated under reduced pressure. The concentrate was purified by silica gel column chromatography (eluting solvent: ethyl acetate/n-hexane=1/2) to obtain the title compound (yielded: 5.20 g, yield: 23%) as a white solid.

Melting point: 160 to 161° C.

$^1$H NMR spectrum (CDCl$_3$) σ: 7.49-7.45 (1H, m), 7.30-7.25 (1H, m), 7.26 (1H, s), 7.07-7.00 (1H, m), 6.87-6.83 (1H, m), 6.78-6.72 (3H, m), 4.57-4.50 (2H, m), 1.23-1.07 (12H, m).

Reference Example 3

Synthesis of N-(2,4-difluorophenyl)-N-isopropyl-5-oxo-4H-1,2,4-triazole-1-carboxamide An aqueous 1 N sodium hydroxide solution (5.42 ml, 5.42 mmol) was added at room temperature (25° C.) to a methanol solution (20 ml) of N,N-bis(2,4-difluorophenyl)-N,N-diisopropyl-5-oxo-1,2,4-triazole-1,4-dicarboxamide (2.60 g, 5.42 mmol), and the solution was stirred at 40° C. for 1 hour. The reaction mixture was poured in an aqueous dilute hydrochloric acid solution and extracted with ethyl acetate. The extract was washed with saturated brine, dried with anhydrous sodium sulfate and then concentrated under reduced pressure. The concentrate was purified by silica gel column chromatography (eluting solvent: ethyl acetate/n-hexane=1/1) to obtain the title compound (yielded: 1.51 g, yield: 99%) as a white solid.

Melting point: 128 to 130° C.

$^1$H NMR spectrum (CDCl$_3$) σ: 11.1 (1H, br. s), 7.28 (1H, s), 7.20-7.15 (1H, m), 6.86-6.80 (2H, m), 4.71-4.62 (1H, m), 1.24-1.18 (6H, m).

Synthesis examples of the compound represented by formula (11) are described below.

Synthesis Example 11

Synthesis of 1-cyclopropylsulfonyl-N-(2,4-difluorophenyl)-N-isopropyl-5-oxo-1,2,4-triazole-4-carboxamide (11-142)

Cesium carbonate (416 mg, 1.28 mmol) and cyclopropanesulfonyl chloride (179 mg, 1.28 mmol) were added to an N,N-dimethylformamide solution (5 ml) of N-(2,4-difluorophenyl)-N-isopropyl-5-oxo-1H-1,2,4-triazole-4-carboxamide (300 mg, 1.06 mmol), and the solution was stirred at room temperature (25° C.) for 2 hours. Water was poured in the reaction mixture, and the resulting solution was extracted with ethyl acetate. The extract was washed with saturated brine, dried with anhydrous sodium sulfate and then concentrated under reduced pressure. The concentrate was purified by a silica gel column chromatography (eluting solvent: ethyl acetate/n-hexane=1/1) to obtain the title compound (yielded: 350 mg, yield: 85%) as a white solid.

The $^1$H NMR spectrum (CDCl$_3$) σ (ppm) value, melting point (° C.), etc. of the compounds according to the present invention produced based on this Synthesis Example and the Production Methods above are shown in Table 4. The $^1$H NMR data was measured by JNM-ECS400 Spectrometer (manufactured by JEOL Ltd.).

TABLE 4

| No. | Physical Properties (mp. ° C.) | Shape | $^1$HNMR Spectrum σ ppm: |
|---|---|---|---|
| 11-1 | | oil | |
| 11-2 | 139-140 | solid | |

TABLE 4-continued

| No. | Physical Properties (mp. °C.) | Shape | ¹HNMR Spectrum σ ppm: |
|---|---|---|---|
| 11-3 | | oil | |
| 11-11 | | oil | |
| 11-12 | | amorphous | |
| 11-14 | | oil | |
| 11-15 | | oil | |
| 11-16 | 110-116 | solid | |
| 11-17 | | oil | |
| 11-19 | 163-173 | solid | |
| 11-20 | | oil | |
| 11-24 | | oil | |
| 11-25 | | oil | |
| 11-26 | | oil | 7.74(1H, s), 7.26-7.22(1H, m), 6.99-6.97(1H, m), 6.93-6.90(1H, m), 4.69-4.62(1H, m), 3.15(3H, s), 2.35(3H, s), 1.31(3H, d, J = 6.8 Hz), 1.16(3H, d, J = 6.8 Hz). |
| 11-29 | | oil | |
| 11-34 | 136-140 | solid | |
| 11-38 | | oil | |
| 11-45 | | oil | |
| 11-46 | | oil | |
| 11-48 | 111-113 | solid | |
| 11-49 | | oil | |
| 11-50 | | oil | |
| 11-58 | | oil | |
| 11-59 | | candy | 7.80(1H, s), 7.45-7.39(1H, m), 6.96-6.85(2H, m), 4.70-4.64(1H, m), 3.55-3.48(1H, m), 1.30-1.09(12H, m). |
| 11-61 | 133-137 | solid | |
| 11-62 | 151-155 | solid | |
| 11-63 | | oil | |
| 11-64 | | oil | |
| 11-66 | | candy | |
| 11-67 | | oil | |
| 11-70 | 105-115 | solid | |
| 11-71 | 109-111 | solid | |
| 11-72 | | oil | |
| 11-73 | 109-111 | solid | |
| 11-74 | | oil | |
| 11-76 | | oil | |
| 11-85 | | solid | |
| 11-86 | 74-76 | solid | |
| 11-91 | | oil | |
| 11-92 | | amorphous | |
| 11-93 | | gum | |
| 11-94 | 108-110 | solid | |
| 11-95 | | oil | |
| 11-98 | | amorphous | |
| 11-109 | | oil | |
| 11-114 | | oil | |
| 11-121 | | oil | |
| 11-123 | | oil | |
| 11-126 | | oil | |
| 11-134 | | oil | |
| 11-140 | | oil | |
| 11-142 | | oil | 7.78(1H, s), 7.44-7.38(1H, m), 7.00-6.85(2H, m), 4.70-4.63(1H, m), 2.73-2.66(1H, m), 1.43-1.06(10H, m). |
| 11-144 | | oil | |
| 11-159 | | oil | 7.63(1H, s), 7.41-7.33(3H, m), 7.17-7.15(2H, m), 4.71-4.65(1H, m), 2.69-2.63(1H, m), 1.26-1.24(10H, m). |
| 11-160 | | oil | |
| 11-161 | | oil | |
| 11-162 | | solid | |
| 11-189 | | oil | |
| 11-191 | | oil | |
| 11-194 | | oil | |
| 11-195 | | oil | |
| 11-197 | | oil | |
| 11-205 | | candy | |
| 11-206 | | oil | |
| 11-209 | | oil | |
| 11-210 | | oil | |
| 11-211 | | oil | |
| 11-212 | 107-109 | solid | |
| 11-213 | | oil | |
| 11-217 | | oil | |

TABLE 4-continued

| No. | Physical Properties (mp. °C.) | Shape | ¹HNMR Spectrum σ ppm: |
|---|---|---|---|
| 11-220 | 126-130 | solid | |
| 11-222 | 153-161 | solid | |
| 11-233 | 103-105 | solid | 8.29(1H, d, J = 2.8 Hz), 7.87(1H, s), 7.73(1H, dd, J = 8.8, 2.8 Hz), 7.29(1H, d, J = 8.8 Hz), 4.64-4.58(1H, m), 2.71-2.66(1H, m), 1.42-1.38(2H, m), 1.35-1.34(6H, m), 1.10-1.04(2H, m). |
| 11-234 | | oil | |
| 11-238 | | oil | |
| 11-239 | | oil | |
| 11-246 | | oil | 7.26-7.21(1H, m), 6.97-6.87(2H, m), 4.67-4.56(1H, m), 2.90-2.83(1H, m), 2.67(3H, s), 1.51-1.48(2H, m), 1.27-1.23(6H, m), 1.14-1.12(2H, m). |
| 11-258 | | gum | 7.76(1H, s), 7.44-7.38(1H, m), 6.95-6.84(2H, m), 4.67-4.64(1H, m), 4.14-4.04(2H, m), 2.54-2.50(1H, m), 2.24-2.18(2H, m), 2.04-1.98(2H, m), 1.31-1.15(6H, m). |
| 11-273 | | oil | 7.78(1H, s), 7.45-7.39(1H, m), 6.96-6.84(2H, m), 4.69-4.65(1H, m), 3.80-3.76(1H, m), 2.07-2.00(2H, m), 1.84-1.80(2H, m), 1.78-1.70(2H, m), 1.62-1.57(2H, m), 1.32-1.15(6H, m). |
| 11-283 | | amorphous | |
| 11-284 | 176-179 | solid | |
| 11-285 | | oil | |
| 11-293 | | oil | |
| 11-294 | | candy | 7.78(1H, s), 7.46-7.40(1H, m), 6.96-6.84(2H, m), 4.70-4.64(1H, m), 3.27-3.32(1H, m), 1.89-1.83(4H, m), 1.47-1.41(2H, m), 1.32-1.09(10H, m). |
| 11-296 | 152-153 | solid | |
| 11-297 | 152-157 | solid | |
| 11-298 | 144-149 | solid | |
| 11-299 | | oil | |
| 11-301 | | candy | |
| 11-305 | 112-117 | solid | |
| 11-306 | | oil | |
| 11-307 | | oil | |
| 11-308 | 156-158 | solid | |
| 11-309 | | oil | |
| 11-311 | | oil | |
| 11-314 | | candy | |
| 11-316 | | oil | |
| 11-327 | 146-148 | solid | |
| 11-352 | | oil | 8.11(2H, d, J = 8.8 Hz), 7.76(1H, s), 7.72(1H, t, J = 8.8 Hz), 7.59(2H, d, J = 8.8 Hz), 3.44-3.39(2H, m), 1.22(3H, t, J = 6.8 Hz). |
| 11-353 | | oil | |
| 11-354 | 169-171 | solid | |
| 11-358 | | amorphous | |
| 11-361 | | amorphous | |
| 11-362 | | amorphous | |
| 11-367 | | solid | |
| 11-391 | | amorphous | |
| 11-392 | 121-129 | solid | |
| 11-401 | 126-134 | solid | |
| 11-404 | | oil | |
| 11-405 | 116-128 | solid | |
| 11-406 | 119-131 | solid | |
| 11-407 | | oil | |
| 11-413 | 165-167 | solid | |
| 11-414 | | oil | |
| 11-415 | | oil | |
| 11-416 | | amorphous | |
| 11-417 | | oil | |
| 11-419 | | oil | |
| 11-426 | | amorphous | |
| 11-427 | 140-142 | solid | |
| 11-428 | 148-150 | solid | |
| 11-437 | 129-142 | solid | |
| 11-440 | | oil | |
| 11-441 | | oil | |
| 11-442 | | oil | |
| 11-443 | | oil | |
| 11-445 | 152-154 | solid | |
| 11-449 | 118-123 | solid | |
| 11-450 | | oil | |
| 11-451 | | oil | |
| 11-452 | 125-127 | solid | |
| 11-453 | | oil | |
| 11-455 | | oil | |

TABLE 4-continued

| No. | Physical Properties (mp. ° C.) | Shape | ¹HNMR Spectrum σ ppm: |
|---|---|---|---|
| 11-460 | | solid | |
| 11-462 | | oil | |
| 11-463 | | solid | |
| 11-464 | | amorphous | |
| 11-465 | | solid | |
| 11-474 | 185-187 | solid | |
| 11-475 | 141-143 | solid | 7.96-7.92(2H, s), 7.71(1H, s), 7.38-7.32(1H, m), 7.22-7.18(2H, m), 6.89-6.84(1H, m), 6.77-6.72(1H, m), 4.63-4.59(1H, m), 1.27(3H, d, J = 6.4 Hz), 1.12(3H, d, J = 6.4 Hz). |
| 11-477 | 134-136 | solid | |
| 11-478 | 159-163 | solid | |
| 11-479 | 139-150 | solid | |
| 11-480 | 136-138 | solid | |
| 11-482 | 150-152 | solid | |
| 11-486 | 175-180 | solid | |
| 11-487 | 154-156 | solid | |
| 11-488 | | oil | |
| 11-489 | 171-173 | solid | |
| 11-490 | 141-145 | solid | |
| 11-492 | 154-156 | solid | |
| 11-497 | | solid | |
| 11-499 | 179-181 | solid | |
| 11-500 | | solid | |
| 11-501 | 149-151 | solid | |
| 11-502 | 166-167 | solid | |
| 11-511 | 142-146 | solid | |
| 11-512 | 159-161 | solid | |
| 11-514 | 132-141 | solid | |
| 11-515 | | oil | |
| 11-516 | | oil | |
| 11-517 | | oil | |
| 11-519 | | candy | |
| 11-523 | | oil | |
| 11-524 | | oil | |
| 11-525 | | oil | |
| 11-526 | | amorphous | |
| 11-527 | | oil | |
| 11-529 | | oil | |
| 11-534 | | solid | |
| 11-536 | | oil | |
| 11-537 | 126-128 | solid | |
| 11-538 | | solid | |
| 11-539 | 156-158 | solid | |
| 11-549 | 179-182 | solid | |
| 11-550 | 123-125 | solid | |
| 11-552 | 118-123 | solid | |
| 11-553 | 149-152 | solid | |
| 11-554 | | oil | |
| 11-555 | | oil | |
| 11-557 | 162-164 | solid | |
| 11-561 | 177-181 | solid | |
| 11-562 | 155-157 | solid | |
| 11-563 | | oil | |
| 11-564 | 137-139 | solid | |
| 11-565 | | oil | |
| 11-567 | | oil | |
| 11-572 | | solid | |
| 11-574 | 187-189 | solid | |
| 11-575 | 129-131 | solid | |
| 11-576 | | solid | |
| 11-577 | 133-135 | solid | |
| 11-578 | 150-155 | solid | |
| 11-579 | | amorphous | |
| 11-580 | 141-148 | solid | |
| 11-587 | 154-158 | solid | |
| 11-588 | | solid | |
| 11-590 | 156-161 | solid | |
| 11-591 | 154-157 | solid | |
| 11-592 | 171-182 | solid | |
| 11-593 | 155-157 | solid | |
| 11-595 | 169-172 | solid | |
| 11-599 | 192-195 | solid | |
| 11-600 | 184-186 | solid | |
| 11-601 | | oil | |
| 11-602 | | solid | |

TABLE 4-continued

| No. | Physical Properties (mp. °C.) | Shape | ¹HNMR Spectrum σ ppm: |
|---|---|---|---|
| 11-603 | 162-166 | solid | |
| 11-605 | 167-169 | solid | |
| 11-608 | 179-180 | solid | |
| 11-610 | | solid | |
| 11-612 | 127-129 | solid | |
| 11-613 | 182-185 | solid | |
| 11-614 | | amorphous | |
| 11-615 | | solid | |
| 11-616 | | solid | |
| 11-619 | | solid | |
| 11-620 | | solid | |
| 11-622 | | solid | |
| 11-623 | | oil | |
| 11-625 | | solid | |
| 11-626 | 155-157 | solid | |
| 11-627 | 131-132 | solid | |
| 11-628 | | oil | |
| 11-636 | | oil | |
| 11-637 | | oil | 7.77(2H, d, J = 8.4 Hz), 7.69(1H, s), 7.38-7.33(1H, m), 7.31(2H, d, J = 8.4 Hz), 6.86-6.82(1H, m), 6.73-6.68(1H, m), 4.68-4.57(1H, m), 2.45(3H, s), 1.26(3H, d, J = 6.4 Hz), 1.11(3H, d, J = 6.4 Hz). |
| 11-639 | 159-171 | solid | |
| 11-640 | 132-147 | solid | |
| 11-641 | 112-123 | solid | |
| 11-642 | | oil | |
| 11-644 | 149-152 | solid | |
| 11-645 | | oil | |
| 11-648 | 146-156 | solid | |
| 11-649 | | oil | |
| 11-650 | | oil | |
| 11-651 | 146-148 | solid | |
| 11-652 | | amorphous | |
| 11-654 | | oil | |
| 11-659 | | solid | |
| 11-661 | | oil | |
| 11-663 | 175-177 | solid | |
| 11-665 | | solid | |
| 11-666 | | oil | |
| 11-670 | | solid | |
| 11-671 | 159-161 | solid | |
| 11-672 | 160-163 | solid | |
| 11-681 | 114-133 | solid | |
| 11-682 | | oil | |
| 11-684 | 154-158 | solid | |
| 11-685 | 156-165 | solid | |
| 11-686 | 179-185 | solid | |
| 11-687 | | oil | |
| 11-689 | 162-164 | solid | |
| 11-693 | 178-185 | solid | |
| 11-694 | 135-137 | solid | |
| 11-695 | | oil | |
| 11-696 | 151-153 | solid | |
| 11-697 | | oil | |
| 11-699 | | oil | |
| 11-704 | | solid | |
| 11-706 | 132-134 | solid | |
| 11-707 | 60> | solid | |
| 11-709 | 187-189 | solid | |
| 11-710 | | solid | |
| 11-711 | | solid | |
| 11-722 | 132-136 | solid | |
| 11-725 | 123-126 | solid | |
| 11-726 | 137-143 | solid | |
| 11-727 | 142-145 | solid | |
| 11-728 | | oil | |
| 11-730 | 183-185 | solid | |
| 11-734 | | oil | |
| 11-735 | 156-158 | solid | |
| 11-737 | 128-130 | solid | |
| 11-743 | 148-150 | solid | |
| 11-745 | 145-146 | solid | |
| 11-748 | | solid | |
| 11-749 | 169-171 | solid | |
| 11-762 | | oil | |
| 11-772 | | oil | |

TABLE 4-continued

| No. | Physical Properties (mp. ° C.) | Shape | ¹HNMR Spectrum σ ppm: |
|---|---|---|---|
| 11-777 | | oil | |
| 11-778 | | oil | |
| 11-780 | | candy | |
| 11-784 | 169-176 | solid | |
| 11-785 | | oil | |
| 11-787 | 88-90 | solid | |
| 11-790 | | oil | |
| 11-797 | 148-150 | solid | |
| 11-800 | 177-179 | solid | |
| 11-801 | 181-182 | solid | |
| 11-810 | 190-194 | solid | |
| 11-814 | 178-186 | solid | |
| 11-815 | | oil | |
| 11-818 | 125-131 | solid | |
| 11-823 | | oil | |
| 11-824 | | oil | |
| 11-825 | 162-164 | solid | |
| 11-835 | | amorphous | |
| 11-837 | | solid | |
| 11-841 | | solid | |
| 11-842 | 146-148 | solid | |
| 11-852 | | oil | |
| 11-853 | | oil | |
| 11-854 | | oil | |
| 11-855 | | solid | |
| 11-862 | | oil | |
| 11-863 | | oil | |
| 11-865 | 150-153 | solid | |
| 11-866 | | oil | |
| 11-867 | | oil | |
| 11-868 | | oil | |
| 11-870 | 152-155 | solid | |
| 11-871 | 155.6-158 | solid | |
| 11-874 | | oil | |
| 11-875 | | oil | |
| 11-876 | | oil | |
| 11-877 | | oil | 7.63(1H, s), 7.18(1H, t, J = 8.4 Hz), 6.92(2H, s), 6.87-6.84(2H, m), 4.63-4.59(1H, m), 2.49(6H, s), 2.35(3H, s), 2.31(3H, s), 1.26(3H, d, J = 6.4 Hz), 1.12(3H, d, J = 6.4 Hz). |
| 11-878 | | oil | |
| 11-880 | | oil | |
| 11-883 | | candy | |
| 11-885 | | solid | |
| 11-887 | | oil | |
| 11-889 | 120-122 | solid | |
| 11-894 | | oil | |
| 11-896 | | oil | |
| 11-897 | 180-182 | solid | |
| 11-898 | 138-139 | solid | |
| 11-907 | | oil | |
| 11-910 | | solid | |
| 11-911 | 131-140 | solid | |
| 11-912 | | oil | |
| 11-913 | | oil | |
| 11-915 | | candy | |
| 11-919 | 117-125 | solid | |
| 11-920 | | oil | |
| 11-921 | | oil | |
| 11-922 | | oil | |
| 11-925 | | oil | |
| 11-930 | | solid | |
| 11-932 | 134-136 | solid | |
| 11-933 | 173-175 | solid | |
| 11-934 | 180-181 | solid | |
| 11-944 | | amorphous | |
| 11-949 | | oil | |
| 11-955 | 138-144 | solid | |
| 11-956 | | oil | |
| 11-957 | | oil | |
| 11-958 | 158-160 | solid | 7.62(1H, s), 7.38-7.29(4H, m), 7.15-7.14(2H, m), 6.99-6.97(1H, m), 6.93-6.91(1H, m), 4.63-4.59(1H, m), 4.51(2H, s), 2.34(3H, s), 1.29(3H, d, J = 6.4 Hz), 1.13(3H, d, J = 6.4 Hz). |
| 11-961 | | oil | |
| 11-966 | 190-194 | solid | |

TABLE 4-continued

| No. | Physical Properties (mp. ° C.) | Shape | ¹HNMR Spectrum σ ppm: |
|---|---|---|---|
| 11-968 | | amorphous | |
| 11-973 | | oil | |
| 11-974 | | oil | |
| 11-975 | 129-136 | solid | |
| 11-985 | | oil | 9.11(1H, s), 8.91(1H, d, J = 4.8 Hz), 8.17(1H, d, J = 8.0 Hz), 7.74(1H, s), 7.49-7.46(1H, m), 7.37-7.29(1H, m), 6.88-6.84(1H, m), 6.75-6.71(1H, m), 4.62-4.59(1H, m), 1.26(3H, d, J = 6.4 Hz), 1.11(3H, d, J = 6.4 Hz). |
| 11-990 | | oil | |
| 11-1007 | 82-98 | solid | |
| 11-1011 | 141-143 | solid | |
| 11-1014 | | solid | |
| 11-1021 | 186-189 | solid | |
| 11-1022 | 147-149 | solid | 7.77-7.73(3H, m), 7.40-7.34(1H, m), 7.13(1H, dd, J = 5.2, 4.0 Hz), 6.90-6.85(1H, m), 6.77-3.71(1H, m), 4.66-4.59(1H, m), 1.27(3H, d, J = 6.8 Hz), 1.2(3H, d, J = 6.8 Hz). |
| 11-1024 | 162-165 | solid | |
| 11-1025 | | oil | |
| 11-1026 | | oil | |
| 11-1027 | | oil | |
| 11-1029 | | candy | |
| 11-1033 | | oil | |
| 11-1034 | | oil | |
| 11-1035 | | oil | |
| 11-1036 | 155-160 | solid | |
| 11-1042 | | candy | |
| 11-1044 | 145-146 | solid | |
| 11-1046 | 108-112 | solid | |
| 11-1047 | 173-175 | solid | |
| 11-1053 | | amorphous | |
| 11-1054 | | oil | |
| 11-1055 | | amorphous | |
| 11-1056 | | candy | |
| 11-1064 | | oil | 7.72(1H, s), 7.45-7.38(1H, m), 6.95-6.81(2H, m), 4.72-4.63(1H, m), 2.86(6H, s), 1.31(3H, d, J = 6.8 Hz), 1.15(3H, d, J = 6.8 Hz). |
| 11-1069 | | oil | |
| 11-1071 | 93-123 | solid | |
| 11-1072 | | oil | |
| 11-1076 | | oil | |
| 11-1078 | 117-119 | solid | |
| 11-1079 | | oil | |
| 11-1081 | | oil | |
| 11-1084 | 168-169 | solid | |
| 11-1086 | | solid | |
| 11-1088 | | oil | |
| 11-1090 | | amorphous | |
| 11-1097 | 166-168 | solid | |
| 11-1098 | | oil | |
| 11-1099 | | oil | |
| 11-1101 | | oil | |
| 11-1102 | | oil | 7.72(1H, s), 7.46-7.40(1H, m), 6.95-6.83(2H, m), 4.69-4.65(1H, m), 3.19-3.17(4H, m), 1.59-1.50(6H, m), 1.31(3H, d, J = 6.4 Hz), 1.15(3H, d, J = 6.4 Hz). |
| 11-1109 | 160-164 | solid | 7.80(1H, s), 7.45-7.39(1H, m), 6.97-6.85(2H, m), 4.70-4.64(1H, m), 4.05-4.02(2H, m), 3.54-3.46(1H, m), 3.34-3.30(2H, m), 1.85-1.75(4H, m), 1.32(3H, d, J = 6.8 Hz), 1.16(3H, d, J = 6.8 Hz). |
| 11-1125 | | oil | |
| 11-1126 | | oil | |
| 11-1127 | | oil | |
| 11-1128 | | oil | |
| 11-1129 | | oil | |
| 11-1130 | | oil | |
| 11-1131 | | oil | |
| 11-1132 | | oil | |
| 11-1133 | | oil | |
| 11-1134 | | oil | |
| 11-1135 | | oil | |
| 11-1136 | | oil | |
| 11-1137 | | oil | |
| 11-1138 | | oil | |
| 11-1139 | | oil | |
| 11-1140 | | oil | |
| 11-1141 | | oil | |

TABLE 4-continued

| No. | Physical Properties (mp. ° C.) | Shape | $^1$HNMR Spectrum σ ppm: |
|---|---|---|---|
| 11-1142 | | oil | |
| 11-1143 | | oil | |
| 11-1144 | | oil | |
| 11-1145 | | oil | |
| 11-1146 | | oil | |
| 11-1147 | | oil | |
| 11-1148 | | oil | |
| 11-1149 | | oil | |
| 11-1150 | | oil | |
| 11-1151 | 148-157 | solid | |
| 11-1152 | | oil | |
| 11-1153 | 164-169 | solid | |
| 11-1154 | | oil | |
| 11-1155 | | oil | |
| 11-1156 | | oil | |
| 11-1157 | | oil | |
| 11-1158 | | oil | |

In the following, although Reference Examples illustrate synthesis examples of synthesizing the starting materials in the syntheses above from commercial products, the present invention is not limited thereto.

Reference Example 11

Synthesis of 1,4-dihydro-1,2,4-triazol-5-one

A 88% formic acid solution (500 ml) of semicarbazide hydrochloride (505 g, 4.53 mol) was stirred at 75° C. for 6 hours. The reaction mixture was concentrated under reduced pressure, and water was added to the obtained sold, followed by heating up to 90° C. This aqueous solution was cooled to room temperature, and the precipitated solid was filtered and dried to obtain the title compound (yielded: 314 g, yield: 81%) as a white solid.
Melting point: 234 to 236° C.
$^1$H NMR spectrum (DMSO-d6) σ: 11.5 (1H, br. s), 11.2 (1H, br. s), 7.69 (1H, s).

Reference Example 12

Synthesis of N-(2,4-difluorophenyl)-N-isopropyl-5-oxo-1H-1,2,4-triazole-4-dicarboxamide Potassium carbonate (4.44 g, 32.1 mmol) was added to an N,N-dimethylformamide solution (50 ml) of 1,4-dihydro-1,2,4-triazol-5-one (5.46 g, 64.2 mmol) synthesized in Reference Example 11, and the solution was stirred at 100° C. for 30 minutes. Subsequently, N-(2,4-difluorophenyl)-N-isopropylcarbamoyl chloride (10.0 g, 42.8 mmol) (prepared by the method described in WO 1998/38176) were added at room temperature (25° C.), and the solution was again stirred at 100° C. for 2 hours. The reaction mixture was poured in an aqueous dilute hydrochloric acid solution and extracted with ethyl acetate. The extract was washed with saturated brine, dried with anhydrous sodium sulfate and then concentrated under reduced pressure. The concentrate was purified by a silica gel column chromatography (eluting solvent: ethyl acetate/n-hexane=1/1) to obtain the title compound (yielded: 5.40 g, yield: 45%) as a yellow solid.
Melting point: 121 to 123° C.
$^1$H NMR spectrum (CDCl$_3$) σ: 9.12 (1H, br. s), 7.62 (1H, s) 7.42-7.36 (1H, m), 6.92-6.80 (2H, m), 4.73-4.63 (1H, m), 1.29-1.16 (6H, m).

The method for formulating the compound represented by formula (1) of the present invention as a herbicide is described more specifically by the following formulation examples. However, the herbicide is not limited to these formulation examples, and the compound may also be formulated by mixing it with other various additives at a freely selected ratio.

Formulation Example 1

(Granule)
To 1 part of the compound of Synthesis Example 1, 1 part of calcium ligninsulfonate, 1 part of lauryl sulfate, 30 parts of bentonite and 67 parts of talc, 15 Parts of water was added, and the mixture was kneaded in a kneader and then granulated in a granulator. The granules were dried in a fluidized bed drier, and a granule containing 1% of the herbicidal active ingredient can thereby be obtained. Furthermore, granules can be obtained by the same method except for using respective compounds shown in Table 1 in place of the compound of Synthesis Example 1.

Formulation Example 2

(Flowable Formulation)
In a wet-type ball mill, 20.0 Parts of the compound of Synthesis Example 1, 2.0 parts of sodium salt of di-2-ethylhexyl sulfosuccinate, 2.0 parts of polyoxyethylene nonylphenyl ether, 5.0 parts of propylene glycol, 0.5 parts of antifoaming agent, and 70.5 parts of water were uniformly mixed and ground, and a flowable formulation containing 20% of the herbicidal active ingredient can thereby be obtained. Furthermore, flowable formulations can be obtained by the same method except for using respective compounds shown in Table 1 in place of the compound of Synthesis Example 1.

Formulation Example 3

(Dry Flowable Formulation)
By uniformly mixing and grinding 75 Parts of the compound of Synthesis Example 1, 10 parts of naphthalene-sulfonic acid-formaldehyde condensate, 5 parts of sodium laurylsulfate, 5 parts of white carbon, and 5 parts of clay, a dry flowable (wet-dispersible granule) formulation containing 75% of the herbicidal active ingredient can be obtained. Furthermore, dry flowable (wet-dispersible granule) formulations can be obtained by the same method except for using respective compounds shown in Table 1 in place of the compound of Synthesis Example 1.

Formulation Example 4

(Wettable Powder)

In a grinding and mixing machine, 15 Parts of the compound of Synthesis Example 1, 15 parts of white carbon, 3 parts of calcium ligninsulfonate, 2 parts of polyoxyethylene alkyl ether, 5 parts of diatomaceous earth, and 60 parts of clay were uniformly mixed, and a wettable powder containing 15% of the herbicidal active ingredient can thereby be obtained. Furthermore, wettable powders can be obtained by the same method except for using respective compounds shown in Table 1 in place of the compound of Synthesis Example 1.

Formulation Example 5

(Emulsifiable Concentrate)

By mixing 20 Parts of the compound of Synthesis Example 1, 18 parts of polyoxyethylene styrylphenyl ether, 2 parts of calcium dodecylbenzenesulfonate, and 60 parts of xylene, an emulsifiable concentrate containing 20% of the herbicidal active ingredient can be obtained. Furthermore, emulsifiable concentrates can be obtained by the same method except for using respective compounds shown in Table 1 in place of the compound of Synthesis Example 1.

Formulation Example 6

(Dust)

By uniformly mixing and grinding 0.5 Parts of the compound of Synthesis Example 1, 0.5 parts of white carbon, 0.5 parts of calcium stearate, 50.0 parts of clay, and 48.5 parts of talc, a dust containing 0.5% of the herbicidal active ingredient can be obtained. Furthermore, dusts can be obtained by the same method except for using respective compounds shown in Table 1 in place of the compound of Synthesis Example 1.

Formulation Example 7

(Jumbo Formulation)

After mixing 15 Parts of the compound of Synthesis Example 1, 2 parts of sodium laurylsulfate, 5 parts of sulfosuccinic acid bis(2-ethylhexyl) ester sodium salt, 5 parts of carboxymethyl cellulose sodium salt, 35 parts of silas balloon, 10 parts of lactose, and 28 parts of expanded perlite, followed by addition of 35 parts of water, the mixture was kneaded in a kneader and then granulated in a granulator. The granules were dried in a fluidized bed drier, and a jumbo formulation containing 15% of the herbicidal active ingredient can thereby be obtained. Furthermore, jumbo formulations can be obtained by the same method except for using respective compounds shown in Table 1 in place of the compound of Synthesis Example 1.

Test Examples are described below for demonstrating the herbicidal effect of the compound represented by formula (1) of the present invention.

Test Example 1

Herbicidal Effect Test by Soil Treatment in Paddy Field

A Wagner pot having an area of 1/10000 are was filled with paddy field soil and after adding water, a chemical fertilizer (N:P:K=17:17:17) was mixed, followed by puddling. Thereafter, 30 grains of each of *Echinochloa crus-galli*, broad-leaved weed (*Lindernia pyxidaria* and *Monochoria vaginalis*) and *Scirpus juncoides* seeds were sown to a depth of 0 to 1 cm. Immediately after the sowing, the pot was flooded, and the depth of water was kept at about 3 cm. The pot was subsequently managed in a glass greenhouse. Just after that, an emulsifiable concentrate prepared according to Formulation Example 5 by using the compound shown in Table 5 below was diluted with water, and a predetermined amount of the water-diluted formulation was added dropwise. The application rate of the active ingredient, by conversion, corresponded to 120 g per 10 are.

This test was performed with two replications per one formulation concentration plot, and 14 days after the formulation treatments, the weed suppression rate (%) was determined according to the following equation (Math. 1).

Weed suppression rate (%)=(1−an average dry weight (g) of plants in treated plots/an average dry weight (g) of plants in untreated plots)×100 [Math. 1]

The results are shown in Table 5 below. The compound numbers in Table 5 are the same as those shown in Table 1 and Table 3.

TABLE 5

| No. | Concentration (g/10a) | *Echinochloa crus-galli* | *Monochoria vaginalis* | *Lindemia pyxidaria* | *Scirpus juncoides* |
| --- | --- | --- | --- | --- | --- |
| 1-54 | 120 | 90 | 80 | 80 | 90 |
| 1-55 | 120 | 90 | 90 | 90 | 90 |
| 1-65 | 120 | 100 | 100 | 100 | 100 |
| 1-73 | 120 | 100 | 90 | 100 | 80 |
| 1-79 | 120 | 90 | 80 | 80 | 90 |
| 1-81 | 120 | 90 | 80 | 80 | 90 |
| 1-90 | 120 | 100 | 80 | 90 | 90 |
| 1-91 | 120 | 100 | 90 | 90 | 90 |
| 1-93 | 120 | 90 | 80 | 100 | 90 |
| 1-97 | 120 | 90 | 90 | 80 | 90 |
| 1-98 | 120 | 100 | 90 | 90 | 90 |
| 1-99 | 120 | 60 | 90 | 80 | 50 |
| 1-101 | 120 | 90 | 80 | 80 | 90 |
| 1-142 | 120 | 100 | 100 | 100 | 100 |
| 1-150 | 120 | 100 | 100 | 100 | 100 |
| 1-168 | 120 | 90 | 80 | 80 | 90 |
| 1-169 | 120 | 100 | 90 | 90 | 90 |
| 1-170 | 120 | 90 | 90 | 100 | 90 |

TABLE 5-continued

| No. | Concentration (g/10a) | Echinochloa crus-galli | Monochoria vaginalis | Lindemia pyxidaria | Scirpus juncoides |
|---|---|---|---|---|---|
| 1-171 | 120 | 100 | 100 | 100 | 100 |
| 1-198 | 120 | 100 | 100 | 100 | 100 |
| 1-200 | 120 | 100 | 80 | 100 | 100 |
| 1-203 | 120 | 100 | 90 | 100 | 100 |
| 1-204 | 120 | 100 | 80 | 100 | 100 |
| 1-206 | 120 | 100 | 90 | 100 | 100 |
| 1-214 | 120 | 90 | 80 | 80 | 90 |
| 1-215 | 120 | 100 | 100 | 100 | 100 |
| 1-218 | 120 | 100 | 80 | 100 | 100 |
| 1-219 | 120 | 100 | 100 | 100 | 100 |
| 1-220 | 120 | 100 | 80 | 100 | 90 |
| 1-221 | 120 | 90 | 90 | 90 | 90 |
| 1-223 | 120 | 100 | 80 | 80 | 90 |
| 1-226 | 120 | 100 | 100 | 100 | 100 |
| 1-229 | 120 | 90 | 80 | 80 | 90 |
| 1-238 | 120 | 90 | 80 | 80 | 90 |
| 1-241 | 120 | 100 | 90 | 90 | 80 |
| 1-242 | 120 | 100 | 90 | 90 | 90 |
| 1-244 | 120 | 100 | 90 | 100 | 90 |
| 1-248 | 120 | 100 | 90 | 100 | 100 |
| 1-249 | 120 | 100 | 90 | 90 | 90 |
| 1-250 | 120 | 90 | 80 | 80 | 90 |
| 1-257 | 120 | 90 | 80 | 80 | 90 |
| 1-269 | 120 | 100 | 100 | 100 | 90 |
| 1-284 | 120 | 100 | 100 | 100 | 100 |
| 1-295 | 120 | 90 | 80 | 80 | 90 |
| 1-296 | 120 | 90 | 80 | 80 | 90 |
| 1-298 | 120 | 90 | 80 | 90 | 90 |
| 1-305 | 120 | 100 | 100 | 100 | 100 |
| 1-306 | 120 | 100 | 100 | 100 | 100 |
| 1-308 | 120 | 100 | 80 | 100 | 100 |
| 1-309 | 120 | 100 | 100 | 100 | 100 |
| 1-310 | 120 | 100 | 100 | 100 | 100 |
| 1-311 | 120 | 100 | 100 | 100 | 100 |
| 1-313 | 120 | 90 | 80 | 80 | 90 |
| 1-314 | 120 | 100 | 80 | 100 | 100 |
| 1-318 | 120 | 100 | 90 | 90 | 100 |
| 1-319 | 120 | 100 | 80 | 80 | 100 |
| 1-320 | 120 | 90 | 90 | 90 | 90 |
| 1-322 | 120 | 90 | 90 | 90 | 90 |
| 1-323 | 120 | 100 | 80 | 100 | 100 |
| 1-328 | 120 | 90 | 80 | 80 | 90 |
| 1-338 | 120 | 100 | 90 | 90 | 100 |
| 1-690 | 120 | 100 | 90 | 100 | 90 |
| 1-899 | 120 | 100 | 90 | 100 | 100 |
| 1-921 | 120 | 90 | 60 | 80 | 70 |
| 1-1052 | 120 | 90 | 80 | 80 | 90 |
| 1-1060 | 120 | 90 | 80 | 80 | 90 |
| 1-1093 | 120 | 90 | 80 | 80 | 90 |
| 1-1095 | 120 | 90 | 80 | 80 | 90 |
| 1-1103 | 120 | 90 | 80 | 80 | 90 |
| 1-1117 | 120 | 90 | 80 | 80 | 90 |
| 1-1128 | 120 | 90 | 60 | 90 | 70 |
| 1-1129 | 120 | 90 | 80 | 80 | 90 |
| 1-1135 | 120 | 90 | 60 | 90 | 90 |
| 1-1136 | 120 | 100 | 90 | 90 | 90 |
| 1-1139 | 120 | 100 | 90 | 90 | 90 |
| 1-1140 | 120 | 90 | 80 | 80 | 90 |
| 1-1142 | 120 | 100 | 80 | 80 | 80 |
| 1-1143 | 120 | 90 | 80 | 80 | 90 |
| 1-1161 | 120 | 90 | 80 | 80 | 90 |

Test Example 2

Herbicidal Effect Test by Treatment During Growing Period in Paddy Field

A Wagner pot having an area of 1/10000 are was filled with paddy field soil and after adding water, a chemical fertilizer (N:P:K=17:17:17) was mixed, followed by puddling. Thereafter, 30 grains of each of Echinochloa crus-galli, broad-leaved weed (Lindernia pyxidaria and Monochoria vaginalis) and Scirpus juncoides seeds were sown to a depth of 0 to 1 cm. Immediately after the sowing, the pot was flooded, and the depth of water was kept at about 3 cm. The pot was subsequently managed in a glass greenhouse. Seven days after sowing, an emulsifiable concentrate prepared according to Formulation Example 5 by using the compound shown in Table 6 below was diluted with water, and a predetermined amount of the water-diluted formulation was added dropwise. The application rate of the active ingredient, by conversion, corresponded to 120 g per 10 are. The test was performed with two replications per one formulation concentration plot, and 14 days after the formulation treatments, the weed suppression rate (%) was determined according to the equation (Math. 1). The results are shown in Table 6.

TABLE 6

| No. | Concentration (g/10a) | Echinochloa crus-galli | Monochoria vaginalis | Lindemia pyxidaria | Scirpus juncoides |
|---|---|---|---|---|---|
| 1-54 | 120 | 90 | 80 | 80 | 90 |
| 1-55 | 120 | 90 | 90 | 90 | 90 |
| 1-65 | 120 | 100 | 90 | 90 | 90 |
| 1-73 | 120 | 100 | 90 | 80 | 100 |
| 1-79 | 120 | 90 | 80 | 80 | 90 |
| 1-81 | 120 | 90 | 80 | 80 | 90 |
| 1-90 | 120 | 100 | 90 | 90 | 90 |
| 1-91 | 120 | 100 | 90 | 90 | 90 |
| 1-93 | 120 | 100 | 90 | 100 | 90 |
| 1-97 | 120 | 90 | 90 | 80 | 80 |
| 1-98 | 120 | 100 | 90 | 80 | 90 |
| 1-99 | 120 | 90 | 80 | 80 | 90 |
| 1-101 | 120 | 90 | 80 | 80 | 90 |
| 1-142 | 120 | 90 | 80 | 80 | 90 |
| 1-150 | 120 | 100 | 90 | 90 | 90 |
| 1-168 | 120 | 90 | 80 | 80 | 90 |
| 1-169 | 120 | 100 | 90 | 80 | 80 |
| 1-170 | 120 | 100 | 90 | 90 | 90 |
| 1-171 | 120 | 100 | 90 | 90 | 90 |
| 1-198 | 120 | 100 | 100 | 100 | 80 |
| 1-200 | 120 | 100 | 90 | 80 | 100 |
| 1-203 | 120 | 100 | 100 | 80 | 100 |
| 1-204 | 120 | 100 | 100 | 80 | 100 |
| 1-206 | 120 | 100 | 90 | 80 | 100 |
| 1-214 | 120 | 90 | 80 | 80 | 90 |
| 1-215 | 120 | 100 | 100 | 100 | 100 |
| 1-218 | 120 | 100 | 80 | 100 | 100 |
| 1-219 | 120 | 100 | 90 | 90 | 100 |
| 1-220 | 120 | 100 | 100 | 90 | 90 |
| 1-221 | 120 | 90 | 80 | 80 | 90 |
| 1-223 | 120 | 90 | 80 | 80 | 90 |
| 1-226 | 120 | 100 | 100 | 80 | 90 |
| 1-229 | 120 | 90 | 80 | 80 | 90 |
| 1-238 | 120 | 90 | 90 | 80 | 90 |
| 1-241 | 120 | 100 | 80 | 90 | 80 |
| 1-242 | 120 | 100 | 90 | 90 | 90 |
| 1-244 | 120 | 100 | 90 | 100 | 90 |
| 1-248 | 120 | 100 | 90 | 90 | 90 |
| 1-249 | 120 | 100 | 90 | 90 | 90 |
| 1-250 | 120 | 90 | 90 | 90 | 80 |
| 1-257 | 120 | 90 | 80 | 80 | 90 |
| 1-269 | 120 | 100 | 90 | 100 | 90 |
| 1-284 | 120 | 90 | 90 | 90 | 90 |
| 1-295 | 120 | 90 | 80 | 80 | 90 |
| 1-296 | 120 | 90 | 90 | 90 | 90 |
| 1-298 | 120 | 90 | 90 | 90 | 90 |
| 1-305 | 120 | 100 | 100 | 100 | 100 |
| 1-306 | 120 | 100 | 100 | 100 | 90 |
| 1-308 | 120 | 100 | 100 | 90 | 100 |
| 1-309 | 120 | 100 | 100 | 80 | 100 |
| 1-310 | 120 | 100 | 100 | 100 | 100 |
| 1-311 | 120 | 100 | 100 | 80 | 90 |
| 1-313 | 120 | 90 | 80 | 80 | 90 |
| 1-314 | 120 | 90 | 90 | 100 | 100 |
| 1-318 | 120 | 100 | 80 | 80 | 80 |
| 1-319 | 120 | 100 | 90 | 80 | 80 |
| 1-320 | 120 | 90 | 80 | 80 | 90 |
| 1-322 | 120 | 90 | 80 | 80 | 90 |
| 1-323 | 120 | 100 | 70 | 70 | 70 |
| 1-328 | 120 | 90 | 80 | 80 | 90 |
| 1-338 | 120 | 90 | 80 | 80 | 90 |
| 1-690 | 120 | 100 | 90 | 90 | 90 |
| 1-899 | 120 | 100 | 100 | 80 | 100 |
| 1-921 | 120 | 80 | 60 | 80 | 70 |
| 1-1052 | 120 | 90 | 80 | 80 | 90 |
| 1-1093 | 120 | 90 | 80 | 80 | 90 |
| 1-1095 | 120 | 90 | 80 | 80 | 90 |
| 1-1103 | 120 | 90 | 80 | 80 | 90 |
| 1-1117 | 120 | 90 | 80 | 80 | 90 |
| 1-1128 | 120 | 90 | 60 | 90 | 70 |
| 1-1129 | 120 | 90 | 80 | 80 | 90 |
| 1-1135 | 120 | 90 | 70 | 60 | 90 |

TABLE 6-continued

| No. | Concentration (g/10a) | Echinochloa crus-galli | Monochoria vaginalis | Lindernia pyxidaria | Scirpus juncoides |
|---|---|---|---|---|---|
| 1-1136 | 120 | 100 | 80 | 90 | 90 |
| 1-1139 | 120 | 90 | 80 | 80 | 90 |
| 1-1142 | 120 | 90 | 80 | 80 | 90 |
| 1-1143 | 120 | 90 | 80 | 80 | 90 |
| 1-1161 | 120 | 90 | 80 | 80 | 90 |

Test Example 3

Herbicidal Effect Test by Soil Treatment in Upland Field

A pot having a size of 36 cm² was filled with field soil (alluvial soil) and after uniformly mixing the soil of the surface layer of 1 cm with 20 grains of each weed seed of crabgrass, *Echinochloa crus-galli*, *Chenopodium album* and *Amaranthus viridis*, the surface layer was pressed lightly. One day after the sowing, an emulsifiable concentrate prepared according to Formulation Example 5 by using the compound shown in Table 7 below was diluted with water, and the water-diluted formulation was sprayed on the soil surface at a ratio of 100 liter per 10 are. The application rate of the active ingredient, by conversion, corresponded to 120 g per 10 are. Fourteen days after the formulation treatment, the herbicidal effect was evaluated by the same criteria as in Test Example 1. The results are shown in Table 7.

Test Example 4

Herbicidal Effect Test by Foliage Treatment in Upland Field

A pot having a size of 36 cm² was filled with field soil (alluvial soil) and after uniformly mixing the soil of the surface layer of 1 cm with 20 grains of each weed seed of crabgrass, *Echinochloa crus-galli*, *Chenopodium album* and *Amaranthus viridis*, the surface layer was pressed lightly. Seven days after the sowing, an emulsifiable concentrate prepared according to Formulation Example 5 by using the compound shown in Table 8 below was diluted with water, and the water-diluted formulation was sprayed on the soil surface at a ratio of 100 liter per 10 are. The application rate of the active ingredient, by conversion, corresponded to 120 g per 10 are. Fourteen days after the formulation treatment, the herbicidal effect was evaluated by the same criteria as in Test Example 1. The results are shown in Table 8.

TABLE 7

| No. | Concentration (g/10a) | Crabgrass | Echinochloa crus-galli | Chenopodium album | Amaranthus viridis |
|---|---|---|---|---|---|
| 1-65 | 120 | 100 | 100 | 90 | 80 |
| 1-79 | 120 | 90 | 80 | 80 | 90 |
| 1-90 | 120 | 100 | 100 | 90 | 90 |
| 1-93 | 120 | 90 | 90 | 40 | 80 |
| 1-98 | 120 | 90 | 80 | 80 | 90 |
| 1-101 | 120 | 90 | 80 | 80 | 90 |
| 1-142 | 120 | 100 | 100 | 100 | 100 |
| 1-150 | 120 | 100 | 100 | 100 | 90 |
| 1-169 | 120 | 90 | 80 | 80 | 90 |
| 1-171 | 120 | 100 | 100 | 100 | 90 |
| 1-198 | 120 | 100 | 100 | 100 | 100 |
| 1-200 | 120 | 100 | 100 | 40 | 40 |
| 1-203 | 120 | 80 | 80 | 60 | 90 |
| 1-214 | 120 | 90 | 80 | 80 | 90 |
| 1-215 | 120 | 80 | 80 | 80 | 80 |
| 1-221 | 120 | 90 | 80 | 80 | 90 |
| 1-229 | 120 | 90 | 80 | 80 | 90 |
| 1-241 | 120 | 90 | 90 | 90 | 90 |
| 1-242 | 120 | 90 | 80 | 80 | 90 |
| 1-244 | 120 | 90 | 80 | 40 | 50 |
| 1-249 | 120 | 90 | 80 | 80 | 90 |
| 1-257 | 120 | 90 | 80 | 80 | 90 |
| 1-269 | 120 | 90 | 90 | 90 | 90 |
| 1-284 | 120 | 90 | 90 | 90 | 60 |
| 1-295 | 120 | 90 | 80 | 80 | 90 |
| 1-298 | 120 | 90 | 80 | 80 | 90 |
| 1-305 | 120 | 100 | 100 | 80 | 80 |
| 1-306 | 120 | 90 | 80 | 80 | 90 |
| 1-308 | 120 | 90 | 90 | 40 | 40 |
| 1-313 | 120 | 90 | 80 | 80 | 90 |
| 1-318 | 120 | 100 | 100 | 50 | 50 |
| 1-899 | 120 | 80 | 80 | 60 | 90 |
| 1-1095 | 120 | 90 | 80 | 80 | 90 |
| 1-1103 | 120 | 100 | 100 | 60 | 60 |
| 1-1117 | 120 | 90 | 80 | 80 | 90 |
| 1-1139 | 120 | 90 | 80 | 80 | 90 |
| 1-1140 | 120 | 90 | 80 | 80 | 90 |
| 1-1142 | 120 | 90 | 80 | 80 | 90 |
| 1-1143 | 120 | 90 | 80 | 80 | 90 |
| 1-1150 | 120 | 100 | 100 | 100 | 100 |

TABLE 8

| No. | Concentration (g/10a) | Crabgrass | Echinochloa crus-galli | Chenopodium album | Amaranthus viridis |
|---|---|---|---|---|---|
| 1-54 | 120 | 90 | 80 | 80 | 90 |
| 1-65 | 120 | 90 | 80 | 80 | 90 |
| 1-79 | 120 | 90 | 80 | 80 | 90 |
| 1-90 | 120 | 90 | 90 | 70 | 50 |
| 1-93 | 120 | 90 | 90 | 0 | 0 |
| 1-98 | 120 | 90 | 80 | 80 | 90 |
| 1-99 | 120 | 90 | 80 | 80 | 90 |
| 1-101 | 120 | 90 | 80 | 80 | 90 |
| 1-142 | 120 | 90 | 80 | 80 | 90 |
| 1-150 | 120 | 90 | 80 | 80 | 90 |
| 1-169 | 120 | 90 | 80 | 80 | 90 |
| 1-170 | 120 | 90 | 80 | 80 | 90 |
| 1-171 | 120 | 90 | 80 | 80 | 90 |
| 1-198 | 120 | 100 | 100 | 80 | 80 |
| 1-200 | 120 | 100 | 100 | 70 | 80 |
| 1-203 | 120 | 100 | 100 | 80 | 100 |
| 1-204 | 120 | 100 | 100 | 60 | 80 |
| 1-206 | 120 | 100 | 100 | 60 | 80 |
| 1-214 | 120 | 90 | 80 | 80 | 90 |
| 1-215 | 120 | 90 | 90 | 60 | 60 |
| 1-226 | 120 | 100 | 100 | 80 | 90 |
| 1-241 | 120 | 90 | 90 | 70 | 50 |
| 1-244 | 120 | 90 | 90 | 40 | 0 |
| 1-249 | 120 | 90 | 80 | 80 | 90 |
| 1-257 | 120 | 90 | 80 | 80 | 90 |
| 1-269 | 120 | 90 | 80 | 80 | 90 |
| 1-284 | 120 | 90 | 80 | 80 | 90 |
| 1-295 | 120 | 90 | 80 | 80 | 90 |
| 1-298 | 120 | 90 | 80 | 80 | 90 |
| 1-305 | 120 | 100 | 90 | 80 | 80 |
| 1-308 | 120 | 90 | 90 | 40 | 60 |
| 1-309 | 120 | 100 | 100 | 80 | 0 |
| 1-311 | 120 | 100 | 100 | 60 | 0 |
| 1-313 | 120 | 90 | 80 | 80 | 90 |
| 1-318 | 120 | 80 | 80 | 60 | 60 |
| 1-319 | 120 | 80 | 70 | 70 | 70 |
| 1-899 | 120 | 100 | 100 | 80 | 100 |
| 1-1095 | 120 | 90 | 80 | 80 | 90 |
| 1-1103 | 120 | 90 | 80 | 80 | 90 |
| 1-1117 | 120 | 90 | 80 | 80 | 90 |
| 1-1136 | 120 | 90 | 80 | 80 | 90 |
| 1-1150 | 120 | 90 | 80 | 80 | 90 |

The method for formulating the compound represented by formula (11) of the present invention as a herbicide is described more specifically by the following formulation examples. However, the herbicide is not limited to these formulation examples, and the compound may also be formulated by mixing it with other various additives at a freely selected ratio.

Formulation Example 11

(Granule)

To 1 part of the compound of Synthesis Example 11, 1 part of calcium ligninsulfonate, 1 part of lauryl sulfate, 30 parts of bentonite and 67 parts of talc, 15 Parts of water was added, and the mixture was kneaded in a kneader and then granulated in a granulator. The granules were dried in a fluidized bed drier, and a granule containing 1% of the herbicidal active ingredient can thereby be obtained. Furthermore, granules can be obtained by the same method except for using respective compounds shown in Table 2 in place of the compound of Synthesis Example 11.

Formulation Example 12

(Flowable Formulation)

In a wet-type ball mill, 20.0 Parts of the compound of Synthesis Example 11, 2.0 parts of sodium salt of sulfosuccinnic acid bis(2-ethylhexyl) ester sodium salt, 2.0 parts of polyoxyethylene nonylphenyl ether, 5.0 parts of propylene glycol, 0.5 parts of antifoaming agent, and 70.5 parts of water were uniformly mixed and ground, and a flowable formulation containing 20% of the herbicidal active ingredient can thereby be obtained. Furthermore, flowable formulations can be obtained by the same method except for using respective compounds shown in Table 2 in place of the compound of Synthesis Example 11.

Formulation Example 13

(Dry Flowable Formulation)

By uniformly mixing and grinding 75 Parts of the compound of Synthesis Example 11, 10 parts of naphthalenesulfonic acid-formaldehyde condensate, 5 parts of sodium laurylsulfate, 5 parts of white carbon, and 5 parts of clay, a dry flowable (wet-dispersible granule) formulation containing 75% of the herbicidal active ingredient can be obtained. Furthermore, dry flowable (wet-dispersible granule) formulations can be obtained by the same method except for using respective compounds shown in Table 2 in place of the compound of Synthesis Example 11.

Formulation Example 14

(Wettable Powder)

In a grinding and mixing machine, 15 Parts of the compound of Synthesis Example 11, 15 parts of white carbon, 3 parts of calcium ligninsulfonate, 2 parts of polyoxyethylene alkyl ether, 5 parts of diatomaceous earth, and 60 parts of clay were uniformly mixed, and a wettable powder containing 15% of the herbicidal active ingredient can thereby be obtained. Furthermore, wettable powders can be obtained by the same method except for using respective compounds shown in Table 2 in place of the compound of Synthesis Example 11.

Formulation Example 15

(Emulsifiable Concentrate)

By mixing 20 Parts of the compound of Synthesis Example 11, 18 parts of polyoxyethylene styrylphenyl ether, 2 parts of calcium dodecylbenzenesulfonate, and 60 parts of xylene, an emulsifiable concentrate containing 20% of the herbicidal active ingredient can be obtained. Furthermore, emulsifiable concentrates can be obtained by the same method except for using respective compounds shown in Table 2 in place of the compound of Synthesis Example 11.

Formulation Example 16

(Dust)

By uniformly mixing and grinding 0.5 Parts of the compound of Synthesis Example 11, 0.5 parts of white carbon, 0.5 parts of calcium stearate, 50.0 parts of clay, and 48.5 parts of talc, a dust containing 0.5% of the herbicidal active ingredient can be obtained. Furthermore, dusts can be obtained by the same method except for using respective compounds shown in Table 2 in place of the compound of Synthesis Example 11.

Formulation Example 17

(Jumbo Formulation)

After mixing 15 Parts of the compound of Synthesis Example 11, 2 parts of sodium laurylsulfate, 5 parts of sulfosuccinic acid bis(2-ethylhexyl) ester sodium salt, 5 parts of carboxymethyl cellulose sodium salt, 35 parts of silas balloon, 10 parts of lactose, and 28 parts of expanded perlite, followed by addition of 35 parts of water, the mixture was kneaded in a kneader and then granulated in a granulator. The granules were dried in a fluidized bed drier, and a jumbo formulation containing 15% of the herbicidal active ingredient can thereby be obtained. Furthermore, jumbo formulations can be obtained by the same method except for using respective compounds shown in Table 2 in place of the compound of Synthesis Example 11.

Test Examples are described below for demonstrating the herbicidal effect of the compound represented by formula (11) of the present invention.

Test Example 11

Herbicidal Effect Test by Soil Treatment in Paddy Field

A Wagner pot having an area of 1/10000 are was filled with paddy field soil and after adding water, a chemical fertilizer (N:P:K=17:17:17) was mixed, followed by puddling. Thereafter, 30 grains of each of *Echinochloa crusgalli*, broad-leaved weed (*Lindernia* pyxidaria, *Monochoria vaginalis*) and *Scirpus juncoides* seeds were sown to a depth of 0 to 1 cm. Immediately after the sowing, the pot was flooded, and the depth of water was kept at about 3 cm. The pot was subsequently managed in a glass greenhouse. Just after that, an emulsifiable concentrate prepared according to Formulation Example 15 by using the compound shown in Table 9 below was diluted with water, and a predetermined amount of the water-diluted formulation was added dropwise. The application rate of the active ingredient, by conversion, corresponded to 120 g per 10 are.

This test was performed with two replications per one formulation concentration plot, and 14 days after the formulation treatments, the weed suppression rate (%) was determined according to the following equation (Math. 2).

Weed suppression rate (%)=(1−average dry weight (g) of plants in treated plots/average dry weight (g) of plants in untreated plots)×100    [Math. 2]

The results are shown in Table 9 below. The compound numbers in Table 9 are the same as those shown in Table 2 and Table 4.

TABLE 9

| No. | Concentration (g/10a) | Echinochloa crus-galli | Monochoria vaginalis | Lindemia pyxidaria | Scirpus juncoides |
|---|---|---|---|---|---|
| 11-1 | 120 | 90 | 80 | 80 | 90 |
| 11-2 | 120 | 90 | 80 | 80 | 90 |
| 11-3 | 120 | 90 | 80 | 80 | 90 |
| 11-11 | 120 | 100 | 100 | 100 | 100 |
| 11-12 | 120 | 100 | 100 | 100 | 100 |
| 11-14 | 120 | 100 | 80 | 100 | 90 |
| 11-15 | 120 | 90 | 60 | 70 | 60 |
| 11-16 | 120 | 100 | 90 | 100 | 90 |
| 11-17 | 120 | 100 | 80 | 90 | 100 |
| 11-19 | 120 | 90 | 80 | 80 | 90 |
| 11-20 | 120 | 70 | 40 | 40 | 80 |
| 11-25 | 120 | 90 | 60 | 70 | 90 |
| 11-26 | 120 | 90 | 80 | 80 | 90 |
| 11-38 | 120 | 100 | 70 | 80 | 70 |
| 11-46 | 120 | 100 | 100 | 100 | 90 |
| 11-48 | 120 | 90 | 80 | 80 | 90 |
| 11-49 | 120 | 90 | 80 | 80 | 90 |
| 11-50 | 120 | 90 | 80 | 80 | 90 |
| 11-58 | 120 | 100 | 100 | 100 | 100 |
| 11-59 | 120 | 100 | 100 | 100 | 100 |
| 11-61 | 120 | 100 | 80 | 100 | 100 |
| 11-62 | 120 | 100 | 90 | 100 | 100 |

TABLE 9-continued

| No. | Concentration (g/10a) | Echinochloa crus-galli | Monochoria vaginalis | Lindernia pyxidaria | Scirpus juncoides |
|---|---|---|---|---|---|
| 11-63 | 120 | 100 | 100 | 100 | 100 |
| 11-64 | 120 | 100 | 90 | 100 | 100 |
| 11-66 | 120 | 90 | 80 | 80 | 90 |
| 11-67 | 120 | 100 | 90 | 90 | 90 |
| 11-70 | 120 | 100 | 90 | 100 | 100 |
| 11-71 | 120 | 100 | 70 | 90 | 100 |
| 11-73 | 120 | 90 | 80 | 80 | 90 |
| 11-74 | 120 | 90 | 80 | 80 | 90 |
| 11-76 | 120 | 100 | 100 | 80 | 60 |
| 11-85 | 120 | 90 | 80 | 80 | 90 |
| 11-86 | 120 | 90 | 80 | 80 | 90 |
| 11-91 | 120 | 90 | 80 | 80 | 90 |
| 11-93 | 120 | 90 | 90 | 90 | 90 |
| 11-94 | 120 | 100 | 100 | 100 | 90 |
| 11-95 | 120 | 100 | 50 | 100 | 100 |
| 11-109 | 120 | 100 | 90 | 100 | 90 |
| 11-123 | 120 | 90 | 80 | 80 | 90 |
| 11-126 | 120 | 100 | 60 | 100 | 30 |
| 11-134 | 120 | 70 | 40 | 40 | 40 |
| 11-140 | 120 | 90 | 70 | 70 | 80 |
| 11-142 | 120 | 100 | 90 | 100 | 100 |
| 11-144 | 120 | 100 | 80 | 90 | 100 |
| 11-159 | 120 | 90 | 80 | 80 | 90 |
| 11-160 | 120 | 100 | 70 | 90 | 90 |
| 11-161 | 120 | 100 | 70 | 100 | 90 |
| 11-162 | 120 | 100 | 90 | 90 | 90 |
| 11-189 | 120 | 100 | 90 | 100 | 90 |
| 11-191 | 120 | 100 | 90 | 100 | 100 |
| 11-194 | 120 | 100 | 100 | 100 | 100 |
| 11-195 | 120 | 100 | 80 | 100 | 100 |
| 11-197 | 120 | 100 | 70 | 100 | 100 |
| 11-205 | 120 | 100 | 90 | 100 | 100 |
| 11-206 | 120 | 100 | 100 | 100 | 100 |
| 11-209 | 120 | 100 | 90 | 100 | 100 |
| 11-210 | 120 | 90 | 80 | 90 | 90 |
| 11-211 | 120 | 100 | 80 | 100 | 90 |
| 11-212 | 120 | 100 | 80 | 90 | 90 |
| 11-213 | 120 | 100 | 60 | 90 | 90 |
| 11-217 | 120 | 100 | 100 | 100 | 80 |
| 11-220 | 120 | 100 | 60 | 90 | 90 |
| 11-222 | 120 | 90 | 80 | 80 | 90 |
| 11-233 | 120 | 100 | 90 | 100 | 90 |
| 11-234 | 120 | 90 | 80 | 90 | 90 |
| 11-238 | 120 | 90 | 80 | 100 | 90 |
| 11-246 | 120 | 90 | 80 | 80 | 90 |
| 11-258 | 120 | 100 | 100 | 100 | 100 |
| 11-273 | 120 | 100 | 90 | 100 | 90 |
| 11-283 | 120 | 100 | 70 | 90 | 90 |
| 11-284 | 120 | 100 | 100 | 100 | 100 |
| 11-285 | 120 | 90 | 80 | 80 | 90 |
| 11-293 | 120 | 100 | 100 | 100 | 100 |
| 11-294 | 120 | 100 | 100 | 100 | 100 |
| 11-296 | 120 | 100 | 70 | 100 | 100 |
| 11-297 | 120 | 100 | 90 | 100 | 100 |
| 11-298 | 120 | 100 | 100 | 100 | 100 |
| 11-299 | 120 | 100 | 70 | 100 | 100 |
| 11-301 | 120 | 90 | 80 | 80 | 90 |
| 11-305 | 120 | 100 | 100 | 100 | 90 |
| 11-306 | 120 | 100 | 60 | 80 | 100 |
| 11-307 | 120 | 80 | 70 | 70 | 80 |
| 11-308 | 120 | 90 | 90 | 90 | 90 |
| 11-309 | 120 | 90 | 80 | 80 | 90 |
| 11-314 | 120 | 90 | 80 | 80 | 90 |
| 11-316 | 120 | 90 | 80 | 80 | 90 |
| 11-352 | 120 | 100 | 50 | 60 | 60 |
| 11-353 | 120 | 90 | 80 | 80 | 90 |
| 11-358 | 120 | 90 | 80 | 80 | 90 |
| 11-361 | 120 | 90 | 80 | 80 | 90 |
| 11-367 | 120 | 100 | 90 | 100 | 90 |
| 11-391 | 120 | 90 | 60 | 80 | 80 |
| 11-392 | 120 | 90 | 80 | 80 | 90 |
| 11-401 | 120 | 100 | 100 | 100 | 90 |
| 11-404 | 120 | 100 | 60 | 30 | 30 |
| 11-405 | 120 | 100 | 100 | 100 | 100 |
| 11-406 | 120 | 100 | 80 | 100 | 80 |
| 11-413 | 120 | 80 | 80 | 90 | 80 |
| 11-415 | 120 | 80 | 70 | 70 | 30 |

TABLE 9-continued

| No. | Concentration (g/10a) | Echinochloa crus-galli | Monochoria vaginalis | Lindemia pyxidaria | Scirpus juncoides |
|---|---|---|---|---|---|
| 11-416 | 120 | 90 | 80 | 80 | 90 |
| 11-419 | 120 | 100 | 60 | 100 | 70 |
| 11-427 | 120 | 100 | 60 | 80 | 60 |
| 11-428 | 120 | 90 | 90 | 90 | 90 |
| 11-437 | 120 | 100 | 80 | 80 | 80 |
| 11-441 | 120 | 100 | 60 | 90 | 100 |
| 11-442 | 120 | 100 | 70 | 80 | 80 |
| 11-443 | 120 | 80 | 70 | 70 | 100 |
| 11-445 | 120 | 100 | 60 | 70 | 100 |
| 11-463 | 120 | 90 | 50 | 50 | 40 |
| 11-464 | 120 | 100 | 60 | 80 | 80 |
| 11-465 | 120 | 90 | 80 | 80 | 90 |
| 11-474 | 120 | 100 | 100 | 100 | 100 |
| 11-475 | 120 | 100 | 90 | 90 | 90 |
| 11-477 | 120 | 100 | 70 | 90 | 100 |
| 11-478 | 120 | 100 | 100 | 100 | 100 |
| 11-479 | 120 | 100 | 80 | 100 | 100 |
| 11-480 | 120 | 100 | 80 | 90 | 90 |
| 11-482 | 120 | 90 | 80 | 80 | 90 |
| 11-486 | 120 | 90 | 80 | 90 | 80 |
| 11-488 | 120 | 100 | 80 | 100 | 100 |
| 11-490 | 120 | 90 | 80 | 80 | 90 |
| 11-500 | 120 | 90 | 50 | 50 | 50 |
| 11-501 | 120 | 100 | 80 | 90 | 90 |
| 11-502 | 120 | 90 | 80 | 80 | 90 |
| 11-511 | 120 | 100 | 90 | 100 | 100 |
| 11-512 | 120 | 100 | 100 | 100 | 100 |
| 11-515 | 120 | 100 | 80 | 90 | 100 |
| 11-516 | 120 | 100 | 80 | 90 | 90 |
| 11-519 | 120 | 100 | 70 | 100 | 100 |
| 11-525 | 120 | 60 | 90 | 90 | 60 |
| 11-526 | 120 | 90 | 80 | 80 | 90 |
| 11-527 | 120 | 90 | 80 | 80 | 90 |
| 11-536 | 120 | 90 | 60 | 90 | 60 |
| 11-538 | 120 | 50 | 40 | 40 | 40 |
| 11-539 | 120 | 80 | 40 | 90 | 40 |
| 11-549 | 120 | 80 | 100 | 90 | 100 |
| 11-550 | 120 | 90 | 80 | 90 | 80 |
| 11-553 | 120 | 100 | 70 | 90 | 30 |
| 11-554 | 120 | 100 | 70 | 90 | 70 |
| 11-563 | 120 | 100 | 90 | 100 | 100 |
| 11-574 | 120 | 90 | 40 | 80 | 50 |
| 11-576 | 120 | 40 | 0 | 0 | 0 |
| 11-577 | 120 | 40 | 0 | 60 | 0 |
| 11-578 | 120 | 90 | 80 | 80 | 90 |
| 11-587 | 120 | 90 | 60 | 80 | 60 |
| 11-588 | 120 | 90 | 90 | 90 | 90 |
| 11-591 | 120 | 100 | 70 | 90 | 60 |
| 11-592 | 120 | 100 | 90 | 100 | 80 |
| 11-593 | 120 | 80 | 60 | 70 | 30 |
| 11-595 | 120 | 90 | 70 | 90 | 60 |
| 11-601 | 120 | 70 | 80 | 80 | 60 |
| 11-612 | 120 | 100 | 70 | 100 | 70 |
| 11-616 | 120 | 90 | 90 | 90 | 90 |
| 11-622 | 120 | 90 | 0 | 40 | 40 |
| 11-623 | 120 | 100 | 90 | 100 | 90 |
| 11-625 | 120 | 100 | 40 | 80 | 60 |
| 11-626 | 120 | 100 | 70 | 90 | 90 |
| 11-627 | 120 | 90 | 80 | 80 | 90 |
| 11-628 | 120 | 90 | 80 | 80 | 90 |
| 11-636 | 120 | 100 | 100 | 100 | 90 |
| 11-637 | 120 | 100 | 100 | 100 | 90 |
| 11-639 | 120 | 100 | 70 | 100 | 100 |
| 11-640 | 120 | 100 | 70 | 100 | 90 |
| 11-641 | 120 | 100 | 80 | 100 | 100 |
| 11-642 | 120 | 100 | 70 | 80 | 70 |
| 11-644 | 120 | 90 | 80 | 80 | 90 |
| 11-645 | 120 | 100 | 90 | 90 | 90 |
| 11-649 | 120 | 90 | 60 | 70 | 60 |
| 11-651 | 120 | 90 | 90 | 90 | 90 |
| 11-652 | 120 | 90 | 80 | 80 | 90 |
| 11-661 | 120 | 100 | 80 | 100 | 90 |
| 11-665 | 120 | 80 | 40 | 40 | 40 |
| 11-666 | 120 | 100 | 90 | 90 | 90 |
| 11-670 | 120 | 50 | 50 | 70 | 60 |
| 11-672 | 120 | 90 | 80 | 80 | 90 |
| 11-681 | 120 | 100 | 80 | 90 | 100 |

TABLE 9-continued

| No. | Concentration (g/10a) | Echinochloa crus-galli | Monochoria vaginalis | Lindemia pyxidaria | Scirpus juncoides |
|---|---|---|---|---|---|
| 11-682 | 120 | 100 | 90 | 90 | 90 |
| 11-685 | 120 | 90 | 100 | 100 | 60 |
| 11-686 | 120 | 90 | 80 | 100 | 100 |
| 11-687 | 120 | 80 | 100 | 100 | 90 |
| 11-689 | 120 | 90 | 70 | 90 | 70 |
| 11-693 | 120 | 80 | 60 | 60 | 60 |
| 11-694 | 120 | 90 | 70 | 80 | 70 |
| 11-696 | 120 | 90 | 80 | 80 | 90 |
| 11-699 | 120 | 90 | 70 | 90 | 30 |
| 11-706 | 120 | 100 | 80 | 100 | 90 |
| 11-710 | 120 | 70 | 40 | 40 | 40 |
| 11-711 | 120 | 90 | 90 | 90 | 90 |
| 11-726 | 120 | 100 | 30 | 90 | 30 |
| 11-727 | 120 | 90 | 60 | 80 | 80 |
| 11-735 | 120 | 100 | 90 | 90 | 100 |
| 11-737 | 120 | 90 | 80 | 80 | 90 |
| 11-749 | 120 | 60 | 70 | 70 | 70 |
| 11-762 | 120 | 90 | 90 | 90 | 40 |
| 11-772 | 120 | 100 | 80 | 90 | 80 |
| 11-777 | 120 | 100 | 80 | 90 | 100 |
| 11-780 | 120 | 60 | 60 | 100 | 100 |
| 11-787 | 120 | 90 | 80 | 80 | 90 |
| 11-790 | 120 | 80 | 30 | 90 | 90 |
| 11-800 | 120 | 90 | 80 | 90 | 90 |
| 11-801 | 120 | 90 | 90 | 90 | 90 |
| 11-814 | 120 | 70 | 70 | 90 | 30 |
| 11-815 | 120 | 100 | 80 | 100 | 100 |
| 11-818 | 120 | 100 | 100 | 100 | 100 |
| 11-825 | 120 | 90 | 80 | 80 | 90 |
| 11-852 | 120 | 100 | 90 | 90 | 90 |
| 11-853 | 120 | 100 | 80 | 90 | 90 |
| 11-854 | 120 | 100 | 80 | 90 | 90 |
| 11-855 | 120 | 100 | 90 | 90 | 90 |
| 11-862 | 120 | 100 | 100 | 100 | 100 |
| 11-863 | 120 | 100 | 100 | 100 | 100 |
| 11-865 | 120 | 80 | 70 | 70 | 70 |
| 11-866 | 120 | 100 | 90 | 100 | 90 |
| 11-867 | 120 | 100 | 80 | 100 | 80 |
| 11-868 | 120 | 100 | 70 | 100 | 100 |
| 11-870 | 120 | 90 | 80 | 80 | 90 |
| 11-876 | 120 | 100 | 100 | 100 | 100 |
| 11-878 | 120 | 90 | 80 | 80 | 90 |
| 11-880 | 120 | 80 | 100 | 80 | 30 |
| 11-889 | 120 | 100 | 80 | 100 | 90 |
| 11-944 | 120 | 90 | 100 | 100 | 90 |
| 11-985 | 120 | 90 | 40 | 60 | 40 |
| 11-1011 | 120 | 90 | 80 | 80 | 90 |
| 11-1014 | 120 | 90 | 80 | 90 | 90 |
| 11-1021 | 120 | 100 | 100 | 100 | 100 |
| 11-1022 | 120 | 100 | 90 | 100 | 100 |
| 11-1024 | 120 | 100 | 70 | 80 | 80 |
| 11-1025 | 120 | 100 | 100 | 100 | 100 |
| 11-1026 | 120 | 100 | 100 | 100 | 100 |
| 11-1027 | 120 | 100 | 90 | 100 | 100 |
| 11-1029 | 120 | 90 | 80 | 80 | 90 |
| 11-1033 | 120 | 100 | 90 | 100 | 100 |
| 11-1034 | 120 | 100 | 70 | 90 | 100 |
| 11-1036 | 120 | 90 | 90 | 90 | 90 |
| 11-1042 | 120 | 90 | 80 | 80 | 90 |
| 11-1044 | 120 | 90 | 90 | 90 | 90 |
| 11-1046 | 120 | 100 | 60 | 80 | 80 |
| 11-1054 | 120 | 90 | 80 | 80 | 90 |
| 11-1056 | 120 | 90 | 80 | 80 | 90 |
| 11-1064 | 120 | 100 | 100 | 100 | 100 |
| 11-1071 | 120 | 90 | 80 | 80 | 90 |
| 11-1072 | 120 | 90 | 80 | 80 | 90 |
| 11-1076 | 120 | 90 | 60 | 60 | 60 |
| 11-1079 | 120 | 90 | 80 | 80 | 90 |
| 11-1084 | 120 | 90 | 80 | 80 | 90 |
| 11-1088 | 120 | 90 | 80 | 80 | 90 |
| 11-1090 | 120 | 100 | 60 | 100 | 90 |
| 11-1098 | 120 | 100 | 80 | 100 | 100 |
| 11-1101 | 120 | 90 | 90 | 90 | 90 |
| 11-1102 | 120 | 100 | 90 | 100 | 90 |
| 11-1109 | 120 | 90 | 80 | 80 | 90 |
| 11-1125 | 120 | 90 | 60 | 60 | 60 |
| 11-1126 | 120 | 100 | 70 | 90 | 100 |

TABLE 9-continued

| No. | Concentration (g/10a) | Echinochloa crus-galli | Monochoria vaginalis | Lindemia pyxidaria | Scirpus juncoides |
|---|---|---|---|---|---|
| 11-1127 | 120 | 100 | 70 | 80 | 80 |
| 11-1129 | 120 | 100 | 100 | 100 | 100 |
| 11-1131 | 120 | 100 | 70 | 100 | 100 |
| 11-1137 | 120 | 100 | 80 | 90 | 100 |
| 11-1140 | 120 | 100 | 90 | 100 | 100 |
| 11-1147 | 120 | 100 | 70 | 100 | 70 |
| 11-1148 | 120 | 100 | 90 | 100 | 100 |
| 11-1149 | 120 | 100 | 100 | 100 | 100 |
| 11-1150 | 120 | 100 | 70 | 100 | 90 |
| 11-1151 | 120 | 100 | 70 | 100 | 80 |
| 11-1152 | 120 | 100 | 100 | 100 | 100 |
| 11-1153 | 120 | 100 | 90 | 100 | 60 |
| 11-1154 | 120 | 100 | 100 | 100 | 100 |
| 11-1155 | 120 | 100 | 80 | 100 | 100 |
| 11-1156 | 120 | 70 | 30 | 80 | 30 |

Test Example 12

Herbicidal Effect Test by Treatment During Growing Period in Paddy Field

A Wagner pot having an area of 1/10000 are was filled with paddy field soil and after adding water, a chemical fertilizer (N:P:K=17:17:17) was mixed, followed by puddling. Thereafter, 30 grains of each of *Echinochloa crus-galli*, broad-leaved weed (*Lindernia* pyxidaria, *Monochoria vaginalis*) and *Scirpus juncoides* seeds were sown to a depth of 0 to 1 cm. Immediately after the sowing, the pot was flooded, and the depth of water was kept at about 3 cm. The pot was subsequently managed in a glass greenhouse. Seven Days after sowing, an emulsifiable concentrate prepared according to Formulation Example 15 by using the compound shown in Table 10 below was diluted with water, and a predetermined amount of the water-diluted formulation was added dropwise. The application rate of the active ingredient, by conversion, corresponded to 120 g per 10 are. The test was performed with two replications per one formulation concentration plot, and 14 days after the formulation treatments, the weed suppression rate (%) was determined according to the equation (Math. 2). The results are shown in Table 10.

TABLE 10

| No. | Concentration (g/10a) | Echinochloa crus-galli | Monochoria vaginalis | Lindemia pyxidaria | Scirpus juncoides |
|---|---|---|---|---|---|
| 11-1 | 120 | 90 | 80 | 80 | 90 |
| 11-2 | 120 | 90 | 80 | 90 | 90 |
| 11-3 | 120 | 90 | 80 | 80 | 90 |
| 11-11 | 120 | 100 | 100 | 80 | 100 |
| 11-12 | 120 | 100 | 90 | 100 | 90 |
| 11-14 | 120 | 100 | 80 | 80 | 100 |
| 11-15 | 120 | 70 | 60 | 60 | 100 |
| 11-16 | 120 | 100 | 100 | 90 | 100 |
| 11-17 | 120 | 100 | 100 | 70 | 100 |
| 11-19 | 120 | 90 | 80 | 80 | 90 |
| 11-20 | 120 | 70 | 60 | 40 | 60 |
| 11-25 | 120 | 100 | 70 | 70 | 100 |
| 11-26 | 120 | 90 | 80 | 80 | 90 |
| 11-38 | 120 | 100 | 80 | 90 | 90 |
| 11-46 | 120 | 100 | 90 | 100 | 90 |
| 11-48 | 120 | 90 | 90 | 70 | 70 |
| 11-49 | 120 | 100 | 90 | 90 | 90 |
| 11-50 | 120 | 90 | 80 | 80 | 90 |
| 11-58 | 120 | 100 | 100 | 100 | 100 |
| 11-59 | 120 | 100 | 100 | 80 | 90 |
| 11-61 | 120 | 100 | 100 | 100 | 80 |
| 11-62 | 120 | 100 | 100 | 80 | 100 |
| 11-63 | 120 | 100 | 100 | 80 | 100 |
| 11-64 | 120 | 100 | 90 | 80 | 100 |
| 11-66 | 120 | 90 | 80 | 80 | 90 |
| 11-67 | 120 | 100 | 90 | 90 | 90 |
| 11-70 | 120 | 100 | 90 | 70 | 100 |
| 11-71 | 120 | 100 | 70 | 70 | 100 |
| 11-73 | 120 | 90 | 80 | 80 | 90 |
| 11-74 | 120 | 90 | 80 | 80 | 90 |
| 11-76 | 120 | 100 | 80 | 60 | 60 |
| 11-85 | 120 | 90 | 90 | 90 | 70 |
| 11-86 | 120 | 90 | 90 | 90 | 90 |
| 11-91 | 120 | 90 | 80 | 80 | 90 |
| 11-93 | 120 | 90 | 90 | 80 | 90 |
| 11-94 | 120 | 100 | 90 | 100 | 90 |
| 11-95 | 120 | 90 | 90 | 60 | 70 |
| 11-109 | 120 | 100 | 90 | 100 | 90 |

TABLE 10-continued

| No. | Concentration (g/10a) | Echinochloa crus-galli | Monochoria vaginalis | Lindemia pyxidaria | Scirpus juncoides |
|---|---|---|---|---|---|
| 11-123 | 120 | 90 | 80 | 80 | 90 |
| 11-134 | 120 | 70 | 40 | 40 | 40 |
| 11-140 | 120 | 100 | 70 | 70 | 100 |
| 11-142 | 120 | 100 | 90 | 80 | 80 |
| 11-144 | 120 | 100 | 100 | 100 | 100 |
| 11-159 | 120 | 90 | 90 | 70 | 80 |
| 11-160 | 120 | 100 | 70 | 90 | 90 |
| 11-161 | 120 | 90 | 80 | 80 | 90 |
| 11-162 | 120 | 90 | 80 | 80 | 90 |
| 11-189 | 120 | 100 | 100 | 80 | 100 |
| 11-191 | 120 | 100 | 90 | 90 | 90 |
| 11-194 | 120 | 100 | 100 | 100 | 100 |
| 11-195 | 120 | 100 | 90 | 70 | 90 |
| 11-197 | 120 | 100 | 100 | 80 | 90 |
| 11-205 | 120 | 100 | 100 | 80 | 100 |
| 11-206 | 120 | 100 | 90 | 90 | 90 |
| 11-209 | 120 | 100 | 90 | 80 | 100 |
| 11-210 | 120 | 90 | 80 | 80 | 90 |
| 11-211 | 120 | 100 | 80 | 80 | 100 |
| 11-212 | 120 | 90 | 80 | 80 | 90 |
| 11-213 | 120 | 90 | 80 | 80 | 90 |
| 11-217 | 120 | 100 | 90 | 80 | 80 |
| 11-220 | 120 | 90 | 90 | 90 | 80 |
| 11-222 | 120 | 90 | 80 | 80 | 90 |
| 11-233 | 120 | 100 | 90 | 90 | 90 |
| 11-234 | 120 | 90 | 90 | 90 | 90 |
| 11-238 | 120 | 100 | 90 | 80 | 90 |
| 11-246 | 120 | 90 | 80 | 80 | 90 |
| 11-258 | 120 | 90 | 90 | 90 | 90 |
| 11-273 | 120 | 100 | 90 | 90 | 90 |
| 11-283 | 120 | 90 | 90 | 90 | 90 |
| 11-284 | 120 | 100 | 100 | 100 | 90 |
| 11-285 | 120 | 90 | 80 | 80 | 90 |
| 11-293 | 120 | 100 | 100 | 100 | 100 |
| 11-294 | 120 | 100 | 90 | 80 | 90 |
| 11-296 | 120 | 100 | 90 | 80 | 90 |
| 11-297 | 120 | 100 | 100 | 70 | 100 |
| 11-298 | 120 | 100 | 80 | 80 | 100 |
| 11-299 | 120 | 100 | 100 | 80 | 100 |
| 11-301 | 120 | 90 | 80 | 80 | 90 |
| 11-305 | 120 | 100 | 100 | 90 | 100 |
| 11-306 | 120 | 90 | 70 | 70 | 100 |
| 11-307 | 120 | 90 | 60 | 70 | 60 |
| 11-308 | 120 | 90 | 80 | 80 | 90 |
| 11-309 | 120 | 90 | 80 | 80 | 90 |
| 11-314 | 120 | 90 | 80 | 80 | 90 |
| 11-316 | 120 | 90 | 80 | 80 | 90 |
| 11-352 | 120 | 100 | 60 | 70 | 60 |
| 11-353 | 120 | 90 | 80 | 80 | 90 |
| 11-358 | 120 | 90 | 80 | 80 | 90 |
| 11-361 | 120 | 90 | 80 | 80 | 90 |
| 11-367 | 120 | 100 | 90 | 90 | 90 |
| 11-391 | 120 | 90 | 80 | 80 | 80 |
| 11-392 | 120 | 90 | 80 | 80 | 90 |
| 11-401 | 120 | 100 | 100 | 80 | 100 |
| 11-404 | 120 | 100 | 70 | 70 | 70 |
| 11-405 | 120 | 100 | 100 | 100 | 100 |
| 11-406 | 120 | 100 | 80 | 70 | 80 |
| 11-413 | 120 | 60 | 70 | 70 | 70 |
| 11-416 | 120 | 90 | 80 | 80 | 90 |
| 11-419 | 120 | 90 | 80 | 60 | 60 |
| 11-427 | 120 | 90 | 90 | 90 | 90 |
| 11-428 | 120 | 90 | 90 | 90 | 90 |
| 11-437 | 120 | 100 | 100 | 100 | 100 |
| 11-441 | 120 | 100 | 80 | 60 | 100 |
| 11-442 | 120 | 100 | 90 | 80 | 80 |
| 11-443 | 120 | 70 | 70 | 70 | 100 |
| 11-463 | 120 | 90 | 80 | 80 | 80 |
| 11-464 | 120 | 90 | 80 | 60 | 90 |
| 11-465 | 120 | 90 | 80 | 80 | 90 |
| 11-474 | 120 | 100 | 90 | 100 | 100 |
| 11-475 | 120 | 90 | 90 | 90 | 90 |
| 11-477 | 120 | 100 | 70 | 60 | 70 |
| 11-478 | 120 | 100 | 90 | 70 | 100 |
| 11-479 | 120 | 100 | 80 | 70 | 80 |
| 11-480 | 120 | 100 | 70 | 80 | 100 |
| 11-482 | 120 | 90 | 80 | 80 | 90 |

TABLE 10-continued

| No. | Concentration (g/10a) | Echinochloa crus-galli | Monochoria vaginalis | Lindemia pyxidaria | Scirpus juncoides |
|---|---|---|---|---|---|
| 11-486 | 120 | 60 | 70 | 70 | 60 |
| 11-488 | 120 | 100 | 100 | 100 | 80 |
| 11-500 | 120 | 80 | 60 | 60 | 60 |
| 11-501 | 120 | 100 | 90 | 80 | 90 |
| 11-502 | 120 | 90 | 80 | 80 | 90 |
| 11-511 | 120 | 100 | 100 | 80 | 100 |
| 11-512 | 120 | 100 | 100 | 100 | 90 |
| 11-515 | 120 | 100 | 100 | 70 | 100 |
| 11-516 | 120 | 100 | 80 | 70 | 70 |
| 11-519 | 120 | 80 | 70 | 70 | 80 |
| 11-526 | 120 | 90 | 80 | 80 | 90 |
| 11-536 | 120 | 90 | 60 | 80 | 90 |
| 11-538 | 120 | 70 | 70 | 70 | 70 |
| 11-550 | 120 | 70 | 90 | 90 | 80 |
| 11-553 | 120 | 100 | 60 | 70 | 30 |
| 11-554 | 120 | 80 | 80 | 80 | 90 |
| 11-563 | 120 | 100 | 80 | 80 | 100 |
| 11-587 | 120 | 90 | 90 | 80 | 90 |
| 11-588 | 120 | 80 | 90 | 90 | 70 |
| 11-591 | 120 | 60 | 70 | 70 | 100 |
| 11-592 | 120 | 100 | 100 | 80 | 80 |
| 11-601 | 120 | 60 | 70 | 70 | 60 |
| 11-612 | 120 | 80 | 70 | 90 | 90 |
| 11-616 | 120 | 50 | 80 | 80 | 60 |
| 11-622 | 120 | 90 | 50 | 50 | 50 |
| 11-623 | 120 | 100 | 100 | 100 | 90 |
| 11-626 | 120 | 90 | 80 | 80 | 90 |
| 11-627 | 120 | 90 | 80 | 80 | 90 |
| 11-628 | 120 | 90 | 80 | 80 | 90 |
| 11-636 | 120 | 100 | 100 | 80 | 100 |
| 11-637 | 120 | 100 | 90 | 90 | 90 |
| 11-639 | 120 | 100 | 70 | 70 | 70 |
| 11-640 | 120 | 80 | 100 | 70 | 90 |
| 11-641 | 120 | 100 | 90 | 80 | 100 |
| 11-642 | 120 | 100 | 90 | 70 | 100 |
| 11-644 | 120 | 90 | 80 | 80 | 90 |
| 11-645 | 120 | 60 | 90 | 90 | 60 |
| 11-648 | 120 | 60 | 70 | 60 | 90 |
| 11-651 | 120 | 90 | 80 | 80 | 90 |
| 11-661 | 120 | 100 | 100 | 100 | 90 |
| 11-665 | 120 | 90 | 60 | 60 | 60 |
| 11-666 | 120 | 100 | 90 | 90 | 90 |
| 11-672 | 120 | 90 | 80 | 80 | 90 |
| 11-681 | 120 | 100 | 100 | 90 | 100 |
| 11-682 | 120 | 90 | 90 | 90 | 80 |
| 11-685 | 120 | 80 | 70 | 60 | 60 |
| 11-686 | 120 | 90 | 70 | 60 | 100 |
| 11-687 | 120 | 100 | 80 | 70 | 70 |
| 11-689 | 120 | 60 | 80 | 70 | 90 |
| 11-694 | 120 | 70 | 70 | 60 | 80 |
| 11-696 | 120 | 90 | 80 | 80 | 90 |
| 11-706 | 120 | 80 | 80 | 80 | 70 |
| 11-710 | 120 | 80 | 40 | 40 | 40 |
| 11-711 | 120 | 60 | 70 | 70 | 60 |
| 11-735 | 120 | 100 | 90 | 90 | 100 |
| 11-737 | 120 | 90 | 80 | 80 | 90 |
| 11-762 | 120 | 80 | 90 | 60 | 80 |
| 11-772 | 120 | 100 | 90 | 70 | 90 |
| 11-777 | 120 | 90 | 80 | 70 | 70 |
| 11-800 | 120 | 90 | 90 | 60 | 90 |
| 11-801 | 120 | 90 | 80 | 60 | 60 |
| 11-815 | 120 | 100 | 70 | 80 | 70 |
| 11-818 | 120 | 100 | 100 | 80 | 100 |
| 11-825 | 120 | 90 | 80 | 80 | 90 |
| 11-852 | 120 | 80 | 90 | 90 | 90 |
| 11-853 | 120 | 90 | 80 | 80 | 90 |
| 11-854 | 120 | 80 | 90 | 90 | 80 |
| 11-855 | 120 | 80 | 80 | 60 | 80 |
| 11-862 | 120 | 100 | 100 | 80 | 100 |
| 11-863 | 120 | 90 | 90 | 90 | 90 |
| 11-866 | 120 | 80 | 90 | 70 | 60 |
| 11-867 | 120 | 100 | 80 | 70 | 80 |
| 11-868 | 120 | 90 | 80 | 90 | 60 |
| 11-870 | 120 | 90 | 80 | 80 | 90 |
| 11-876 | 120 | 100 | 100 | 100 | 100 |
| 11-889 | 120 | 100 | 80 | 70 | 90 |
| 11-944 | 120 | 90 | 90 | 90 | 90 |

TABLE 10-continued

| No. | Concentration (g/10a) | Echinochloa crus-galli | Monochoria vaginalis | Lindernia pyxidaria | Scirpus juncoides |
|---|---|---|---|---|---|
| 11-1011 | 120 | 90 | 80 | 80 | 90 |
| 11-1014 | 120 | 90 | 80 | 80 | 90 |
| 11-1021 | 120 | 100 | 90 | 80 | 100 |
| 11-1022 | 120 | 90 | 90 | 90 | 90 |
| 11-1024 | 120 | 100 | 90 | 80 | 90 |
| 11-1025 | 120 | 100 | 100 | 80 | 100 |
| 11-1026 | 120 | 100 | 100 | 80 | 100 |
| 11-1027 | 120 | 100 | 90 | 80 | 100 |
| 11-1029 | 120 | 90 | 80 | 80 | 90 |
| 11-1033 | 120 | 100 | 100 | 100 | 100 |
| 11-1034 | 120 | 90 | 70 | 70 | 70 |
| 11-1036 | 120 | 90 | 80 | 80 | 90 |
| 11-1042 | 120 | 90 | 80 | 80 | 90 |
| 11-1044 | 120 | 90 | 80 | 80 | 90 |
| 11-1046 | 120 | 100 | 90 | 90 | 90 |
| 11-1054 | 120 | 90 | 80 | 80 | 90 |
| 11-1056 | 120 | 90 | 80 | 80 | 90 |
| 11-1064 | 120 | 100 | 90 | 90 | 90 |
| 11-1069 | 120 | 90 | 70 | 70 | 60 |
| 11-1071 | 120 | 90 | 80 | 80 | 90 |
| 11-1072 | 120 | 100 | 60 | 90 | 90 |
| 11-1076 | 120 | 90 | 30 | 60 | 60 |
| 11-1079 | 120 | 90 | 80 | 80 | 90 |
| 11-1084 | 120 | 90 | 80 | 80 | 90 |
| 11-1088 | 120 | 90 | 80 | 80 | 90 |
| 11-1090 | 120 | 100 | 60 | 90 | 90 |
| 11-1098 | 120 | 100 | 80 | 70 | 70 |
| 11-1101 | 120 | 90 | 80 | 80 | 90 |
| 11-1102 | 120 | 100 | 80 | 70 | 90 |
| 11-1109 | 120 | 90 | 80 | 80 | 90 |
| 11-1125 | 120 | 90 | 60 | 70 | 30 |
| 11-1126 | 120 | 100 | 70 | 70 | 100 |
| 11-1127 | 120 | 100 | 70 | 70 | 100 |
| 11-1129 | 120 | 100 | 80 | 70 | 100 |
| 11-1131 | 120 | 100 | 90 | 70 | 80 |
| 11-1134 | 120 | 80 | 70 | 70 | 100 |
| 11-1137 | 120 | 100 | 80 | 70 | 100 |
| 11-1140 | 120 | 100 | 90 | 80 | 100 |
| 11-1141 | 120 | 90 | 80 | 70 | 60 |
| 11-1147 | 120 | 100 | 90 | 70 | 100 |
| 11-1148 | 120 | 100 | 90 | 90 | 100 |
| 11-1149 | 120 | 100 | 100 | 80 | 100 |
| 11-1150 | 120 | 100 | 90 | 100 | 60 |
| 11-1151 | 120 | 100 | 90 | 80 | 90 |
| 11-1152 | 120 | 100 | 100 | 100 | 100 |
| 11-1153 | 120 | 100 | 100 | 70 | 90 |
| 11-1154 | 120 | 100 | 90 | 80 | 80 |
| 11-1155 | 120 | 100 | 90 | 80 | 90 |
| 11-1156 | 120 | 90 | 60 | 90 | 30 |

Test Example 13

Herbicidal Effect Test by Soil Treatment in Upland Field

A pot having a size of 36 cm² was filled with field soil (alluvial soil) and after mixing the soil of the surface layer of 1 cm with 20 grains of each weed seed of crabgrass, *Echinochloa crus-galli*, *Chenopodium album* and *Amaranthus viridis*, the surface layer was pressed lightly. One day after the sowing, an emulsifiable concentrate prepared according to Formulation Example 15 by using the compound shown in Table 11 below was diluted with water, and the water-diluted formulation was sprayed on the soil surface at a ratio of 100 liter per 10 are. The application rate of the active ingredient, by conversion, corresponded to 120 g per 10 are. Fourteen Days after the formulation treatment, the herbicidal effect was evaluated by the same criteria as in Test Example 11. The results are shown in Table 11.

TABLE 11

| No. | Concentration (g/10a) | Crabgrass | Echinochloa crus-galli | Chenopodium album | Amaranthus viridis |
|---|---|---|---|---|---|
| 11-1 | 120 | 90 | 80 | 80 | 90 |
| 11-11 | 120 | 90 | 80 | 30 | 30 |
| 11-12 | 120 | 100 | 100 | 90 | 100 |
| 11-14 | 120 | 100 | 100 | 60 | 70 |
| 11-16 | 120 | 100 | 100 | 70 | 100 |
| 11-19 | 120 | 90 | 80 | 80 | 90 |
| 11-25 | 120 | 100 | 80 | 30 | 30 |
| 11-26 | 120 | 90 | 80 | 80 | 90 |

TABLE 11-continued

| No. | Concentration (g/10a) | Crabgrass | Echinochloa crus-galli | Chenopodium album | Amaranthus viridis |
|---|---|---|---|---|---|
| 11-38 | 120 | 90 | 90 | 40 | 0 |
| 11-46 | 120 | 100 | 100 | 100 | 100 |
| 11-48 | 120 | 90 | 80 | 80 | 90 |
| 11-58 | 120 | 90 | 100 | 70 | 70 |
| 11-59 | 120 | 100 | 100 | 100 | 90 |
| 11-61 | 120 | 100 | 100 | 80 | 90 |
| 11-62 | 120 | 70 | 70 | 60 | 100 |
| 11-63 | 120 | 100 | 100 | 90 | 90 |
| 11-64 | 120 | 100 | 100 | 60 | 60 |
| 11-66 | 120 | 90 | 80 | 80 | 90 |
| 11-73 | 120 | 90 | 80 | 80 | 90 |
| 11-85 | 120 | 100 | 100 | 60 | 90 |
| 11-86 | 120 | 90 | 80 | 80 | 90 |
| 11-93 | 120 | 90 | 80 | 80 | 90 |
| 11-94 | 120 | 100 | 100 | 90 | 80 |
| 11-95 | 120 | 70 | 70 | 0 | 0 |
| 11-109 | 120 | 100 | 100 | 100 | 90 |
| 11-123 | 120 | 90 | 80 | 80 | 90 |
| 11-142 | 120 | 90 | 80 | 80 | 90 |
| 11-159 | 120 | 90 | 80 | 80 | 90 |
| 11-160 | 120 | 90 | 80 | 80 | 90 |
| 11-162 | 120 | 90 | 80 | 80 | 90 |
| 11-189 | 120 | 100 | 100 | 90 | 100 |
| 11-191 | 120 | 100 | 100 | 70 | 70 |
| 11-194 | 120 | 90 | 90 | 70 | 100 |
| 11-195 | 120 | 100 | 100 | 90 | 90 |
| 11-211 | 120 | 100 | 100 | 70 | 70 |
| 11-212 | 120 | 100 | 100 | 60 | 60 |
| 11-222 | 120 | 90 | 80 | 80 | 90 |
| 11-233 | 120 | 90 | 80 | 50 | 80 |
| 11-234 | 120 | 90 | 80 | 80 | 90 |
| 11-238 | 120 | 90 | 80 | 80 | 90 |
| 11-258 | 120 | 100 | 100 | 100 | 100 |
| 11-273 | 120 | 100 | 90 | 90 | 60 |
| 11-283 | 120 | 90 | 80 | 80 | 90 |
| 11-284 | 120 | 90 | 80 | 80 | 90 |
| 11-294 | 120 | 90 | 80 | 80 | 90 |
| 11-296 | 120 | 100 | 100 | 70 | 60 |
| 11-297 | 120 | 90 | 90 | 70 | 100 |
| 11-298 | 120 | 100 | 100 | 60 | 60 |
| 11-301 | 120 | 90 | 80 | 80 | 90 |
| 11-308 | 120 | 90 | 80 | 80 | 90 |
| 11-309 | 120 | 90 | 80 | 80 | 90 |
| 11-352 | 120 | 80 | 80 | 40 | 0 |
| 11-358 | 120 | 90 | 80 | 80 | 90 |
| 11-367 | 120 | 100 | 100 | 40 | 40 |
| 11-406 | 120 | 90 | 100 | 30 | 30 |
| 11-427 | 120 | 90 | 70 | 60 | 40 |
| 11-463 | 120 | 90 | 90 | 100 | 80 |
| 11-475 | 120 | 100 | 100 | 90 | 80 |
| 11-477 | 120 | 100 | 100 | 70 | 70 |
| 11-482 | 120 | 90 | 80 | 80 | 90 |
| 11-488 | 120 | 70 | 60 | 60 | 60 |
| 11-500 | 120 | 80 | 80 | 0 | 0 |
| 11-501 | 120 | 90 | 40 | 0 | 0 |
| 11-512 | 120 | 100 | 100 | 50 | 70 |
| 11-538 | 120 | 60 | 80 | 40 | 40 |
| 11-550 | 120 | 90 | 90 | 0 | 0 |
| 11-588 | 120 | 60 | 80 | 80 | 40 |
| 11-616 | 120 | 40 | 80 | 80 | 80 |
| 11-622 | 120 | 80 | 90 | 40 | 40 |
| 11-623 | 120 | 90 | 100 | 0 | 0 |
| 11-625 | 120 | 80 | 80 | 0 | 0 |
| 11-626 | 120 | 90 | 90 | 70 | 50 |
| 11-637 | 120 | 90 | 100 | 40 | 40 |
| 11-644 | 120 | 90 | 80 | 80 | 90 |
| 11-665 | 120 | 80 | 80 | 0 | 0 |
| 11-666 | 120 | 90 | 100 | 100 | 40 |
| 11-670 | 120 | 70 | 70 | 0 | 0 |
| 11-682 | 120 | 80 | 90 | 40 | 40 |
| 11-706 | 120 | 80 | 80 | 50 | 50 |
| 11-710 | 120 | 80 | 100 | 60 | 40 |
| 11-711 | 120 | 90 | 100 | 50 | 50 |
| 11-762 | 120 | 90 | 80 | 60 | 60 |
| 11-800 | 120 | 90 | 60 | 70 | 70 |
| 11-818 | 120 | 100 | 100 | 60 | 60 |
| 11-852 | 120 | 80 | 80 | 60 | 60 |

TABLE 11-continued

| No. | Concentration (g/10a) | Crabgrass | Echinochloa crus-galli | Chenopodium album | Amaranthus viridis |
|---|---|---|---|---|---|
| 11-863 | 120 | 70 | 60 | 50 | 50 |
| 11-870 | 120 | 90 | 80 | 80 | 90 |
| 11-876 | 120 | 100 | 100 | 100 | 70 |
| 11-944 | 120 | 90 | 90 | 0 | 0 |
| 11-985 | 120 | 80 | 80 | 0 | 0 |
| 11-1021 | 120 | 100 | 90 | 70 | 70 |
| 11-1022 | 120 | 100 | 100 | 100 | 70 |
| 11-1024 | 120 | 100 | 70 | 60 | 60 |
| 11-1029 | 120 | 90 | 80 | 80 | 90 |
| 11-1056 | 120 | 90 | 80 | 80 | 90 |
| 11-1064 | 120 | 100 | 100 | 90 | 90 |
| 11-1071 | 120 | 90 | 80 | 80 | 90 |
| 11-1090 | 120 | 90 | 80 | 50 | 50 |
| 11-1098 | 120 | 100 | 100 | 100 | 90 |
| 11-1101 | 120 | 90 | 80 | 80 | 90 |
| 11-1102 | 120 | 100 | 100 | 100 | 90 |
| 11-1109 | 120 | 100 | 100 | 100 | 100 |
| 11-1148 | 120 | 100 | 100 | 90 | 100 |
| 11-1149 | 120 | 70 | 70 | 30 | 30 |
| 11-1150 | 120 | 100 | 100 | 80 | 90 |
| 11-1154 | 120 | 100 | 100 | 80 | 90 |
| 11-1155 | 120 | 90 | 90 | 30 | 30 |

Test Example 14

Herbicidal Effect Test by Foliage Treatment in Upland Field

A pot having a size of 36 cm² was filled with field soil (alluvial soil) and after uniformly mixing the soil of the surface layer of 1 cm with 20 grains of each weed seed of crabgrass, *Echinochloa crus-galli*, *Chenopodium album* and *Amaranthus viridis*, the surface layer was pressed lightly. Seven Days after the sowing, an emulsifiable concentrate prepared according to Formulation Example 15 by using the compound shown in Table 12 below was diluted with water, and the water-diluted formulation was sprayed on the soil surface at a ratio of 100 liter per 10 are. The application rate of the active ingredient, by conversion, corresponded to 120 g per 10 are. Fourteen Days after the formulation treatment, the herbicidal effect was evaluated by the same criteria as in Test Example 11. The results are shown in Table 12.

TABLE 12

| No. | Concentration (g/10a) | Crabgrass | Echinochloa crus-galli | Chenopodium album | Amaranthus viridis |
|---|---|---|---|---|---|
| 11-1 | 120 | 90 | 80 | 80 | 90 |
| 11-11 | 120 | 100 | 100 | 70 | 60 |
| 11-12 | 120 | 90 | 90 | 90 | 80 |
| 11-14 | 120 | 100 | 100 | 30 | 30 |
| 11-16 | 120 | 100 | 100 | 70 | 30 |
| 11-17 | 120 | 60 | 70 | 30 | 100 |
| 11-19 | 120 | 90 | 80 | 80 | 90 |
| 11-26 | 120 | 90 | 80 | 80 | 90 |
| 11-38 | 120 | 90 | 90 | 0 | 0 |
| 11-46 | 120 | 100 | 100 | 90 | 60 |
| 11-48 | 120 | 100 | 90 | 70 | 40 |
| 11-49 | 120 | 90 | 80 | 80 | 90 |
| 11-58 | 120 | 100 | 90 | 70 | 30 |
| 11-59 | 120 | 90 | 80 | 80 | 90 |
| 11-61 | 120 | 100 | 100 | 70 | 70 |
| 11-62 | 120 | 100 | 100 | 90 | 100 |
| 11-63 | 120 | 100 | 100 | 70 | 60 |
| 11-64 | 120 | 100 | 90 | 60 | 60 |
| 11-66 | 120 | 90 | 80 | 80 | 90 |
| 11-67 | 120 | 90 | 90 | 60 | 60 |
| 11-71 | 120 | 100 | 100 | 70 | 60 |
| 11-73 | 120 | 90 | 80 | 80 | 90 |
| 11-74 | 120 | 90 | 80 | 80 | 90 |
| 11-76 | 120 | 100 | 100 | 60 | 80 |
| 11-85 | 120 | 90 | 80 | 80 | 90 |
| 11-86 | 120 | 90 | 80 | 80 | 90 |
| 11-93 | 120 | 90 | 80 | 80 | 90 |
| 11-94 | 120 | 90 | 90 | 90 | 50 |
| 11-109 | 120 | 90 | 90 | 40 | 40 |
| 11-123 | 120 | 90 | 80 | 80 | 90 |
| 11-134 | 120 | 70 | 40 | 40 | 40 |
| 11-142 | 120 | 90 | 80 | 80 | 90 |
| 11-144 | 120 | 80 | 80 | 60 | 80 |
| 11-159 | 120 | 90 | 80 | 80 | 90 |
| 11-160 | 120 | 90 | 80 | 80 | 90 |

TABLE 12-continued

| No. | Concentration (g/10a) | Crabgrass | Echinochloa crus-galli | Chenopodium album | Amaranthus viridis |
|---|---|---|---|---|---|
| 11-162 | 120 | 90 | 80 | 80 | 90 |
| 11-189 | 120 | 100 | 100 | 80 | 60 |
| 11-191 | 120 | 100 | 100 | 60 | 60 |
| 11-194 | 120 | 100 | 100 | 80 | 90 |
| 11-195 | 120 | 100 | 100 | 70 | 30 |
| 11-205 | 120 | 100 | 100 | 70 | 70 |
| 11-206 | 120 | 90 | 90 | 60 | 60 |
| 11-209 | 120 | 90 | 90 | 60 | 30 |
| 11-212 | 120 | 90 | 80 | 80 | 90 |
| 11-213 | 120 | 90 | 80 | 80 | 90 |
| 11-217 | 120 | 100 | 100 | 70 | 60 |
| 11-233 | 120 | 90 | 90 | 50 | 40 |
| 11-234 | 120 | 90 | 80 | 80 | 90 |
| 11-238 | 120 | 90 | 80 | 80 | 90 |
| 11-258 | 120 | 90 | 80 | 80 | 90 |
| 11-273 | 120 | 90 | 80 | 80 | 90 |
| 11-283 | 120 | 90 | 80 | 80 | 90 |
| 11-285 | 120 | 90 | 80 | 80 | 90 |
| 11-293 | 120 | 100 | 90 | 70 | 60 |
| 11-294 | 120 | 90 | 80 | 80 | 90 |
| 11-296 | 120 | 100 | 100 | 70 | 90 |
| 11-297 | 120 | 100 | 100 | 60 | 90 |
| 11-298 | 120 | 100 | 100 | 70 | 60 |
| 11-299 | 120 | 100 | 100 | 60 | 60 |
| 11-301 | 120 | 90 | 80 | 80 | 90 |
| 11-306 | 120 | 100 | 60 | 70 | 70 |
| 11-311 | 120 | 100 | 90 | 30 | 60 |
| 11-367 | 120 | 90 | 90 | 40 | 40 |
| 11-391 | 120 | 90 | 60 | 40 | 40 |
| 11-405 | 120 | 90 | 90 | 60 | 70 |
| 11-427 | 120 | 90 | 40 | 60 | 40 |
| 11-463 | 120 | 60 | 70 | 0 | 40 |
| 11-464 | 120 | 90 | 60 | 50 | 50 |
| 11-475 | 120 | 90 | 70 | 40 | 40 |
| 11-482 | 120 | 90 | 80 | 80 | 90 |
| 11-500 | 120 | 40 | 40 | 50 | 40 |
| 11-501 | 120 | 90 | 70 | 0 | 0 |
| 11-512 | 120 | 90 | 80 | 50 | 40 |
| 11-623 | 120 | 60 | 80 | 40 | 40 |
| 11-626 | 120 | 90 | 40 | 90 | 60 |
| 11-637 | 120 | 80 | 80 | 0 | 0 |
| 11-641 | 120 | 90 | 100 | 70 | 60 |
| 11-644 | 120 | 90 | 80 | 80 | 90 |
| 11-661 | 120 | 70 | 90 | 0 | 0 |
| 11-666 | 120 | 90 | 90 | 40 | 40 |
| 11-686 | 120 | 90 | 90 | 60 | 30 |
| 11-706 | 120 | 50 | 0 | 40 | 70 |
| 11-735 | 120 | 100 | 60 | 70 | 70 |
| 11-762 | 120 | 90 | 90 | 60 | 70 |
| 11-800 | 120 | 90 | 90 | 100 | 100 |
| 11-815 | 120 | 100 | 70 | 80 | 70 |
| 11-852 | 120 | 90 | 60 | 70 | 60 |
| 11-863 | 120 | 60 | 70 | 70 | 50 |
| 11-870 | 120 | 90 | 80 | 80 | 90 |
| 11-876 | 120 | 100 | 90 | 30 | 30 |
| 11-1011 | 120 | 90 | 80 | 80 | 90 |
| 11-1022 | 120 | 70 | 90 | 40 | 0 |
| 11-1025 | 120 | 100 | 100 | 60 | 60 |
| 11-1026 | 120 | 90 | 90 | 70 | 30 |
| 11-1029 | 120 | 90 | 80 | 80 | 90 |
| 11-1033 | 120 | 90 | 90 | 60 | 60 |
| 11-1046 | 120 | 100 | 0 | 40 | 60 |
| 11-1056 | 120 | 90 | 80 | 80 | 90 |
| 11-1064 | 120 | 90 | 90 | 80 | 70 |
| 11-1071 | 120 | 90 | 80 | 80 | 90 |
| 11-1072 | 120 | 90 | 80 | 80 | 90 |
| 11-1090 | 120 | 90 | 90 | 40 | 40 |
| 11-1098 | 120 | 90 | 80 | 80 | 90 |
| 11-1099 | 120 | 90 | 80 | 80 | 90 |
| 11-1101 | 120 | 90 | 80 | 80 | 90 |
| 11-1102 | 120 | 90 | 80 | 80 | 90 |
| 11-1109 | 120 | 90 | 80 | 80 | 90 |
| 11-1129 | 120 | 90 | 70 | 60 | 70 |
| 11-1148 | 120 | 100 | 100 | 80 | 70 |
| 11-1149 | 120 | 80 | 70 | 70 | 30 |
| 11-1150 | 120 | 100 | 100 | 60 | 50 |
| 11-1152 | 120 | 100 | 100 | 80 | 90 |

TABLE 12-continued

| No. | Concentration (g/10a) | Crabgrass | Echinochloa crus-galli | Chenopodium album | Amaranthus viridis |
|---|---|---|---|---|---|
| 11-1154 | 120 | 100 | 100 | 80 | 30 |
| 11-1155 | 120 | 100 | 90 | 60 | 30 |

INDUSTRIAL APPLICABILITY

According to the present invention, a novel 1-(N,N-disubstituted carbamoyl)4-(substituted sulfonyl)triazolin-5-one derivative, a novel 4-(N,N-disubstituted carbamoyl)1-(substituted sulfonyl)triazolin-5-one derivative, and a herbicide containing the derivative as an active ingredient and showing an excellent herbicidal effect can be provided.

While the invention has been described in detail and with reference to specific embodiments thereof, it will be apparent to one skilled in the art that various changes and modifications can be made therein without departing from the spirit and scope of the invention.

This application is based on Japanese Patent Application (Patent Application No. 2017-167829) filed on Aug. 31, 2017 and Japanese Patent Application (Patent Application No. 2017-167830) filed on Aug. 31, 2017, the contents of which are incorporated herein by way of reference.

The invention claimed is:

1. A 1-(N,N-disubstituted carbamoyl)4-(substituted sulfonyl)triazolin-5-one derivative represented by formula (1):

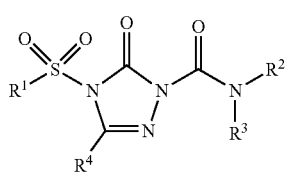

wherein in formula (1),
$R^1$ represents a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C8 cycloalkyl group which may be monosubstituted or polysubstituted by a halogen atom, a C1-C6 alkyl group, a C1-C6 alkoxy group, a C3-C8 cycloalkyl group, a C3-C6 cycloalkyl C1-C6 alkyl group, a phenyl group, or a C7-C11 aralkyl group, a C3-C6 cycloalkyl C1-C6 alkyl group, a C1-C6 alkoxy C1-C6 alkyl group, a C1-C6 haloalkoxy C1-C6 alkyl group, a phenyl group which may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group, a C7-C11 aralkyl group which may be monosubstituted or polysubstituted by a halogen atom, a C1-C6 alkyl group, or a C1-C6 alkoxy group, a heterocyclic ring which may be monosubstituted or polysubstituted by a halogen atom, a C1-C6 alkyl group, or a C1-C6 alkoxy group, a C1-C6 alkylamino group, a di C1-C6 alkylamino group in which alkyl groups may be the same or different and the alkyl groups may also combine with each other via an alkylene group to form a 3-membered ring, a 4-membered ring, a 5-membered ring and a 6-membered ring, a tetrahydropyranyl group, a tetrahydrofuryl group, a tetrahydropyranylmethyl group, or a tetrahydrofurfuryl group;
each of $R^2$ and $R^3$ independently represents a C1-C6 alkyl group, a C1-C6 haloalkyl group, a C2-C6 alkenyl group, a C2-C6 alkynyl group, a C3-C6 cycloalkyl group, a C3-C6 cycloalkyl C1-C6 alkyl group, a C1-C6 alkoxy C1-C6 alkyl group, a C1-C6 haloalkoxy C1-C6 alkyl group, a phenyl group which may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group, a C7-C11 aralkyl group which may be monosubstituted or polysubstituted by a halogen atom, a C1-C6 alkyl group, or a C1-C6 alkoxy group, or a heterocyclic ring which may be monosubstituted or polysubstituted by a halogen atom, a C1-C6 alkyl group, a C1-C6 haloalkyl group, or a C1-C6 alkoxy group, and when $R^2$ and $R^3$ are C1-C6 alkyl groups, these may also combine with each other to form a 3-membered ring, a 4-membered ring, a 5-membered ring, and a 6-membered ring with an alkylene group having from 2 to 5 carbon atoms as ring members; and
$R^4$ represents a hydrogen atom, a halogen atom, a C1-C6 alkyl group, a C1-C6 haloalkyl group, a C1-C6 alkoxy group, or a C1-C6 haloalkoxy group.

2. The 1-(N,N-disubstituted carbamoyl)4-(substituted sulfonyl)triazolin-5-one derivative according to claim 1, wherein in formula (1),
$R^1$ represents a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C8 cycloalkyl group which may be monosubstituted or polysubstituted by a halogen atom, a C1-C6 alkyl group, a C1-C6 alkoxy group, a C3-C8 cycloalkyl group, a C3-C6 cycloalkyl C1-C6 alkyl group, a phenyl group, or a C7-C11 aralkyl group, a C3-C6 cycloalkyl C1-C6 alkyl group, a C1-C6 alkoxy C1-C6 alkyl group, a C1-C6 haloalkoxy C1-C6 alkyl group, a phenyl group which may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group, a C7-C11 aralkyl group which may be monosubstituted or polysubstituted by a halogen atom, a C1-C6 alkyl group, or a C1-C6 alkoxy group, a pyridine ring which may be monosubstituted or polysubstituted by a halogen atom, a C1-C6 alkyl group, or a C1-C6 alkoxy group, a thiophene ring which may be monosubstituted or polysubstituted by a halogen atom, a C1-C6 alkyl group, or a C1-C6 alkoxy group, a C1-C6 alkylamino group, a di C1-C6 alkylamino group in which alkyl groups may be the same or different and the alkyl groups may also combine with each other via an alkylene group to form a 3-membered ring, a 4-membered ring, a 5-membered ring and a 6-membered ring, a tetrahydropyranyl group, a tetrahydrofuryl group, a tetrahydropyranylmethyl group, or a tetrahydrofurfuryl group;

$R^2$ represents a C1-C6 alkyl group, a C1-C6 haloalkyl group, a C2-C6 alkenyl group, a C2-C6 alkynyl group, a C3-C6 cycloalkyl group, a C3-C6 cycloalkyl C1-C6 alkyl group, a C1-C6 alkoxy C1-C6 alkyl group, a C1-C6 haloalkoxy C1-C6 alkyl group, a phenyl group which may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group, a C7-C11 aralkyl group which may be monosubstituted or polysubstituted by a halogen atom, a C1-C6 alkyl group, or a C1-C6 alkoxy group, or a pyridine ring which may be monosubstituted or polysubstituted by a halogen atom, a C1-C6 alkyl group, a C1-C6 haloalkyl group, or a C1-C6 alkoxy group;

$R^3$ represents a C1-C6 alkyl group, a C3-C6 cycloalkyl group, a phenyl group which may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group, a C7-C11 aralkyl group which may be monosubstituted or polysubstituted by a halogen atom, a C1-C6 alkyl group, or a C1-C6 alkoxy group, a pyridine ring which may be monosubstituted or polysubstituted by a halogen atom, a C1-C6 alkyl group, a C1-C6 haloalkyl group, or a C1-C6 alkoxy group, an isoxazole ring which may be monosubstituted or polysubstituted by a halogen atom, a C1-C6 alkyl group, a C1-C6 haloalkyl group, or a C1-C6 alkoxy group, a thiazole ring which may be monosubstituted or polysubstituted by a halogen atom, a C1-C6 alkyl group, a C1-C6 haloalkyl group, or a C1-C6 alkoxy group, or a pyrazole ring which may be monosubstituted or polysubstituted by a halogen atom, a C1-C6 alkyl group, a C1-C6 haloalkyl group, or a C1-C6 alkoxy group, and when $R^2$ and $R^3$ are C1-C6 alkyl groups, these may also combine with each other to form a 3-membered ring, a 4-membered ring, a 5-membered ring, and a 6-membered ring with an alkylene group having from 2 to 5 carbon atoms as ring members; and $R^4$ represents a hydrogen atom, a halogen atom, a C1-C6 alkyl group, a C1-C6 haloalkyl group, a C1-C6 alkoxy group, or a C1-C6 haloalkoxy group.

3. The 1-(N,N-disubstituted carbamoyl)4-(substituted sulfonyl)triazolin-5-one derivative according to claim 1, wherein in formula (1), $R^1$ represents a C1-C6 alkyl group, a C1-C6 haloalkyl group, a C2-C6 alkenyl group, a C3-C8 cycloalkyl group which may be monosubstituted or polysubstituted by a halogen atom, a C1-C6 alkyl group, a C1-C6 alkoxy group, a C3-C8 cycloalkyl group, a C3-C6 cycloalkyl C1-C6 alkyl group, a phenyl group, or a C7-C11 aralkyl group, a phenyl group which may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group, a C7-C11 aralkyl group which may be monosubstituted or polysubstituted by a halogen atom, a C1-C6 alkyl group, or a C1-C6 alkoxy group, a pyridine ring which may be monosubstituted or polysubstituted by a halogen atom, a C1-C6 alkyl group, or a C1-C6 alkoxy group, a thiophene ring which may be monosubstituted or polysubstituted by a halogen atom, a C1-C6 alkyl group, or a C1-C6 alkoxy group, a di C1-C6 alkylamino group in which alkyl groups may be the same or different and the alkyl groups may also combine with each other via an alkylene group to form a 3-membered ring, a 4-membered ring, a 5-membered ring and a 6-membered ring, a tetrahydropyranyl group, or a tetrahydrofuryl group;

$R^2$ represents a C1-C6 alkyl group;

$R^3$ represents a C1-C6 alkyl group, a phenyl group which may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group, a C7-C11 aralkyl group which may be monosubstituted or polysubstituted by a halogen atom, a C1-C6 alkyl group, or a C1-C6 alkoxy group, a pyridine ring which may be monosubstituted or polysubstituted by a halogen atom, a C1-C6 alkyl group, a C1-C6 haloalkyl group, or a C1-C6 alkoxy group, or an isoxazole ring which may be monosubstituted or polysubstituted by a halogen atom, a C1-C6 alkyl group, a C1-C6 haloalkyl group, or a C1-C6 alkoxy group); and $R^4$ represents a hydrogen atom, a C1-C6 alkyl group, or a C1-C6 alkoxy group.

4. A 4-(N,N-disubstituted carbamoyl)1-(substituted sulfonyl)triazolin-5-one derivative represented by formula (11):

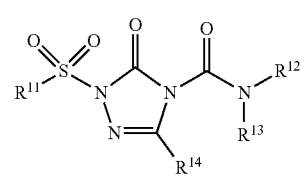

(11)

wherein in formula (11), $R^{11}$ represents a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C8 cycloalkyl group which may be monosubstituted or polysubstituted by a halogen atom, a C1-C6 alkyl group, a C1-C6 alkoxy group, a C3-C8 cycloalkyl group, a C3-C6 cycloalkyl C1-C6 alkyl group, a phenyl group, or a C7-C11 aralkyl group), a C3-C6 cycloalkyl C1-C6 alkyl group, a C1-C6 alkoxy C1-C6 alkyl group, a C1-C6 haloalkoxy C1-C6 alkyl group, a phenyl group which may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group, a C7-C11 aralkyl group which may be monosubstituted or polysubstituted by a halogen atom, a C1-C6 alkyl group, or a C1-C6 alkoxy group, a heterocyclic ring which may be monosubstituted or polysubstituted by a halogen atom, a C1-C6 alkyl group, or a C1-C6 alkoxy group, a C1-C6 alkylamino group, a di C1-C6 alkylamino group in which alkyl groups may be the same or different and the alkyl groups may also combine with each other via an alkylene group to form a 3-membered ring, a 4-membered ring, a 5-membered ring and a 6-membered ring, a tetrahydropyranyl group, a tetrahydrofuryl group, a tetrahydropyranylmethyl group, or a tetrahydrofurfuryl group;

each of $R^{12}$ and $R^{13}$ independently represents a C1-C6 alkyl group, a C1-C6 haloalkyl group, a C2-C6 alkenyl group, a C2-C6 alkynyl group, a C3-C6 cycloalkyl group, a C3-C6 cycloalkyl C1-C6 alkyl group, a C1-C6 alkoxy C1-C6 alkyl group, a C1-C6 haloalkoxy C1-C6 alkyl group, a phenyl group which may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group, a C7-C11 aralkyl group which may be monosubstituted or polysubstituted by a halogen atom, a C1-C6 alkyl group, or a C1-C6 alkoxy group, or a heterocyclic ring which may be monosubstituted or polysubstituted by a halogen atom, a C1-C6 alkyl group, a C1-C6 haloalkyl group, or a C1-C6 alkoxy group, and when $R^{12}$ and $R^{13}$ are a C1-C6 alkyl group, these may also combine with each other to form a 3-membered ring, a 4-membered ring, a 5-membered ring, and a 6-membered ring with an alkylene group having from 2 to 5 carbon atoms as ring members; and $R^{14}$ represents a hydrogen atom, a halogen atom, a C1-C6 alkyl group, a C1-C6 haloalkyl group, a C1-C6 alkoxy group, or a C1-C6 haloalkoxy group.

5. The 4-(N,N-disubstituted carbamoyl)1-(substituted sulfonyl)triazolin-5-one derivative according to claim 4, wherein in formula (11), $R^{11}$ represents a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C8 cycloalkyl group which may be monosubstituted or polysubstituted by a halogen atom, a C1-C6 alkyl group, a C1-C6 alkoxy group, a C3-C8 cycloalkyl group, a C3-C6 cycloalkyl C1-C6 alkyl group, a phenyl group, or a C7-C11 aralkyl group, a C3-C6 cycloalkyl C1-C6 alkyl group, a C1-C6 alkoxy C1-C6 alkyl group, a C1-C6 haloalkoxy C1-C6 alkyl group, a phenyl group which may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group, a C7-C11 aralkyl group which may be monosubstituted or polysubstituted by a halogen atom, a C1-C6 alkyl group, or a C1-C6 alkoxy group, a pyridine ring which may be monosubstituted or polysubstituted by a halogen atom, a C1-C6 alkyl group, or a C1-C6 alkoxy group, a thiophene ring which may be monosubstituted or polysubstituted by a halogen atom, a C1-C6 alkyl group, or a C1-C6 alkoxy group, a C1-C6 alkylamino group, a di C1-C6 alkylamino group in which alkyl groups may be the same or different and the alkyl groups may also combine with each other via an alkylene group to form a 3-membered ring, a 4-membered ring, a 5-membered ring and a 6-membered ring, a tetrahydropyranyl group, a tetrahydrofuryl group, a tetrahydropyranylmethyl group, or a tetrahydrofurfuryl group;

$R^{12}$ represents a C1-C6 alkyl group, a C1-C6 haloalkyl group, a C2-C6 alkenyl group, a C2-C6 alkynyl group, a C3-C6 cycloalkyl group, a C3-C6 cycloalkyl C1-C6 alkyl group, a C1-C6 alkoxy C1-C6 alkyl group, a C1-C6 haloalkoxy C1-C6 alkyl group, a phenyl group which may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group, a C7-C11 aralkyl group which may be monosubstituted or polysubstituted by a halogen atom, a C1-C6 alkyl group, or a C1-C6 alkoxy group, or a pyridine ring which may be monosubstituted or polysubstituted by a halogen atom, a C1-C6 alkyl group, a C1-C6 haloalkyl group, or a C1-C6 alkoxy group;

$R^{13}$ represents a C1-C6 alkyl group, a C3-C6 cycloalkyl group, a phenyl group which may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group, a C7-C11 aralkyl group which may be monosubstituted or polysubstituted by a halogen atom, a C1-C6 alkyl group, or a C1-C6 alkoxy group, a pyridine ring which may be monosubstituted or polysubstituted by a halogen atom, a C1-C6 alkyl group, a C1-C6 haloalkyl group, or a C1-C6 alkoxy group, an isoxazole ring which may be monosubstituted or polysubstituted by a halogen atom, a C1-C6 alkyl group, a C1-C6 haloalkyl group, or a C1-C6 alkoxy group, a thiazole ring which may be monosubstituted or polysubstituted by a halogen atom, a C1-C6 alkyl group, a C1-C6 haloalkyl group, or a C1-C6 alkoxy group, or a pyrazole ring which may be monosubstituted or polysubstituted by a halogen atom, a C1-C6 alkyl group, a C1-C6 haloalkyl group, or a C1-C6 alkoxy group, and when $R^{12}$ and $R^{13}$ are C1-C6 alkyl groups, these may also combine with each other to form a 3-membered ring, a 4-membered ring, a 5-membered ring, and a 6-membered ring with an alkylene group having from 2 to 5 carbon atoms as ring members; and $R^{14}$ represents a hydrogen atom, a halogen atom, a C1-C6 alkyl group, a C1-C6 haloalkyl group, a C1-C6 alkoxy group, or a C1-C6 haloalkoxy group.

6. The 4-(N,N-disubstituted carbamoyl)1-(substituted sulfonyl)triazolin-5-one derivative according to claim 4, wherein in formula (11), $R^{11}$ represents a C1-C6 alkyl group, a C1-C6 haloalkyl group, a C2-C6 alkenyl group, a C3-C8 cycloalkyl group which may be monosubstituted or polysubstituted by a halogen atom, a C1-C6 alkyl group, a C1-C6 alkoxy group, a C3-C8 cycloalkyl group, a C3-C6 cycloalkyl C1-C6 alkyl group, a phenyl group, or a C7-C11 aralkyl group, a phenyl group which may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group, a C7-C11 aralkyl group which may be monosubstituted or polysubstituted by a halogen atom, a C1-C6 alkyl group, or a C1-C6 alkoxy group, a pyridine ring which may be monosubstituted or polysubstituted by a halogen atom, a C1-C6 alkyl group, or a C1-C6 alkoxy group, a thiophene ring which may be monosubstituted or polysubstituted by a halogen atom, a C1-C6 alkyl group, or a C1-C6 alkoxy group, a di C1-C6 alkylamino group in which alkyl groups may be the same or different and the alkyl groups may also combine with each other via an alkylene group to form a 3-membered ring, a 4-membered ring, a 5-membered ring and a 6-membered ring, or a tetrahydropyranyl group;

$R^{12}$ represents a C1-C6 alkyl group or a C1-C6 haloalkyl group;

$R^{13}$ represents a C1-C6 alkyl group, a C3-C8 cycloalkyl group, a phenyl group which may be monosubstituted or polysubstituted by a halogen atom, cyano, nitro, a C1-C6 alkyl group, a C1-C6 haloalkyl group, a C1-C6 alkoxy group, a C1-C6 haloalkoxy group, a C1-C6 alkylthio group, or a C1-C6 haloalkylthio group, a C7-C11 aralkyl group which may be monosubstituted or polysubstituted by a halogen atom, a C1-C6 alkyl group, or a C1-C6 alkoxy group, a pyridine ring which may be monosubstituted or polysubstituted by a halogen atom, a C1-C6 alkyl group, a C1-C6 haloalkyl group, or a C1-C6 alkoxy group), or an isoxazole ring which may be monosubstituted or polysubstituted by a halogen atom, a C1-C6 alkyl group, a C1-C6 haloalkyl group, or a C1-C6 alkoxy group, and when $R^{12}$ and $R^{13}$ are C1-C6 alkyl groups, these may also combine with each other to form a 3-membered ring, a 4-membered ring, a 5-membered ring, and a 6-membered ring with an alkylene group having from 2 to 5 carbon atoms as ring members; and $R^{14}$ represents a hydrogen atom or a C1-C6 alkyl group.

7. A herbicide comprising as an active ingredient the 1-(N,N-disubstituted carbamoyl)4-(substituted sulfonyl)triazolin-5-one derivative according to claim 1.

8. A herbicide comprising as an active ingredient the 4-(N,N-disubstituted carbamoyl)1-(substituted sulfonyl)triazolin-5-one derivative according to claim 4.

9. A herbicide comprising as an active ingredient the 1-(N,N-disubstituted carbamoyl)4-(substituted sulfonyl)triazolin-5-one derivative according to claim 2.

10. A herbicide comprising as an active ingredient the 1-(N,N-disubstituted carbamoyl)4-(substituted sulfonyl)triazolin-5-one derivative according to claim 3.

11. A herbicide comprising as an active ingredient the 4-(N,N-disubstituted carbamoyl)1-(substituted sulfonyl)triazolin-5-one derivative according to claim 5.

12. A herbicide comprising as an active ingredient the 4-(N,N-disubstituted carbamoyl)1-(substituted sulfonyl)triazolin-5-one derivative according to claim 6.

* * * * *